United States Patent
Gaillard et al.

(10) Patent No.: US 7,465,736 B2
(45) Date of Patent: Dec. 16, 2008

(54) AZOLE METHYLIDENE CYANIDE DERIVATIVES AND THEIR USE AS PROTEIN KINASE MODULATORS

(75) Inventors: Pascale Gaillard, St-Julien-en-Genevois (FR); Jean-Pierre Gotteland, Beaumont (FR); Isabelle Jeanclaude-Etter, Bellevue (CH); Matthias Schwarz, Geneva (CH); Russel J. Thomas, Siena (IT)

(73) Assignee: Laboratoires Serono S.A., Coinsins (CH)

(*) Notice: Subject to any disclaimer, the term of this patent is extended or adjusted under 35 U.S.C. 154(b) by 276 days.

(21) Appl. No.: 10/516,330

(22) PCT Filed: Jun. 13, 2003

(86) PCT No.: PCT/EP03/50225

§ 371 (c)(1),
(2), (4) Date: Sep. 22, 2005

(87) PCT Pub. No.: WO03/106455

PCT Pub. Date: Dec. 24, 2003

(65) Prior Publication Data

US 2007/0123530 A1    May 31, 2007

(30) Foreign Application Priority Data

Jun. 14, 2002 (EP) .................................. 02100710

(51) Int. Cl.
| | |
|---|---|
| *C07D 417/06* | (2006.01) |
| *C07D 417/08* | (2006.01) |
| *C07D 417/14* | (2006.01) |
| *A61K 31/427* | (2006.01) |
| *A61P 3/04* | (2006.01) |
| *A61P 3/10* | (2006.01) |
| *C07D 413/06* | (2006.01) |
| *C07D 413/14* | (2006.01) |
| *A61K 31/4523* | (2006.01) |
| *A61K 31/497* | (2006.01) |
| *A61K 31/502* | (2006.01) |

(52) U.S. Cl. .................. 514/256; 514/258.1; 514/269; 514/274; 514/275; 514/252.01; 514/252.1; 514/336; 544/253; 544/299; 544/323; 544/326; 544/333; 544/334; 544/335; 544/238; 544/239; 544/240; 544/241; 544/336

(58) Field of Classification Search ............... 544/253, 544/299, 333, 334, 323, 326, 335; 514/256, 514/258.1, 269, 274, 275

See application file for complete search history.

(56) References Cited

U.S. PATENT DOCUMENTS 4,371,734 A * 2/1983 Seybold ...................... 544/300

FOREIGN PATENT DOCUMENTS

| | | |
|---|---|---|
| EP | 0 169 502 | 1/1986 |
| EP | 1 110 957 | 6/2001 |
| WO | 00/35906 | 6/2000 |
| WO | 00/35909 | 6/2000 |
| WO | 00/35921 | 6/2000 |
| WO | 00/64872 | 11/2000 |
| WO | 01/47920 | 7/2001 |
| WO | 02/10141 | 2/2002 |
| WO | 02/20495 | 3/2002 |
| WO | 02/22608 | 3/2002 |

OTHER PUBLICATIONS

Cecil Textbook of Medicine, edited by Bennet, J.C., and Plum F., 20th edition, vol. 1, 1004-1010, 1996.*
Mass, R. D., Int. J. Radiation Oncology Bio. Phys.vol. 58(3); 932-940, 2004.*
Fabbro et al. Pharmacology & therapeutics 93, 79-98, 2002.*
Patel et al. Biochem. Soc. Trans. 32(5), 803-808, 2004.*
Jope et al., Trends in Biochemical Sciences, 20(2); 95-102, 2004.*
Cohen et al., Nature Reviews/Molecular Biology 2: 769-776, 2001.*
Turner et al., Current Pharmaceutical Design. 2, 209-224, 1996.*
Sugar et al., Diagn. Microbiol. Infect. Dis. 21: 129-133, 1995.*
Snyder et al., J. Med. Liban 48(4); 208-214, 2000.*
Blyumin et al., Tetrahedron, 58(28), 5733-5740, 2002.*
Xie, Xiaoling et al. "Crystal structure of JNK3: a kinase implicated in neuronal apoptosis", Structure, vol. 6, No. 8, pp. 983-991 1998.
Kumagae, Yoshihiro et al. "Human c-Jun N-terminal kinase expression and activation in the nervous system", Molecular Brain Research, vol. 67, No. 1, pp. 10-17 1999.
Yang, Derek D. et al. "Absence of excitotoxicity-induced apoptosis in the hippocampus of mice lacking the Jnk3 gene", Nature, vol. 389, pp. 865-870 1997.

(Continued)

*Primary Examiner*—Venkataraman Balasubram
(74) *Attorney, Agent, or Firm*—Oblon, Spivak, McClelland, Maier & Neustadt, P.C.

(57) ABSTRACT

An azole derivative of formula (I)

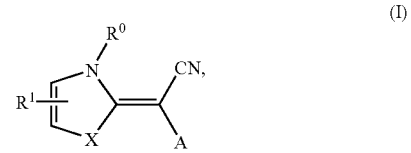

a medicament that contains the azole derivative of formula (I), a method of treating a disease with the azole derivative of formula (I), and a method of preparing the azole derivative of formula (I).

18 Claims, No Drawings

OTHER PUBLICATIONS

Yang, Derek D. et al. "Differentiation of CD4+ T Cells to Th1 Cells Requires MAP Kinase JNK2", Immunity, vol. 9, pp. 575-585 1998.

Sabapathy, Kanaga et al. "JNK2 is required for efficient T-cell activation and apoptosis but not for normal lymphocyte development", Current Biology, vol. 9, No. 3, pp. 116-125 1999.

Woodgett, James R. "A common denominator linking glycogen metabolism, nuclear oncogenes and development", TIBS, vol. 16, pp. 177-181 1991.

Saito, Yuji et al. "The mechanism by which epidermal growth factor inhibits glycogen synthase kinase 3 in A431 cells", Biochem. J., vol. 303, pp. 27-31 1994.

Welsh, Gavin I. et al. "Glycogen synthase kinase-3 is rapidly inactivated in response to insulin and phosphorylates eukaryotic initiation factor eIF-2B", Biochem. J., vol. 294, pp. 625-629 1993.

Cross, Darren A.E. et al. "The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf", Biochem. J., vol. 303, pp. 21-26 1994.

Grimes, C.A. et al., Progress in Neurobiology, vol. 65, pp. 393-426 2001.

Klein, Peter S. et al. "A molecular mechanism for the effect of lithium on development", Proc. Natl. Acad. Sci., vol. 93, pp. 8455-8459 1996.

Flueckiger-Isler, Rosina E. et al. "Stimulation of rat liver glycogen synthesis by the adenosine kinase inhibitor 5-iodotubercidin", Biochem. J., vol. 292, pp. 85-91 1993.

Massillon, Duna et al. "Identification of the glycogenic compound 5-iodotubercidin as a general protein kinase inhibitor", Biochem. J., vol. 299, pp. 123-128 1994.

Lovestone, Simon et al. "Alzheimer's disease-like phosphorylation of the microtubule-associated protein tau by glycogen synthase kinase-3 in transfected mammalian cells", Current Biology, vol. 4, No. 12, pp. 1077-1086 1994.

Brownlees, Janet et al. "Tau phosphorylation in transgenic mice expressing glycogen synthase kinase-3beta transgenes", NeuroReport, vol. 8, pp. 3251-3255 1997.

Stambolic, Vuk et al. "Lithium inhibits glycogen synthase kinase-3 activity and mimics Wingless signalling in intact cells", Current Biology, vol. 6, No. 12, pp. 1664-1668 1996.

Chen, Guang et al. "The Mood-Stabilizing Agent Valproate Inhibits the Activity of Glycogen Synthase Kinase-3", Journal of Neurochemistry, vol. 72, pp. 1327-1330 1999.

Takashima, Akihiko et al. "Presenilin 1 associates with glycogen synthase kinase-3beta and its substrate tau", Proc. Natl. Acad. Sci., vol. 95, pp. 9637-9641 1998.

Zhang, Zhuohua et al. "Destabilization of beta-catenin by mutations in presenilin-1 potentiates neuronal apoptosis", Nature, vol. 395, pp. 698-702 1998.

Takashima, Akihiko et al. "Tau protein kinase I is essential for amyloid beta-protein-induced neurotoxicity", Proc. Natl. Acad. Sci., vol. 90, pp. 7789-7793 1993.

Pei, Jin-Jing et al. "Distribution, Levels, and Activity of Glycogen Synthase Kinase-3 in the Alzheimer Disease Brain", Journal of Neuropathology and Experimental Neurology, vol. 56, No. 1, pp. 70-78 1997.

Nonaka, Shigeyuki et al. "Chronic lithium treatment robustly protects neurons in the central nervous system against excitotoxicity by inhibiting N-methyl-D-aspartate receptor-mediated calcium influx", Proc. Natl. Acad. Sci., vol. 95, pp. 2642-2647 1998.

Thomas, Robert Joseph. "Excitatory Amino Acids in Health and Disease", JAGS, vol. 43, pp. 1279-1289 1995.

Sasaki, Chihoko et al. "Different expression of glycogen synthase kinase-3beta between young and old rat brains after transient middle cerebral artery occlusion", Neurological Research, vol. 23, pp. 588-592 2001.

Cross, Darren A.E. "Selective small-molecule inhibitors of glycogen synthase kinase-3 activity protect primary neurones from death", Journal of Neurochemistry, vol. 77, pp. 94-102 2001.

Ali, Adnan et al. "Glycogen Synthase Kinase-3: Properties, Functions, and Regulation", American Chemical Society, pp. A-N 2000.

Naerum, Lars et al. "Scaffold Hopping and Optimization towards Libraries of Glycogen Synthase Kinase-3 Inhibitors", Bioorganic & Medicinal Chemistry Letters, vol. 12, pp. 1525-1528 2002.

Chabaka, Laila M. et al. "Facile Synthesis of 2-Furyl-, 2-Pyrrolyl-, 2-Imidazolyl- and Pyrrolo-Azoles from 2-Substituted Methylazoles", Polish J. Chem., vol. 68, pp. 1317-1325 1994.

Abdelhamid, Abdou O. et al. "Reactions with Hydrazonoyl Halides. Part 10. Formation of Thiohydrazide, Hydrazonoyl Sulfide and Arylazothiazole Derivatives", J. Chem. Research (S), pp. 144-145 1995.

Brown, Michael D. et al. "A New General Synthesis of 2-(N-Mono- and N-Di-substituted Amino)thiazoles", J. Chem. Soc. Perkin. Trans. I, vol. 52, No. 5, pp. 1623-1626 1985.

Dawood, Kamal M. et al. "Polyheterocyclic ring systems with bridgehead nitrogen atoms: a facile route to some novel Azolo-1,2,4-triazine derivatives", J. Chem. Research (S), pp. 206-207 2000.

Gaudry, M. et al. "Enolisation des Cetones Dissymetriques-III", Tetrahedron, vol. 26, pp. 5611-5615, with English abstract 1970.

"Exploratory Library (Catalog)", Ambinter, Chemical Abstracts Service, Database accession No. 2002:2290627, XP002218003 2002.

"Exploratory Library (Catalog)", Ambinter, Chemical Abstracts Service, Database accession No. 2002:2290629, XP002218005 2002.

"Exploratory Library (Catalog)", Ambinter, Chemical Abstracts Service, Database accession No. 2002:2290615. XP002218009 2002.

Blyumin, E.V. et al. "Reaction of 2-hetarylacetonitriles with ethyl 2-alkylsulfanyl-4-chloro-5-pyrimidinecarboxylates. Synthesis of new condensed pyrimidines", Tetrahedron, vol. 58, No. 28, pp. 5733-5740, XP004369422 2002.

"Exploratory Library (Catalog)", Ambinter, Chemical Abstracts Service, Database accession No. 2002:2832472, XP002218001 2002.

"Exploratory Library (Catalog)", Ambinter, Chemical Abstracts Service, Database accession No. 2002:2290610, XP002218002 2002.

"Exploratory Library (Catalog)", Ambinter, Chemical Abstracts Service, Database accession No. 2002:2833110, XP002218004 2002.

"Exploratory Library (Catalog)", Ambinter, Chemical Abstracts Service, Database accession No. 2002:2290614, XP002218006 2002.

"Exploratory Library (Catalog)", Ambinter, Chemical Abstracts Service, Database accession No. 2001:2009866, XP002218007 2002.

"Exploratory Library (Catalog)", Ambinter, Chemical Abstracts Service, Database accession No. 2002:2290631, XP002218008 2002.

"Exploratory Library (Catalog)", Ambinter, Chemical Abstracts Service, Database accession No. 2002:2290611, XP002218010 2002.

Fischer, E. et al. "Cyclisierungsreaktionen von 1-[2-Amino-1-cyan-2-thio-]ethylene-pyridiniumbetainen", Journal f. prakt. Chemie, vol. 321, No. 3, pp. 429-436, XP008009779, with English abstract 1979.

\* cited by examiner

SEQUENCE LISTING

```
<160> NUMBER OF SEQ ID NOS: 1

<210> SEQ ID NO 1
<211> LENGTH: 26
<212> TYPE: PRT
<213> ORGANISM: Artificial
<220> FEATURE:
<223> OTHER INFORMATION: Phospho GS2 peptide
<220> FEATURE:
<221> NAME/KEY: MISC_FEATURE
<222> LOCATION: (21)..(21)
<223> OTHER INFORMATION: X=Phosphorylated Serine

<400> SEQUENCE: 1

Tyr Arg Arg Ala Ala Val Pro Pro Ser Pro Ser Leu Ser Arg His Ser
1               5                   10                  15

Ser Pro His Gln Xaa Glu Asp Glu Glu Glu
            20                  25
```

AZOLE METHYLIDENE CYANIDE DERIVATIVES AND THEIR USE AS PROTEIN KINASE MODULATORS

CROSS REFERENCES TO RELATED APPLICATIONS

This application is a national stage application of International Patent Application No. PCT/EP03/50225, filed on Jun. 13, 2003, and claims priority to European Patent Application No. EP 02100710.9, filed on Jun. 14, 2002, both of which are incorporated herein by reference in their entireties.

FIELD OF THE INVENTION

The present invention is related to novel azole methylidene cyanide derivatives and their tautomers, as well as pharmaceutical compositions containing such azole derivatives. In particular, the present invention is related to the modulation, notably the inhibition of the protein kinase pathway by using azole methylidene cyanide derivatives of the present invention. Preferred protein kinases are c-Jun N-terminal kinase (JNK) and Glycogen Synthase Kinase 3 (GSK3). The compounds of the present invention are particularly useful in the treatment of neurodegenerative diseases, neuronal disorders, inflammatory diseases, cardiovascular diseases, cancer or metabolic disorders mediated by insulin resistance or hyperglycemia, comprising diabetes type I and/or II, inadequate glucose tolerance, insulin resistance, obesity, polycystic ovary syndrome (PCOS). The present invention is furthermore related methods for the preparation of the novel azole methylidene cyanide derivatives.

BACKGROUND OF THE INVENTION

Cellular signaling has become a major research theme in biology and medicine over the past twenty years. The complex pathways and protein components in signal transduction are emerging with increasing clarity. Over the last 15 years, the protein kinases, such as the protein tyrosine kinases, have been identified as key players in cellular regulation. They are involved in immune, endocrine, and nervous system physiology and pathology and thought to be important in the development of many cancers. As such they serve as drug targets for many different diseases. Members of protein kinase family include for example c-Jun N-terminal kinase or Glycogen Synthase Kinase 3 (GSK3).

C-Jun N-Terminal kinase (JNK) is a member of the MAP Kinase family that includes the extracellular regulated kinases (ERKs) and p38 kinases. It is a serine/threonine kinase that phosphorylates c-Jun, a transcription factor activator protein-1 (AP-1) component. AP-1 regulates the transcription of several genes including inflammatory enzymes (COX-2), matrix metalloproteinases (MMP-13), cytokines (TNF), growth factors (VEGF) and immunoglobulins. Three JNK isoforms, JNK-1, -2 and -3, have been identified in humans and they appear to mediate critical phosphorylation events involved in the regulation of apoptosis and the immune response.

In a publication of Xie X et al, (*Structure* 6 (8) p. 983-991 (1998)) it has been suggested that activation of stress-activated signal transduction pathways are required for neuronal apoptosis induced by NGF withdrawal in rat PC-12 and superior cervical ganglia (SCG) sympathetic neuronal cells. Inhibition of specific kinases, namely MAP kinase kinase 3 (MKK3) and MAP kinase kinase 4 (MKK4), or c-Jun (part of the MKK-4 cascade) may be sufficient to block apoptosis (see also Kumagae Y et al, in *Brain Res*, 67(1), 10-17 (1999) and Yang DD et al in *Nature*, 389 p. 865-870 (1997)).

It has been reported that the JNK signalling pathway is implicated in cell proliferation and could play an important role in autoimmune diseases (Yang et al, *Immunity* 9, 575-585 (1998); Sabapathy et al. *Current Biology* 3, 116-125 (1999)) which are mediated by T-cell activation and proliferation.

One of the first compounds that inhibits the JNK pathway is Cephalon's CEP-1347 which was found to be neuroprotective in a number of in vivo models of neurodegenerative disease. Several compounds are reported in the patent literature to inhibit JNKs. Hoffmann-La Roche claimed 4-heteroaryl, 4-arylindolinones and annulated indolinones (WO 0035921, WO 0035909 and WO 0035906). Vertex Pharmaceuticals disclosed oxime derivatives as a JNK3 inhibitor (WO 0064872). Applied Research Systems has disclosed benzazole derivatives (EP 1110957) as JNK inhibitors.

Glycogen synthase kinase 3 (GSK3) is a serine/threonine kinase for which two isoforms, $\alpha$ and $\beta$, have been identified (Woodgett et al. *Trends Biochem. Sci.*, 16 p. 177-81 (1991)). Both GSK3 isoforms are constitutively active in resting cells. GSK3 was originally identified as a kinase that inhibits glycogen synthase by direct phosphorylation. Upon insulin activation, GSK3 is inactivated, thereby allowing the activation of glycogen synthase and possibly other insulin-dependent events, such glucose transport. Subsequently, it has been shown that GSK3 activity is also inactivated by other growth factors that, like insulin, signal through receptor tyrosine kinases (RTKs). Examples of such signalling molecules include IGF-1 and EGF (Saito et al. *Biochem. J.*, 303 p. 27-31 (1994), Welsh et al., *Biochem. J.*, 294 p. 625-29 (1993) and Cross et al., *Biochem. J.*, 303 p. 21-26 (1994)). GSK3 beta activity is regulated by serine (inhibitory) and tyrosine (stimulatory) phosphorylation, by protein complex formation, and by its intracellular localization. GSK3 beta phosphorylates and thereby regulates the functions of many metabolic, signalling and structural proteins (Carol Grimes, Richard Jope, *Prog. Neurobiol.* 65(4) p. 391-426 (2001)). Notable among the signalling proteins regulated by GSK3 beta are the many transcription factors, including activator protein-1 cells, Myc, beta-catenin, CCAAT/enhancer binding protein, and NFkappaB.

Agents that inhibit GSK3 activity are useful in the treatment of disorders that are mediated by GSK3 activity. In addition, inhibition of GSK3 mimics the activation of growth factor signalling pathways and consequently GSK3 inhibitors are useful in the treatment of diseases in which such pathways are insufficiently active. Examples of diseases that can be treated with GSK3 inhibitors, such as diabetes, neurodegenerative diseases (e.g. Alzheimer's disease), inflammatory diseases, ischemia and cancer are described below.

In the patent literature, several GSK3 inhibitors have already been disclosed (WO 02/20495, Chiron Corporation; WO 02/10141, Pfizer Products Inc.; WO 02/22608, Vertex Pharmaceuticals Inc.).

Diabetes mellitus is a serious metabolic disease that is defined by the presence of chemically elevated levels of blood glucose (hyperglycemia). The term diabetes mellitus encompasses several different hyperglycemic states. These states include Type 1 (insulin-dependent diabetes mellitus or IDDM) and Type 2 (non-insulin dependent diabetes mellitus or NIDDM) diabetes. The hyperglycemia present in individuals with Type 1 diabetes is associated with deficient, reduced, or nonexistent levels of insulin that are insufficient to maintain blood glucose levels within the physiological range. Conventionally, Type 1 diabetes is treated by administration of replacement doses of insulin, generally by a parenteral route.

Type 2 diabetes is an increasingly prevalent disease of aging. It is initially characterized by decreased sensitivity to insulin and a compensatory elevation in circulating insulin concentrations, the latter of which is required to maintain normal blood glucose levels. As described above, GSK3 inhibition stimulates insulin-dependent processes and is consequently useful in the treatment of type 2 diabetes. Recent data obtained using lithium salts provides evidence for this notion. The lithium ion has recently been reported to inhibit GSK3 activity (Peter Klein, Douglas Melton PNAS 93 p. 8455-9 (1996)). However, lithium has not been widely accepted for use in the inhibition of GSK3 activity, possibly because of its documented effects on molecular targets other than GSK3. The purine analog 5-iodotubercidin, also a GSK3 inhibitor, likewise stimulates glycogen synthesis and antagonizes inactivation of glycogen synthase by glucagon and vasopressin in rat liver cells (Fluckiger-Isler et al., Biochem. J. 292 p. 85-91 (1993) and Massillon et al., Biochem. J. 299 p. 123-8 (1994)). However, this compound has also been shown to inhibit other serine/threonine and tyrosine kinases (Biochem. J. 299 p. 123-8 (1994)).

GSK(3 is also involved in biological pathways relating to Alzheimer's disease (AD). The characteristic pathological features of AD are extracellular plaques of an abnormally processed form of the amyloid precursor protein (APP), so-called β-amyloid peptide (β-AP) and the development of intracellular neurofibrillary tangles containing paired helical filaments (PHF) that consists largely of hyperphosphorylated tau protein. GSK3 is one of a number of a number of kinases that have been found to phosphorylate tau protein in vitro on the abnormal sites characteristic of PHF tau, and is the only kinase also demonstrated to do this in living cells and in animals (Lovestone et al., Current Biology 4 p. 1077-86 (1994) and Brownlees et al., Neuroreport 8 p. 3251-55 (1997)). Furthermore, the GSK3 kinase inhibitor, LiCl, blocks tau hyperphosphorylation in cells (Stambolic et al., Current Biology 6 p. 1664-8 (1996)). Thus GSK3 activity may contribute to the generation of neurofibrillary tangles and consequently to disease progression. Recently it has been shown that GSK3b associates with another key protein in AD pathogenesis, presenillin 1 (PS1) (Takashima et al., PNAS 95 p. 9637-41 (1998)). Mutations in the PS1 gene lead to increased production of β-AP, but the authors also demonstrate that the mutant PS1 proteins bind more tightly to GSK3β and potentiate the phosphorylation of tau, which is bound to the same region of PS1. Interestingly it has also been shown that another GSK3 substrate, β-catenin, binds to PS1 (Zhang et al., Nature 395 p. 698-702 (1998)). Cytosolic β-catenin is targeted for degradation upon phosphorylation by GSK3 and reduced β-catenin activity is associated with increased sensitivity of neuronal cells to β-AP induced neuronal apoptosis. Consequently, increased association of GSKβ with mutant PS1 may account for the reduced levels of β-catenin that have been observed in the brains of PS1-mutant AD patients and to the disease related increase in neuronal cell-death. Consistent with these observations, it has been shown that injection of GSK3 antisense but not sense, blocks the pathological effects of β-AP on neurons in vitro, resulting in a 24 hr delay in the onset of cell death (Takashima et al., PNAS 90 p. 7789-93 (1993)). In these latter studies, the effects on cell-death are preceded (within 3-6 hours of β-AP administration) by a doubling of intracellular GSK3 activity, suggesting that genetic mechanisms may increase GSK3 activity. Further evidence for a role for GSK3 in AD is provided by the observation that the protein expression level (but, in this case, not specific activity) of GSK3 is increased by 50% in postsynaptosomal supernatants of AD vs. normal brain tissue (Pei et al., J Neuropathol. Exp. 56 p. 70-78 (1997)). Thus, it is believed that specific inhibitors of GSK3 will act to slow the progression of Alzheimer's Disease.

It has also been described an involvement of GSK3 activity in the etiology of bipolar disorder. In support of this notion it was recently shown that valproate, another drug commonly used in the treatment of said disease, is also a GSK3 inhibitor (Chen et al. J Neurochemistry 72 p. 1327-30 (1999)). One mechanism by which lithium and other GSK3 inhibitors may act to treat bipolar disorder is to increase the survival of neurons subjected to aberrantly high levels of excitation induced by the neurotransmitter, glutamate (Nonaka et al, PNAS 95 p. 2642-47 (1998)).

Glutamate-induced neuronal excitotoxicity is also believed to be a major cause of neurodegeneration associated with acute damage such as in cerebral ischemia, traumatic brain injury and bacterial infection. Furthermore, it is believed that excessive glutamate signalling is a factor in the chronic neuronal damage seen in diseases such as Alzheimer's, Huntingdon's, Parkinson's, AIDS associated dementia, amyotrophic lateral sclerosis (AML) and multiple sclerosis (MS) (Thomas et al., J. Am. Geriatr. Soc. 43 p. 1279-89 (1995)). Consequently, GSK3 inhibitors are believed to be a useful treatment in these and other neurodegenerative disorders.

Sasaki et al. disclosed that GSK3 beta may have a role in ischemic neuronal cell death (Sasaki C. et al., Neurol. Res. 23(6) p. 588-92 (2001). Cross et al. described selective small-molecule inhibitors of glycogen synthase kinase-3 activity protecting primary neurones from death (Cross et al., Journal of Neurochemistry 77 p. 94-102 (2001)).

It has also been reported that debromohymenialdisine (DBH), considered as inhibitors of GSK3, exhibit anti-inflammatory activity in a model of adjuvant-induced arthritis in the rat. (A. Ali et al., American Chemical Society p. A-N (December 2000)).

SUMMARY OF THE INVENTION

The present invention relates to new azole methylidene cyanide derivatives of formula (I)

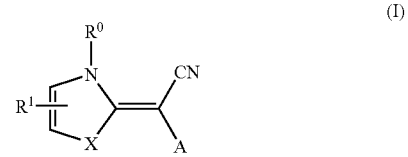

their pharmaceutically acceptable salts, as well as use thereof for the preparation of pharmaceutical compositions in the treatment and/or prevention of neuronal disorders, neurodegenerative diseases, cardiovascular diseases, inflammatory diseases, metabolic disorders, cancer or metabolic disorders mediated by insulin resistance or hyperglycemia, comprising diabetes type I and/or II, inadequate glucose tolerance, insulin resistance, obesity, polycystic ovary syndrome (PCOS). Compounds of this invention are inhibitors of the protein kinases

DESCRIPTION OF THE INVENTION

It has now been found that compounds of the present invention are modulators of protein kinases, particularly of the c-Jun N-terminal kinases, and Glycogen Synthase Kinase 3

(GSK3). When the protein kinase is bound by the compounds of the present invention, said kinase is inhibited by being blocked from its substrate and thus being unable to exert its biological or pharmacological effects. The compounds of the present invention are therefore useful for example in the treatment and/or prevention of neuronal disorders, neurodegenerative diseases, cardiovascular diseases, inflammatory diseases, cancer or metabolic disorders mediated by insulin resistance or hyperglycemia, comprising diabetes type I and/or II, inadequate glucose tolerance, insulin resistance, obesity, polycystic ovary syndrome (PCOS).

In particular, compounds of the present invention are useful in the treatment and prevention of protein kinases, particularly c-Jun kinases N-terminal and Glycogen Synthase Kinase 3 related disorders of mammals and especially humans.

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazoly, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=CH$_2$), n-2-propenyl (allyl, —CH$_2$CH=CH$_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"heterocycloalkyl" refers to a $C_3$-$C_8$-cycloalkyl group according to the definition above, in which 1 to 3 carbon atoms are replaced by heteroatoms chosen from the group consisting of O, S, NR, R being defined as hydrogen or $C_1$-$C_6$ alkyl. Preferred heterocycloalkyl include pyrrolidine, piperidine, piperazine, 1-methylpiperazine, morpholine, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"$C_1$-$C_6$-alkyl carboxy" refers to $C_1$-$C_6$-alkyl groups having a carboxy substituent, including 2-carboxyethyl and the like.

"Acyl" refers to the group —C(O)R where R includes H, "$C_1$-$C_6$-alkyl", "$C_2$-$C_6$-alkenyl", "$C_2$-$C_6$-alkynyl", "$C_3$-$C_8$-cycloalkyl", heterocycloalkyl"heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynyl heteroaryl", "$C_1$-$C_6$-alkyl cycloalkyl", "$C_1$-$C_6$-alkyl heterocycloalkyl".

"$C_1$-$C_6$-alkyl acyl" refers to $C_1$-$C_6$-alkyl groups having an acyl substituent, including 2-acetylethyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"$C_3$-$C_8$-(hetero)cycloalkyl acyl" refers to 3 to 8 membered cycloalkyl or heterocycloalkyl groups having an acyl substituent.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloatkyl", "$C_1$-$C_6$-alkyl heterocycloalkyl".

"$C_1$-$C_6$-alkyl acyloxy" refers to $C_1$-$C_6$-alkyl groups having an acyloxy substituent, including 2-(acetyloxy)ethyl and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxy" refers to $C_1$-$C_6$-alkyl groups having an alkoxy substituent, including 2-ethoxyethyl and the like.

"Alkoxycarbonyl" refers to the group —C(O)OR where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$- alkynyl aryl", "C$_2$-C$_6$-alkynylheteroaryl", "C$_1$-C$_6$-alkyl cycloalkyl", "C$_1$-C$_6$-alkyl heterocycloalicyl".

"C$_1$-C$_6$-alkyl alkoxycarbonyl" refers to C$_1$-C$_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl aminocarbonyl" refers to C$_1$-C$_6$-alkyl groups having an aminocarbonyl substituent, including 2-(dimethylaminocarbonyl)ethyl and the like.

"Acylamino" refers to the group —NRC(O)R' where each R, R' is independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl acylamino" refers to C$_1$-C$_6$-alkyl groups having an acylamino substituent, including 2-(propionylamino)ethyl and the like.

"Ureido" refers to the group —NRC(O)NR'R" where each R, R', R" is independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl", and where R' and R", together with the nitrogen atom to which they are attached, can optionally form a 3-8-membered heterocycloalkyl ring.

"C$_1$-C$_6$-alkyl ureido" refers to C$_1$-C$_6$-alkyl groups having an ureido substituent, including 2-(N'-methylureido)ethyl and the like.

"Carbamate" refers to the group —NRC(O)OR' where each R,R' is independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"Amino" refers to the group —NRR' where each R, R' is independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl", and where R and R', together with the nitrogen atom to which they are attached, can optionally form a 3-8-membered heterocycloalkyl ring.

"C$_1$-C$_6$-alkyl amino" refers to C$_1$-C$_6$-alkyl groups having an amino substituent, including 2-(1-pyrrolidinyl)ethyl and the like.

"Ammonium" refers to a positively charged group —N$^+$RR'R", where each R, R',R" is independently, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl", and where R and R', together with the nitrogen atom to which they are attached, can optionally form a 3-8-membered heterocycloalkyl ring.

"C$_1$-C$_6$-alkyl ammonium" refers to C$_1$-C$_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —OSO$_2$—R wherein R is selected from H, "C$_1$-C$_6$-alkyl", "C$_1$-C$_6$-alkyl" substituted with halogens, e.g., an —OSO$_2$—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfonyloxy" refers to C$_1$-C$_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "C$_1$-C$_6$-alkyl", "C$_1$-C$_6$-alkyl" substituted with halogens, e.g., an —SO$_2$—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfonyl" refers to C$_1$-C$_6$-alkyl groups having a sulfonyl substituent, including 2-(methylsulfonyl)ethyl and the like.

"Sulfinyl" refers to a group "—S(O)—R" wherein R is selected from H, "C$_1$-C$_6$-alkyl", "C$_1$-C$_6$-alkyl" substituted with halogens, e.g., an —SO—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfinyl" refers to C$_1$-C$_6$-alkyl groups having a sulfinyl substituent, including 2-(methylsulfinyl)ethyl and the like.

"Sulfanyl" refers to groups —S—R where R includes H, "C$_1$-C$_6$-alkyl", "C$_1$-C$_6$-alkyl" substituted with halogens, e.g., an —SO—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl". Preferred sulfanyl groups include methylsulfanyl, ethylsulfanyl, and the like.

"C$_1$-C$_6$-alkyl sulfanyl" refers to C$_1$-C$_6$-alkyl groups having a sulfanyl substituent, including 2-(ethylsulfanyl)ethyl and the like.

"Sulfonylamino" refers to a group —NRSO$_2$—R' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfonylamino" refers to C$_1$-C$_6$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl aminosulfonyl" refers to C$_1$-C$_6$-alkyl groups having an aminosulfonyl substituent, including 2-(cyclohexylaminosulfonyl)ethyl and the like.

"2-pyridyl, 3-pyridyl, 4-pyridyl" refers to pyridyl moieties of the following structure:

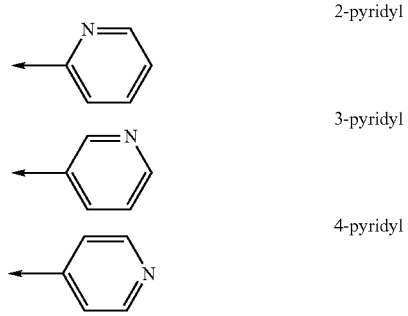

"Substituted or unsubstittited": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "C$_1$-C$_6$-alkyl", "C$_2$-C$_6$-alkenyl", "C$_2$-C$_6$-alkynyl", "cycloalkyl", "heterocycloalkyl", "C$_1$-C$_6$-alkyl aryl", "C$_1$-C$_6$-alkyl heteroaryl", "C$_1$-C$_6$-alkyl cycloalkyl", "C$_1$-C$_6$-alkyl heterocycloalkyl", "amino", "ammonium", "acyl", "acyloxy", "acylamino", "aminocarbonyl", "alkoxycarbonyl", "ureido", "carbamate", "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formulae (I), (Ia) and (Ib) that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, methanesulfonic acid and poly-galacturonic acid. Said compounds can also be administered as pharmaceutically acceptable quaternary salts known by a person skilled in the art, which specifically include the quaternary ammonium salt of the formula —NR,R',R"$^+$Z$^-$, wherein R, R', R" is independently hydrogen, alkyl, or benzyl, C$_1$-C$_6$-alkyl, C$_2$-C$_6$-alkenyl, C$_2$-C$_6$-alkynyl, C$_1$-C$_6$-alkyl aryl, C$_1$-C$_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

Said formula also comprises its tautomers, its geometrical isomers, its optically active forms as enantiomers, diastereomers and its racemate forms, as well as pharmaceutically acceptable salts thereof. Preferred pharmaceutically acceptable salts of the formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

A first aspect of the invention consists in new azole methylidene cyanide derivatives of formula I

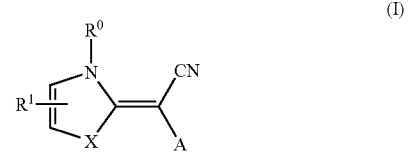

as well as its tautomers, its geometrical isomers, its optically active forms as enantiomers, diastereomers and its racemate forms and pharmaceutically acceptable salts thereof.

Where R$^0$ is H, such tautomers undergo transformation in solution and an equilibrium between azole derivatives of formula (IA) is established with those of formula (IB).

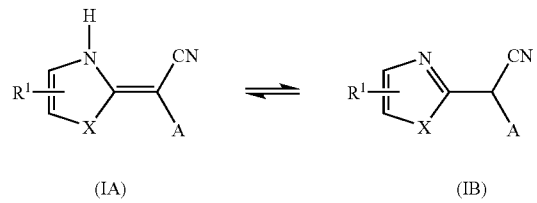

Said tautomers are comprised by the present invention.

The substituents within formula (I) are defined as follows:

X is O, S or NR$^0$, with R$^0$ being as defined below. More preferred compounds are 1,3-thiazoles, i.e. compounds of formula (I) wherein X is S.

A is an unsubstituted or substituted 2-pyridyl, 3-pyridyl, 4-pyridyl, an unsubstituted or substituted pyridazinyl, an unsubstituted or substituted pyrimidinyl, an unsubstituted or substituted pyrazinyl or an unsubstituted or substituted triazinyl group, each of the above-mentioned groups may be fused with an aryl or a heteroaryl group. Preferably, A is an unsubstituted or substituted pyrimidinyl group.

Each of said heterocyclic groups A may be substituted by at least one, preferably one, moiety R$^2$.

$R^2$ is selected from the group comprising or consisting of hydrogen, sulfonyl, amino, unsubstituted or substituted $C_1$-$C_6$-alkyl, unsubstituted or substituted $C_2$-$C_6$-alkenyl, unsubstituted or substituted $C_2$-$C_6$-alkynyl or substituted aryl, unsubstituted or substituted heteroaryl, unsubstituted or substituted saturated or unsaturated 3-8-membered cycloalkyl, unsubstituted or substituted heterocycloalkcyl, wherein said cycloalkyl, heterocycloalkyl, aryl or heteroaryl groups may be fused with 1-2 further cycloalkyl, heterocycloalkyl, aryl or heteroaryl group, an acyl moiety, unsubstituted or substituted $C_1$-$C_6$-alkyl aryl, unsubstituted or substituted $C_1$-$C_6$-alkyl heteroaryl, unsubstituted or substituted $C_1$-$C_6$-alkenyl aryl, unsubstituted or substituted $C_1$-$C_6$-alkenyl heteroaryl, unsubstituted or substituted $C_1$-$C_6$-alkynyl aryl, unsubstituted or substituted $C_1$-$C_6$-alkynyl heteroaryl, unsubstituted or substituted $C_1$-$C_6$-alkyl cycloalkyl, unsubstituted or substituted $C_1$-$C_6$-alkyl heterocycloalkyl, unsubstituted or substituted $C_1$-$C_6$-alkenyl cycloalkyl, unsubstituted or substituted $C_1$-$C_6$-alkenyl heterocycloalkyl, unsubstituted or substituted $C_1$-$C_6$-alkynyl cycloalkyl, unsubstituted or substituted $C_1$-$C_6$-alkynyl heterocycloalkyl, substituted or unsubstituted alkoxycarbonyl, substituted or unsubstituted aminocarbonyl, substituted or unsubstituted $C_1$-$C_6$-alkyl carboxy, substituted or unsubstituted $C_1$-$C_6$-alkyl acyl, substituted or unsubstituted aryl acyl, substituted or unsubstituted heteroaryl acyl, substituted or unsubstituted $C_3$-$C_8$-(hetero)cycloalkyl acyl, unsubstituted or substituted $C_1$-$C_6$-alkyl acyloxy, unsubstituted or substituted $C_1$-$C_6$-alkyl alkoxy, unsubstituted or substituted $C_1$-$C_6$-alkyl alkoxycarbonyl, unsubstituted or substituted $C_1$-$C_6$-alkyl aminocarbonyl, unsubstituted or substituted $C_1$-$C_6$-alkyl acylamino, acylamino, unsubstituted or substituted $C_1$-$C_6$-alkyl ureido, substituted or unsubstituted $C_1$-$C_6$-alkyl carbamate, unsubstituted or substituted $C_1$-$C_6$-alkyl amino, unsubstituted or substituted $C_1$-$C_6$-alkyl ammonium, unsubstituted or substituted $C_1$-$C_6$-alkyl sulfonyloxy, unsubstituted or substituted $C_1$-$C_6$-alkyl sulfonyl, unsubstituted or substituted $C_1$-$C_6$-alkyl sulfinyl, unsubstituted or substituted $C_1$-$C_6$-alkyl sulfanyl, unsubstituted or substituted $C_1$-$C_6$-alkyl sulfonylamino, unsubstituted or substituted $C_1$-$C_6$-alkyl aminosulfonyl, hydroxy, halogen (e.g. chlorine, bromine or fluorine), cyano.

According to a specific embodiment $R^2$ is an amino group of the formula —$NR^3R^4$ wherein $R^3$ and $R^4$ are each independently from each other H, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted $C_1$-$C_6$-alkoxy, unsubstituted or substituted $C_1$-$C_6$-sulfanyl, unsubstituted or substituted primary, secondary or tertiary amino groups, aminoacyl, aminocarbonyl, unsubstituted or substituted $C_1$-$C_6$ alkoxycarbonyl, unsubstituted or substituted aryl, unsubstituted or substituted heteroaryl, carboxy, hydroxy, sulfinyl, sulfonyl, or sulfonamides.

Other specific substituents $R^2$ are those wherein $R^2$ is an amino moiety of the formula —$NHR^4$ with $R^4$ being an unsubstituted straight or branched $C_1$-$C_6$ alkyl which may be substituted by unsubstituted or substituted cycloalkyl, unsubstituted or substituted heterocycloalkyl, unsubstituted or substituted aryl, unsubstituted or substituted heteroaryl, amino, alkoxycarbonyl, acylamino, diacylamino.

More specific $R^2$ are those wherein $R^2$ is —$NHR^4$ in which $R^4$ is a straight or branched $C_2$-$C_4$ alkyl, in particular an ethylene or propylene moiety, optionally substituted with an unsubstituted or substituted heteroaryl group, e.g., an unsubstituted or substituted pyridyl or a 2-pyrrolidinone (2-oxopyrrolidine) or a triazolyl moiety.

In a further embodiment $R^2$ is —$NHR^4$ in which $R^4$ is a straight or branched $C_2$-$C_3$ alkyl which is substituted by an amine or a cyclic amine like $R^0$ is selected from the group comprising or consisting of hydrogen, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted $C_1$-$C_6$-alkyl-aryl, unsubstituted or substituted aryl or unsubstituted or substituted heteroaryl, unsubstituted or substituted $C_1$-$C_6$-alkyl-heteroaryl, —C(O)—$OR^5$, —C(O)—$R^5$, —C(O)—$NR^5R^{5'}$, —($SO_2$)$R^5$, with $R^5$ and $R^{5'}$ being independently selected from the group comprising or consisting of hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted aryl, unsubstituted or substituted heteroaryl, unsubstituted or substituted $C_1$-$C_6$-alkyl unsubstituted or substituted aryl, or unsubstituted or substituted $C_1$-$C_6$-alkyl heteroaryl wherein said heteroaryl is an unsubstituted or substituted moiety. In a particular embodiment, $R^0$ is hydrogen.

$R^1$ is selected from the group comprising or consisting of hydrogen, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted $C_1$-$C_6$-alkoxy, unsubstituted or substituted $C_1$-$C_6$-sulfanyl, primary, secondary or tertiary amino groups, aminoacyl, aminocarbonyl, unsubstituted or substituted $C_1$-$C_6$ alkoxycarbonyl, unsubstituted or substituted $C_3$-$C_8$-cycloalkyl, unsubstituted or substituted heterocycloalkyl, unsubstituted or substituted aryl, unsubstituted or substituted heteroaryl, carboxyl, cyano, halogen, hydroxy, nitro, sulfinyl, sulfonyl, sulfonamide or hydrazide.

According to a further embodiment, $R^1$ is selected from unsubstituted or substituted $C_3$-$C_8$-cycloalkyl, unsubstituted or substituted heterocycloalkyl, unsubstituted or substituted aryl or unsubstituted or substituted heteroaryl group wherein each of the above-mentioned groups may be substituted with at least one moiety selected from the group consisting of $C_1$-$C_6$-alkyl, $C_2$-$C_6$-alkenyl, $C_2$-$C_6$-alkynyl, $C_1$-$C_6$-alkoxy, $C_1$-$C_6$-sulfanyl, primary, secondary or tertiary amino groups, acylamino, aminocarbonyl, $C_1$-$C_6$ alkoxycarbonyl, $C_3$-$C_8$-cycloalkyl, $C_3$-$C_8$ heterocycloalkyl, aryl, heteroaryl, carboxy, cyano, halogen, hydroxy, nitro, sulfinyl, sulfonyl, sulfonamide or hydrazide.

In a more specific embodiment, $R^1$ is either a phenyl group which may be substituted by straight or branched $C_1$-$C_6$ alkyl or a halogen including fluorine, chlorine. Alternatively, $R^1$ may be a straight or branched $C_1$-$C_6$ alkyl, including methyl, ethyl, propyl isopropyl, t-butyl.

In a more specific embodiment according to the invention, $R^1$ is unsubstituted or substituted ($C_3$-$C_8$)-cycloalkyl, unsubstituted or substituted ($C_3$-$C_8$)-heterocycloalkyl, unsubstituted or substituted aryl or unsubstituted or substituted heteroaryl group which may be substituted with at least one moiety selected from the group consisting of unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted $C_1$-$C_6$-alkoxy, $C_1$-$C_6$-sulfanyl, primary, secondary or tertiary amino groups, aminoacyl, aminocarbonyl, $C_1$-$C_6$ alkoxycarbonyl, unsubstituted or substituted $C_3$-$C_8$-cycloalkyl, unsubstituted or substituted $C_3$-$C_8$ heterocycloalkcyl, unsubstituted or substituted aryl, unsubstituted or substituted heteroaryl, carboxyl, cyano, halogen, hydroxy, nitro, sulfinyl, sulfonyl, sulfonamide or hydrazide, while X is as above defined, A is a pyrimidinyl group which is substituted by halogen or —$NHR^4$ with $R^4$ being an unsubstituted or substituted straight or branched $C_1$-$C_6$ alkyl in which said alkyl is substituted with unsubstituted or substituted $C_3$-$C_8$-cycloalkyl, unsubstituted or substituted heterocycloalkyl, unsubstituted or substituted aryl or unsubstituted or substituted heteroaryl straight or branched $C_1$-$C_6$ alkyl group substituted with an unsubstituted or substituted heteroaryl group and $R^0$ is hydrogen.

An even more specific embodiment according to the invention relates to compounds of the following formula (I'):

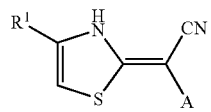

(I')

$R^1$ is an unsubstituted or substituted phenyl or a straight or branched $C_1$-$C_6$ alkyl, or a halogen, A is a pyrimidinyl group which may be substituted with $R^2$ wherein $R^2$ is halogen or —$NHR^4$ in which $R^4$ is an unsubstituted or substituted straight or branched $C_1$-$C_6$ alkyl group which may be substituted with an unsubstituted or substituted pyridyl group.

The following compounds appear to be not novel as they are listed in a commercial library ("Explorarory Library", Ambinter, 21.1.2002):

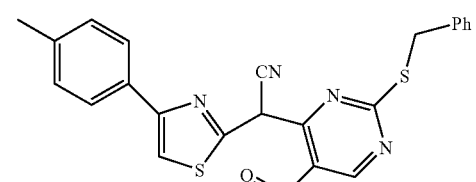

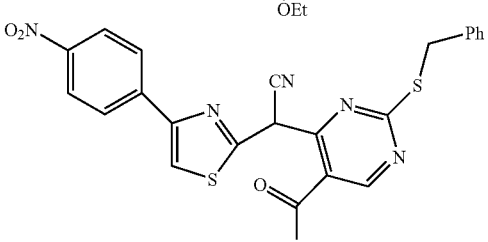

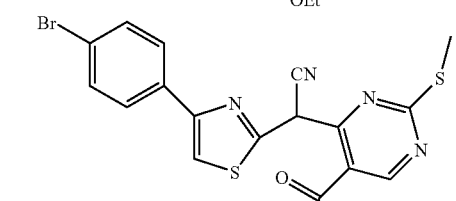

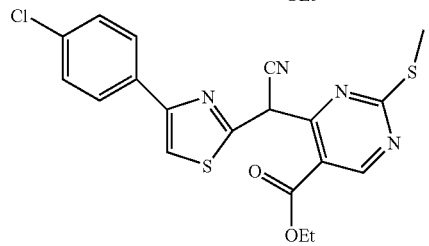

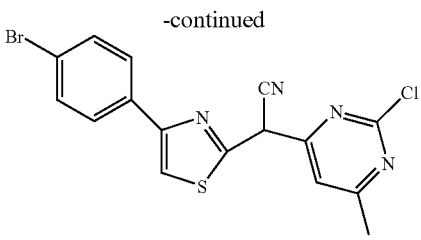

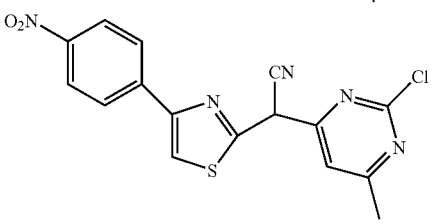

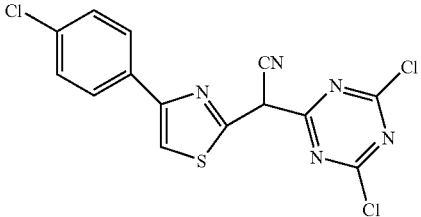

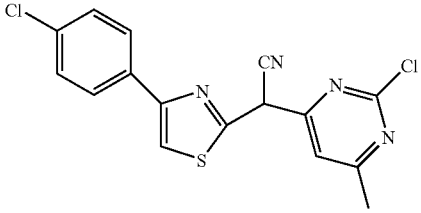

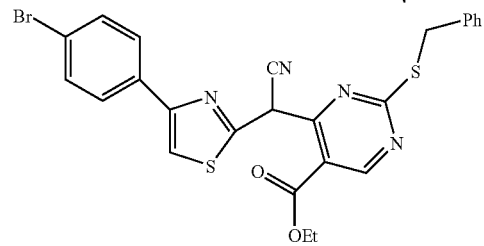

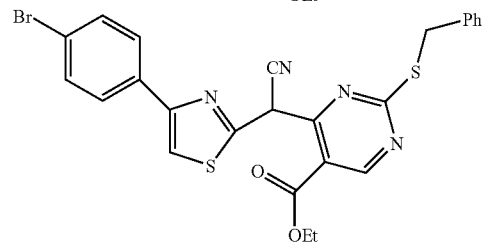

No medical use and no biological activity is disclosed for the above compounds, though.

Specific azole derivatives according to formula (I) are:
(2-chloropyrimidin-4-yl)-(4-ethyl-3H-thiazol-2ylidene)-acetonitrile
[4-(4-chlorophenyl)-1,3-thiazol-2(3H)-ylidene](2-chloropyrimidin-4-yl)acetonitrile
(2-chloropyrimidin-4-yl)(4-phenyl-1,3-thiazol-2(3H)-ylidene)acetonitrile
(2-chloropyrimidin-4-yl)(4-methyl-1,3-thiazol-2(3H)-ylidene)acetonitrile
(2-chloropyrimidin-4-yl)[4-(4-methoxyphenyl)-1,3-thiazol-2(3H)-ylidene]acetonitrile ethyl-2-[(2-chloropyrimidin-4-yl)(cyano)methylene]-2,3-dihydro-1,3-thiazole-4-carboxylate
methyl-2-[(2-chloropyrimidin-4-yl)(cyano)methylene]-2,3-dihydro-1,3-thiazole-4-carboxylate
(2-chloropyrimidin-4-yl)[4-(3-methoxyphenyl)-1,3-thiazol-2-yl]acetonitrile
(2-chloropyrimidin-4-yl)[4-(2-methoxyphenyl)-1,3-thiazol-2(3H)-ylidene]acetonitrile
(2-chloropyrimidin-4-yl)[4-(4-fluorophenyl)-1,3-thiazol-2(3H)-ylidene]acetonitrile
(2-chloro-5-methylpyrimidin-4-yl)(4-ethyl-1,3-thiazol-2(3H)-ylidene)acetonitrile
(2-chloropyrimidin-4-yl)[4-(3,4-dichlorophenyl)-1,3-thiazol-2(3H)-ylidene]acetonitrile
(2-chloropyrimidin-4-yl)[4-(4-methylphenyl)-1,3-thiazol-2(3H)-ylidene]acetonitrile
(4-{[3-(2-oxopyrrolidin-1-yl)propyl]amino}pyrimidin-2-yl)(4-phenyl-1,3-thiazol-2(3H)-ylidene)acetonitrile
4-{2-[(2-chloropyrimidin-4-yl)(cyano)methylene]-2,3-dihydro-1,3-thiazol-4-yl}benzonitrile
[4-(2-chlorophenyl)-1,3-thiazol-2(3H)-ylidene](2-chloropyrimidin-4-yl)acetonitrile
[4-(3-chlorophenyl)-1,3-thiazol-2-3H)-ylidene](2-chloropyrimidin-4-yl)acetonitrile
(2-chloropyrimidin-4-yl)[4-(4-methoxyphenyl)-1,3-thiazol-2(3H)-ylidene]acetonitrile
(2-chloropyrimidin-4-yl)[4-(pentafluoroethyl)-1,3-thiazol-2(3H)-ylidene]acetonitrile
(2-chloro-5-methylpyrimidin-4-yl)(4-methyl-1,3-thiazol-2(3H)-ylidene)acetonitrile
(4-tert-butyl-1,3-thiazol-2(3H)-ylidene)(2-chloro-5-methylpyrimidin-4-yl)acetonitrile
(4-tert-butyl-1,3-thiazol-2(3H)-ylidene)(2-chloropyrimidin-4-yl)acetonitrile
(2-chloropyrimidin-4-yl)(4-isopropyl-1,3-thiazol-2(3H)-ylidene)acetonitrile
(2-chloro-5-methylpyrimidin-4-yl)[4-(4-chlorophenyl)-1,3-thiazol-2(3H)-ylidene]acetonitrile
(4-chloro-6-morpholin-4-yl-1,3,5-triazin-2-yl)(4-phenyl-1,3-thiazol-2(3H)-ylidene)acetonitrile
[4-chloro-6-(dimethylamino)-1,3,5-triazin-2-yl](4-phenyl-1,3-thiazol-2(3H)-ylidene)acetonitrile
[4-chloro-6-(methylamino)-1,3,5-triazin-2-yl](4-phenyl-1,3-thiazol-2(3H)-ylidene)acetonitrile
(2-chloro-6-methylpyrimidin-4-yl)(4-phenyl-1,3-thiazol-2(3H)-ylidene)acetonitrile
(2-chloro-5-methylpyrimidin-4-yl)(4-phenyl-1,3-thiazol-2(3H)-ylidene)acetonitrile
(6-chloropyrimidin-4-yl)(4-methyl-1,3-thiazol-2(3H)-ylidene)acetonitrile
[4-chloro-6-(methylamino)-1,3,5-triazin-2-yl](4-methyl-1,3-thiazol-2(3H)-ylidene)acetonitrile
(2-chloro-6-methylpyrimidin-4-yl)(4-methyl-1,3-thiazol-2(3H)-ylidene)acetonitrile
{2-chloro-6-[methyl(phenyl)amino]pyrimidin-4-yl}(4-methyl-1,3-thiazol-2(3H)-ylidene)acetonitrile
(4-chloro-6-morpholin-4-yl-1,3,5-triazin-2-yl)(4-methyl-1,3-thiazol-2(3H)-ylidene)acetonitrile
(4-ethyl-1,3-thiazol-2(3H)-ylidene)(2-{[3-(2-oxopyrrolidin-1-yl)propyl]amino}pyrimidin-4-yl)acetonitrile
[4-(4-chlorophenyl)-1,3-thiazol-2(3H)-ylidene]{2-[(2-pyridin-3-ylethyl)amino]pyrimidin-4-yl}acetonitrile
(4-phenyl-1,3-thiazol-2(3H)-ylidene){2-[(2-pyridin-3-ylethyl)amino]pyrimidin-4-yl}acetonitrile
{2-[(3-aminopropyl)amino]pyrimidin-4-yl}(4-ethyl-1,3-thiazol-2(3H)-ylidene)acetonitrile
(2-{[2-(6-aminopyridin-3-yl)ethyl]amino}pyrimidin-4-yl)(4-ethyl-1,3-thiazol-2(3H)-ylidene)acetonitrile
{2-[(3-aminopropyl)amino]pyrimidin-4-yl}(4-ethyl-1,3-thiazol-2(3H)-ylidene)acetonitrile
{2-[(3-aminopropyl)amino]pyrimidin-4-yl}(4-tert-butyl-1,3-thiazol-2(3H)-ylidene)acetonitrile
ethyl-2-[cyano(2-{[3-(2-oxopyrrolidin-1-yl)propyl]amino}pyrimidin-4-yl)methylene]-2,3-dihydro-1,3-thiazole-4-carboxylate
(4-methyl-1,3-thiazol-2(3H)-ylidene){2-[(2-pyridin-3-ylethyl)amino]pyrimidin-4-yl}acetonitrile
4-(4-methoxyphenyl)-1,3-thiazol-2(3H)-ylidene){2-[(2-pyridin-3-ylethyl)amino]pyrimidin-4-yl}acetonitrile
2-[cyano(2-{[3-(2-oxopyrrolidin-1-yl)propyl]amino}pyrimidin-4-yl)methylene]-2,3-dihydro-1,3-thiazole-4-carboxylic acid
methyl-2-[cyano(2-{[3-(2-oxopyrrolidin-1-yl)propyl]amino}pyrimidin-4-yl)methylene]-2,3-dihydro-1,3-thiazole-4-carboxylate
methyl-2-(cyano{2-[(2-pyridin-3-ylethyl)amino]pyrimidin-4-yl}methylene)-2,3-dihydro-1,3-thiazole-4-carboxylate
[2-(cyclopropylamino)pyrimidin-4-yl](4-methyl-1,3-thiazol-2(3H)-ylidene)acetonitrile
4-[2-({4-[cyano(4-methyl-1,3-thiazol-2(3H)-ylidene)methyl]pyrimidin-2-yl}amino)ethyl]benzenesulfonamide
[4-(pentafluoroethyl)-1,3-thiazol-2(3H)-ylidene]{2-[(2-pyridin-3-ylethyl)amino]pyrimidin-4-yl}acetonitrile
[2-(cyclopropylamino)pyrimidin-4-yl][4-(pentafluoroethyl)-1,3-thiazol-2(3H)-ylidene]acetonitrile
(2-{[3-(2-oxopyrrolidin-1-yl)propyl]amino}pyrimidin-4-yl)(4-phenyl-1,3-thiazol-2(3H)-ylidene)acetonitrile
(4-ethyl-1,3-thiazol-2(3H)-ylidene){2-[(2-pyridin-3-ylethyl)amino]pyrimidin-4-yl}acetonitrile
[4-(3-methoxyphenyl)-1,3-thiazol-2(3H)-ylidene]{2-[(2-pyridin-3-ylethyl)amino]pyrimidin-4-yl}acetonitrile
[4-(3-methoxyphenyl)-1,3-thiazol-2(3H)-ylidene](2-{[3-(2-oxopyrrolidin-1-yl)propyl]amino}pyrimidin-4-yl)acetonitrile
methyl 4-[2-({4-[cyano(4-ethyl-1,3-thiazol-2(3H)-ylidene)methyl]pyrimidin-2-yl}amino)ethyl]benzoate
6-{[2-({4-[-cyano(4-ethyl-1,3-thiazol-2(3H)-ylidene)methyl]pyrimidin-2-yl}amino)ethyl]amino}nicotinonitrile
[2-({2-[6-(dimethylamino)pyridin-3-yl]ethyl}amino)pyrimidin-4-yl](4-ethyl-1,3-thiazol-2(3H)-ylidene)acetonitrile
4-[2-({4-[cyano(4-ethyl-1,3-thiazol-2(3H)-ylidene)methyl]pyrimidin-2-yl}amino)ethyl]benzenesulfonamide
(2-{[2-(4-aminophenyl)ethyl]amino}pyrimidin-4-yl)(4-ethyl-1,3-thiazol-2(3H)-ylidene)acetonitrile
(4-ethyl-1,3-thiazol-2(3H)-ylidene)(2-{[2-(6-morpholin-4-ylpyridin-3-yl)ethyl]amino}pyrimidin-4-yl)acetonitrile
(4-ethyl-1,3-thiazol-2(3H)-ylidene)[2-({2-[6-(4-methylpiperazin-1-yl)pyridin-3-yl]ethyl}amino)pyrimidin-4-yl]acetonitrile
[2-(cyclopropylamino)pyrimidin-4-yl](4-ethyl-1,3-thiazol-2(3H)-ylidene)acetonitrile
[4-(2-methoxyphenyl)-1,3-thiazol-2(3H)-ylidene]{2-[(2-pyridin-3-ylethyl)amino]pyrimidin-4-yl}acetonitrile
[4-(2-methoxyphenyl)-1,3-thiazol-2(3H)-ylidene](2-{[3-(2-oxopyrrolidin-1-yl)propyl]amino}pyrimidin-4-yl)acetonitrile
[4-(4-fluorophenyl)-1,3-thiazol-2(3H)-ylidene]{2-[(2-pyridin-3-ylethyl)amino]pyrimidin-4-yl}acetonitrile
[4-(4-fluorophenyl)-1,3-thiazol-2(3H)-ylidene](2-{[3-(2-oxopyrrolidin-1-yl)propyl]amino}pyrimidin-4-yl)acetonitrile (4-ethyl-1,3-thiazol-2(3H)-ylidene){5-methyl-2-[(2-pyridin-3-ylethyl)amino]pyrimidin-4-yl}acetonitrile (4-ethyl-1,3-thiazol-2(3H)-ylidene)(5-methyl-2-{[3-(2-oxopyrrolidin-1-yl)propyl]amino}pyrimidin-4-yl)acetonitrile

[2-(cyclopropylamino)-5-methylpyrimidin-4-yl](4-ethyl-1,3-thiazol-2(3H)-ylidene)acetonitrile (4-ethyl-1,3-thiazol-2(3H)-ylidene){2-[(3-pyrrolidin-1-ylpropyl)amino]pyrimidin-4-yl}acetonitrile

[2-({2-[(5-nitropyridin-2-yl)amino]ethyl}amino)pyrimidin-4-yl](4-phenyl-1,3-thiazol-2(3H)-ylidene)acetonitrile 6-{[2-({4-[cyano(4-phenyl-1,3-thiazol-2(3H)-ylidene)methyl]pyrimidin-2-yl}amino)ethyl]amino}nicotinonitrile tert-butyl 4-({4-[cyano(4-phenyl-1,3-thiazol-2(3H)-ylidene)methyl]pyrimidin-2-yl}amino)butanoate

[4-(4-methoxyphenyl)-1,3-thiazol-2(3H)-ylidene](2-{[3-(2-oxopyrrolidin-1-yl)propyl]amino}pyrimidin-4-yl)acetonitrile (4-methyl-1,3-thiazol-2(3H)-ylidene)(2-{[3-(2-oxopyrrolidin-1-yl)propyl]amino}pyrimidin-4-yl)acetonitrile (4-tert-butyl-1,3-thiazol-2(3H)-ylidene)(2-{[3-(2-oxopyrrolidin-1-yl)propyl]amino}pyrimidin-4-yl)acetonitrile (4-tert-butyl-1,3-thiazol-2(3H)-ylidene){2-[(2-pyridin-3-ylethyl)amino]pyrimidin-4-yl}acetonitrile (4-tert-butyl-1,3-thiazol-2(3H)-ylidene)[2-(cyclohexylamino)pyrimidin-4-yl]acetonitrile (4-tert-butyl-1,3-thiazol-2(3H)-ylidene)[2-(cyclopropylamino)pyrimidin-4-yl]acetonitrile

[4-(4-chlorophenyl)-1,3-thiazol-2(3H)-ylidene](2-{[3-(2-oxopyrrolidin-1-yl)propyl]amino}pyrimidin-4-yl)acetonitrile

[4-(4-chlorophenyl)-1,3-thiazol-2(3H)-ylidene][2-(cyclopropylamino)pyrimidin-4-yl]acetonitrile

[4-(3,4-dichlorophenyl)-1,3-thiazol-2(3H)-ylidene](2-{[3-(2-oxopyrrolidine-1yl)propyl]amino}pyrimidin-4-yl)acetonitrile

[4-(3,4-dichlorophenyl)-1,3-thiazol-2(3H)-ylidene]{2-[(2-pyridin-3-ylethyl)amino]pyrimidin-4-yl}acetonitrile

[2-(cyclopropylamino)pyrimidin-4-yl][4-(3,4-dichlorophenyl)-1,3-thiazol-2(3H)-ylidene]acetonitrile

[4-(4-methylphenyl)-1,3-thiazol-2(3H)-ylidene](2-{[3-(2-oxopyrrolidin-1-yl)propyl]amino}pyrimidin-4-yl)acetonitrile

[4-(4-methylphenyl)-1,3-thiazol-2(3H)-ylideiie]{2-[(2-pyridin-3-ylethyl)amino]pyrimidin-4-yl}acetonitrile

[2-(cyclopropylamino)pyrimidin-4-yl][4-(4-metlylphenyl)-1,3-thiazol-2(3H)-ylidene]acetonitrile {2-[(3-aminopropyl)amino]pyrimidin-4-yl}(4-tert-butyl-1,3-thiazol-2(3H)-ylidene)acetonitrile {2-[(2-aminoethyl)amino]pyrimidin-4-yl}(4-tert-butyl-1,3-thiazol-2(3H)-ylidene)acetonitrile {2-[(piperidin-4-yl)amino]pyrimidin-4-yl}(4-ethyl-1,3-thiazol-2(3H)-ylidene)acetonitrile methyl N-{4-[(4-tert-butyl-1,3-thiazol-2(3H)-ylidene)(cyano)methyl]pyrimidin-2-yl}-beta-alaninate (2-{[3-(2-oxopyrrolidin-1-yl)propyl]amino}pyrimidin-4-yl)[4-(pentafluoroethyl)-1,3-thiazol-2(3H)-ylidene]acetonitrile {5-methyl-2-[(2-pyridin-3-ylethyl)amino]pyrimidin-4-yl}(4-methyl-1,3-thiazol-2(3H)-ylidene)acetonitrile (5-methyl-2-{[3-(2-oxopyrrolidin-1-yl)propyl]amino}pyrimidin-4-yl)(4-methyl-1,3-thiazol-2(3H)-ylidene)acetonitrile

[2-(cyclopropylamino)-5-methylpyrimidin-4-yl](4-methyl-1,3-thiazol-2(3H)-ylidene)acetonitrile (4-tert-butyl-1,3-thiazol-2(3H)-ylidene){5-methyl-2-[(2-pyridin-3-ylethyl)amino]pyrimidin-4-yl}acetonitrile (4-tert-butyl-1,3-thiazol-2(3H)-ylidene)(5-methyl-2-{[3-(2-oxopyrrolidin-1-yl)propyl]amino}pyrimidin-4-yl)acetonitrile (4-tert-butyl-1,3-thiazol-2(3H)-ylidene)[2-(cyclopropylamino)-5-methylpyrimidin-4-yl]acetonitrile (4-tert-butyl-1,3-thiazol-2(3H)-ylidene)(5-methyl-2-{[3-(1H-1,2,4-triazol-1-yl)propyl]amino}pyrimidin-4-yl)acetonitrile N-[3-({4-[(4-tert-butyl-1,3-thiazol-2(3H)-ylidene)(cyano)methyl]pyrimidin-2-yl}amino)propyl]-2-ethoxy-N-glycoloylacetamide N-[3-({4-[cyano(4-isopropyl-1,3-thiazol-2(3H)-ylidene)methyl]pyrimidin-2-yl}amino)propyl]-2-ethoxy-N-glycoloylacetamide

[2-(cyclohexylamino)pyrimidin-4-yl](4-ethyl-1,3-thiazol-2(3H)-ylidene)acetonitrile

[2-(cyclopentylamino)pyrimidin-4-yl](4-ethyl-1,3-thiazol-2(3H)-ylidene)acetonitrile (4-ethyl-1,3-thiazol-2(3H)-ylidene)[2-(isobutylamino)pyrimidin-4-yl]acetonitrile (4-tert-butyl-1,3-thiazol-2(3H)-ylidene)(2-{[3-(1H-1,2,4-triazol-1-yl)propyl]amino}pyrimidin-4-yl)acetonitrile (4-isopropyl-1,3-thiazol-2(3H)-ylidene)(2-{[3-(2-oxopyrrolidin-1-yl)propyl]amino}pyrimidin-4-yl)acetonitrile (4-isopropyl-1,3-thiazol-2(3H)-ylidene){2-[(2-pyridin-3-ylethyl)amino]pyrimidin-4-yl}acetonitrile

[2-(cyclopropylamino)pyrimidin-4-yl](4-isopropyl-1,3-thiazol-2(3H)-ylidene)acetonitrile methyl 4-({4-[(4-tert-butyl-1,3-thiazol-2(3H)-ylidene)(cyano)methyl]pyrimidin-2-yl}amino)butanoate 4-{2-[cyano(2-{[3-(2-oxopyrrolidin-1-yl)propyl]amino}pyrimidin-4-yl)methylene]-2,3-dihydro-1,3-thiazol-4-yl}benzonitrile 4-[2-(cyano{2-[(2-pyridin-3-ylethyl)amino]pyrimidin-4-yl}methylene)-2,3-dihydro-1,3-thiazol-4-yl]benzonitrile 4-(2-{cyano[2-(cyclopropylamino)pyrimidin-4-yl]methylene}-2,3-dihydro-1,3-thiazol-4-yl)benzonitrile

[4-(2-chlorophenyl)-1,3-thiazol-2(3H)-ylidene](2-{[3-(2-oxopyrrolidin-1-yl)propyl]amino}pyrimidin-4-yl)acetonitrile

[4-(3-chlorophenyl)-1,3-thiazol-2(3H)-ylidene](2-{[3-(2-oxopyrrolidin-1-yl)propyl]amino}pyrimidin-4-yl)acetonitrile

[4-(3-chlorophenyl)-1,3-thiazol-2(3H)-ylidene]{2-[(2-pyridin-3-ylethyl)amino]pyrimidin-4-yl}acetonitrile

[4-(2-chlorophenyl)-1,3-thiazol-2(3H)-ylidene]{2-[(2-pyridin-3-ylethyl)amino]pyrimidin-4-yl}acetonitrile

[2-(cyclopropylamino)pyrimidin-4-yl][4-(4-methoxyphenyl)-1,3-thiazol-2(3H)-ylidene]acetonitrile

[4-(2-chlorophenyl)-1,3-thiazol-2(3H)-ylidene][2-(cyclopropylamino)pyrimidin-4-yl]acetonitrile N-[3-({4-[cyano(4-ethyl-1,3-thiazol-2(3H)-ylidene)methyl]pyrimidin-2-yl}(amino)propyl]acetamide N-[2-({4-[(4-tert-butyl-1,3-thiazol-2(3H)-ylidene)(cyano)methyl]pyrimidin-2-yl}amino)ethyl]acetamide {2-[(1-acetylpiperidin-4-yl)amino]pyrimidin-4-yl}(4-ethyl-1,3-thiazol-2(3H)-ylidene)acetonitrile (4-tert-butyl-1,3-thiazol-2(3H)-ylidene)(2-{[3-(2,5-dioxopyrrolidin-1-yl)propyl]amino}pyrimidin-4-yl)acetonitrile (2-{[3-(2,5-dioxopyrrolidin-1-yl)propyl]amino}pyrimidin-4-yl)(4-ethyl-1,3-thiazol-2(3H)-ylidene)acetonitrile (4-ethyl-1,3-thiazol-2(3H)-ylidene)(2-{[1-(methylsulfonyl)piperidin-4-yl]amino}pyrimidin-4-yl)acetonitrile trifluoroacetate N~3~-{4-[(4-tert-butyl-1,3-thiazol-2(3H)-ylidene)(cyano)
methyl]pyrimidin-2-yl}-N~1~,N~1~-dimethyl-beta-
alaninamide
N-{3-[{4-[(4-tert-butyl-1,3-thiazol-2(3H)-ylidene)(cyano)
methyl]pyrimidin-2-yl}(methyl)amino]propyl}acetamide
N-[3-({4-[(4-tert-butyl-3-methyl-1,3-thiazol-2(3H)-ylidene)
(cyano)methyl]pyrimidin-2-yl}amino)propyl]acetamide
(4-ethyl-1,3-thiazol-2(3H)-ylidene)(2-{[4-(morpholin-4-yl-
methyl)benzyl]oxy}pyrimidin-4-yl)acetonitrile
{2-[3-(dimethylamino)propoxy]pyrimidin-4-yl}(4-ethyl-1,
3-thiazol-2(3H)-ylidene)acetonitrile
[4-(4-chlorophenyl)-1,3-thiazol-2(3H)-ylidene]{5-methyl-
2-[(3-pyrrolidin-1-ylpropyl)amino]pyrimidin-4-
yl}acetonitrile
[4-(4-chlorophenyl)-1,3-thiazol-2(3H)-ylidene]{2-[(3-pyr-
rolidin-1-ylpropyl) amino]pyrimidin-4-yl}acetonitrile
[4-(dimethylamino)-6-(octahydroquinolin-1(2H)-yl)-1,3,5-
triazin-2-yl](4-phenyl-1,3-thiazol-2(3H)-ylidene)acetoni-
trile
[2-(cyclohexylamino)-5-methylpyrimidin-4-yl](4-phenyl-1,
3-thiazol-2(3H)-ylidene)acetonitrile
[2-(cyclohexylamino)pyrimidin-4-yl](4-phenyl-1,3-thiazol-
2(3H)-ylidene)acetonitrile
[4-(methylamino)-6-(4-methylpiperidin-1-yl)-1,3,5-triazin-
2-yl](4-methyl-1,3-thiazol-2(3H)-ylidene)acetonitrile
[4-(cyclohexylamino)-6-(methylamino)-1,3,5-triazin-2-yl]
(4-methyl-1,3-thiazol-2(3H)-ylidene)acetonitrile
[5-methyl-2-(4-methylpiperidin-1-yl)pyrimidin-4-yl](4-
phenyl-1,3-thiazol-2(3H)-ylidene)acetonitrile
[2-(cyclopropylamino)-5-methylpyrimidin-4-yl](4-phenyl-
1,3-thiazol-2(3H)-ylidene)acetonitrile
[2-(cyclopropylamino)pyrimidin-4-yl](4-phenyl-1,3-thia-
zol-2(3H)-ylidene)acetonitrile
[2-(cyclopentylamino)-5-methylpyrimidin-4-yl](4-phenyl-
1,3-thiazol-2(3H)-ylidene)acetonitrile
{5-methyl-2-[(1-methylbutyl)amino]pyrimidin-4-yl}(4-
phenyl-1,3-thiazol-2(3H)-ylidene)acetonitrile
[2-(cyclopentylamino)pyrimidin-4-yl](4-phenyl-1,3-thia-
zol-2(3H)-ylidene)acetonitrile
{5-methyl-2-[(3-pyrrolidin-1-ylpropyl)amino]pyrimidin-4-
yl}(4-phenyl-1,3-thiazol-2(3H)-ylidene)acetonitrile
{2-[(1-methylbutyl)amino]pyrimidin-4-yl}(4-phenyl-1,3-
thiazol-2(3H)-ylidene)acetonitrile
{6-[(2-furylmethyl)amino]pyrimidin-4-yl}(4-methyl-1,3-
thiazol-2(3H)-ylidene)acetonitrile
[6-(4-ethylpiperazin-1-yl)pyrimidin-4-yl](4-methyl-1,3-
thiazol-2(3H)-ylidene)acetonitrile
(4-phenyl-1,3-thiazol-2(3H)-ylidene){2-[(3-pyrrolidin-1-yl
propyl)amino]pyrimidin-4-yl}acetonitrile
[2-(cyclopentylamino)-6-methylpyrimidin-4-yl](4-phenyl-
1,3-thiazol-2(3H)-ylidene)acetonitrile
[4-(4-ethylpiperazin-1-yl)-6-morpholin-4-yl-1,3,5-triazin-2-
yl](4-phenyl-1,3-thiazol-2(3H)-ylidene)acetonitrile
{2-[(cyclohexylmethyl)amino]pyrimidin-4-yl}(4-phenyl-1,
3-thiazol-2(3H)-ylidene)acetonitrile
{2-[(cyclohexylmethyl)amino]-5-methylpyrimidin-4-yl}(4-
phenyl-1,3-thiazol-2(3H)-ylidene)acetonitrite
[2-(4-ethylpiperazin-1-yl)-5-methylpyrimidin-4-yl](4-phe-
nyl-1,3-thiazol-2(3H)-ylidene)acetonitrile
[4-(cyclopentylamino)-6-(methylamino)-1,3,5-triazin-2-yl]
(4-methyl-1,3-thiazol-2(3H)-ylidene)acetonitrile
[4-(cyclopropylamino)-6-morpholin-4-yl-1,3,5-triazin-2-yl]
(4-phenyl-1,3-thiazol-2(3H)-ylidene)acetonitrile
[4-(cyclopropylamino)-6-(methylamino)-1,3,5-triazin-2-yl]
(4-phenyl-1,3-thiazol-2(3H)-ylidene)acetonitrile
[4-(cyclopropylamino)-6-(methylamino)-1,3,5-triazin-2-yl]
(4-methyl-1,3-thiazol-2(3H)-ylidene)acetonitrile
[2-(1,4-dioxa-8-azaspiro[4.5]dec-8-yl)-5-methylpyrimidin-
4-yl](4-phenyl-1,3-thiazol-2(3H)-ylidene)acetonitrile
(5-methyl-2-{[3-(1H-1,2,4-triazol-1-yl)propyl]
amino}pyrimidin-4-yl)(4-phenyl-1,3-thiazol-2(3H)-
ylidene)acetonitrile
{2-[(1,4-dimethylpentyl)amino]-5-methylpyrimidin-4-yl}
(4-phenyl-1,3-thiazol-2(3H)-ylidene)acetonitrile
(5-methyl-2-{[2-(1H-pyrazol-1-yl)ethyl]amino}pyrimidin-
4-yl)(4-phenyl-1,3-thiazol-2(3H)-ylidene)acetonitrile
(4-phenyl-1,3-thiazol-2(3H)-ylidene)(2-{[3-(1H-1,2,4-tria-
zol-1-yl)propyl]amino}pyrimidin-4-yl)acetonitrile
(4-phenyl-1,3-thiazol-2(3H)-ylidene)(2-{[2-(1H-pyrazol-1-
yl)ethyl]amino}pyrimidin-4-yl)acetonitrile
[2-(dipropylamino)-5-methylpyrimidin-4-yl](4-phenyl-1,3-
thiazol-2(3H)-ylidene)acetonitrile
{2-[(1,4-dimethylpentyl)amino]pyrimidin-4-yl}(4-phenyl-
1,3-thiazol-2(3H)-ylidene)acetonitrile
[2-(methylamino)pyrimidin-4-yl](4-phenyl-1,3-thiazol-2
(3H)-ylidene)acetonitrile
[4-[(1,4-dimethylpentyl)amino]-6-(methylamino)-1,3,5-tri-
azin-2-yl](4-phenyl-1,3-thiazol-2(3H)-ylidene)acetoni-
trile
[4-{[(6-aminopyridin-3-yl)methyl]amino}-6-(methy-
lamino)-1,3,5-triazin-2-yl](4-methyl-1,3-thiazol-2(3H)-
ylidene)acetonitrile
[2-(methylamino)pyrimidin-4-yl](4-methyl-1,3-thiazol-2
(3H)-ylidene)acetonitrile
[2-(cyclopentylamino)pyrimidin-4-yl](4-methyl-1,3-thia-
zol-2(3H)-ylidene)acetonitrile
[2-(cyclohexylamino)pyrimidin-4-yl](4-methyl-1,3-thiazol-
2(3H)-ylidene)acetonitrile
{2-[(1-methylbutyl)amino]pyrimidin-4-yl}(4-methyl-1,3-
thiazol-2(3H)-ylidene)acetonitrile
[2-(cyclopentylamino)-6-methylpyrimidin-4-yl](4-methyl-
1,3-thiazol-2(3H)-ylidene)acetonitrile
{2-[(cyclohexylmethyl)amino]pyrimidin-4-yl}(4-methyl-1,
3-thiazol-2(3H)-ylidene)acetonitrile
{6-[methyl(phenyl)amino]-2-[(2-pyridin-3-ylethyl)amino]
pyrimidin-4-yl}(4-methyl-1,3-thiazol-2(3H)-ylidene)ac-
etonitrile
{2-[(2,3-dimethylcyclohexyl)amino]pyrimidin-4-yl}(4-me-
thyl-1,3-thiazol-2(3H)-ylidene)acetonitrile
(4-methyl-1,3-thiazol-2(3H)-ylidene){2-[(pyridin-3-ylm-
ethyl)amino]pyrimidin-4-yl}acetonitrile
{6-methyl-2-[(2-pyridin-2-ylethyl)amino]pyrimidin-4-yl}
(4-methyl-1,3-thiazol-2(3H)-ylidene)acetonitrile
[2-(isopropylamino)pyrimidin-4-yl](4-methyl-1,3-thiazol-2
(3H)-ylidene)acetonitrile
{2-[(1,2-dimethylpropyl)amino]pyrimidin-4-yl}(4-methyl-
1,3-thiazol-2(3H)-ylidene)acetonitrile
(4-methyl-1,3-thiazol-2(3H)-ylidene){2-[4-(pyrimidin-2-
ylamino)piperidin-1-yl]pyrimidin-4-yl}acetonitrile
{2-[(1-ethylpropyl)amino]pyrimidin-4-yl}(4-methyl-1,3-
thiazol-2(3H)-ylidene)acetonitrile
{2-[(3-butoxypropyl)amino]-6-[methyl(phenyl)amino]pyri-
midin-4-yl}(4-methyl-1,3-thiazol-2(3H)-ylidene)acetoni-
trile
{4-[(3-butoxypropyl)amino]-6-morpholin-4-yl-1,3,5-tri-
azin-2-yl}(4-methyl-1,3-thiazol-2(3H)-ylidene)acetoni-
trile
{2-(isopropylamino)-6-[methyl(phenyl)amino]pyrimidin-4-
yl}(4-methyl-1,3-thiazol-2(3H)-ylidene)acetonitrile
{2-[(3-isopropoxypropyl)amino]pyrimidin-4-yl}(4-methyl-
1,3-thiazol-2(3H)-ylidene)acetonitrile
[4-(4-chlorophenyl)-1,3-thiazol-2(3H)-ylidene][2-(cyclo-
propylamino)pyrimidin-4-yl]acetonitrile

[4-(4-chlorophenyl)-1,3-thiazol-2(3H)-ylidene][2-(cyclopentylamino)pyrimidin-4-yl]acetonitrile

[4-(4-chlorophenyl)-1,3-thiazol-2(3H)-ylidene]{2-[(cyclohexylmethyl)amino]-5-methylpyrimidin-4-yl}acetonitrile Compounds of formula (I) are suitable for the use as medicament, in particular for the treatment and/or prevention of neurodegenerative diseases, neuronal disorders including epilepsy, Alzheimer's disease, amyotrohic lateral sclerosis, parkinsonism-dementia of Gaum, corticobasal degeneration, dementia pugilistica and head trauma, Down's syndrome, postencephalatic parkinsoism, progressive supranuclear palsy, Parkinson's disease, amyotrophic lateral sclerosis, Huntington's Disease, HIV dementia, ischemic stroke and head trauma retinal diseases, spinal cord injury, head trauma, mood disorders, particularly bipolar (mood) disorders, multiple sclerosis or amyotrophic lateral sclerosis, diabetes, particularly type II diabetes and obesity, asthma, septic shock, transplant rejection, cerebrovascular accident, glaucoma, cardiovascular diseases including stroke, arteriosclerosis, myocardial infarction, myocardial reperfusion injury, ischemia, cancer and inflammatory diseases including arteriosclerosis, arthritis, Inflammatory Bowel Disease or rheumatoid arthritis.

A further aspect of the present invention is related to the use of the azole derivatives according to formula (I) for the preparation of pharmaceutical compositions for the modulation— notably of the inhibition—of a protein kinase mediated signalling pathways as well as for preventive and therapeutic treatment of diseases caused by abnormal protein kinase activity. Preferably, this protein kinase is a c-Jun Kinase. More preferably said protein is a Glycogen Synthase Kinase 3, particularly Glycogen Synthase Kinase 3 beta. The compounds according to formula I could be employed alone or in combination with further pharmaceutical agents.

Specifically, the compounds pursuant to formula (I) are useful in the preparation of a medicament for the prevention and/or treatment of pathological states and diseases in which inhibition of protein kinases, particularly of Jun Kinase and/or Glycogen Synthase Kinase 3 is required. These diseases are selected in the group consisting of neurodegenerative diseases, neuronal disorders including epilepsy, Alzheimer's disease, Parkinson's disease, retinal diseases, spinal cord injury, head trauma, multiple sclerosis or amyotrophic lateral sclerosis, diabetes, particularly type II diabetes and obesity, asthma, septic shock, transplant rejection, cerebrovascular accident, glaucoma, cardiovascular diseases including stroke, arteriosclerosis, myocardial infarction, myocardial reperfusion injury, ischemia, cancer and inflammatory diseases including arteriosclerosis, arthritis, Inflammatory Bowel Disease or rheumatoid arthritis.

Specifically, the compounds of formula I are suitable for use in treating disorders of the immune system and neuronal system of mammals, notably of human beings. Such neuronal system disorders include for example neurodegenerative diseases e.g. Alzheimer's disease, Huntington's disease, Parkinson's disease, retinal diseases, spinal cord injury, multiple sclerosis or amyotrophic lateral sclerosis, head trauma, epilepsy and seizures, ischemic and hemorrhagic brain strokes.

Also, the compounds of formula I are suitable for use in the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS).

Immune system disorders include for example asthma, transplant rejection, inflammatory processes such as inflammatory bowel disease (IBD), cartilage and bone erosion disorders, rheumatoid arthritis, septic shock.

The compounds according to formula I are also suitable for use in treating cancers, such as breast, colorectal, pancreatic, prostate, testicular, ovarian, lung, liver and kidney cancers.

In another embodiment, the compounds according to formula I may be used for treating cardiovascular diseases including atherosclerosis, restenosis, glaucoma, stroke, ischemia, e.g. cerebral ischemia, myocardial reperfiusion injury or myocardial infarction.

In another embodiment, the compounds according to formula I may be used for treating various ischemic conditions including heart and kidney failures, hepatic disorders and brain reperfusion injuries.

Another object of the present invention is a method for the treatment of disease states mediated by protein kinase comprising the administration to the patient of a pharmaceutically active amount of an azole derivative according to formula (I).

Still a further object of the present invention is a process for preparing the novel azole derivatives according to formula I.

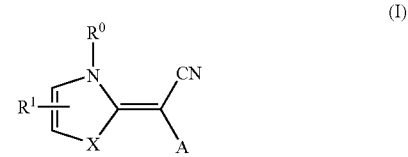

The azole methylidene cyanide exemplified in this invention may be prepared from readily available starting materials using the following general methods and procedures. It will be appreciated that where typical or preferred experimental conditions (i.e., reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

Generally, azole methylidene cyanide derivatives according to the general formula I may be obtained by several processes using solution-phase chemistry protocols.

According to one process, azole methylidene cyanide derivatives according to the general formula I, whereby the substituents X, A and $R^1$ are as above defined and $R^0$ is H, are prepared from the corresponding acetonitrile derivatives II and chloro derivatives III, by well known solution-phase chemistry protocols, such as those described in the Examples and shown in Scheme 1, below.

Scheme 1

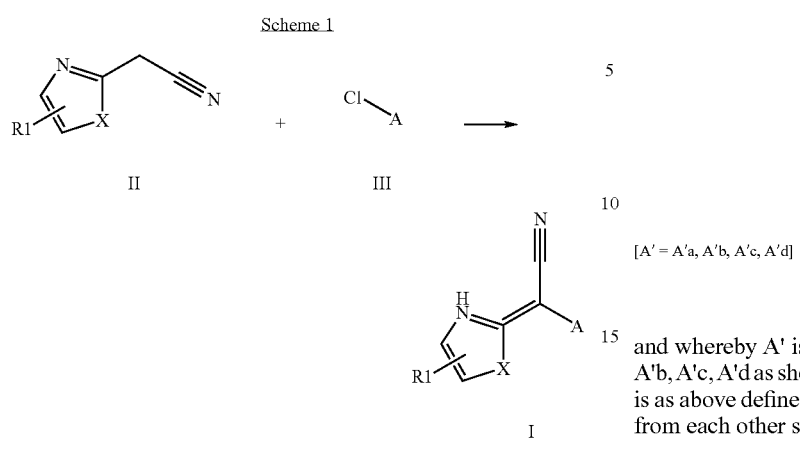

The chloro derivatives III can be obtained either through commercial sources or can be prepared from known compounds by conventional procedures known by one skilled in the art. Preferred chloro derivatives III are defined such as shown in the scheme 2 below.

The azole methylidene cyanide of general formula I are prepared according to a general process outlined above, and also starting from the azole acetonitrile derivatives II, whereby X and $R^1$ are as above defined and $R^0$ is hydrogen, which was reacted with the bis-chloro derivatives III', where A' is as above defined, to give the intermediate of synthesis II'. In a subsequent step, the intermediate II' was treated with the amines IV, whereby the substituents $R^3, R^4$ are as above defined to give the final azole methylidene cyanide derivatives I, utilizing well known solution-phase chemistry protocols, such as those described in the Examples and shown in Scheme 2, below

Scheme 2

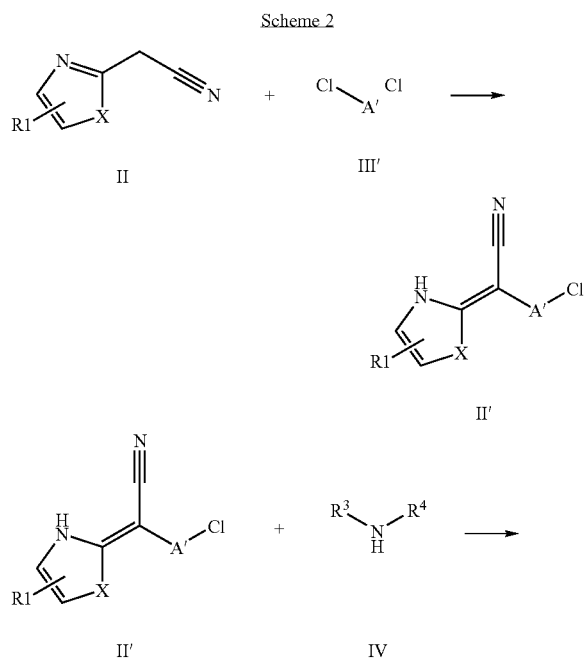

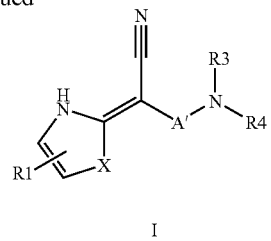

[A' = A'a, A'b, A'c, A'd]

and whereby A' is either a pyrimidinyl or triazinyl core A'a, A'b, A'c, A'd as shown in the Scheme 3 below, and whereby $R^2$ is as above defined and also $G^1$, $G^2$ and $G^3$ are independently from each other selected from N and CH.

Scheme 3

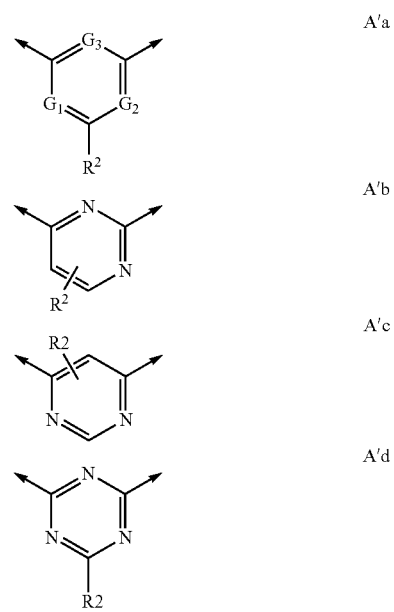

The azole methylidene cyanide derivatives according to the general formula Ia, whereby the substituent X and R1 are as above defied and $R^0$ is hydrogen, were obtained in two subsequent steps as shown in Scheme 4. In a first step, the chloro azole methylidene cyanide derivatives II'a were isolated after condensation of the azole acetonitrile compound II with a bis-chloro derivative III'a, whereby the heteroaromatic core is A'a, and $R^2$ is as above defied and also $G^1$, $G^2$ and $G^3$ are independently from each other selected from N and CH. This first reaction step was performed using, e.g. lithium hydride or sodium hydride or similar reagents in appropriate solvent such as THF or DMF in an anhydrous inert atmosphere. This reaction can be performed at various temperatures (range of about −78° C. to 160° C., *Pol. J. Chem.* by Chabaka L. M. et al. p. 1317-1326 (1994)) or reaction times depending of the intrinsic reactivity of compounds II and III'a, by traditional thermic method or using microwave technology, using standard conditions well known to the person skilled in the art, such as those described hereinafter in the Examples. In a subsequent step, the chloro azole methylidene cyanide derivatives II'a were treated with various amines IV to give the expected azole methylidene cyanide Ia. The nucleophilic displacement of the chloro atom of the heterocyclic moiety by the amine IV, is accomplished by treatment with several equivalents of the amines IV in presence or absence of sodium iodine as catalyst and a base such as triethylamine or diisopropylethylamine or similar reagents. This reaction can be performed at various temperatures depending of the intrinsic reactivity of compounds IV and II'a, by traditional thermic method or using microwave technology, using standard conditions well known to the person skilled in the art, such as those described hereinafter in the Examples.

or similar reagents in an appropriate solvent such as THF or DMF. This reaction can be performed at various temperature depending of the intrinsic reactivity of compounds II and III'b, by traditional thermic method or using microwave technology, using standard conditions well known to the person skilled in the art, such as those described hereinafter in the Examples. In a subsequent step, chloro azole methylidene cyanide derivatives II'b were treated with various amines IV to give the azole methylidene cyanide derivatives Ib. The nucleophilic displacement of the chloro atom of the pyrimidinyl moiety by the amine IV, is accomplished by treatment with several equivalents of the amines IV in presence or absence of sodium iodine as catalyst and a base such as triethylamine or diisopropylethylamine or similar reagents. This reaction can be performed at various temperatures depending of the intrinsic reactivity of compounds IV and II'b, by traditional thermic method or using microwave technology, using standard conditions well known to the person skilled in the art, such as those described hereinafter in the Examples.

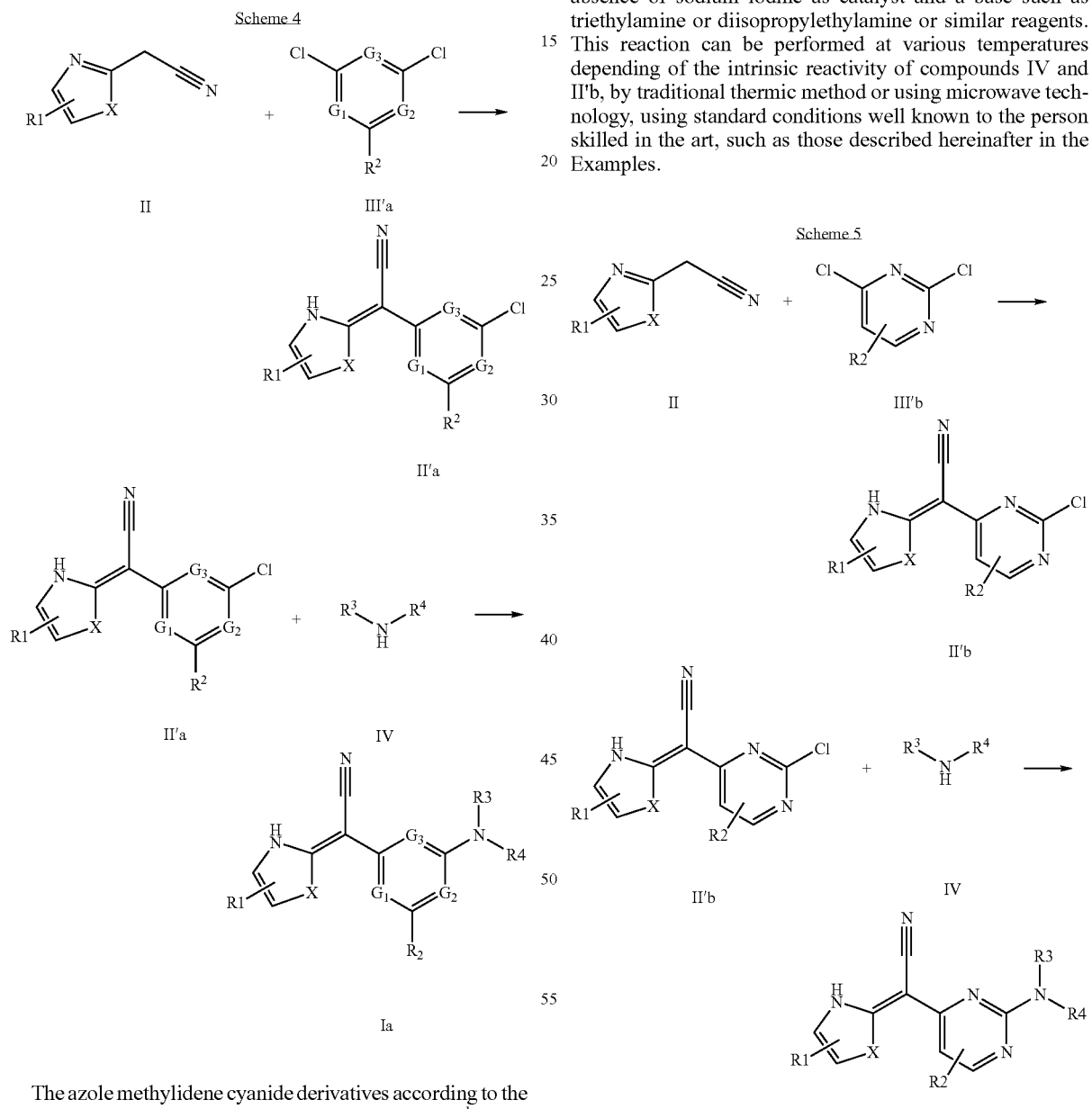

The azole methylidene cyanide derivatives according to the general formula Ib, whereby the substituent X and $R^1$ are as above defined and $R^0$ is hydrogen, were obtained in two subsequent steps as shown in Scheme 5. In a first step, the chloro azole methylidene cyanide derivatives II'b were isolated after condensation of the azole acetonitrile compound II with bis-chloro derivative III'b, whereby the heteroaromatic core is A'b, and $R^2$ is as above defined. This first reaction step was performed, using, e.g. lithium hydride or sodium hydride The azole methylidene cyanide derivatives according to the general formula Ic, whereby the substituent X and R1 are as above defined and $R^0$ is hydrogen, were obtained in two subsequent steps as shown in Scheme 6. In a first step, the azole methylidene cyanide derivatives II'c were isolated after condensation of the azole acetonitrile compound II with a bis-chloro derivative III'c, whereby the heteroaromatic core is A'c, and $R^2$ is as above defined. This first reaction step was performed, using, e.g. lithium hydride or sodium hydride or similar reagents in an appropriate solvent such as THF or DMF. This reaction can be performed at various temperatures depending of the intrinsic reactivity of compounds II and III'c, by traditional thermic method or using microwave technology, using standard conditions well known to the person skilled in the art, such as those described hereinafter in the Examples. In a subsequent step, the chloro azole methylidene cyanide derivatives II'c were treated with various amines IV to give the expected azole methylidene cyanide acetonitriles derivatives Ic. The nucleophilic displacement of the chloro atom of the pyrimidinyl moiety by the amine IV, is accomplished by treatment with several equivalents of the amines IV in presence or absence of sodium iodine as catalyst and a base such as triethylamine or diisopropylethylamine or similar reagents. This reaction can be performed at various temperatures depending of the intrinsic reactivity of compounds IV and II'c, by traditional thermic method or using microwave technology, using standard conditions well known to the person skilled in the art, such as those described hereinafter in the Examples.

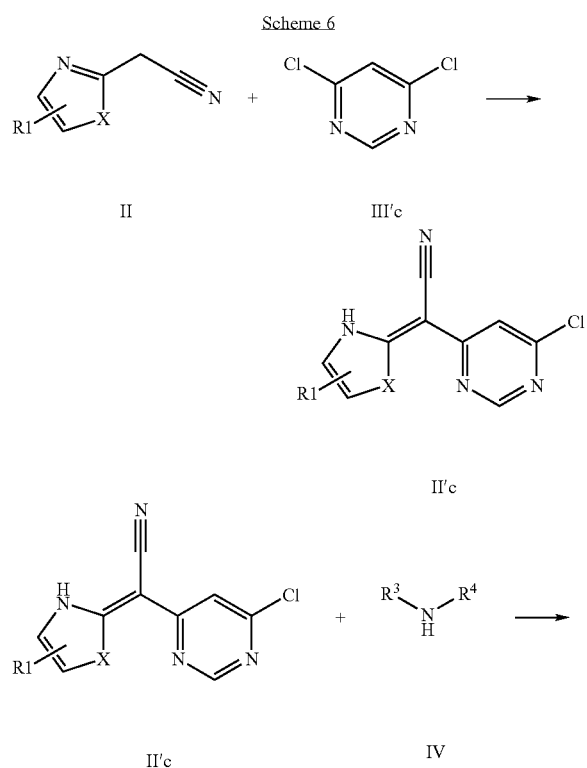

Scheme 6

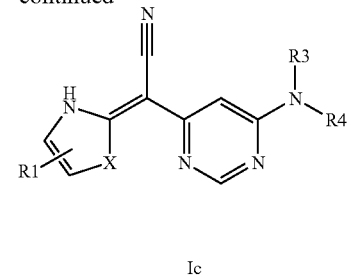

Ic

The azole methylidene cyanide derivatives according to the general formula Id, whereby the substituent X and $R^1$ is as above defined and $R^0$ is hydrogen, were obtained in two subsequent steps as shown in Scheme 7. In a first step, the azole methylidene cyanide derivatives II'd were isolated after condensation of the azole acetonitrile compound II with a bis-chloro derivative III'd, whereby the heteroaromatic core is A'd, and $R^2$ is as above defined. This first reaction step was performed, using, e.g. lithium hydride or sodium hydride or similar reagents in an appropriate solvent such as THF or DMF. This reaction can be performed at various temperature depending of the intrinsic reactivity of compounds II and III'd, by traditional thermic method or using microwave technology, using standard conditions well known to the person skilled in the art, such as those described hereinafter in the Examples. In a subsequent step, the chloro azole methylidene cyanide derivatives II'd were treated with various amines IV to give the expected azole methylidene cyanide derivatives Id. The nucleophilic displacement of the chloro atom of the triazinyl moiety by the amine IV, is accomplished by treatment with several equivalents of the amines IV in presence or absence of sodium iodine as catalyst and a base such as triethylamine or diisopropylethylamine or similar reagents. This reaction can be performed at various temperature depending of the intrinsic reactivity of compounds IV and II'd, by traditional thermic method or using microwave technology, using standard conditions well known to the person skilled in the art, such as those described hereinafter in the Examples.

Scheme 7

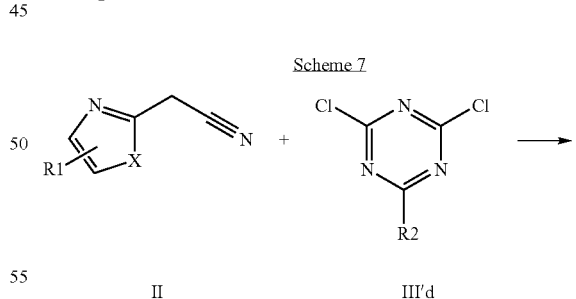

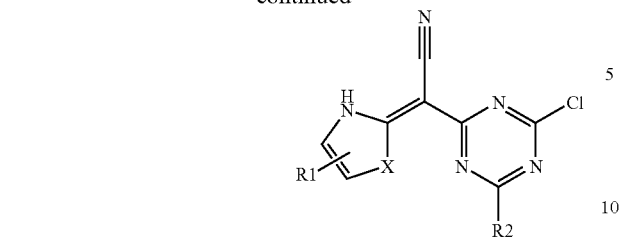

II'd

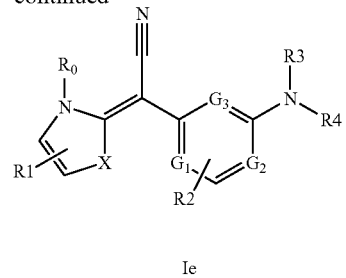

Ie

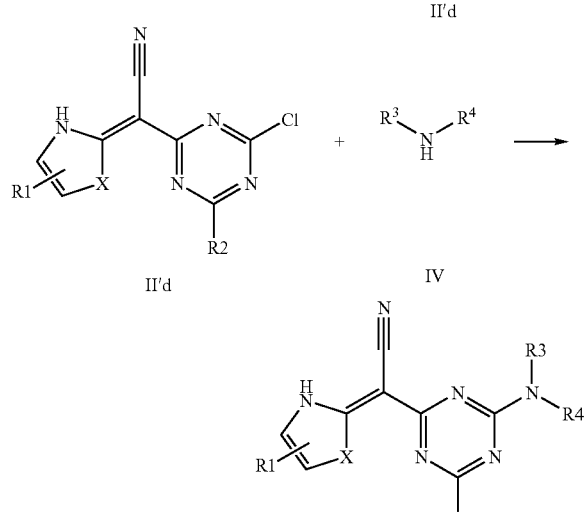

Id

The azole methylidene cyanide derivatives according to the general formula Ie, whereby the substituent X, $R^0$ and $R^1$ is as above defined, were obtained in one step as shown in Scheme 8, by the treatment of the azole methylidene cyanide derivatives II'a with electrophiles Y—$R^0$ such as alkyl, benzyl halides or acyl chlorides at a temperature in the range of 25° C. to 80° C. in the presence of a base such as potassium carbonate, potassium terbutoxide, sodium hydride and the like in a solvent such as DMSO, DMF, acetone and the like in an anhydrous inert atmosphere.

Electrophiles Y—$R^0$ are either commercially available or can be prepared from known compounds by conventional procedures known by one skilled in the art. Preferred electrophiles as starting materials include methyl iodide and acetyl chloride.

Scheme 8

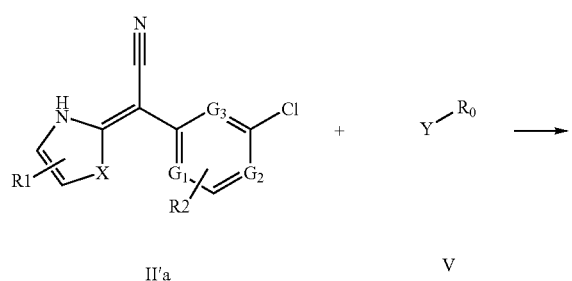

The azole acetonitrile components II are either obtained from commercial sources or prepared in one step by conventional procedures from the condensation of the corresponding α-bromo or chloro ketones VI and thioamide derivatives VII as outlined in scheme 9 (*J. Chem. Research* (S) by Abdelhamid, A. O. et al, 144-145 (1995); EP0169502 A2, *J. Chem. Soc. Perkin Trans I* by Brown M. D. et al 52(5) p. 1623-1626 (1985); *J. Chem. Research* by Dawood K. M. et al (S), 206-201 (2000)). The α-bromo ketones VI are either obtained from commercial sources or prepared in one step by conventional procedures known by one skilled in the art by bromination of the corresponding acetone derivatives VIII (Ref: Gaudry M. and Marquet A., Tetrahedron, 1970, 26, 5611-5615)

Scheme 9

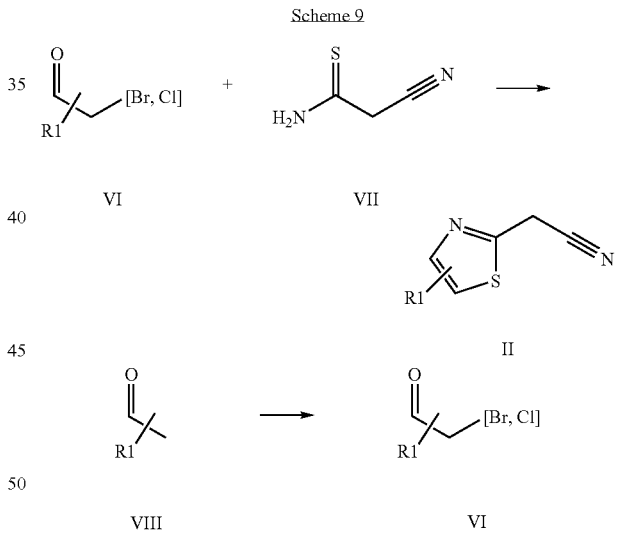

The dichloro heterocycles III'a and dichloropyrimidyl components III'b are obtained from commercial sources. The chloropyrimidinyl derivatives III'c are obtained from commercial sources or made from the dichloro pyrimidinyl derivatives IX by treatment of the latter with primary or secondary amines IV, using standard conditions well known to the practitioner skilled in the art, to yield products of formula III'c, as shown in scheme 11. The dichlorotriazinyl derivatives III'd are obtained from commercial sources or made from cyanuric chloride X, by treatment of the latter with primary or secondary amines IV, using standard conditions well known to the practitioner skilled in the art, to yield products of formula III'd, as shown in scheme 11.

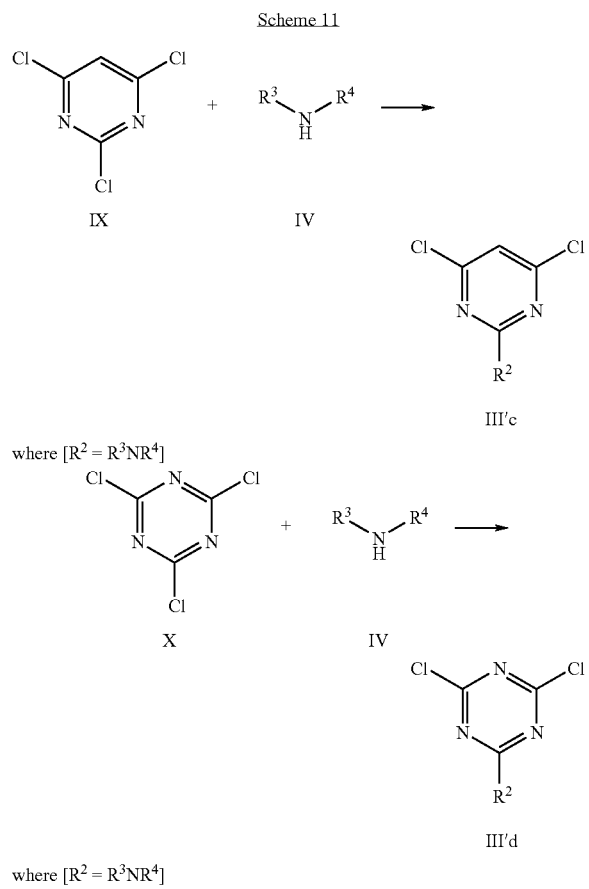

Scheme 11 where [R² = R³NR⁴]

where [R² = R³NR⁴]

If the above set out general synthetic methods are not applicable for the obtention of compounds of formula I, suitable methods of preparation known by a person skilled in the art should be used.

When employed as pharmaceuticals, the azole derivatives of the present invention are typically administered in the form of a pharmaceutical composition. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides compounds for use as a medicament. In particular, the invention provides the compounds of formula I for use as protein kinase inhibitor, particularly c-Jun N-terminal Kinase inhibitor and particularly Glycogen Synthase Kinase 3 inhibitor, for the treatment of disorders and/or diseases as above-mentioned in mammals, notably of humans, either alone or in combination with other medicaments.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, azole derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, intrathecal, intraperitoneal and intranasal. Depending on the intended route of delivery, the compounds are preferably formulated as either injectable, topical or oral compositions. The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the azole compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the benzazole derivatives of formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20th Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention.

The following abbreviations are hereinafter used in the accompanying examples: min (minute), hr (hour), g (gram), mmol (millimole), m.p. (melting point), eq (equivalents), mL (milliliter), μL (microliters), mL (milliliters), L (Liters), Acetone-d6 (deuteriated actenone), ACN (Acetonitrile), Boc (butoxycarbonyl), Br2 (Bromine), CDCl$_3$ (deuteriated chloroform), CHCl$_3$ (Chloroform), CsCO$_3$ (Cesium carbonate), cHex (Cyclohexanes), CCl$_4$ (carbon tetrachloride) DCM (Dichloromethane), DIPEA (Diisopropylethylamine), DMA (Dimethylacetamide), DMAP (4-Dimethylaminopyridine) DMF (Dimethylformamide), DMSO (Dimethylsulfoxide), DMSO-d$_6$ (deuterated dimethylsulfoxide), Et$_3$N (Triethylamine), EtOAc (Ethyl acetate), EtOH (Ethanol), Et$_2$O (Diethyl ether), HBr (Hydrobromic acid), HCl (Hydrochloric acid), iPrOH (Isopropanol), K$_2$CO$_3$ (potassium carbonate), LAH (lithium aluminum hydride), LiH (Lithium Hydride), MeOH (Methanol), MeOD (deuteriated methanol), NaI (Sodium Iodine), NaH (Sodium hydride), NaHCO$_3$ (Sodium bicarbonate), NaOD (deuteriated sodium hydride), NaOH (sodium hydride), Na$_2$SO$_4$ (Sodium sulphate), NH$_4$Cl (Ammonium chloride), NBS (N-bromo succinimide), NMM (N-methylmorpholine), pet ether (Petrol ether), TEA (Triethyl amine), TFA (Trifluoro-acetic acid), THF (Tetrahydrofuran), TMA (Trimethylaluminum), MgSO$_4$ (Magnesium sulfate), r.t. (room temperature), Rt (Retention time).

The HPLC, NMR and MS data provided in the examples described below were obtained as followed: HPLC: column Waters Symmetry C8 50×4.6 mm, Conditions: MeCN/H$_2$O, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The purifications were obtained as followed: Preparative HPLC Waters Prep LC 4000 System equipped with columns Prep Nova-Pak®HR C186 μm 60 Å, 40×30 mm (up to 100 mg) or 40×300 mm (up to 1 g). All the purifications were performed with a gradient of MeCN/H$_2$O 0.09% TFA.

EXAMPLES

Procedure A

Intermediate 1:
4,6-dichloro-N-methyl-1,3,5-triazin-2-amine

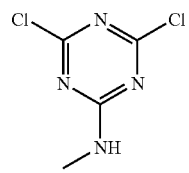

Cyanuric chloride (10 g, 54.3 mmol, 1 equiv.) was dissolved in THF (200 mL) and cooled to −70° C. DIPEA (36.3 mL, 1.42 mmol, 2 equiv.) and methylamine hydrochloride (3.7 g, 1 equiv.) were added to the reaction mixture, which was stirred 2 h at −70° C. and 1 h at rt. The THF was removed under reduced pressure and the remaining material was taken up in DCM and washed with water. The organic layer was dried with MgSO$_4$ and the DCM removed to give a colourless powder (9.5 g, 97%).

MS(ESI$^+$): 181.2; MS(ESI$^-$): 179.2.

Intermediate 2:
4,6-dichloro-N-dimethyl-1,3,5-triazin-2-amine

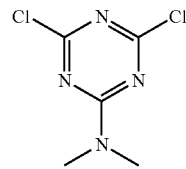

Following the general strategies and protocols outlined in the procedure A, the title compound was obtained from cyanuric chloride and dimethylamine in the presence of K$_2$CO$_3$ for 2 h at −70° C. and 1 h at rt in THF (86%).

MS(ESI$^+$): 194.3; MS(ESI$^-$): 192.3.

Intermediate 3:
4,6-dichloro-N-morpholinyl-1,3,5-triazin-2-amine

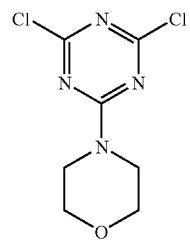

Following the general strategies and protocols outlined in the procedure A, the title compound was obtained from cyanuric chloride and morpholine in the presence of DIPEA for 2 h at −70° C. and 1 h at rt in THF (98%).

MS(ESI$^+$): 236.1; MS(ESI$^-$): 234.1.

Intermediate 4:
6-[(2-Aminoethyl)amino]nicotinonitrile

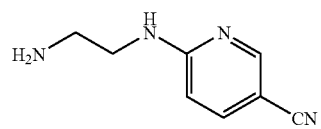

To 100 mL of ethylene diamine at 50° C. under nitrogen was added 2-chloro-5-cyanopyridine (10 g, 0.0722 mol) in small portions over a period of 3 h. The reaction mixture was stirred at 50° C. for an additional 5 h. The reaction mixture was concentrated to near dryness under reduced pressure and the crude residue obtained was purified by chromatography using chloroform/methanol (9/1) as eluent to afford 9 g of the title compound as a solid (77%).

$^1$H NMR (DMSO-d6) δ 8.37 (d, J=2.2 Hz, 1H), 7.66-7.58 (m, 2H), 6.54 (d, J=9.0 Hz, 1H), 3.28-3.16 (m, 2H), 2.68 (t, J=6.4 Hz, 2H), 1.78-1.40 (br s, 2H).

M⁻(ES): 161.4.

Intermediate 5:
3-(1H-1,2,4-triazol-1-yl)propan-1-amine

Step-1: 3-(1H-1,2,4-triazol-1-yl)propanenitrile

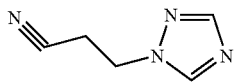

A mixture of 1,2,4-triazole (25 g, 0.362 mol) and acrylonitrile (100 mL, 4 w/v) was heated up to 80° C. under nitrogen for 16 h. The reaction mixture was then concentrated under reduced pressure to remove the excess of acrylonitrile affording 41 g of the title compound as a colourless liquid (93%). It was used in the next step without further purification.

Step-2: 3-(1H-1,2,4-triazol-1-yl)propan-1-amine

To a mixture of 3-(1H-1,2,4-triazol-1-yl)-propanenitrile (25 g, 0.204 mol) and Raney-Nickel (5 g, 0.2 w/w, wet) in methanol (300 mL) was added a solution of 25% aqueous NH$_4$OH (75 mL). The above reaction mixture was hydrogenated under pressure (75 psi of hydrogen) for a period of 6 h. The catalyst was then filtered off and the filtrate was concentrated under reduced pressure. The residue obtained was taken up in DCM (150 mL) then triturated 4 times and the combined organic layer was concentrated under reduced pressure to yield 22 g of the title compound as a liquid (85%). The above compound was converted to its hydrochloride using HCl gas in a mixture of ether/methanol (9.5/0.5) to yield 20 g of the product as its dihydrochloride.

$^1$H NMR (DMSO-d$_6$) δ 8.89 (s, 1H), 8.26 (s, 1H), 7.83 (s, 2H exchangeable), 4.33 (t, J=6.8 Hz, 2H), 2.85-2.74 (m, 2H), 2.13-2.03 (m, 2H).

Intermediate 6:
4-(3-Aminopropyl)morpholine-3,5-dione.HCl

Step 1: Tert-Butyl-3-aminopropyl carbamate

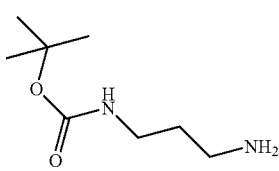

To a stirred solution of 1,3-diaminopropane (10 g, 1.34 mol) in dry THF (1 L) at 0° C. was added Boc-anhydride (98 g, 0.45 mol) and the resulting solution was stirred at rt for 24 h under N$_2$. The reaction mixture was concentrated under reduced pressure and the crude residue obtained was dissolved in EtOAc (2 L). The organic layer was washed with brine (3×250 mL), dried with MgSO$_4$ and concentrated to near dryness. The crude product was purified by column chromatography over silica gel (chloroform/methanol and methanol) to give 65 g of tert-butyl-3-aminopropyl carbamate (82%).

Step 2: Tert-Butyl-3-(3,5-dioxomorpholin-4-yl)propylcarbamate

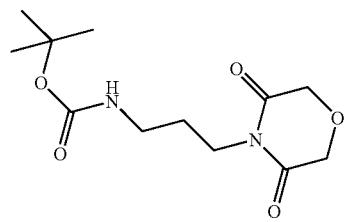

A mixture of diglycolic anhydride (22 g, 0.188 mol), tert-butyl-3-aminopropylcarbamate (65 g, 0.377 mol) and NMM (21 mL, 0.188 mol) in DMA (300 mL) was heated up to 120° C. for 48 h. The reaction mixture was cooled down to r.t and diluted with EtOAc (1.5 L). The solution was washed with brine (5×150 mL), dried with MgSO$_4$ and concentrated under reduced pressure. The crude was purified by column chromatography over silica gel (15% ethylacetate in chloroform) affording 15 g of the title compound (30%).

Step 3: 4-(3-Aminopropyl)morpholine-3,5-dione hydrochloric salt.

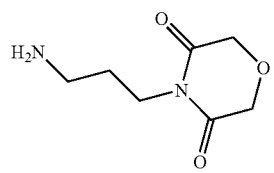

To a solution of tert-butyl-3-(3,5-dioxomorpholin-4-yl) propylcarbamate (15 g) in dry ether (150 mL) was added a saturated solution of dry HCl (gas) in diethylether (300 mL) at 0° C. and the solution was then slowly warmed up to r.t. The precipitate obtained was filtered, washed with cold ether and dried under vacuum to give 11 g of the title compound (94%).

$^1$H NMR (DMSO-d$_6$) δ 8.08 (br s, 3H exchangeable), 4.42 (s, 4H), 3.70 (t, J=7.1 Hz, 2H), 2.79-2.72 (m, 2H), 1.84-1.74 (m, 2H).

Procedure B

Intermediate 7:
2-[6-morpholin-4-yl-pyridin-3-yl]ethanamine

Step 1: 2-Bromopicoline

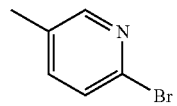

To a stirred solution of 2-amino-5-picoline (120 g, 1.10 mol) in 1.5 L of 48% HBr was added 160 mL of Br$_2$ (498 g, 3.1 mol) at −20° C. over a period of 1 h and then allowed to stir at same temperature for 2 h. To this mixture was added slowly a solution of NaNO$_2$ (204 g, 2.95 mol, in 300 mL of water) and the resulting solution was allowed to stir for another 1 h at −20° C. The reaction mixture was quenched at −20° C. by addition of aqueous NaOH (1.2 Kg of NaOH in 2 L of water) then extracted with diethyl ether (3×1 L). The organic layer was washed with water, brine, dried with Na$_2$SO$_4$ and concentrated to give a crude residue. After purification by distillation (bath temp. 130° C., vacuum temp. 85-90° C., vacuum=0.01 mm), 172 g 2-bromopicoline were obtained as off white low melting solid (90%). [TLC, R$_f$=0.8, diethyl ether]

Step 2: 2-Bromo-5-bromomethylpyridine

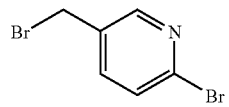

To a suspension of 2-bromo-5-methylpyridine (170 g, 0.95 mol) in CCl$_4$ (2 L) was added NBS (193 g, 1.08 mol) and benzoylperoxide (15 g) and the mixture was refluxed for 6 h. The reaction mixture was cooled down to rt and the solid formed was filtered off. The filtrate was concentrated affording 275 g of crude 2-bromo-5-bromomethylpyridine which was used without further purification in the next step (mixture of mono-bromo and di-bromo). [TLC, R$_f$=0.7, pet. ether/ethylacetate 9:1].

Step 3: (6-Bromopyridin-3-yl) acetonitrile

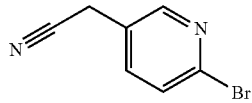

To a stirred solution of NaCN (117 g, 2.38 mol) in dioxane (1 L) and water (1 L), was added the above crude 2-bromo-5-bromomethylpyridine (275 g) and the mixture was stirred at rt for 15 h. The reaction mixture was quenched with cold water (15 L) and extracted with EtOAc (3×1 L). The organic layer was washed with water (3×1 L), brine (2×1 L), dried with Na$_2$SO$_4$ and concentrated under reduced pressure to give crude title compound. The crude residue was purified by column chromatography over silica gel (pet. ether/ethylacetate, 7:3) to give 95 g (6-bromopyridin-3-yl)acetonitrile as a pale yellow solid (49%). [TLC, R$_f$=0.5, pet. ether/ethylacetate 7:3]

Step 4: (6-Morpholin-pyridin-3-yl) acetonitrile

A mixture of (6-bromopyridin-3-yl) acetonitrile (30 g, 0.15 mol) and morpholin (100 mL) was heated to 120° C. for 4 h. After completion of the reaction, the morpholin was distilled off under reduce pressure to give crude product which was purified by column chromatography (pet. ether/ethylacetate, 7:3) to give 18 g (6-morpholin-pyridin-3-yl) acetonitrile as yellow solid (58%). [TLC, R$_f$=0.6, pet. ether/EtOAc 6:4]

Step 5: 2-(6-Morpholin-4-yl pyridin-3-yl)-ethanamine

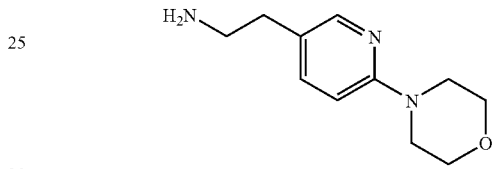

To a solution of (6-morpholin-pyridin-3-yl) acetonitrile (16 g, 0.078 mol) in MeOH (200 mL) and 25% NH$_4$OH solution (150 mL) was added Raney-Ni (20 g wet) in MeOH (100 mL) and the mixture was hydrogenated under 5 Kg of pressure for 18 h at rt using a parr-shaker. The reaction mixture was filtered through celite, washed with methanol (2×200 mL) and the combined filtrate was concentrated under reduced pressure to give a crude residue. It was purified by column chromatography over silica gel (CHCl$_3$/MeOH, 4:1) to give 9 g of 2-(6-morpholin-4-yl pyridin-3-yl)-ethanamine as a low melting solid (54%). [TLC, R$_f$=0.15, CHCl$_3$/MeOH 4:1]

$^1$H NMR (DMSO-d$_6$) δ 8.02-7.95 (m, 1H), 7.47-7.38 (m, 1H), 6.79-6.72 (m, 1H), 3.75-3.62 (m, 4H), 3.40-3.33 (m, 4H), 2.85-2.63 (m, 4H [2+2]), 2.60-2.45 (m, 2H); MS (ES+) 208.4.

Intermediate 8:
2-(N,N-dimethylamino)-5-aminoethyl pyridine

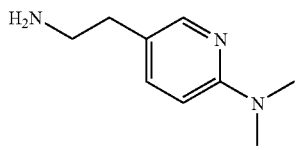

Following the general strategies and protocols outlined in the procedure B, the title compound was obtained from the corresponding starting materials (Y: Step 1: 86%, Steps 2/3/4/5: 22%).

$^1$H NMR (DMSO-d$_6$) δ 7.95-7.89 (m, 1H), 7.40-7.32 (m, 1H), 6.60-6.55 (m, 1H), 2.97 (s, 6H), 2.75-2.65 (m, 2H), 2.55-2.45 (m, 2H), 1.90-1.60 (brs, 2H, exchangeable); MS (ES+) 166.

Intermediate 9: ((tert-butoxy)-N-)5-aminoetyl)(2-pyridyl)carboxamide

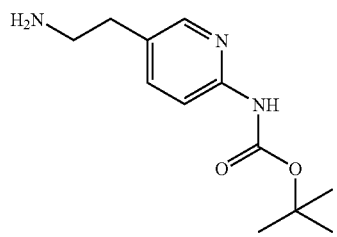

Step 1: (tert-butoxy)-N-(5-metyl-(2-pyridyl))carboxamide

To a solution of 2-amino-5-picoline (27 g, 250 mmol) in DCM (250 mL) were added DMAP (4.6 g, 37.5 mmol) and Boc anhydride (65.5 g, 300 mmol). The reaction mixture was allowed to stir at rt for 16 h, then the solvent was removed under reduced pressure. The residue obtained was recrystallized from ACN to give 24 g of (tert-butoxy)-N-(5-metyl-(2-pyridyl))carboxamide (44%).

Following the general strategies and protocols outlined in the procedure B (Steps 2 to 4; Step 2: 73%, step 3: 93%, Step 4: 77%), the title compound was obtained from the corresponding starting materials as a white solid.

$^1$H NMR (CDCl$_3$) δ 9.45 (s, 1H), 8.21 (d, J=1.8 Hz, 1H), 7.94 (d, J=8.7 Hz, 1H), 7.52 (dd, J=8.4 and 2.4 Hz, 1H), 2.94 (t, J=6.9 Hz, 2H), 2.68 (t, J=6.9 Hz, 2H), 1.55 (s, 9H), 1.14 (brs, 2H); MS (ES+) 237.9.

Intermediate 10: 2-[6-(4-methylpiperazin-1-yl-pyridin-3-yl]ethanamine

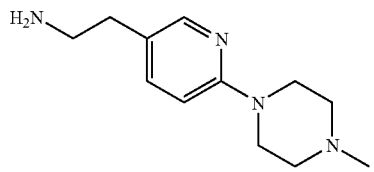

Following the general strategies and protocols outlined in the procedure B, the title compound was obtained from the corresponding starting materials as a thick liquid (Y: Steps 1/2/3/4: 51%, Step 5: 69%).

$^1$H NMR (DMSO-d$_6$) δ 7.98-7.92 (m, 1H), 7.45-7.35 (m, 1H), 6.79-6.70 (m, 1H), 3.90-3.75 (m, 2H), 3.45-3.35 (m, 4H), 2.85-2.63 (m, 2H), 2.60-2.48 (m, 2H), 2.41-2.32 (m, 4H), 2.19 (s, 3H); MS (ES+) 221.4.

Intermediate 11: 4-morpholinomethylbenzyl alcohol

Step 1: Synthesis of methyl 4-bromomethylbenzoate

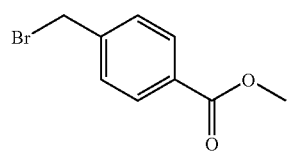

To a suspension of 150 g of methyl p-toluate and 195.5 g of NBS in CCl$_4$ (1.67 L) under N$_2$ at 50° C. was added portion wise over 30 min, solid benzoyl peroxide (5.0 g). No exothermic reaction was observed. After heating for 2 hours at 50° C., the yellow solution was heated up at 65° C. for 1 d. After cooling down to rt, the precipitate formed was filtered off and washed with 150 mL of CCl$_4$ and the filtrate was concentrated to afford a yellow oil that solidified on standing. The title compound, containing a small fraction of starting material was used in the next step without further purification.

Step 2: Synthesis of methyl 4-morpholinomethylbenzoate

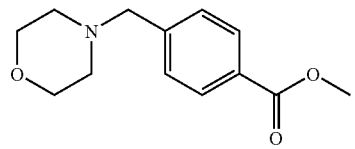

To a solution of 66.6 g of morpholine and 269 mL of triethylamine in 1.5 L of abs. EtOH under N$_2$ at 0° C. was added dropwise over 30 min a solution of methyl 4-bromomethylbenzoate in 450 mL of abs. EtOH. The resulting solution was stirred at 0° C. for 2 h then slowly warmed up to rt over 4 h and stirred at rt overnight. The HPLC showed no unreacted methyl 4-bromomethylbenzoate but the remaining methyl p-toluate from the previous reaction. The solvent was removed under reduced pressure and the residue was taken up in 2 L of 1.5 N HCl. The acidic phase was washed with 3×350 mL of diethyl ether then with 1×350 mL of EtOAc and was neutralized to pH 7 with NaOH and then to pH 7.5 with 10% NaHCO$_3$ in water. The product was extracted with 3×700 mL of EtOAc. The organic phase was dried over anhydrous Na$_2$SO$_4$ and concentrated under reduce pressure, affording an orange oil. The excess EtOAc was removed by toluene distillation. The title compound was used in the next step without further purification.

Step 3: Synthesis of 4-morpholinomethylbenzyl alcohol

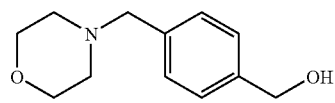

To a suspension of 33.9 g of LAH in 1.6 L of dry THF under N$_2$ at 0° C. was added drop wise a solution of methyl 4-methylmorpholinobenzoate in 233 mL of dry THF over 30 min. The temperature remained under 15° C. during the addition.

The reaction was allowed to stir at rt overnight. It was then cooled to 0° C. and quenched with 220 mL of 10% aqueous NaOH. The NaOH was added drop wise (over 30 min) keeping the temperature below 10° C. It was then warmed up to rt and stirred for 2 h. The precipitate formed was filtered off and washed with 200 mL of THF. The filtrate was concentrated affording a white solid that was taken up in EtOAc (1 L) and heated up at 65° C. for 45 min then cooled down to rt. The EtOAc solution was washed with brine (250 mL). Then 700 mL of the solvent were removed to give a suspension of the product and 300 mL of hexane were added. The solution was cooled down to 4° C. and held for 12 h. The crystals were filtered off and washed with a cold 1:1 mixture of EtOAc/:hexane (200 mL) then dried at 40° C. under vacuum overnight, affording 107.5 g of the title compound as white crystals (52% yield from methyl p-toluate).

Intermediate 12: 1-bromoacetone

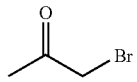

In a 100 mL flask, 1-bromo-2,2-dimethoxy-propane (7.3 mmol, 1.02 ml) was added to a solution of HCl (1M; 5.2 mL) in EtOH (47 mL). The solution was left stirring at r.t for 3 days. The pH was brought to 7 with Et$_3$N and the solution was used as such in the next step Intermediate 13: 1-Bromo-3-methyl-2-butanone

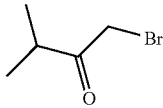

To a solution of 3-methyl-2-butanone (43 g, 0.5 mol) in dry methanol (300 mL) at 0° C. was added Br$_2$ (80 g, 0.5 mol) slowly at the same temperature and then allowed to stir at 10° C. for 1 h. The reaction mixture became colourless, then quenched with water (150 mL) and allowed to stir at rt for 20 h. The reaction mixture was further diluted with water (450 mL) and extracted with diethylether (2×500 mL). The ether layer was washed with water, 10% aqueous K$_2$CO$_3$ solution, water, brine and dried with Na$_2$SO$_4$. The solvent was removed at rt to give 67 g of 1-bromo-3-methyl-2-butanone as a liquid (75%).

Procedure C

Intermediate 14:
(4-ethyl-1,3-thiazol-2-yl)acetonitrile

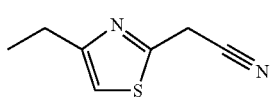

To a solution of 1-bromo-2-butanone (10.3 g, 57.98 mmol) in EtOH (200 mL) were added 2-cyanothioacetamide (5.8 g, 57.98 mmol) and triethylamine (1.59 mL, 11.6 mmol) and the solution was stirred under reflux for 1 h. After cooling down to r.t., the solvent was removed. The orange solid obtained was washed with AcOEt then cyclohexane, and recrystallized from EtOH to afford 7.2 g of the title compound as orange needles (Y=81%).

$^1$H NMR (CD$_3$OD) δ 7.56 (t, J=0.75 Hz, 1H), 4.91 (s, 2H), 2.89 (dq, J=0.75 Hz, J=7.54 Hz, 2H), 1.34 (t, J=7.54 Hz, 3H).
HPLC (max plot) 98%; Rt: 1.66 min Intermediate 15:
(4-methyl-1,3-thiazol-2-yl)acetonitrile

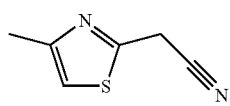

Following the general strategies and protocols outlined in the procedure C, the title compound was obtained from 1-bromoacetone (Intermediate 12) and 2-cyanothioacetamide in the presence of triethylamine for 12 h at 90° C. in EtOH (76.4%).

$^1$H NMR (DMSO-d$_6$) δ 7.32 (d, J=1.13 Hz, 1H), 4.5 (s, 2H), 2.39 (d, J=1.13 Hz, 3H).
hu 13C NMR (DMSO-d$_6$) δ 158.10 (C), 152.63 (C), 117.45 (C), 115.98 (CH), 21.71 (CH2), 16.96 (CH3)
HPLC (max plot) 90%; Rt: 1.23 min.

Intermediate 16:
(4-Isopropyl-1,3-thiazol-2-yl)acetonitrile

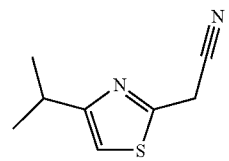

Following the general strategies and protocols outlined in the procedure C, the title compound was obtained from 1-bromo-3-methyl-2-butanone (Intermediate 13) and 2-cyanothioacetamide in the presence of triethylamine for 4 h at 90° C. in EtOH The crude was purified by flash chromatography over silica gel (5% ethylacetate in pet. Ether) (33% as a brown liquid).
$^1$H NMR (DMSO-d$_6$) δ 7.27 (s, 1H), 4.52 (s, 2H), 3.04-2.99 (m, 1H), 1.26 (d, J=6.8 Hz, 6H).
M$^-$(ES): 165.4; M$^+$(ES): 167.4.

Intermediate 17:
[4-(4-methoxyphenyl)-1,3-thiazol-2-yl]acetonitrile

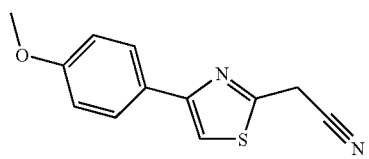

Following the general strategies and protocols outlined in the procedure C, the title compound was obtained from 2-bromo-4'-methoxyacetophenone and 2-cyanothioacetamide in the presence of triethylamine for 2 h at 90° C. in EtOH (71.4%).

$^1$H NMR (CDCl$_3$) δ 7.75 (d, J=9.04 Hz, J=4.9 Hz, 2H), 7.19 (s, 1H), 6.89 (d, J=8.67 Hz, J=4.9 Hz, 2H), 4.14 (s, 1H), 3.79 (s, 3H), 1.73 (H2O, 2.64H)-13C (ppm, CDCl3, 300 MHz): 160.32 (C), 157.45 (C), 156.41 (C), 128.10 (CH), 126.97 (C), 115.81 (C), 114.60 (CH), 112.57 (CH), 55.75 (CH3), 22.88 (CH2)

M$^-$(ES): 229; M$^+$(ES): 231; HPLC (max plot) 96.4%; Rt: 3.27 min.

Intermediate 18: ethyl 2-(cyanomethyl)-1,3-thiazole-4-carboxylate

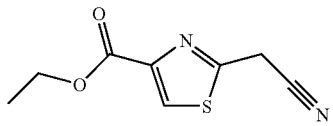

Following the general strategies and protocols outlined in the procedure C using microwave technology, the title compound was obtained from ethyl-bromopyruvate and 2-cyanothioacetamide in the presence of triethylamine for 2 min at 155° C. in EtOH (54.3%).

$^1$H NMR (DMSO-d$_6$) δ 8.53 (s, 1H); 4.62 (s, 2H); 4.31 (q, J=7.2 Hz, 2H), 1.30 (t, J=7.2 Hz, 3H)

M$^-$(ES): 195; M$^+$(ES): 197; HPLC (max plot) 100%; Rt: 1.56 min.

Intermediate 19: methyl 2-(cyanomethyl)-1,3-thiazole-4-carboxylate

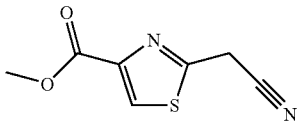

Following the general strategies and protocols outlined in the procedure C using microwave technology, the title compound was obtained from methyl-bromopyruvate and 2-cyanothioacetamide in the presence of triethylamine for 2.5 min at 145° C. in MeOH (35.9%).

$^1$H NMR (DMSO-d) δ 8.54 (s, 1H); 4.61 (s, 2H); 3.83 (s, 3H)

M$^-$(ES): 183; M$^+$(ES): 181; HPLC (max plot) 100%; Rt: 1.09 min.

Intermediate 20: [4-(pentafluoroethyl)-1,3-thiazol-2-yl]acetonitrile

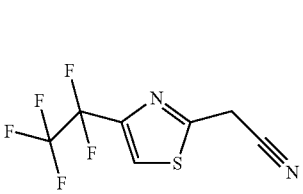

Following the general strategies and protocols outlined in the procedure C, the title compound was obtained from 1-bromo-3,3,4,4,4-pentafluoro-2-butanone and 2-cyanothioacetamide in the presence of triethylamine for 12 h at 80° C. in EtOH (26.6%).

$^1$H NMR (CDCl3) δ 7.87 (s, 1H), 4.20 (s, 2H).

M$^-$(ES): 241; HPLC (max plot) 82%; Rt: 3.20 min.

Intermediate 21: [4-(3-methoxyphenyl)-1,3-thiazol-2-yl]acetonitrile

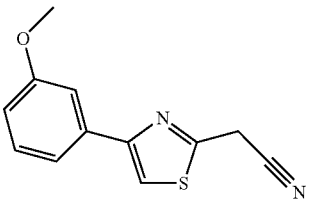

Following the general strategies and protocols outlined in the procedure C, the title compound was obtained from 2-bromo-3'methoxyacetophenone and 2-cyanothioacetamide in the presence of triethylamine for 1 h at reflux in EtOH (99%).

$^1$H NMR (DMSO-d$_6$) δ 8.16 (s, 1H), 7.54-7.48 (m, 2H), 7.39-7.33(m, 1H), 6.95-6.91 (m, 1H), 4.62 (s, 2H), 3.81 (s, 3H).

HPLC (max plot) 88%; Rt: 3.18 min

Intermediate 22: [4-(2-methoxyphenyl)-1,3-thiazol-2-yl]acetonitrile

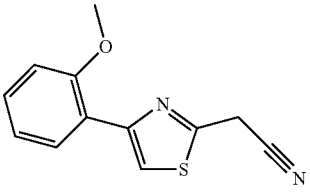

Following the general strategies and protocols outlined in the procedure C, the title compound was obtained from 2-bromo-2'methoxyacetophenone and 2-cyanothioacetamide in the presence of triethylamine for 1 h at reflux in EtOH (79.6%).

$^1$H NMR (DMSO-d$_6$) δ 8.12 (dd, J=1.9 Hz, 7.9 Hz, 1H), 8.08 (s, 1H), 7.38-7.32 (m, 1H), 7.16-7.13 (m, 1H), 7.08-7.02 (m, 1H), 4.61 (s, 2H), 3.92 (s, 3H).

M⁺(ES): 231.3; HPLC (max plot) 96.7%; Rt: 3.35 min

Intermediate 23:
[4-(4-fluorophenyl)-1,3-thiazol-2-yl]acetonitrile

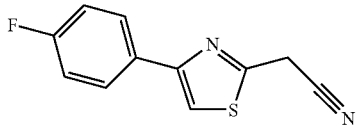

Following the general strategies and protocols outlined in the procedure C, the title compound was obtained from 2-bromo-4'fluoroacetophenone and 2-cyanothioacetamide in the presence of triethylamine for 1 h at reflux in EtOH (83.2%).

$^1$H NMR (DMSO-$d_6$) δ 8.12 (s, 1H), 8.01-7.97 (m, 2H), 7.31-7.25 (m, 2H), 4.62 (s, 2H).

M⁺(ES): 219.2; HPLC (max plot) 97.4%; Rt: 3.22 min

Intermediate 24:
[4-(4-chlorophenyl)-1,3-thiazol-2-yl]acetonitrile

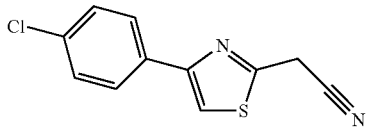

Following the general strategies and protocols outlined in the procedure C, the title compound was obtained from 2-bromo-4'-chloroacetophenone and 2-cyanothioacetamide in the presence of triethylamine for 1 h 30 at reflux in EtOH (82.6%).

$^1$H NMR (CDCl13) δ 7.84 (d, J=8.67 Hz, 2H), 7.48 (s, 1H); 7.42 (d, J=8.67 Hz, 2H,) 4.19 (s, 2H).

M⁻(ES): 233; M⁺(ES): 235; HPLC (max plot) 99.2%; Rt: 3.80 min.

Intermediate 25: [4-(3,4-dichlorophenyl)-1,3-thiazol-2-yl]acetonitrile

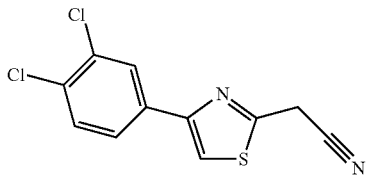

Following the general strategies and protocols outlined in the procedure C, the title compound was obtained from 3,4-dichlorophenacyl bromide and 2-cyanothioacetamide in the presence of triethylamine for 1 h 30 at Reflux in EtOH (76.4%).

$^1$H NMR (DMSO-$d_6$) δ 8.34 (s, 1H), 8.2 (d, J=2.26 Hz, 1H), 7.99 (dd, J=8.29 Hz, J=2.27 Hz, 1H), 7.78 (d, J=8.29 Hz, 1H), 4.64 (s, 2H).

HPLC (max plot) 95.2%; Rt: 4.18 min.

Intermediate 26:
[4-(4-methylphenyl)-1,3-thiazol-2-yl]acetonitrile

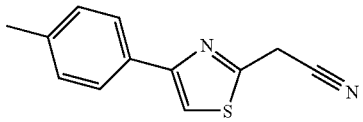

Following the general strategies and protocols outlined in the procedure C, the title compound was obtained from 4-methylphenacyl bromide and 2-cyanothioacetamide in the presence of triethylamine for 1 h 30 at reflux in EtOH (83%).

$^1$H NMR (DMSO-$d_6$) δ 8.05 (s, 1H), 7.85 (d, J=7.91 Hz, 2H), 7.27 (d, J=7.91 Hz, 2H), 4.62 (s, 2H), 2.33 (s, 3H)

M⁻(ES): 213.2; M⁺(ES): 215.3; HPLC (max plot) 100%; Rt: 3.59 min.

Intermediate 27:
(4-tert-butyl-1,3-thiazol-2-yl)acetonitrile

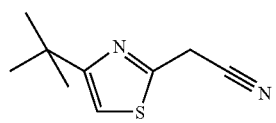

Following the general strategies and protocols outlined in the procedure C, the title compound was obtained from 1-bromopinacolone and 2-cyanothioacetamide in the presence of triethylamine for overnight at r.t. in EtOH (87%).

$^1$H NMR (DMSO-$d_6$) δ 7.27 (s, 1H), 4.51 (s, 2H), 1.27 (s, 9H)

HPLC (max plot) 100%; Rt: 2.98 min.

Intermediate 28:
4-[2-(cyanomethyl)-1,3-thiazol-4-yl]benzonitrile

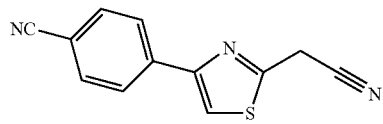

Following the general strategies and protocols outlined in the procedure C, the title compound was obtained from 2-bromo-4'-cyano acetophenone and 2-cyanothioacetamide in the presence of triethylamine for 1 h 30 at reflux in EtOH (84.4%).

$^1$H NMR (DMSO-$d_6$) δ 8.41 (s, 1H), 8.16-8.13 (m, 2H), 7.94-7.91 (m, 2H), 4.65 (s, 2H).

M⁺(ES): 226.3; HPLC (max plot) 99.1%; Rt: 3.00 min.

Intermediate 29:
[4-(2-chlorophenyl)-1-3-thiazol-2-yl]acetonitrile

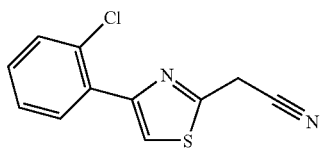

Following the general strategies and protocols outlined in the procedure C, the title compound was obtained from 2-chlorophenacyl bromide and 2-cyanothioacetamide in the presence of triethylamine for 1 h 30 at reflux in EtOH (78.6%).

$^1$H NMR(DMSO-d$_6$) δ 8.10 (s, 1H), 7.86-7.83 (m, 1H), 7.59-7.56 (m, 1H), 7.48-7.38 (m, 2H), 4.63 (s, 2H).

M$^-$(ES): 233.2; M$^+$(ES): 235.2; HPLC (max plot) 100%; Rt: 3.47 min.

Intermediate 30:
[4-(3-chlorophenyl-1,3-thiazol-2-yl]acetonitrile

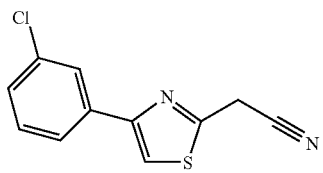

Following the general strategies and protocols outlined in the procedure C, the title compound was obtained from 3-chlorophenacyl bromide and 2-cyanothioacetamide in the presence of triethylamine for 1 h 30 at reflux in EtOH (82.5%).

$^1$H NMR (DMSO-d$_6$) δ 8.28 (s, 1H), 8.00 (t, J=1.5 Hz, 1H), 7.92 (dt, J=7.5 Hz, J=1.5 Hz, 1H), 7.49 (t, J=7.9 Hz, 1H), 7.44-7.40 (m, 1H), 4.63 (s, 2H).

M$^-$(ES): 233.2; M$^+$(ES): 235.2; HPLC (max plot) 99.3%; Rt: 3.77 min.

Procedure D

Example 1

(2-chloropyrimidin-4-yl)-(4-ethyl-3H-thiazol-2ylidene)-acetonitrile

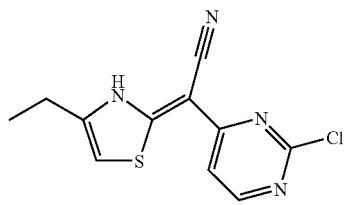

To a suspension of LiH (699 mg, 87.90 mmol) in anhydrous THF was added dropwise a suspension of (4-ethyl-1,3-thiazol-2-yl)acetonitrile (6.69 g, 43.95 mmol) in THF (60 mL) and the suspension was stirred for 1 h at 0° C. A suspension of 2,4-dichloropyrimidine (7.2 g, 48.34 mmol) in THF (60 mL) was added dropwise to the pale red suspension at 0° C. and the resulting mixture was stirred at rt for 7 h. The reaction was quenched by addition water (10 mL) at 0° C. then the solution obtained was left overnight under stirring. The THF was removed under reduced pressure then 80 mL of water were added and the suspension was acidified with 1N HCl. The precipitate formed was filtered off and washed with water until neutral pH to afford 9.96 g of the title compound as a beige powder (Y=85.5%).

$^1$H NMR (DMSO-d$_6$) δ 12.97 (br s, 1H), 8.23 (d, J=5.7 Hz, 1H), 7.05 (d, J=5.7 Hz, 1H), 6.87 (s, 1H), 2.66 (q, J=7.5 Hz, 2H), 1.19 (t, J=7.5 Hz, 3H).

M$^-$(ES): 263.2; M$^+$(ES): 265.2; HPLC (max plot) 99.6%; Rt: 3.28 min.

Example 2

[4-(4-chlorophenyl)-1,3-thiazol-2(3H)-ylidene](2-chloropyrimidin-4-yl)acetonitrile

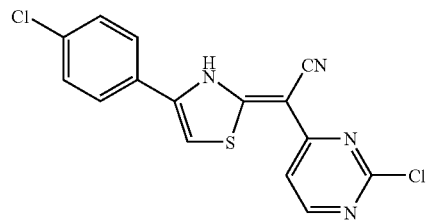

Following the general strategies and protocols outlined in the procedure D, the title. compound was obtained from (4-(4-chlorophenyl)-1,3-thiazol-2-yl)acetonitrile and 2,4-dichloropyrimidine in the presence of NaH overnight at 60° C. in THF (70%).

$^1$H NMR (DMSO d6) δ 7.92 (d, J=8.5 Hz, 2H); 7.79 (m, 2H); 7.52 (d, J=8.5 Hz, 2H); 6.79 (br d, 1H);

M$^+$(ES): 346.9; HPLC (max plot) 99%, Rt. 4.30 min.

Example 3

Preparation of (2-chloropyrimidin-4-yl)(4-phenyl-1,3-thiazol-2(3H)-ylidene)acetonitrile

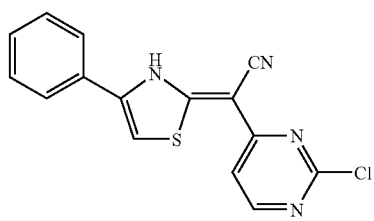

Following the general strategies and protocols outlined in the procedure D, the title compound was obtained from (4-phenyl-1,3-thiazol-2-yl)acetonitrile and 2,4-dichloropyrimidine in the presence of NaH for 4 d at 70° C. in THF (66%).

$^1$H NMR (DMSO-d6) δ 7.92 (br d, 1H), 7.85 (d, J=7.1 Hz, 2H), 7.69-7.37 (m, 3H), 6.89 (br d, 1H), M$^+$(ES): 313; HPLC (max plot) 98%; Rt. 4.72 min.

Example 4

(2-chloropyrimidin-4-yl)(4-methyl-1,3-thiazol-2

(3H)-ylidene)acetonitrile 2,3-dihydro-1,3-thiazole-4-carboxylate

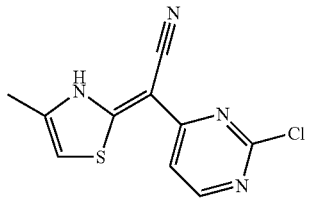

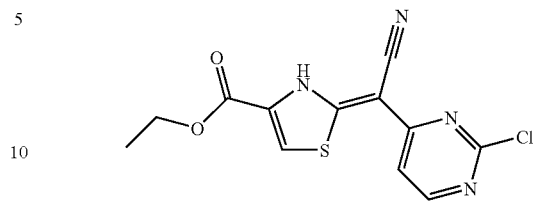

Following the general strategies and protocols outlined in the procedure D, the title compound was obtained from (4-methyl-1,3-thiazol-2-yl)acetonitrile and 2,4-dichloropyrimidine in the presence of NaH for 5 h at r.t. in THF. A purification step was performed using aminomethyl polystyrene resin in DMA at 70° C. allowing to specifically remove the regioisomer resulting from the displacement of the chlorine in the 2 position of the pyrimidine (69.6%).

$^1$H NMR (MeOD+NaOD) δ 7.62 (d, J=6.03 Hz, 1H), 6.72 (d, J=6.03 Hz, 1H9, 6.55 (d, J=0.75 Hz, 1H), 2.31 (d, J=0.75 Hz, 3H).

M$^-$(ES): 249; M$^+$(ES): 251; HPLC (max plot) 96%; Rt: 2.90 min.

Following the general strategies and protocols outlined in the procedure D, the title compound was obtained from ethyl 2-(cyanomethyl)-1,3-thiazole-4-carboxylate and 2,4-dichloropyrimidine in the presence of LiH for overnight at 0° C. to r.t. in THF (80%).

$^1$H NMR (DMSO-d$_6$) δ 7.88 (s, 1H), 7.71 (d, J=6 Hz, 1H), 6.78(d, J=6 Hz, 1H), 3.61 (q, J=7.16 Hz, 2H), 1.18 (t, J=7.15 Hz, 3H)

M$^-$(ES): 307; M$^+$(ES): 309; HPLC (max plot) 99%; Rt: 3.44 min.

Example 7 methyl-2-[(2-chloropyrimidin-4-yl)(cyano)methylene]-2,3-dihydro-1,3-thiazole-4-carboxylate Example 5

(2-chloropyrimidin-4-yl)[4-(4-methoxyphenyl)-1,3-thiazol-2(3H)-ylidene]acetonitrile

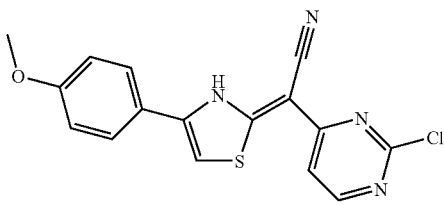

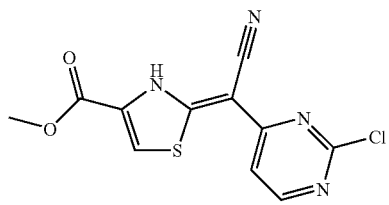

Following the general strategies and protocols outlined in the procedure D, the title compound was obtained from [4-(4-methoxyphenyl)-1,3-thiazol-2-yl]acetonitrile and 2,4-dichloropyrimidine in the presence of NaH for 24 h at r.t. in THF (94.4%).

$^1$H NMR (DMSO-d$_6$) δ 8.01 (br s, 1H), 7.75 (d, J=8.3 Hz, 2H), 7.49 (s, 1H), 7.03 (d, J=8.3 Hz, 2H), 6.92 (br s, 1H), 3.79 (s, 3H).

M$^-$(ES): 341; M$^+$(ES): 343; HPLC (max plot) 100%; Rt: 4.40 min.

Example 6 ethyl-2-[(2-chloropyrimidin-4-yl)(cyano)methylene]-

Following the general strategies and protocols outlined in the procedure D, the title compound was obtained from methyl 2-(cyanomethyl)-1,3-thiazole-4-carboxylate and 2,4-dichloropyrimidine in the presence of LiH for 36 h at 0° to r.t. in THF (46.3%).

$^1$H NMR (DMSO-d$_6$) δ 8.16 (s, 1H); 7.68 (br s, 1H); 6.68 (br s, 1H); 3.77 (s, 3H)

M$^-$(ES): 293; M$^+$(ES): 295; HPLC (max plot) 99%; Rt: 2.93 min.

Example 8

(2-chloropyrimidin-4-yl)[4-(3-methoxyphenyl)-1,3-thiazol-2-yl]acetonitrile

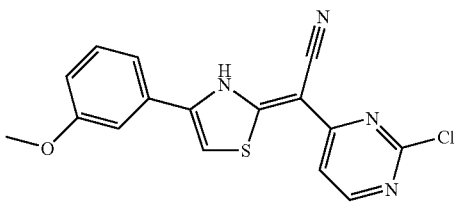

Following the general strategies and protocols outlined in the procedure D, the title compound was obtained from [4-(3-methoxyphenyl)-1,3-thiazol-2-yl]acetonitrile and 2,4-dichloropyrimidine in the presence of LiH for overnight at r.t. in THF (68%).

¹H NMR (DMSO-d₆) δ 8.05-7.85 (br d, 1H), 7.73 (s, 1H), 7.41-7.36 (m, 3H), 6.98-6.96 (m, 1H), 6.90 (br d, 1H), 3.82 (s, 3H).

HPLC (max plot) 97%; Rt: 4.32 min.

Example 9

(2-chloropyrimidin-4-yl)[4-(2-methoxyphenyl)-1,3-thiazol-2(3H)-ylidene]acetonitrile

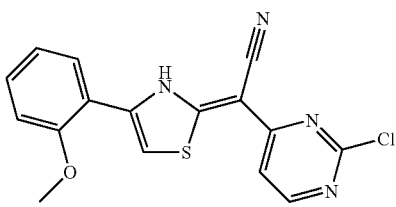

Following the general strategies and protocols outlined in the procedure D, the title compound was obtained from [4-(2-methoxyphenyl)-1,3-thiazol-2-yl]acetonitrile and 2,4-dichloropyrimidine in the presence of LiH for overnight at 0° C. to r.t. in THF (72.9%).

¹H NMR (DMSO-d₆) δ 13.45 (br s, 1H), 8.38-8.04 (m, 1H), 7.71-7.44 (m, 3H), 7.23-7.02 (m, 3H), 3.93 (g, 3H).

M⁺(ES): 343.2; HPLC (max plot): 98.1%; Rt: 4.32 min.

Example 10

(2-chloropyrimidin-4-yl)[4-(4-fluorophenyl)-1,3-thiazol-2(3H)-ylidene]acetonitrile

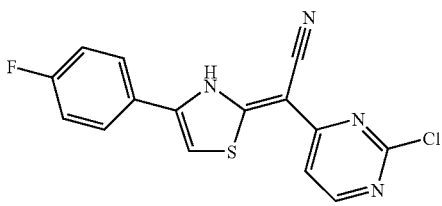

Following the general strategies and protocols outlined in the procedure D, the title compound was obtained from [4-(4-fluorophenyl)-1,3-thiazol-2-yl]acetonitrile and 2,4-dichloropyrimidine in the presence of LiH for overnight at 0° C. to r.t. in THF (60.7%).

¹H NMR (DMSO-d₆) δ 7.94-7.89 (m, 4H), 7.70 (s, 1H), 7.33-7.27 (m, 2H), 6.85 (br d, 1H).

M⁺(ES): 331.1; HPLC (max plot) 99.2%; Rt: 4.20 min.

Example 11

(2-chloro-5-methylpyrimidin-4-yl)(4-ethyl-1,3-thiazol-2(3H)-ylidene)acetonitrile

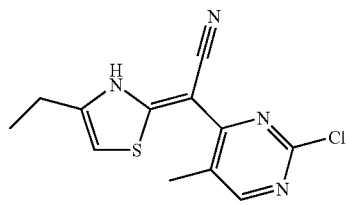

Following the general strategies and protocols outlined in the procedure D, the title compound was obtained from (4-ethyl-1,3-thiazol-2-yl)acetonitrile and 2,4-dichloro-5-methylpyrimidine in the presence of LiH for 4 h at 0° C. to r.t. in THF (60.4%).

¹H NMR (DMSO-d₆) δ 12.72 (br s, 1H), 8.02 (s, 1H), 6.85 (s, 1H), 2.71-2.63 (m, 2H), 2.41 (d, J=0.7 Hz, 3H), 1.18 (t, J=7.5 Hz, 3H).

M⁻(ES): 277.1; M⁺(ES): 279.2; UPLC (max plot) 95.2%; Rt: 3.66 min.

Example 12

(2-chloropyrimidin-4-yl)[4-(3,4-dichlorophenyl)-1,3-thiazol-2(3H)-ylidene]acetonitrile

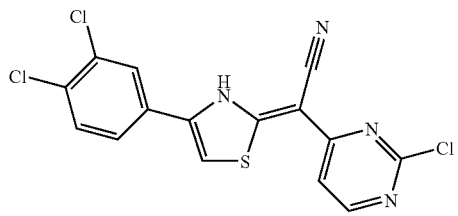

Following the general strategies and protocols outlined in the procedure D, the title compound was obtained from [4-(3,4-dichlorophenyl)-1,3-thiazol-2-yl]acetonitrile and 2,4-dichloropyrimidine in the presence of LiH for overnight at r.t. in THF (69.6%).

¹H NMR (DMSO-d₆) δ 8.16 (s, 1H), 7.98 (s, 1H), 7.92 (d, J=7.54 Hz, 1H), 7.72 (d, J=8.29 Hz, 2H), 6.77 (s, 1H)

M⁻(ES): 381; M⁺(ES): 382.9; HPLC (max plot) 100%; Rt: 4.76 min.

Example 13

(2-chloropyrimidin-4-yl)[4-(4-methylphenyl-1,3-thiazol-2(3H)-ylidene]acetonitrile

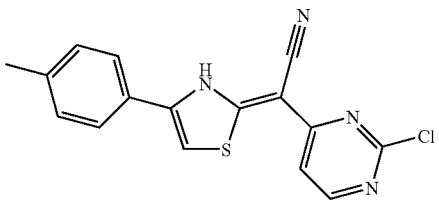

Following the general strategies and protocols outlined in the procedure D, the title compound was obtained from [4-(4-methylphenyl)-1,3-thiazol-2-yl]acetonitrile and 2,4-dichloropyrimidine in the presence of LiH for overnight at r.t. in THF (69.5%).

$^1$H NMR (DMSO-d$_6$) δ 8.05 (s, 1H), 7.73 (d, J=7.16 Hz, 2H), 7.61 (s, 1H), 7.29 (d, J=7.53 Hz, 2H), 6.92 (br s, 1H), 2.35 (s, 3H)

M$^-$(ES): 325.2; M$^+$(ES): 327.1; HPLC (max plot) 97%; Rt: 4.58 min.

Example 14

(4-{[3-(2-oxopyrrolidin-1-yl)propyl]amino}pyrimidin-2-yl)(4-phenyl-1,3-thiazol-2(3H)-ylidene)acetonitrile

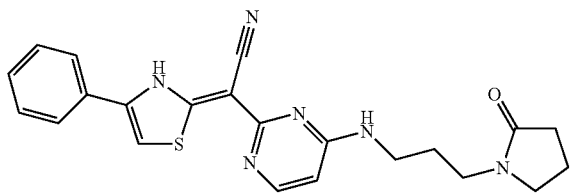

Following the general strategies and protocols outlined in the procedure D, the title compound was obtained from (4-phenyl-1,3-thiazol-2-yl)acetonitrile and 1-{3-[(2-chloropyrimidin-4-yl)amino]propyl}pyrrolidin-2-one in the presence of sodium hydride for overnight at 50° C. in THF as a light yellow powder (19%).

$^1$H NMR (DMSO-d$_6$) δ 12.75 (br s, 1H), 8.15-8.00 (m, 1H), 7.81-7.65 (m, 2H), 7.40-7.33 (s, 1H), 7.23-7.08 (m, 3H), 5.73 (d, J=7.1 Hz, 1H), 3.15-3.01 (m, 6H), 2.00-1.95 (m, 2H), 1.72-1.48 (m, 4H).

M$^+$(ES): 419.4; HPLC (max plot) 99%; Rt: 2.63 min.

Example 15

4-{2-[(2-chloropyrimidin-4-yl)(cyano)methylene]-2,3-dihydro-1,3-thiazol-4-yl}benzonitrile

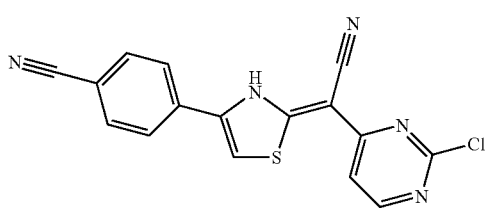

Following the general strategies and protocols outlined in the procedure D, the title compound was obtained from 4-[2-(cyanomethyl)-1,3-thiazol-4-yl]benzonitrile and 2,4-dichloropyrimidine in the presence of LiH for overnight at r.t. in THF (65.3%).

$^1$H NMR (DMSO-d6) δ 8.12 (d, J=8.6 Hz, 2H), 8.05 (s, 1H), 7.9 (d, J=8.6 Hz, 2H), 7.72 (br d, 1H), 6.73 (br d, 1H).

M$^-$(ES): 336.1; M$^+$(ES): 338.2; HPLC (max plot) 99.8%; Rt: 3.96 min.

Example 16

[4-(2-chlorophenyl)-1,3-thiazol-2(3H)-ylidene](2-chloropyrimidin-4-yl)acetonitrile

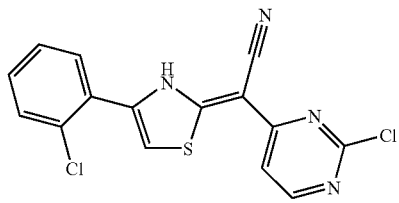

Following the general strategies and protocols outlined in the procedure D, the title compound was obtained from [4-(2-chlorophenyl)-1,3-thiazol-2-yl]acetonitrile and 2,4-dichloropyrimidine in the presence of LiH for overnight at r.t. in THF (65.2%).

$^1$H NMR (DMSO-d6) δ 8.08 (s, 1H), 7.59 (m, 3H), 7.48 (m, 3H), 6.97 (s, 1H).

M$^-$(ES): 347; M$^+$(ES): 348.9; HPLC (max plot) 100%; Rt: 4.32 min.

Example 17

[4-(3-chlorophenyl)-1,3-thiazol-2(3H)-ylidene](2-chloropyrimidin-4-yl)acetonitrile

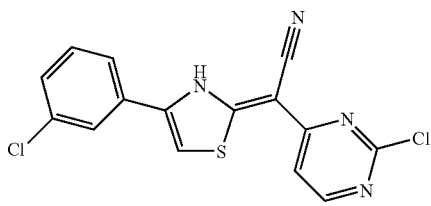

Following the general strategies and protocols outlined in the procedure D, the title compound was obtained from [4-(3-chlorophenyl)-1,3-thiazol-2-yl]acetonitrile and 2,4-dichloropyrimidine in the presence of LiH for overnight at r.t. in TKF (41.2%).

$^1$H NMR (DMSO-d6) δ 7.9 (m, 5H), 7.46 (m, 2H), 6.81 (s, 1H).

M$^-$(ES): 346.9; M$^+$(ES): 348; HPLC (max plot) 99.6%; Rt: 4.51 min.

Example 18

(2-chloropyrimidin-4-yl)[4-(4-methoxyphenyl)-1,3-thiazol-2(3H)-ylidene]acetonitrile

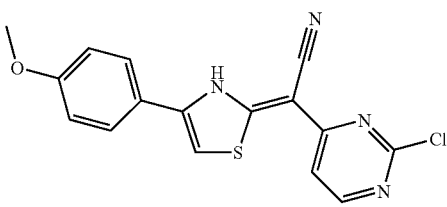

Following the general strategies and protocols outlined in the procedure D, the title compound was obtained from [4-(4-methoxyphenyl)-1,3-thiazol-2-yl]acetonitrile and 2,4-dichloropyrimidine in the presence of NaH for 24 h at r.t. °C. in THF (94.4%).

¹H NMR (MeOD+NaOD aq) δ 7.83 (d, J=9.04 Hz, 2H), 7.63 (d, J=6.4 Hz, 1H), 7.13 (s, 1H), 6.94 (d, J=8.67 Hz, 2H), 6.76 (d, J=6.03 Hz, 1H), 3.82 (s, 3H)

M⁺(ES): 343; HPLC (max plot) 94%; Rt: 4.40 min.

Example 19

(2-chloropyrimidin-4-yl)[4-(pentafluoroethyl)-1,3-thiazol-2(3H)-ylidene]acetonitrile

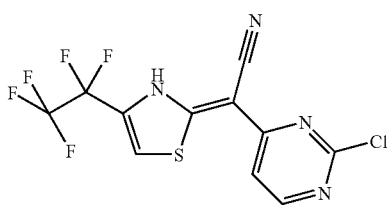

Following the general strategies and protocols outlined in the procedure D, the title compound was obtained from [4-(pentafluoroethyl)-1,3-thiazol-2-yl]acetonitrile and 2,4-dichloropyrimidine in the presence of LiH for 4 d at 0° C. to r.t. in THF. A purification step was performed using aminomethyl polystyrene resin in DMA at 70° C. allowing to specifically remove the regioisomer resulting from the displacement of the chlorine in the 2 position of the pyrimidine (55.8%).

¹H NMR (DMSO-d6) δ14.5 (br s, 1H), 7.85 (d, J=6.4 Hz, 1H), 7.64 (s, 1H), 6.97 (s, 1H)

HPLC (max plot) 85%; Rt: 4.04 min.

Example 20

(2-chloro-5-methylpyrimidin-4-yl)(4-methyl-1,3-thiazol-2(3H)-ylidene)acetonitrile

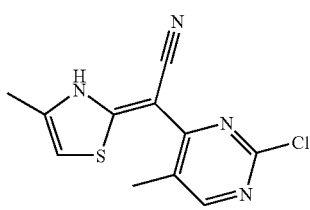

Following the general strategies and protocols outlined in the procedure D, the title compound was obtained from (4-methyl-1,3-thiazol-2-yl)acetonitrile and 2,4-dichloro-5-methylpyrimidine in the presence of LiH for 2 d at 0° C. to r.t. in THF. A purification step was performed using aminomethyl polystyrene resin in DMA at 70° C. allowing to specifically remove the regioisomer resulting from the displacement of the chlorine in the 2 position of the pyrimidine (72.7%).

¹H NMR (DMSO-d6) δ12.71(s, 1H), 8.04 (s, 1H), 6.86 (d, J=1.1 Hz, 1H), 2.43 (s, 3H), 2.30 (d, J=1.1 Hz, 3H)

M⁺(ES): 265; HPLC (max plot) 97%; Rt: 3.12 min.

Example 21

(4-tert-butyl-1,3-thiazol-2(3H)-ylidene)(2-chloro-5-methylpyrimidin-4-yl)acetonitrile

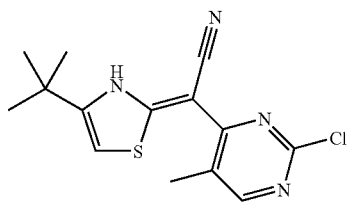

Following the general strategies and protocols outlined in the procedure D, the title compound was obtained from (4-tert-butyl-1,3-thiazol-2-yl)acetonitrile and 2,4-dichloro-5-methylpyrimidine in the presence of NaH for 2.5 d at r.t. in THF (92.3%).

¹H NMR (DMSO-d6) δ 13.58 (br s, 1H), 8.09 (s, 1H), 6.93 (s, 1H), 2.40 (s, 3H), 1.34 (s, 9H).

HPLC (max plot) 98.5%.

Example 22

(4-tert-butyl-1,3-thiazol-2(3H)-ylidene(2-chloropyrimidin-4-yl)acetonitrile

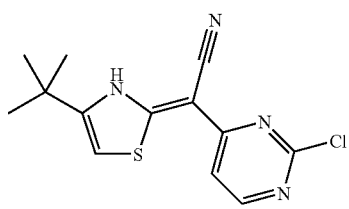

Following the general strategies and protocols outlined in the procedure D, the title compound was obtained from (4-tert-butyl-1,3-thiazol-2-yl)acetonitrile and 2,4-dichloropyrimidine in the presence of NaH overnight at r.t. in THF (57.8%).

¹H NMR (DMSO-d6) δ 13.10 (br s, 1H), 8.26 (br d, 1H), 7.03 (br d, 1H), 6.91 (s, 1H), 1.33 (s, 9H).

HPLC (max plot) 100%.

Example 23

(2-chloropyrimidin-4-yl)(4-isopropyl-1,3-thiazol-2(3H)-ylidene)acetonitrile

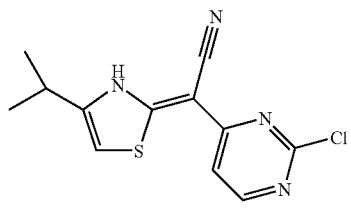

Following the general strategies and protocols outlined in the procedure D, the title compound was obtained from (4-isopropyl-1,3-thiazol-2-yl)acetonitrile and 2,4-dichloropyrimidine in the presence of NaH overnight at 0° C. to rt in THF (38.6%).

$^1$H NMR (DMSO-d6) δ 12.98 (s, 1H), 8.24 (d, J=5.7 Hz, 1H), 7.05 (d, J=5.7 Hz, 1H), 6.88 (d, J=0.7 Hz, 1H), 3.05 (sept., J=6.8 Hz, 1H), 1.22 (d, J=6.8 Hz, 6H)

HPLC (max plot) 100%; Rt: 3.82 min.

Example 24

(2-chloro-5-methylpyrimidin-4-yl)[4-(4-chlorophenyl)-1,3-thiazol-2(3H)-ylidene]acetonitrile

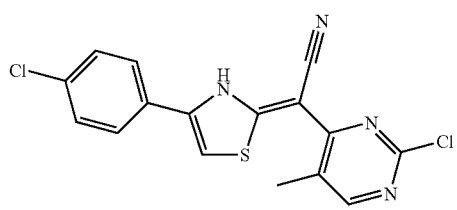

Following the general strategies and protocols outlined in the procedure D, the title compound was obtained from [4-(4-chlorophenyl-1,3-thiazol-2-yl)]acetonitrile and 2,4-dichloro-5-methyl-pyrimidine in the presence of NaH in THF (78%).

M$^+$(ES): 361.2

Example 25

(4-chloro-6-morpholin-4-yl-1,3,5-triazin-2-yl)(4-phenyl-1,3-thiazol-2(3H)-ylidene)acetonitrile

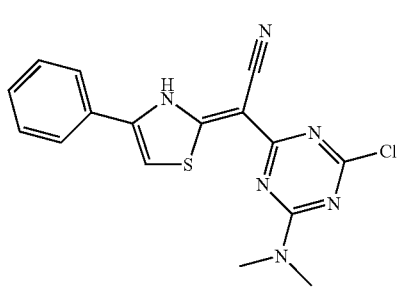

Following the general strategies and protocols outlined in the procedure D, the title compound was obtained from (4-phenyl-1,3-thiazol-2-yl)acetonitrile and 2,4-dichloro-6-morpholin-4-yl-1,3,5-triazine in the presence of NaH in THF (99%).

M$^+$(ES): 399.3; LC (215 nm): 44%

Example 26

[4-chloro-6-(dimethylamino)-1,3,5-triazin-2-yl](4-phenyl-1,3-thiazol-2(3H)-ylidene)acetonitrile Following the general strategies and protocols outlined in the procedure D, the title compound was obtained from (4-phenyl-1,3-thiazol-2-yl)acetonitrile and 4,6-dichloro-N,N-dimethyl-1,3,5-triazin-2-amine in the presence of NaH in THF (87%).

M$^+$(ES): 357.25; LC (215 nm): 92%

Example 27

[4-chloro-6-(methylamino)-1,3,5-triazin-2-yl](4- phenyl-1,3-thiazol-2(3H)-ylidene)acetonitrile

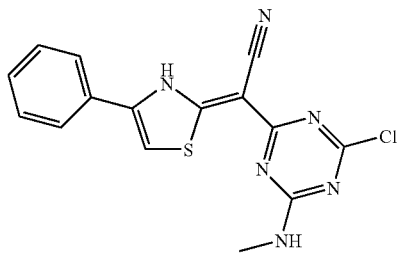

Following the general strategies and protocols outlined in the procedure D, the title compound was obtained from (4-phenyl-1,3-thiazol-2-yl)acetonitrile and 4,6-dichloro-N-methyl-1,3,5,triazin-2-amine in the presence of NaH in THF (92%).

M⁺(ES): 343; LC (215 nm): 92%

Example 28

(2-chloro-6-methylpyrimidin-4-yl)(4-phenyl-1,3-thiazol-2(3H-ylidene)acetonitrile

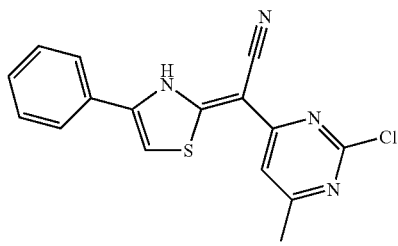

Following the general strategies and protocols outlined in the procedure D, the title compound was obtained from (4-phenyl-1,3-thiazol-2-yl)acetonitrile and 2,4-6-methyl-pyrimidine in the presence of NaH in THF (79%).

M⁺(ES): 327.27; LC (215 nm): 95%

Example 29

(2-chloro-5-methylpyrimidin-4-yl)(4-phenyl-1,3-thiazol-2(3H)-ylidene)acetonitrile

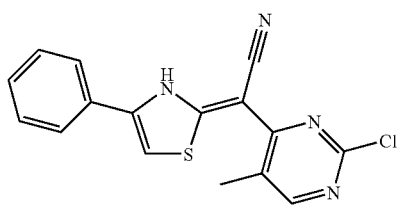

Following the general strategies and protocols outlined in the procedure D, the title compound was obtained from (4-phenyl-1,3-thiazol-2-yl)acetonitrile and 2,4-5-methyl-pyrimidine in the presence of NaH in THF (93%).

M⁺(ES): 327.27; LC (215 nm): 52%

Example 30

(6-chloropyrimidin-4-yl(4-methyl-1,3-thiazol-2(3H)-ylidene)acetonitrile

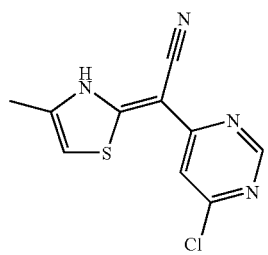

Following the general strategies and protocols outlined in the procedure D, the title compound was obtained from (4-methyl-1,3-thiazol-2-yl)acetonitrile and 4,6-dichloropyrimidine in the presence of NaH in THF (80%).

M⁺(ES): 251.21; LC (215 nm): 84%

Example 31

[4-chloro-6-(methylamino)-1,3,5-triazin-2-yl](4-methyl-1,3-thiazol-2(3H)-ylidene)acetonitrile

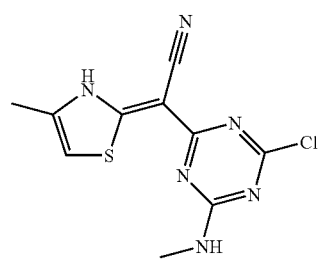

Following the general strategies and protocols outlined in the procedure D, the title compound was obtained from (4-methyl-1,3-thiazol-2-yl)acetonitrile and 4,6-dichloro-N-methyl-1,3,5-triazin-2-amine in the presence of NaH in THF (56%).

M⁺(ES): 281.26; LC (215 nm): 78%

Example 32

(2-chloro-6-methylpyrimidin-4-yl)(4-methyl-1,3-thiazol-2(3H)-ylidene)acetonitrile

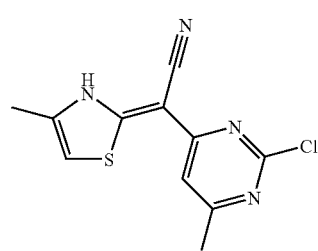

Following the general strategies and protocols outlined in the procedure D, the title compound was obtained from (4-methyl-1,3-thiazol-2-yl)acetonitrile and 2,4-6-methyl-pyrimidine in the presence of NaH in THF (65%).

M+(ES): 265.2; LC (215 mn): 42%

Example 33

{2-chloro-6-[methyl(phenyl)amino]pyrimidin-4-yl}(4-methyl-1,3-thiazol-2(3H)-ylidene)acetonitrile

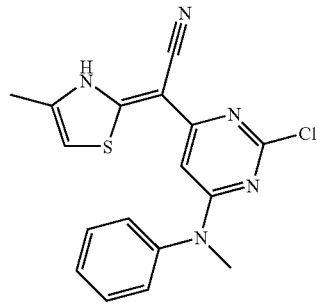

Following the general strategies and protocols outlined in the procedure D, the title compound was obtained from (4-methyl-1,3-thiazol-2-yl)acetonitrile and 2,6-dichloro-N-methyl-N-phenylpyrimidin-4-amine in the presence of NaH in THF (83%).

M+(ES): 356.28; LC (215 nm): 95%

Example 34

(4-chloro-6-morpholin-4-yl-1,3,5-triazin-2-yl)(4-methyl-1,3-thiazol-2(3H)-ylidene)acetonitrile

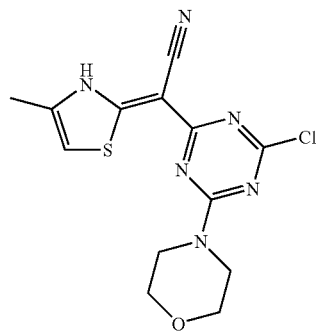

Following the general strategies and protocols outlined in the procedure D, the title compound was obtained from (4-methyl-1,3-thiazol-2-yl)acetonitrile and 2,4-dichloro-6-morpholin-4-yl-1,3,5-triazine in the presence of NaH in THF (99%).

M+(ES): 337.27; LC (215 nm): 40%

Procedure E

Example 35

(4-ethyl-1,3-thiazol-2(3H)-ylidene)(2-{[3-(2-oxopyrolidin-1-yl)propyl]amino}pyrimidin-4-yl)acetonitrile TFA salt

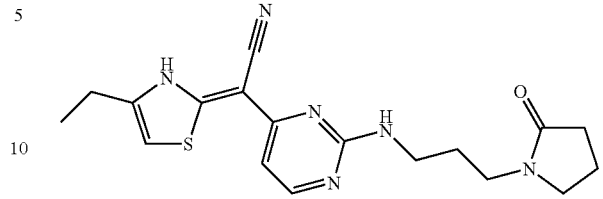

To a suspension of (2-chloropyrimidin-4-yl)(4-ethyl-1,3-thiazol-2(3H)-ylidene)acetonitrile in EtOH in 4 microwave tubes (250 mg in each tube) were added N-(3'-aminopropyl)-2-pyrrolidinone and Et₃N and the resulting suspension was heated up to 155° C. for 4 min. After cooling down to rt, the yellow precipitate formed was filtered off, washed with water (3×) and dried under vacuum at 40° C., affording 1.29 g of the title compound as a yellow solid (HPLC purity: 96.8%).

The crude solid was taken up in DCM and excess TFA was added. After addition of ether a yellow precipitate formed and was filtered off then washed with ether (3×) and dried under vacuum at 40° C. overnight, affording the salt form of the title compound with 97.5% purity. After purification by preparative HPLC and lyophilization, 1.3 g of the title compound was obtained as a TFA salt (Y=70.2%).

$^1$H NMR (DMSO-$d_6$) δ 8.06 (br s, 1H), 7.68 (d, J=7.1 Hz, 1H), 7.02 (s, 1H), 6.44 (d, J=7.1 Hz, 1H), 3.55-3.43 (m, 2H), 3.35-3.26 (m, 4H), 2.73-2.66 (m, 2H), 2.22-2.16 (m, 2H), 1.94-1.78 (m, 4H), 1.23-1.18 (m, 3H).

M+(ES): 371.2; HPLC (max plot) 99.6%; Rt: 2.22 min.

Example 36

[4-(4-chlorophenyl)-1,3-thiazol-2(3H)-ylidene]{2-[(2-pyridin-3-ylethyl)amino]pyrimidin-4-yl}acetonitrile

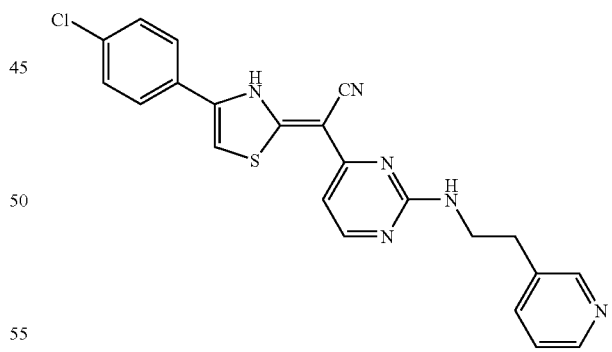

Following the general strategies and protocols outlined in the procedure E, the title compound was obtained from (2-chloropyrimidin-4-yl)(4-(4-chlorophenyl)-1,3-thiazol-2(3H)-ylidene)acetonitrile and 3-(2-aminoethyl)pyridine in the presence of triethylamine for 4 d at 70° C. in EtOH (20%).

1H NMR (DMSO-d6) δ 10.77 (br s, 1H), 8.76 (s, 1H), 8.71 (br d, 1H), 8.28 (d, J=7.9 Hz, 1H), 7.97 (d, J=8.7 Hz, 2H), 7.83 (dd, J=7.9 Hz, J=5.3 Hz, 1H), 7.72 (s, 1H), 7.55 (br s, 1H), 7.48 (d, J=8.7 Hz, 2H), 7.34 (d, J=7.5 Hz, 1H), 6.28 (d, J=7.5 Hz, 1H), 3.89 (br t, 2H), 3.12 (t, J=6.8 Hz, 2H).

M+(ES): 433.3, HPLC (max plot) 100%, Rt. 2.58 min.

Example 37

(4-phenyl-1,3-thiazol-2(3H)-ylidene){2-[(2-pyridin-3-ylethyl)amino]pyrimidin-4-yl}acetonitrile

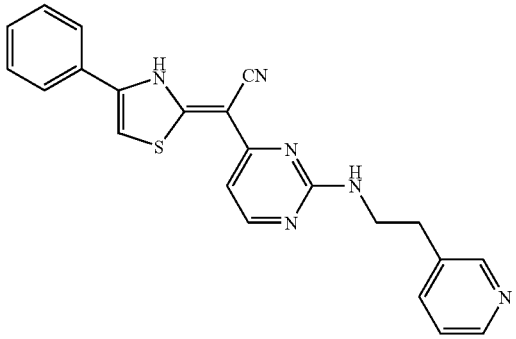

Following the general strategies and protocols outlined in the procedure E, the title compound was obtained from (2-chloropyrimidin-4-yl)(4-phenyl-1,3-thiazol-2(3H)-ylidene)acetonitrile and 3-(2-aminoethyl)pyridine in the presence of triethylariine for 5 mm at 155° C. in EtOH (19%).

$^1$H NMR (DMSO-d6) δ 10.71 (br s, 1H), 8.75 (s, 1H), 8.70 (d, J=5.3 Hz, 1H), 8.27 (d, J=7.5 Hz, 1H), 7.95 (d, J=7.2 Hz, 2H), 7.82 (dd, J=7.5 Hz, J=5.3 Hz, 1H), 7.65 (s, 1H), 7.52 (br s, 1H), 7.42 (d, J=7.5 Hz, 2H), 7.35-7.27 (m, 2H), 6.28 (d, J=7.6 Hz, 1H), 3.89 (br t, 2H), 3.12 (t, J=6.8 Hz, 2H).

M+(APCI): 399.0; HPLC (max plot) 99%, Rt. 2.08 min.

Intermediate 31: 1-{3-[(2-chloropyrimidin-4-yl)amino]propyl}pyrrolidin-2-one

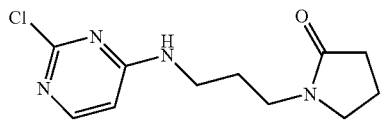

Following the general strategies and protocols outlined in the procedure E, the title compound was obtained from 2,4-dichloropyrimidine and N-(3'-aminopropyl)-2-pyrrolidinone in the presence of triethylamine for 4 h at 70° C. in EtOH (50.8%).

NMR-1H (DMSO) 7.87 (m, 2H), 6.43 (br d, 11H), 3.35-3.28 (m, 4H), 3.23-3.19 (m, 2H), 2.23-2.17 (m, 2H), 1.96-1.86 (m, 2H), 1.72-1.63(m, 2H)

HPLC (max plot) 100%.

Example 38

{2-[(3-aminopropyl)amino]pyrimidin-4-yl}(4-ethyl-1,3-thiazol-2(3H)-ylidene)acetonitrile

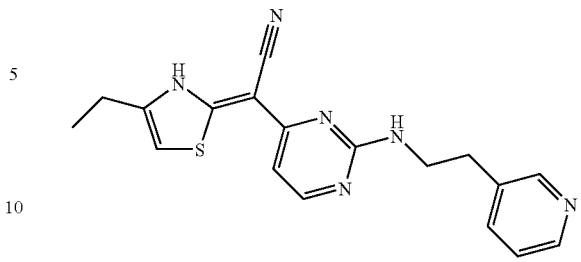

Following the general strategies and protocols outlined in the procedure E, the title compound was obtained from (2-chloropyrimidin-4-yl)(4-ethyl-1,3-thiazol-2(3H)-ylidene)acetonitrile and 3-(2-aminoethyl)pyridine in the presence of triethylamine for 5 min at 155° C. in EtOH (74%).

$^1$H NMR (DMSO-d$_6$) δ 7.46 (d, J=6 Hz, 1H), 6.41 (s, 1H), 6.11 (d, J=6 Hz, 1H), 3.60-3.10 (m, 2H+2H exchangeable), 2.80 (t, J=7.1 Hz, 2H), 2.56 (q, J=7.5 Hz, 2H), 1.81-1.77 (m, 2H), 1.17 (t, J=7.5 Hz, 3H).

M−(ES): 301.2; M+(ES): 303.3; HPLC (max plot) 67.8%; Rt: 1.41 min.

Example 39

(2-{[2-(6-aminopyridin-3-yl)ethyl]amino}pyrimidin-4-yl)(4-ethyl-1,3-thiazol-2(3H)-ylidene)acetonitrile

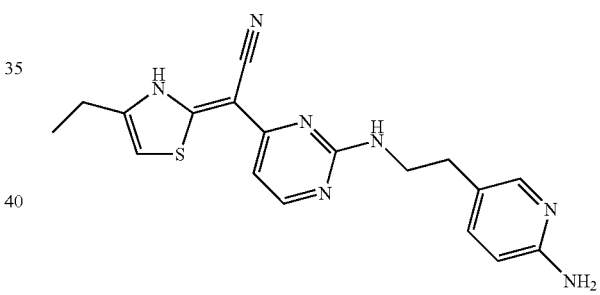

Following the general strategies and protocols outlined in the procedure E, the title compound was obtained from (2-chloropyrimidin-4-yl)(4-ethyl-1,3-thiazol-2(3H)-ylidene)acetonitrile and (tert-butoxy)-N-))5-aminoethyl)(2-pyridyl))carboxamide in the presence of triethylamine for overnight at 70° C. in EtOH (75.4%).

M+(ES): 466.0; HPLC (max plot) 87.7%; Rt: 2.30 min.

The Boc protected intermediate tert-butyl 5-[2-({4-[cyano(4-ethyl-1,3-thiazol-2(3H)-ylidene)methyl]pyrimidin-2-yl}amino)ethyl]pyridin-2-ylcarbamate was treated with a solution of 20% TFA in DCM overnight at rt, affording the title compound as a diTFA salt after evaporation of the solvent (yellow powder, 61.1%).

$^1$H NMR (DMSO-$_6$) δ 8.03-7.91 (m, 3H), 7.89-7.85 (m, 1H), 7.80 (br d, 1H), 7.64-7.54 (m, 1H), 6.95-6.92 (m, 2H), 6.38 (d, J=7.2 Hz, 1H), 3.82-3.68 (m, 2H), 2.85-2.81 (m, 2H), 2.68 (q, J=7.5 Hz, 2H), 1.20 (t, J=7.5 Hz, 3H).

M+(ES): 366.2; HPLC (max plot) 100%; Rt: 1.75 min.

Example 40

{2-[(3-aminopropyl)amino]pyrimidin-4-yl}(4-ethyl-1,3-thiazol-2(3H)-ylidene)acetonitrile

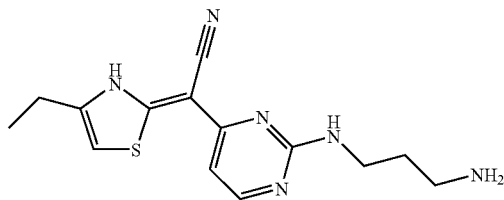

Following the general strategies and protocols outlined in the procedure E, the title compound was obtained from (2-chloropyrimidin-4-yl)(4-ethyl-1,3-thiazol-2(3H)-ylidene)acetonitrile and 1,3-diaminopropane in the presence of triethylamine for 4 min at 155° C. in EtOH (67%).

$^1$H NMR (DMSO-d$_6$) δ 7.47 (br d, 1H), 6.41 (s, 1H), 6.11 (br d, 1H), 3.52-3.39 (m, 2H), 2.82-2.77 (m, 2H), 2.56 (q, J=7.5 Hz, 2H), 1.83-1.72 (m, 2H), 1.17 (t, J=7.5 Hz, 3H).

HPLC (max plot) 77.2%; Rt: 1.43 min.

Example 41

{2-[(3-aminopropyl)amino]pyrimidin-4-yl}(4-tert-butyl-1,3-thiazol-2(3H)-ylidene)acetonitrile

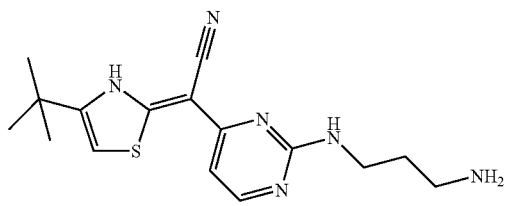

Following the general strategies and protocols outlined in the procedure E, the title compound was obtained from (4-tert-butyl-1,3-thiazol-2(3H)-ylidene)(2-chloropyrimidin-4-yl)acetonitrile and 1,3-diaminopropane in the presence of triethylamine for 2 min at 155° C. in EtOH (73.1%).

$^1$H NMR (DMSO-d$_6$) δ 7.50-7.35 (m, 2H, 1 exchangeable), 6.40 (s, 1H), 6.11 (d, J=6 Hz, 1H), 3.80-3.20 (m, 2H), 2.95-2.65 (m, 2H), 1.95-1.65 (m, 2H), 1.24 (s, 9H).

M$^-$(ES): 329; M$^+$(ES): 331; HPLC (max plot) 78%; Rt: 1.79 min.

Example 42 ethyl-2-[cyano(2-{[3-(2-oxopyrrolidin-1-yl)propyl]amino}pyrimidin-4-yl)methylene]-2,3-dihydro-1,3-thiazole-4-carboxylate

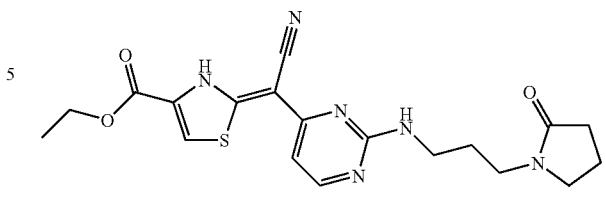

Following the general strategies and protocols outlined in the procedure E, the title compound was obtained from ethyl-2-[(2-chloropyrimidin-4-yl)(cyano)methylene]-2,3-dihydro-1,3-thiazole-4-carboxylate and N-(3'-aminopropyl)-2-pyrrolidinone in the presence of triethylamine for 10 min at 155° C. in EtOH as a yellow fluffy solid (51.4%).

$^1$H NMR (DMSO-d$_6$) δ 10.82 (s, 1H), 8.06 (s, 1H), 7.43 (s, 1H), 7.37 (d, J=6.8 Hz, 1H), 6.27 (d, J=5.5 Hz, 1H), 4.28 (q, J=7.2 Hz, 2H), 3.48 (m, 2H), 3.32 (t, J=7.2 Hz, 2H), 3.27 (t, J=7.2 Hz, 2H), 2.19 (t, J=7.9 Hz, 2H), 1.88 (quint, J=7.1 Hz, 2H), 1.79 (quint, J=6.8 Hz, 2H), 1.29 (t, J=7.1 Hz, 3H).

M$^-$(ES): 413; M$^+$(ES): 415; HPLC (max plot) 99.2%; Rt: 2.47 min.

Example 43

(4-methyl-1,3-thiazol-2(3H)-ylidene){2-[(2-pyridin-3-ylethyl)amino]pyrimidin-4-yl}acetonitrile

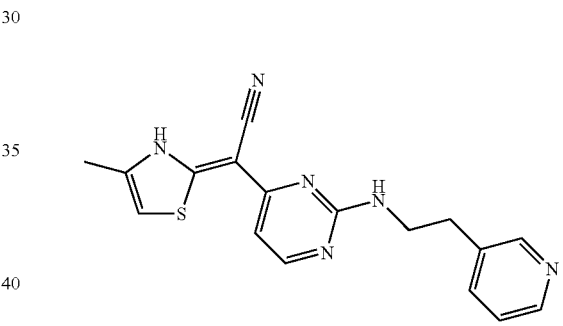

Following the general strategies and protocols outlined in the procedure E, the title compound was obtained from (2-chloropyrimidin-4-yl)(4-methyl-1,3-thiazol-2(3H)-ylidene)acetonitrile and 3-(2-aminoethyl)pyridine in the presence of triethylamine for 33 min at 155° C. in mixture of iPrOH/EtOH as a light yellow powder (66.1%).

$^1$H NMR (DMSO-d$_6$) δ 8.66 (d, J=1.5 Hz, 1H); 8.61 (dd, J=1.5 Hz, J=5.3 Hz, 1H); 8.07 (d, J=7.9 Hz, 1H); 7.66 (m, 2H), 7.01 (s, 1H); 6.45 (d, J=7.2 Hz, 1H); 3.86 (s, 2H); 3.07 (t, J=6.4 Hz, 2H); 2.33 (d, J=0.8 Hz, 3H)

M$^-$(ES): 335; M$^+$(ES): 337; HPLC (max plot) 80%; Rt: 1.35 min.

Example 44

[4-(4-methoxyphenyl)-1,3-thiazol-2(3H)-ylidene]{2-[(2-pyridin-3-ylethyl)amino]pyrimidin-4- yl}acetonitrile

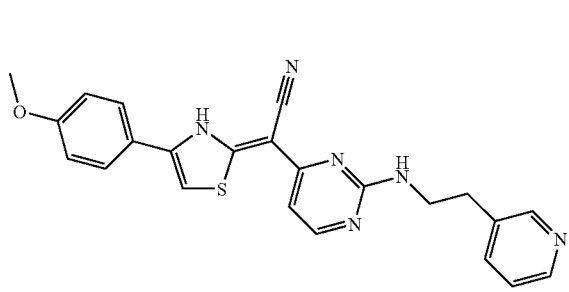

Following the general strategies and protocols outlined in the procedure E, the title compound was obtained from (2-chloropyrimidin-4-yl)[4-(4-methoxyphenyl)-1,3-thiazol-2(3H)-ylidene]acetonitrile and 3-(2-aminoethyl)pyridine in the presence of triethylamine for 33 min at 155° C. in EtOH as a dark yellow powder (47.8%).

$^1$H NMR (DMSO-d$_6$) δ 10.73 (br s, 1H); 8.76 (s, 1H); 8.70 (d, J=4.5 Hz, 1H); 8.26 (d, J=8.3 Hz, 1H); 7.88 (d, J=8.6 Hz, 2H); 7.82 (dd, J=7.9 Hz, J=5.3 Hz, 1H); 7.53 (d, J=7.2 Hz, 1H); 7.49 (s, 1H); 7.34 (d, J=7.5Hz 1H); 6.98 (d, J=9.1 Hz, 2H); 6.28 (d, J=7.2 Hz, 1H); 3.90 (d, J=5.6 Hz, 2H); 3.79 (s, 3H); 3.13(t, J=6.8 Hz, 2H)

M$^-$(ES): 427; M$^+$(ES): 429; HPLC (max plot) 94.5%; Rt: 2.14 min.

Example 45

2-[cyano(2-{[3-(2-oxopyrrolidin-1-yl)propyl]amino}pyrimidin-4-yl)methylene]-2,3-dihydro-1,3-thiazole-4-carboxylic acid

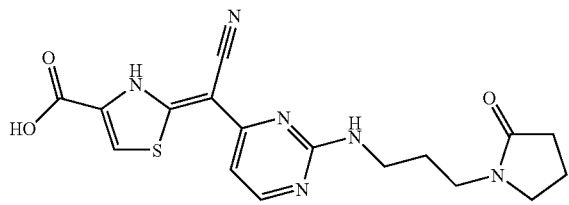

Following the general strategies and protocols outlined in the procedure E, the title compound was obtained from ethyl 2-[(2-chloropyrimidin-4-yl)(cyano)methylene]-2,3-dihydro-1,3-thiazole-4-carboxylate and N-(3'-aminopropyl)-2-pyrrolidinone in the presence of triethylamine for 70 h at 70° C. in EtOH as a yellow powder (61.5%).

$^1$H NMR (DMSO-d$_6$) δ 12.65 (br s, 1H); 10.80 (s, 1H); 8.01 (s, 1H); 7.36 (d, 1H, J=7.2 Hz); 7.36 (br s, 1H); 6.27 (d, J=7.1Hz; 1H); 3.38 (m, 6H); 2.20 (t, J=7.6 Hz, 2H); 2.08 (quint, J=7.5 Hz, 2H); 1.99 (quint, J=6.8 Hz, 2H)

M$^-$(ES): 341; M$^+$(ES): 387; HPLC (max plot) 93%; Rt: 1.82 min.

Example 46 methyl-2-[cyano(2-{[3-(2-oxopyrrolidin-1-yl)propyl]amino}pyrimidin-4-ylmethylene]-2,3-dihydro-1,3-thiazole-4-carboxylate

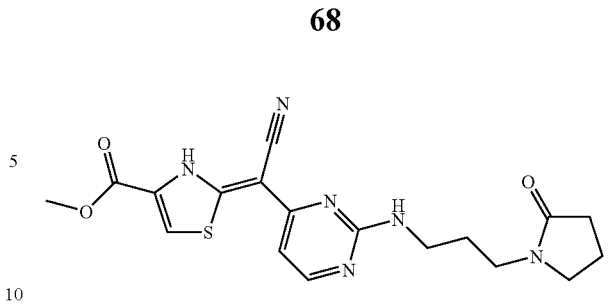

Following the general strategies and protocols outlined in the procedure E, the title compound was obtained from methyl 2-[(2-chloropyrimidin-4-yl)(cyano)methylene]-2,3-dihydro-1,3-thiazole-4-carboxylate and N-(3'-aminopropyl)-2-pyrrolidinone in the presence of triethylamine for 10 min at 145° C. in MeOH as a yellow powder (68.9%).

$^1$H NMR (DMSO-d$_6$) δ 10.78 (s, 1H); 8.04 (s, 1H); 7.38 (s, 1H); 7.32 (d, J=6.8 Hz, 1H); 6.22 (d, J=7.1 Hz, 1H); 3.75 (s, 3H); 3.43 (d, J=4.9 Hz, 2H); 3.28 (t, J=6.8 Hz, 2); 3.22 (t, J=7.2 Hz, 2H); 2.14 (t, J=7.9 Hz, 2H); 1.84 (m, 2H); 1.75 (m, 2H)

M$^-$(ES): 399; M$^+$(ES): 401; HPLC (max plot) 99%; Rt: 2.24 min.

Example 47 methyl-2-(cyano{2-[(2-pyridin-3-ylethyl)amino]pyrimidin-4-yl}methylene)-2,3-dihydro-1,3-thiazole-4-carboxylate

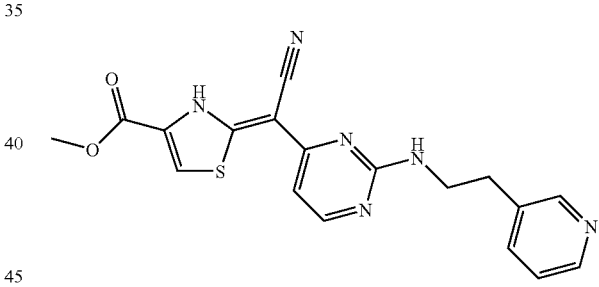

Following the general strategies and protocols outlined in the procedure E, the title compound was obtained from methyl-2-[(2-chloropyrimidin-4-yl)(cyano)methylene]-2,3-dihydro-1,3-thiazole-4-carboxylate and 3-(2-aminoethyl)pyridine in the presence of triethylamine for 10 min at 145° C. in MeOH as a yellow powder (54.3%).

$^1$H NMR (DMSO-d$_6$) δ 10.82 (s, 1H); 8.71 (s, 1H); 8.66 (d, J=4.9 Hz, 1H); 8.18 (d, J=7.9 Hz, 1H); 8.08 (s, 1H); 7.75 (dd, J=7.5 Hz, J=5.2 Hz, 1H); 7.57 (br s, 1H); 7.38 (d, J=7.2 Hz, 1H); 6.29 (d, J=7.1 Hz, 1H); 3.86 (m, 2H); 3.81 (s, 3H); 3.08 (t, J=6.8 Hz, 2H)

M$^-$(ES): 379; M$^+$(ES): 381; HPLC (max plot) 97%; Rt: 1.63 min.

Example 48

[2-(cyclopropylamino)pyrimidin-4-yl](4-methyl-1,3-thiazol-2(3H)-ylidene)acetonitrile

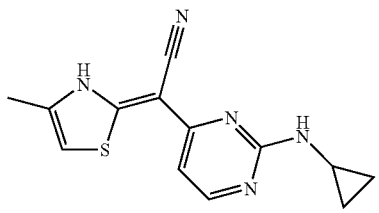

Following the general strategies and protocols outlined in the procedure E, the title compound was obtained from (2-chloropyrimidin-4-yl)(4-methyl-1,3-thiazol-2(3H)-ylidene)acetonitrile and cyclopropyl amine in the presence of triethylamine for 10 min at 155° C. in EtOH as a yellow powder (73.1%).

1H NMR (Acetone-d$_6$) δ 14 (br s, 1H); 10.15 (s, 1H); 7.79 (d, J=7.2 Hz, 1H); 7.04 (s, 1H); 6.56 (d, J=6.8 Hz, 1H); 3.05 (br s, 1H); 2.47 (s, 3H); 0.99 (d, J=5.2 Hz, 2H); 0.77 (s, 2H).

M$^-$(ES): 270; M$^+$(ES): 272; HPLC (max plot) 95%; Rt: 2.00 min.

Example 49

4-[2-({4-[cyano(4-methyl-1,3-thiazol-2(3H)-ylidene)methyl]pyrimidin-2-yl}amino)ethyl]benzenesulfonamide

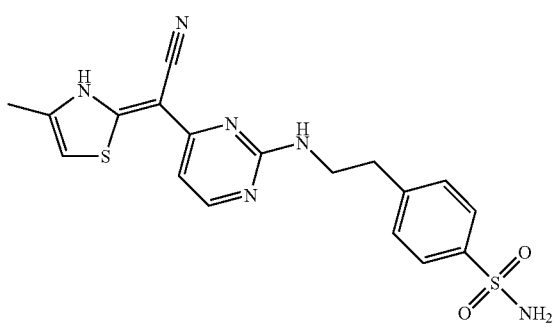

Following the general strategies and protocols outlined in the procedure E, the title compound was obtained from (2-chloropyrimidin-4-yl)(4-methyl-1,3-thiazol-2(3H)-ylidene)acetonitrile and 4-(2-aminoethyl)benzenesulfonamide in the presence of triethylamine for 10 min at 155° C. in EtOH as a yellow powder (69.4%).

$^1$H NMR (DMSO-d$_6$) δ 7.90 (br s, 1H); 7.77 (d, J=8.3 Hz, 2H); 7.67 (d, J=6.4 Hz, 1H); 7.47 (d, J=7.9 Hz, 2H); 7.31 (s, 2H); 7.02 (s, 1H); 6.46 (d, J=6.8 Hz, 1H); 3.84 (s, 2H); 3.03 (t, J=6.8 Hz, 2H); 2.33 (d, J=0.7 Hz, 3H)

M$^-$(ES): 415; M$^+$(ES): 413; HPLC (max plot) 92%; Rt: 2.13 min.

Example 50

[4-(pentafluoroethyl)-1,3-thiazol-2(3H)-ylidene{2-[(2-pyridin-3-ylethyl)amino]pyrimidin-4-yl}acetonitrile

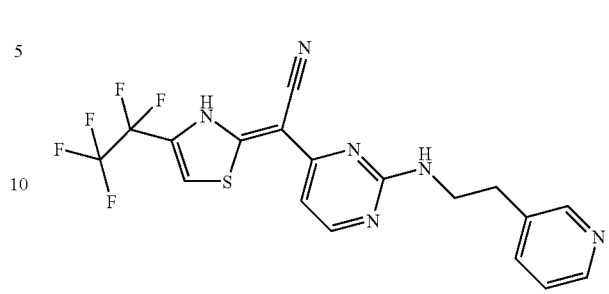

Following the general strategies and protocols outlined in the procedure E, the title compound was obtained from (2-chloropyrimidin-4-yl)[4-(pentafluoroethyl)-1,3-thiazol-2(3H)-ylidene]acetonitrile and 3-(2-aminoethyl)pyridine in the presence of triethylamine for 3 min at 155° C. in EtOH as a yellow powder (56.1%).

$^1$H NMR (DMSO-d$_6$) δ 10.96 (s, 1H); 8.72 (d, J=1.5 Hz, 1H); 8.67 (dd, J=4.2 Hz, J=1.1 Hz, 1H); 8.20 (d, J=8.3 Hz, 1H); 7.97 (s, 1H); 7.76 (dd, J=5.3 Hz, J=7.9 Hz, 1H); 7.67 (br s, 1H); 7.42 (m, 1H); 6.32 (d, J=7.2 Hz, 1H); 3.86 (s, 2H); 3.09 (t, J=6.8 Hz, 2H)

M$^+$(ES): 441.1; HPLC (max plot) 99.4%; Rt: 2.90 min.

Example 51

[2-(cyclopropylamino)pyrimidin-4-yl][4-(pentafluoroethyl)-1,3-thiazol-2(3H)-ylidene]acetonitrile

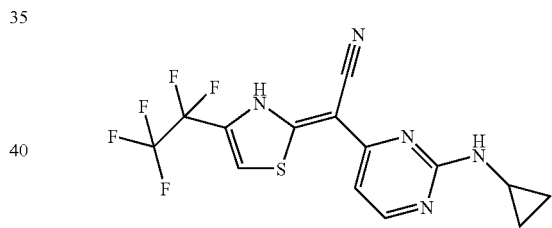

Following the general strategies and protocols outlined in the procedure E, the title compound was obtained from (2-chloropyrimidin-4-yl)[4-(pentafluoroethyl)-1,3-thiazol-2(3H)-ylidene]acetonitrile and cyclopropyl amine in the presence of triethylamine for 3 min at 155° C. in EtOH as a yellow powder (95.3%).

$^1$H NMR (DMSO-d$_6$) δ 10.81 (s, 1H), 7.95 (s, 1H), 7.40 (d, J=7.2 Hz, 1H), 6.34 (d, J=7.1 Hz, 1H), 2.81 (br s, 1H), 0.85 (m, 2H), 0.62 (m, 2H).

M$^-$(ES): 374; M$^+$(ES): 376; HPLC (max plot) 99.9%; Rt: 3.88 min.

Example 52

(2-{[3-(2-oxopyrrolidin-1-yl)propyl]amino}pyrimidin-4-yl)(4-phenyl-1,3-thiazol-2(3H)-ylidene)acetonitrile

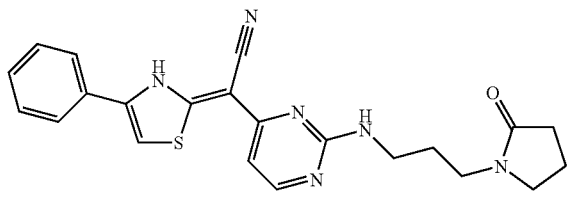

Following the general strategies and protocols outlined in the procedure E, the title compound was obtained from (2-chloropyrimidin-4-yl)(4-phenyl-1,3-thiazol-2(3H)-ylidene)acetonitrile and N-(3'-aminopropyl)-2-pyrrolidinone in the presence of triethylamine for 4.5 d at 70° C. in EtOH as a yellow powder (86%).

$^1$H NMR (DMSO-d$_6$) δ 7.88 (d, J=7.1 Hz, 2H), 7.62 (s, 1H), 7.38-7.24 (m, 5H), 6.23 (d, J=7.1 Hz, 1H), 3.51-3.41 (m, 2H), 3.31-3.21 (m, 4H), 2.18-2.12 (m, 2H), 1.86-1.74 (m, 4H).

M$^+$(ES): 419.3; HPLC (max plot) 97%; Rt: 2.63 min.

Example 53

(4-ethyl-1,3-thiazol-2(3H)-ylidene){2-[(2-pyridin-3-ylethyl)amino]pyrimidin-4-yl}acetonitrile

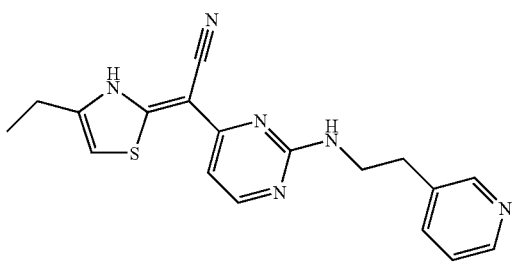

Following the general strategies and protocols outlined in the procedure E, the title compound was obtained from (2-chloropyrimidin-4-yl)(4-ethyl-1,3-thiazol-2(3H)-ylidene)acetonitrile and 3-(2-aminoethyl)pyridine in the presence of triethylamine for overnight at 70° C. in EtOH as a beige powder (71%).

$^1$H NMR (DMSO-d$_6$) δ 8.68 (d, J=1.5 Hz, 1H), 8.62 (dd, J=5 Hz, J=1.5 Hz, 2H), 8.10 (br d, 1H), 7.69-7.65 (m, 2H), 6.99 (s, 1H), 6.43 (d, J=7.2 Hz, 1H), 3.93-3.80 (m, 2H), 3.09-3.05 (m, 2H), 2.73-2.66 (m, 2H), 1.20 (t, J=7.5 Hz, 3H).

M$^+$(ES): 351.3; HPLC (max plot) 97%; Rt: 1.58 min.

Example 54

[4-(3-methoxyphenyl)-1,3-thiazol-2(3H)-ylidene]{2-[(2-pyridin-3-ylethyl)amino]pyrimidin-4-yl}acetonitrile

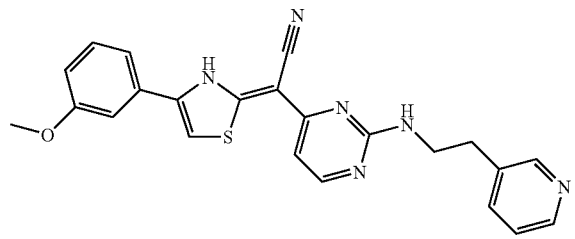

Following the general strategies and protocols outlined in the procedure E, the title compound was obtained from (2-chloropyrimidin-4-yl)[4-(3-methoxyphenyl)-1,3-thiazol-2(3H)-ylidene]acetonitrile and 3-(2-aminoethyl)pyridine in the presence of triethylamine for 5 min at 165° C. in EtOH as a yellow powder (46%).

1H NMR (DMSO-d$_6$) δ 8.78 (d, J=1.5 Hz, 1H), 8.73-8.71 (m, 1H), 8.32 (br d, 1H), 7.88-7.84 (m, 1H), 7.67 (s, 1H), 7.54-7.49 (m, 3H), 7.36-7.30 (m, 2H), 6.90-6.87 (m, 1H), 6.28 (d, J=7.2 Hz, 1H), 3.91-3.80 (m, 2H), 3.80 (s, 3H), 3.13 (t, J=6.8 Hz, 2H).

M$^+$(ES): 429.2; HPLC (max plot) 99%; Rt: 2.19 min.

Example 55

[4-(3-methoxyphenyl)-1,3-thiazol-2(3H)-ylidene](2-{[3-(2-oxopyrrolidin-1-yl)propyl]amino}pyrimidin-4-yl)acetonitrile

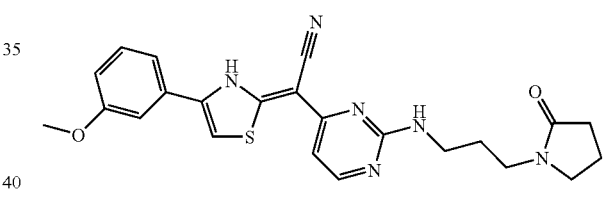

Following the general strategies and protocols outlined in the procedure E, the title compound was obtained from (2-chloropyrimidin-4-yl)[4-(3-methoxyphenyl)-1,3-thiazol-2(3H)-ylidene]acetonitrile and N-(3'-aminopropyl)-2-pyrrolidinone in the presence of triethylamine for 5 min at 165° C. in EtOH as a green powder (88%).

$^1$H NMR (DMSO-d$_6$) δ 10.86 (br s, 1H), 7.69 (s, 1H), 7.53-7.49 (m, 2H), 7.37-7.30 (m, 3H), 6.69-6.87 (m, 1H), 6.28 (d, J=7.1 Hz, 1H), 3.80 (s, 3H), 3.52-3.51 (m, 2H), 3.36-3.26 (m, 4H), 2.24-2.18 (m, 2H), 1.92-1.79 (m, 4H).

M$^+$(ES): 449.3; HPLC (max plot) 96%; Rt: 2.79 min.

Example 56 methyl 4-[2-({4-[cyano(4-ethyl-1,3-thiazol-2(3H)-ylidene)methyl]pyrimidin-2-yl}aminoethyl]benzoate

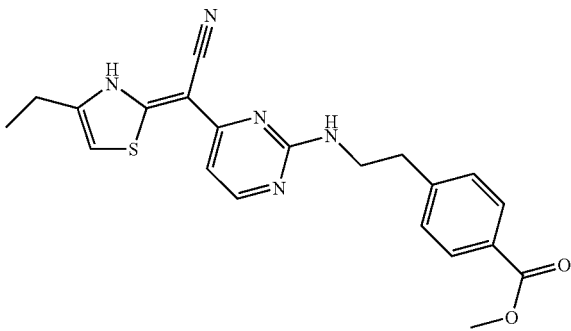

Following the general strategies and protocols outlined in the procedure E, the title compound was obtained from (2-chloropyrimidin-4-yl)(4-ethyl-1,3-thiazol-2(3H)-ylidene)acetonitrile and HCl salt of methyl-4-(2-aminoethyl) benzoate in the presence of triethylamine for 5 min at 155° C. in EtOH as a yellow powder (41.4%).

$^1$H NMR (DMSO-d$_6$) δ 7.92 (d, J=8.3 Hz, 2H), 7.93-7.90 (br s, 1H), 7.62 (br d, 1H), 7.43 (d, J=8.3 Hz, 2H), 6.42 (d, J=7.2 Hz, 1H), 3.90-3.78 (m, 2H), 3.83 (s, 3H), 3.02 (br t, 2H), 2.68 (q, J=7.5 Hz, 2H), 1.20 (t, J=7.5 Hz, 3H).

M$^+$(ES): 408.1; HPLC (max plot) 99.2%; Rt: 2.97 min.

Example 57

6-{[2-({4-[-cyano(4-ethyl-1,3-thiazol-2(3H)-ylidene) methyl]pyrimidin-2-yl}amino)ethyl] amino}nicotinonitrile

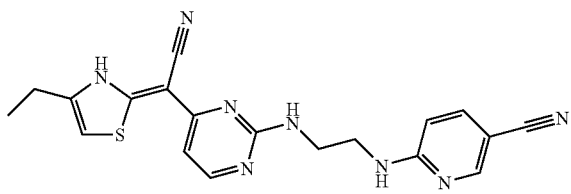

Following the general strategies and protocols outlined in the procedure E, the title compound was obtained from (2-chloropyrimidin-4-yl)(4-ethyl-1,3-thiazol-2(3H)-ylidene)acetonitrile and 6-[(2-aminoethyl)amino]pyridine-3-carbonitrile in the presence of triethylamine for 5 min at 155° C. in EtOH as a yellow powder (68.7%).

$^1$H NMR (DMSO-d$_6$) δ 8.37 (d, J=1.8 Hz, 1H), 8.05 (br s, 1H), 7.75-7.63 (m, 3H), 6.97 (s, 1H), 6.53 (d, J=9 Hz, 1H), 6.45 (d, J=7.1 Hz, 1H), 3.71-3.55 (m, 4H), 2.69 (q, J=7.5 Hz, 2H), 1.21 (t, J=7.5 Hz, 3H).

M$^+$(ES): 391.3; HPLC (max plot) 99.3%; Rt: 2.24 min.

Example 58

[2-({2-[6-(dimethylamino)pyridin-3-yl]ethyl}amino) pyrimidin-4-yl](4-ethyl-1,3-thiazol-2(3H)-ylidene) acetonitrile

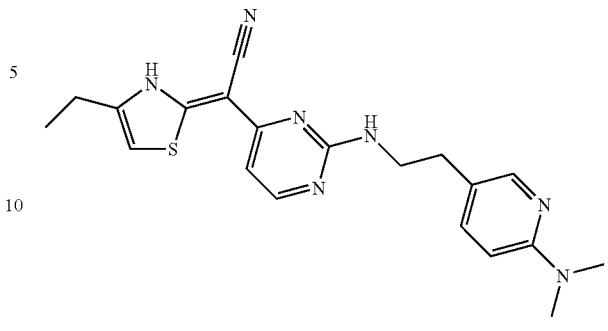

Following the general strategies and protocols outlined in the procedure E, the title compound was obtained from (2-chloropyrimidin-4-yl)(4-ethyl-1,3-thiazol-2(3H)-ylidene)acetonitrile and 2-(N,N-dimethylamino)-5-aminoethyl pyridine in the presence of triethylamine for 5 min at 155° C. in EtOH as a yellow powder (97.4%).

$^1$H NMR (DMSO-d$_6$) δ 8.07 (brs, 1H), 7.91-7.88 (m, 2H), 7.84 (s, 1H), 7.64 (br d, 1H), 6.15 (d, J=9 Hz, 2H), 7.00 (s, 1H), 6.42 (d, J=7.2 Hz, 1H), 3.78 (br t, 2H), 3.15 (s, 6H), 2.88 (t, J=6.4 Hz, 2H), 2.70 (q, J=7.5 Hz, 2H), 1.21 (t, J=7.5 Hz, 3H).

M$^+$(ES): 394.3; HPLC (max plot) 99.9%; Rt: 1.76 min.

Example 59

4-[2-({4-[cyano(4-ethyl-1,3-thiazol-2(3H)-ylidene) methyl]pyrimidin-2-yl}amino)ethyl]benzenesulfona- mide

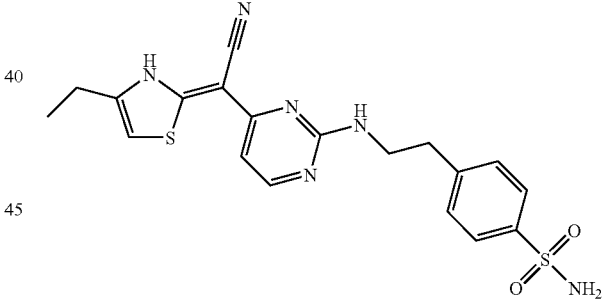

Following the general strategies and protocols outlined in the procedure E, the title compound was obtained from (2-chloropyrimidin-4-yl)(4-ethyl-1,3-thiazol-2(3H)-ylidene)acetonitrile and 4-(2-aminoethyl)benzenesulfonamide in the presence of triethylamine for 5 min at 155° C. in EtOH as a yellow powder (85.7%).

$^1$H NMR (DMSO-d$_6$) δ 7.88 (brs, 1H), 7.76 8 d, J=8.2 Hz, 2H), 7.62 (br d, 1H), 7.46 (d, J=8.2 Hz, 2H), 7.29 (s, 2H), 7.00 (s, 1H), 6.41 (d, J=7.1 Hz, 1H), 4.00-3.70 (m, 2H), 3.02 (t, J=6.8 Hz, 2H), 2.69 (q, J=7.5 Hz, 2H), 1.21 (t, J=7.5 Hz, 3H).

M$^+$(ES): 429.3; HPLC (max plot) 99.7%; Rt: 2.28 min.

Example 60

(2-{[2-(4-aminophenyl)ethyl]amino}pyrimidin-4-yl) (4-ethyl-1,3-thiazol-2(3H)-ylidene)acetonitrile

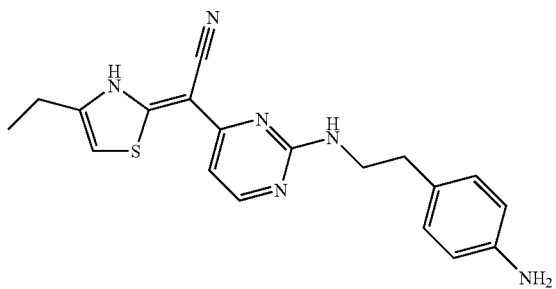

Following the general strategies and protocols outlined in the procedure E, the title compound was obtained from (2-chloropyrimidin-4-yl)(4-ethyl-1,3-thiazol-2(3H)-ylidene)acetonitrile and 4-(tert-butoxycarbonylamino)phenylethylamine in the presence of triethylamine for 5 min at 155° C. in EtOH. The Boc protected intermediate was treated with a solution of 20% TFA in DCM overnight at rt, affording the title compound as a diTFA salt after evaporation of the solvent (yellow powder, 87.4%).

$^1$H NMR (DMSO-$d_6$) δ 8.12 (br s, 1H), 7.68 (br d, 1H), 7.30 (d, J=8.3 Hz, 2H), 7.14 (d, J=8.3 Hz, 2H), 7.01 (s, 1H), 6.45 (d, J=7.2 Hz, 1H), 3.85-3.72 (m, 2H), 2.93 (br t, 2H), 2.69 (q, J=7.5 Hz, 2H), 1.20 (t, J=7.5 Hz, 3H).

M$^+$(ES): 365.2; HPLC (max plot) 98%; Rt: 1.76 min.

Example 61

(4-ethyl-1,3-thiazol-2(3H)-ylidene)(2-{[2-(6-morpholin-4-ylpyridin-3-yl)ethyl]amino}pyrimidin-4-yl)acetonitrile

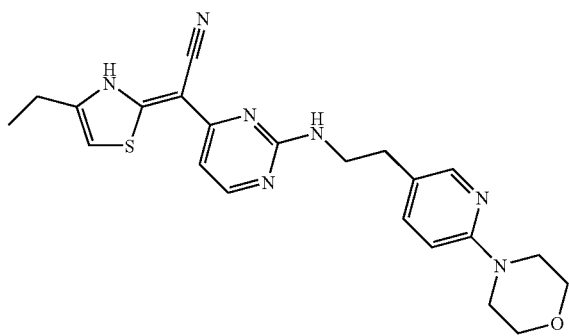

Following the general strategies and protocols outlined in the procedure E, the title compound was obtained from (2-chloropyrimidin-4-yl)(4-ethyl-1,3-thiazol-2(3H)-ylidene)acetonitrile and 2-[6-morpholin-4-yl-pyridin-3-yl]ethanamine in the presence of triethylamine for 5 min at 155° C. in EtOH as a yellow powder (97.6%).

$^1$H NMR (DMSO-$d_6$) δ 8.05 (br s, 1H), 7.97 (d, J=1.9 Hz, 1H), 7.72-7.69 (m, 2H), 7.04-7.02 (m, 2H), 6.47 (d, J=7.1 Hz, 1H), 3.77 (br t, 2H), 3.71 (t, J=4.9 Hz, 4H), 3.46 (t, J=4.9 Hz, 4H), 2.86 (t, J=6.4 Hz, 2H), 2.71 (q, J=7.5 Hz, 2H), 1.21 (t, J=7.5 Hz, 3H).

M$^+$(ES): 436.3; HPLC (max plot) 98.5%; Rt: 1.74 min.

Example 62

(4-ethyl-1,3-thiazol-2(3H)-ylidene)[2-({2-[6-(4-methylpiperazin-1-yl)pyridin-3-yl]ethyl}amino)pyrimidin-4-yl]acetonitrile

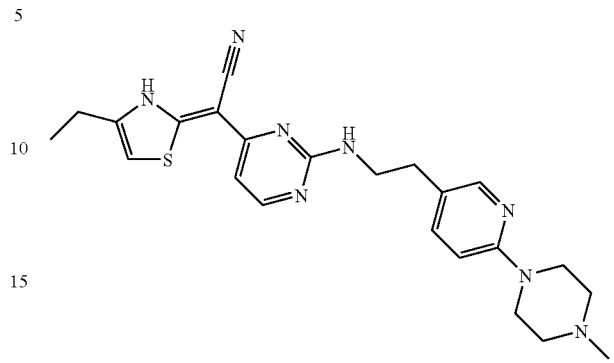

Following the general strategies and protocols outlined in the procedure E, the title compound was obtained from (2-chloropyrimidin-4-yl)(4-ethyl-1,3-thiazol-2(3H)-ylidene)acetonitrile and 2-[6-(4-methylpiperazin-1-yl-pyridin-3-yl]ethanamine in the presence of triethylamine for 5 min at 155° C. in EtOH as a yellow powder (29.3%).

$^1$H NMR (DMSO-$d_6$) δ 8.06 (d, J=2.3 Hz, 1H), 7.93 (br s, 1H), 7.61 (br d, 1H), 7.57 (dd, J=2.3 Hz, J=8.7 Hz, 1H), 6.97 (s, 1H), 6.93 (d, J=8.7 Hz, 1H), 6.41 (d, J=6.8 Hz, 1H), 4.35-4.32 (m, 2H), 3.82-3.68 (m, 2H), 3.51-3.48 (m, 2H), 3.06-3.03 (m, 4H), 2.84 (s, 3H), 2.84-2.81 (m, 2H), 2.69 (q, J=7.5 Hz, 2H), 1.20 (t, J=7.5 Hz, 3H).

M$^+$(ES): 449.1; HPLC (max plot) 87.8%; Rt: 1.52 min.

Example 63

[2-(cyclopropylamino)pyrimidin-4-yl](4-ethyl-1,3-thiazol-2(3H)-ylidene)acetonitrile

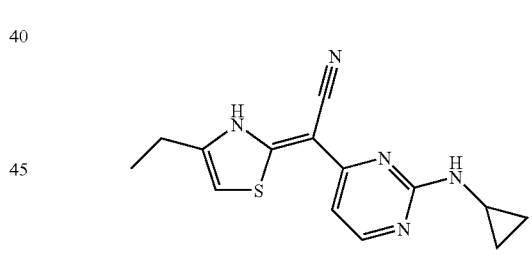

Following the general strategies and protocols outlined in the procedure E, the title compound was obtained from (2-chloropyrimidin-4-yl)(4-ethyl-1,3-thiazol-2(3H)-ylidene)acetonitrile and cyclopropyl amine in the presence of triethylamine for 5 min at 155° C. in EtOH as a yellow powder (78.6%).

$^1$H NMR (DMSO-$d_6$) δ 8.63 (br s, 1H), 7.71 (d, J=6.8 Hz, 1H), 7.04 (s, 1H), 6.48 (d, J=6.8 Hz, 1H), 2.91-2.77 (m, 1H), 2.69 (q, J=7.6 Hz, 2H), 1.20 (t, J=7.6 Hz, 3H), 0.93-0.86 (m, 2H), 0.68-0.62 (m, 2H).

M$^+$(ES): 286.3; HPLC (max plot) 97.5%; Rt: 1.66 min.

Example 64

[4-(2-methoxyphenyl)-1,3-thiazol-2(3H)-ylidene]{2-[(2-pyridin-3-ylethyl)amino]pyrimidin-4-yl}acetonitrile

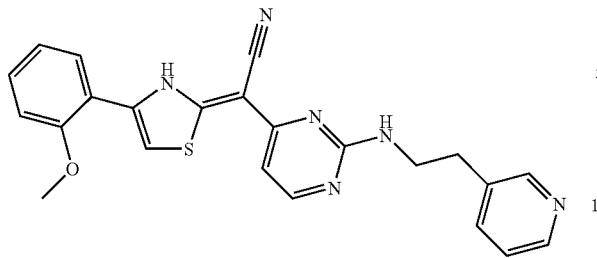

Following the general strategies and protocols outlined in the procedure E, the title compound was obtained from (2-chloropyrimidin-4-yl)[4-(2-methoxyphenyl)-1,3-thiazol-2(3H)-ylidene]acetonitrile and 3-(2-aminoethyl)pyridine in the presence of triethylamine for 5 min at 155° C. in EtOH as a yellow powder (28.4%).

$^1$H NMR (DMSO-$d_6$) δ 8.74 (br d, 1H), 8.68-8.67 (m, 1H), 8.23-8.17 (m, 2H), 7.80-7.75 (m, 1H), 7.70 (s, 1H), 7.51 (br t, 1H), 7.35-7.27 (m, 2H), 7.12-7.01 (m, 2H), 6.28 (d, J=7.6 Hz, 1H), 3.91 (s, 3H), 3.91-3.85 (m, 2H), 3.13-3.09 (m, 2H).

M$^+$(ES): 429.1; HPLC (max plot) 98.3%; Rt: 2.20 min.

Example 65

[4-(2-methoxyphenyl)-1,3-thiazol-2(3H)-ylidene](2-{[3-(2-oxopyrrolidin-1-yl)propyl]amino}pyrimidin-4-yl)acetonitrile

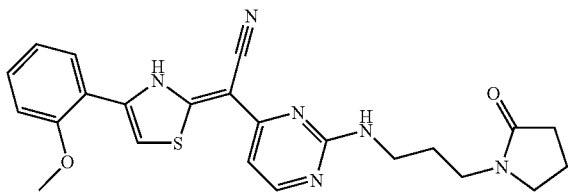

Following the general strategies and protocols outlined in the procedure E, the title compound was obtained from (2-chloropyrimidin-4-yl)[4-(2-methoxyphenyl)-1,3-thiazol-2(3H)-ylidene]acetonitrile and N-(3'-aminopropyl)-2-pyrrolidinone in the presence of triethylamine for 5 min at 155° C. in EtOH as a yellow powder (71.9%).

$^1$H NMR (DMSO-$d_6$) δ 8.07 (br d, 1H), 7.70 (s, 1H), 7.53 (br t, 1H), 7.43 (d, J=7.2 Hz, 1H), 7.36-7.30 (m, 1H), 7.12 (d, J=8 Hz, 1H), 7.05 (dt, J=0.8 Hz, J=7.5 Hz, 1H), 6.32 (d, J=7.2 Hz, 1H), 3.90 (s, 3H), 3.52-3.51 (m, 2H), 3.36-3.27 (m, 4H), 2.23-2.18 (m, 2H), 1.92-1.79 (m, 4H).

M$^+$(ES): 449.2; HPLC (max plot) 99.1%; Rt: 2.85 min.

Example 66

[4-(4-fluorophenyl)-1,3-thiazol-2(3H)-ylidene]{2-[(2-pyridin-3-ylethyl)amino]pyrimidin-4-yl}acetonitrile

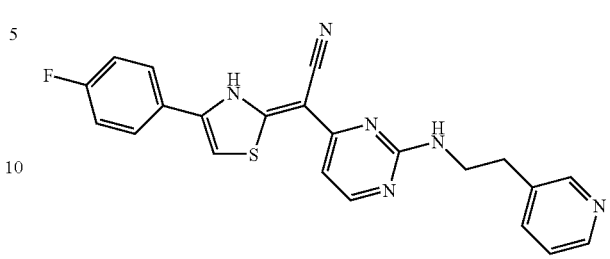

Following the general strategies and protocols outlined in the procedure E, the title compound was obtained from (2-chloropyrimidin-4-yl)[4-(4-fluorophenyl)-1,3-thiazol-2(3H)-ylidene]acetonitrile and 3-(2-aminoethyl)pyridine in the presence of triethylamine for 4 min at 155° C. in EtOH as a yellow powder (60.3%).

$^1$H NMR (DMSO-$d_6$) δ 10.79 (br s, 1H), 8.79 (d, J=1.5 Hz, 1H), 8.74-8.72 (m, 1H), 8.34-8.31 (m, 1H), 8.01-7.96 (m, 2H), 7.89-7.84 (m, 1H), 7.63 (s, 1H), 7.56 (br t, 1H), 7.34 (d, J=7.1 Hz, 1H), 7.28-7.22 (m, 2H), 6.28 (d, J=7.1 Hz, 1H), 3.91-3.89 (m, 2H), 3.16-3.11 (m, 2H).

M$^+$(ES): 416.8; HPLC (max plot) 99.9%; Rt: 2.16 min.

Example 67

[4-(4-fluorophenyl)-1,3-thiazol-2(3H)-ylidene](2-{[3-(2-oxopyrrolidin-1-yl)propyl]amino}pyrimidin-4-yl)acetonitrile

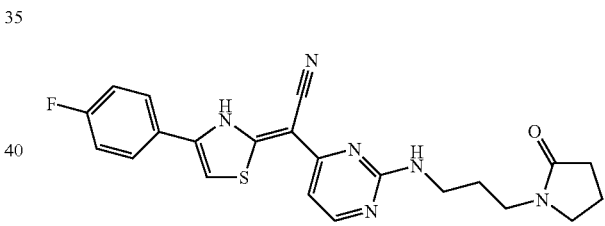

Following the general strategies and protocols outlined in the procedure E, the title compound was obtained from (2-chloropyrimidin-4-yl)[4-(4-fluorophenyl)-1,3-thiazol-2(3H)-ylidene]acetonitrile and N-(3'-aminopropyl)-2-pyrrolidinone in the presence of triethylamine for 4 min at 155° C. in EtOH as a yellow powder (95.3%).

$^1$H NMR (DMSO-$d_6$) δ 10.77 (br s, 1H), 8.00-7.95 (m, 2H), 7.65 (s, 1H), 7.39 (br t, 1H), 7.35 (d, J=7.5 Hz, 1H), 7.27-7.21 (m, 2H), 6.28 (d, J=7.5 Hz, 1H), 3.52-3.50 (m, 2H), 3.36-3.26 (m, 4H), 2.24-2.18 (m, 2H), 1.92-1.79 (m, 4H).

M$^+$(ES): 437.2; HPLC (max plot) 98.2%; Rt: 2.77 min.

Example 68

(4-ethyl-1,3-thiazol-2(3H)-ylidene){5-methyl-2-[(2- pyridin-3-ylethyl)amino]pyrimidin-4-yl}acetonitrile

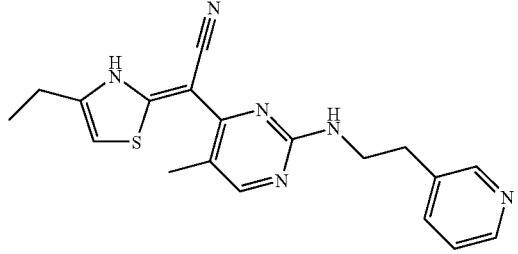

Following the general strategies and protocols outlined in the procedure E, the title compound was obtained from (2-chloro-5-methylpyrimidin-4-yl)(4-ethyl-1,3-thiazol-2(3H)-ylidene)acetonitrile and 3-(2-aminoethyl)pyridine in the presence of triethylamine for 16 min at 155° C. in EtOH as a yellow powder (82.5%).

$^1$H NMR (DMSO-d$_6$) δ 8.70 (d, J=1.5 Hz, 1H), 8.65-8.64 (m, 1H), 8.16-8.13 (m, 1H), 8.04 (br t, 1H), 7.73-7.69 (m, 1H), 7.56 (s, 1H), 7.03 (s, 1H), 3.88-3.75 (m, 2H), 3.08-3.04 (m, 2H), 2.71 (q, J=7.6 Hz, 2H), 2.33 (s, 3H), 1.19 (t, J=7.6 Hz, 3H).

M$^+$(ES): 365.2; HPLC (max plot) 97.5%; Rt: 1.74 min.

Example 69

(4-ethyl-1,3-thiazol-2(3H)-ylidene)(5-methyl-2-{[3-(2-oxopyrrolidin-1-yl)propyl]amino}pyrimidin-4-yl)acetonitrile

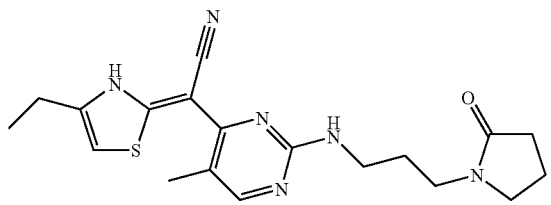

Following the general strategies and protocols outlined in the procedure E, the title compound was obtained from (2-chloro-5-methylpyrimidin-4-yl)(4-ethyl-1,3-thiazol-2(3H)-ylidene)acetonitrile and N-(3'-aminopropyl)-2-pyrrolidinone in the presence of triethylamine for 2×4 min at 155° C. in EtOH as a yellow powder (86.2%).

$^1$H NMR (DMSO-d$_6$) δ 8.04 (br t, 1H), 7.59 (s, 1H), 7.08 (s, 1H), 3.52-3.39 (m, 2H), 3.35-3.26 (m, 4H), 2.74 (q, J=7.5 Hz, 2H), 2.33 (s, 3H), 2.19 (t, J=7.9 Hz, 2H), 1.92-1.77 (m, 4H), 1.20 (t, J=7.5 Hz, 3H).

M$^+$(ES): 385.3; HPLC (max plot) 97.8% ; Rt: 2.37 min.

Example 70

[2-(cyclopropylamino)-5-methylpyrimidin-4-yl](4-ethyl-1,3-thiazol-2(3H)-ylidene)acetonitrile

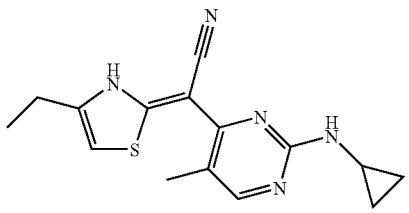

Following the general strategies and protocols outlined in the procedure E, the title compound was obtained from (2-chloro-5-methylpyrimidin-4-yl)(4-ethyl-1,3-thiazol-2(3H)-ylidene)acetonitrile and cyclopropyl amine in the presence of triethylamine for 4 min at 155° C. in EtOH as a yellow powder (77%).

$^1$H NMR (DMSO-d$_6$) δ 8.55 (br t, 1H), 7.57 (s, 1H), 7.07 (s, 1H), 2.82-2.67 (m, 3H), 2.34 (s, 3H), 1.20 (t, J=7.5 Hz, 3H), 0.89-0.86 (m, 2H), 0.65-0.63 (m, 2H).

M$^+$(ES): 300.2; HPLC (max plot) 97.8%; Rt: 2.44 min.

Example 71

(4-ethyl-1,3-thiazol-2(3H)-ylidene){2-[(3-pyrrolidin-1-ylpropyl)amino]pyrimidin-4-yl}acetonitrile

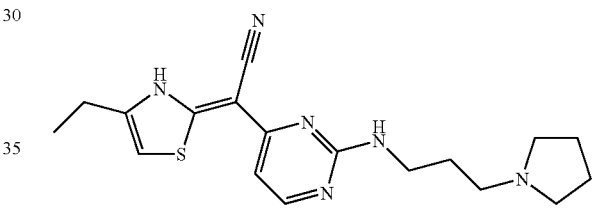

Following the general strategies and protocols outlined in the procedure E, the title compound was obtained from (2-chloropyrimidin-4-yl)(4-ethyl-1,3-thiazol-2(3H)-ylidene)acetonitrile and 1-(3-aminopropyl)pyrrolidine in the presence of triethylamine for 4 min at 155° C. in EtOH as a yellow powder (46.4%).

$^1$H NMR (DMSO-d$_6$) δ 9.60 (br s, 1H), 8.09 (br s, 1H), 7.62 (br d, 1H), 6.98 (s, 1H), 6.41 (d, J=6.7 Hz, 1H), 3.64-3.45 (m, 4H), 3.24-3.18 (m, 2H), 3.06-2.88 (m, 2H), 2.69 (q, J=7.5 Hz, 2H), 2.06-1.74 (m, 6H), 1.21 (t, J=7.5 Hz, 3H).

M$^+$(ES): 357.2; HPLC (max plot) 99.9%; Rt: 1.58 min.

Example 72

[2-({2-[(5-nitropyridin-2-yl)amino]ethyl}amino)pyrimidin-4-yl](4-phenyl-1,3-thiazol-2(3H)-ylidene)acetonitrile

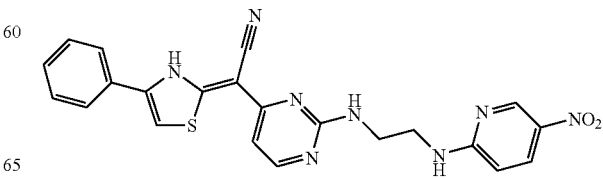

Following the general strategies and protocols outlined in the procedure E, the title compound was obtained from (2-chloropyrimidin-4-yl)(4-phenyl-1,3-thiazol-2(3H)-ylidene)acetonitrile and 2-(2-aminoethylamino)-5-nitro-pyridine in the presence of triethylamine for 24 h at 70° C. in EtOH as a green powder (26%).

$^1$H NMR (DMSO-d$_6$) δ 11.80-11.70 (br s, 1H exchangeable), 8.92 (d, J=2.7, 1H), 8.35-8.27 (br s, 1H exchangeable), 8.15-8.05 (m, 1H1), 7.96-7.88 (m, 2H), 7.62 (s, 1H), 7.58-7.51 (br s, 1H exchangeable), 7.46-7.24 (m, 4H [3+1]), 6.59 (d, J=9.4 Hz, 1H), 6.30 (d, J=7.2 Hz, 1H), 4.70-3.85 (br s, 2 H exchangeable), 3.80-3.60 (m, 4H).

M$^+$(ES): 459.4; HPLC (max plot) 91%; Rt: 3.05 min.

Example 73

6-{[2-({4-[cyano(4-phenyl-1,3-thiazol-2(3H)-ylidene)methyl]pyrimidin-2-yl}amino)ethyl]amino}nicotinonitrile

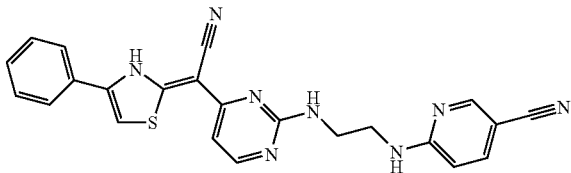

Following the general strategies and protocols outlined in the procedure E, the title compound was obtained from (2-chloropyrimidin-4-yl)(4-phenyl-1,3-thiazol-2(3H)-ylidene)acetonitrile and 2-(2-aminoethylamino)-5-cyano-pyridine in the presence of triethylamine for overnight at 70° C. in EtOH as a yellow powder (54%).

$^1$H NMR (DMSO-d$_6$) δ 11.85-11.75 (br s, 1H exchangeable), 8.41(d, J=2.2, 1H), 7.96-7.88 (m, 2H), 7.85-7.75 (br s, 1H exchangeable), 7.72-7.61(m, 2H), 7.60-7.50 (br s, 1H exchangeable), 7.46-7.24 (m, 4H [3+1]), 6.57 (d, J=9.0 Hz, 1H), 6.30 (d, J=7.2 Hz, 1H), 5.50-4.20 (br s, 2 H exchangeable), 3.80-3.60 (m, 4H).

M$^+$(ES): 439.2 HPLC (max plot) 98%; Rt: 2.78 min.

Example 74 tert-butyl 4-({4-[cyano(4-phenyl-1,3-thiazol-2(3H)-ylidene)methyl]pyrimidin-2-yl}amino)butanoate

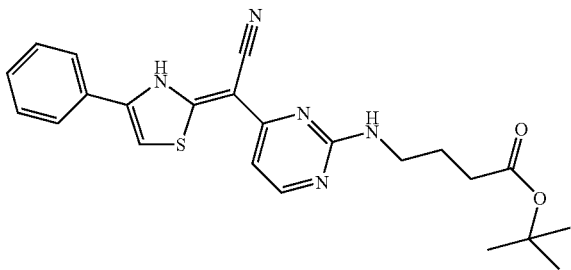

Following the general strategies and protocols outlined in the procedure E, the title compound was obtained from (2-chloropyrimidin-4-yl)(4-phenyl-1,3-thiazol-2(3H)-ylidene)acetonitrile and 4-amino-N-butyric acid tert-butyl ester hydrochloride in the presence of triethylamine for 36 h at 70° C. in EtOH as a yellow powder (49.6%).

$^1$H NMR (DMSO-d$_6$) δ 10.8-10.4 (br s, 1H exchangeable), 7.98-7.90 (m, 2H), 7.68 (s, 1H), 7.53-7.48 (br s, 1H exchangeable), 7.46-7.24 (m, 5H [3+1+1]), 6.29 (d, J=7.2 Hz, 1H), 5.40-4.10 (br s, 1H exchangeable), 3.65-3.45 (br s, 2H), 2.32 (t, J=7.5 Hz, 2H), 1.85 (q, J=7.1 Hz, 2H), 1.38 (s, 9H).

M$^-$(ES): 434.3; M$^+$(ES): 436.3; HPLC (max plot) 99%; Rt: 3.54 min.

Example 75

[4-(4-methoxyphenyl)-1,3-thiazol-2(3H)-ylidene](2-{[3-(2-oxopyrrolidin-1-yl)propyl]amiino}pyrimidin-4-yl)acetonitrile

Following the general strategies and protocols outlined in the procedure E, the title compound was obtained from (2-chloropyrimidin-4-yl)[4-(4-methoxyphenyl)-1,3-thiazol-2(3H)-ylidene]acetonitrile and 1-(3-aminopropyl)-2-pyrrolidinone in the presence of triethylamine for overnight at 70° C. in EtOH as a yellow powder (16.7%).

$^1$H NMR (DMSO-d$_6$) δ 11.0-10.65 (br s, 1H exchangeable), 7.86 (d, J=8.6 Hz, 2H), 7.51 (s, 1H), 7.55-7.45 (m, 2H [1+1 exchangeable]), 6.98 (d, J=9.1 Hz, 2H), 6.27 (d, J=7.2 Hz, 1H), 4.24-3.62 (m, 4H [3+1 exchangeable]), 3.58-3.45 (m, 2H), 3.40-3.22 (m, 2H), 2.25-2.15 (t, J=7.9 Hz, 2H), 1.98-1.79 (m, 4H).

M$^-$(ES): 447.3; M$^+$(ES): 449.3; HPLC (max plot) 98%; Rt: 2.76 min.

Example 76

(4-methyl-1,3-thiazol-2(3H)-ylidene)(2-{[3-(2-oxopyrrolidin-1-yl)propyl]amino}pyrimidin-4-yl)acetonitrile

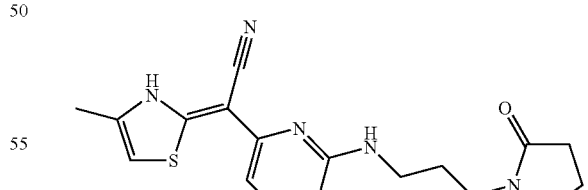

Following the general strategies and protocols outlined in the procedure E, the title compound was obtained from (2-chloropyrimidin-4-yl)(4-methyl-1,3-thiazol-2(3H)-ylidene)acetonitrile and 1-(3-aminopropyl)-2-pyrrolidinone in the presence of triethylamine for 5 min at 155° C. in EtOH as a yellow powder (50.4%).

$^1$H NMR (DMSO-d$_6$) δ 8.10-7-95 (br s, 1H, exchangeable), 7.69 (d, J=7.2 Hz, 1H), 7.03 (s, 1H), 6.44 (d, J=7.1 Hz, 1H), 4.50-3.40 (br s, 1H+H2O), 3.60-3.45 (m, 2H), 3.38-3.20 (m, 4H), 2.33 (d, J=0.7 Hz, 3H), 2.30-2.10 (m, 2H), 2.00-1.75 (m, 4H [2+2]).

HPLC (max plot) 96.7%; Rt: 1.97 min.

Example 77

(4-tert-butyl-1,3-thiazol-2(3H)-ylidene)(2-{[3-(2-oxopyrrolidin-1-yl)propyl]amino}pyrimidin-4-yl)acetonitrile

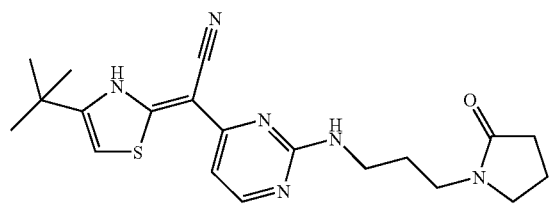

Following the general strategies and protocols outlined in the procedure E, the title compound was obtained from (4-tert-butyl-1,3-thiazol-2(3H)-ylidene)(2-chloropyrimidin-4-yl)acetonitrile and 1-(3-aminopropyl)-2-pyrrolidinone in the presence of triethylamine for 4 min at 155° C. in iPrOH as a yellow powder (49.5%).

$^1$H NMR (DMSO-d$_6$) δ 11.06 (br s, 1H, exchangeable), 7.80-7.10 (m, 2H, including 1 exchangeable), 6.82 (s, 1H), 6.26 (d, J=7.2Hz), 4.70-3.45 (br s, 1H, exchangeable), 3.50-3.10 (m, 6H [2+4]), 2.15 (t, J=7.9 Hz, 2H), 1.90-1.65 (m, 4H), 1.22 (s, 9H).

M$^-$(ES): 397; M$^+$(ES): 399; HPLC (max plot) 99%; Rt: 2.60 min.

Example 78

(4-tert-butyl-1,3-thiazol-2(3H)-ylidene){2-[(2-pyridin-3-ylethyl)amino]pyrimidin-4-yl}acetonitrile

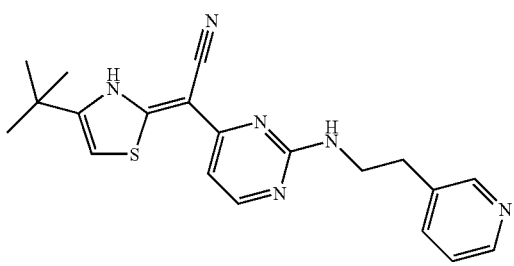

Following the general strategies and protocols outlined in the procedure E, the title compound was obtained from (4-tert-butyl-1,3-thiazol-2(3H)-ylidene)(2-chloropyrimidin-4-yl)acetonitrile and 3-(2-aminoethyl)pyridine in the presence of triethylamine for 5 min at 165° C. in iPrOH as a yellow powder (72.7%).

$^1$H NMR (DMSO-d$_6$) δ 8.80-8.65 (m, 2H), 8.71 (d, J=7.9 Hz, 1H), 7.90-7.65 (m, 2H, including 1 exchangeable), 7.42 (d, J=7.2 Hz, 1H), 6.84 (s, 1H), 6.32 (d, J=7.2 Hz, 1H), 3.95-3.80 (m, 2H), 3.15-3.05 (m, 2H), 1.28 (m, 9H).

M$^-$(ES): 377; M$^+$(ES): 379; HPLC (max plot) 98%; Rt: 1.90 min.

Example 79

(4-tert-butyl-1,3-thiazol-2(3H)-ylidene)[2-(cyclohexylamino)pyrimidin-4-yl]acetonitrile

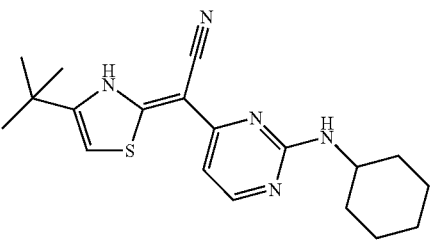

Following the general strategies and protocols outlined in the procedure E, the title compound was obtained from (4-tert-butyl-1,3-thiazol-2(3H)-ylidene)(2-chloropyrimidin-4-yl)acetonitrile and cyclohexyl amine in the presence of triethylamine for 5 min at 165° C. in iPrOH as a bright yellow powder (54.9%).

$^1$H NMR (DMSO-d$_6$) δ 10.61 (br s, 1H, exchangeable), 7.75-7.35 (m, 2H, including 1 exchangeable), 6.97 (s, 1H), 6.32 (d, J=6.8 Hz, 1H), 4.10-3.95 (m, 1H), 2.10-1.85 (m, 2H), 1.80-1.50 (m, 2H), 1.48-1.10 (m, 14H, [9+5]).

M$^-$(ES): 354; M$^+$(ES): 356; HPLC (max plot) 99.9%; Rt: 3.34 min.

Example 80

(4-tert-butyl -1,3-thiazol-2(3H)-ylidene)[2-(cyclopropylamino)pyrimidin-4-yl]acetonitrile

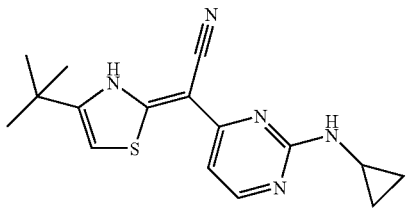

Following the general strategies and protocols outlined in the procedure E, the title compound was obtained from (4-tert-butyl-1,3-thiazol-2(3H)-ylidene)(2-chloropyrimidin-4-yl)acetonitrile and cyclopropyl amine in the presence of triethylamine for 3 min at 155° C. in EtOH as a yellowish powder (78.6%).

$^1$H NMR (DMSO-d$_6$) δ 11.0 (br s, 1H, exchangeable), 8.26 (br s, 1H, exchangeable), 7.52 (s, 1H), 6.93 (s, 1H), 6.42 (d, J=6.8 Hz [from D2O spectrum], 1H), 3.00-2.75 (m, 1H), 1.29 (s, 9H), 0.95-0.78 (m, 2H), 0.72-0.52 (m, 2H).

M$^-$(ES): 312; M$^+$(ES): 314; HPLC (max plot) 98.5%; Rt: 2.68 min.

Example 81

[4-(4-chlorophenyl)-1,3-thiazol-2(3H)-ylidene](2-{[3-(2-oxopyrrolidin-1-yl)propyl]amino}pyrimidin-4-yl)acetonitrile

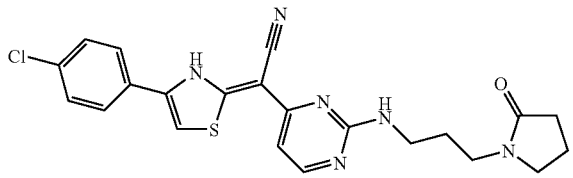

Following the general strategies and protocols outlined in the procedure E, the title compound was obtained from [4-(4-chlorophenyl)-1,3-thiazol-2(3H)-ylidene](2-chloropyrimidin-4-yl)acetonitrile and 1-(3-aminopropyl)-2-pyrrolidinone in the presence of triethylamine for 5 min at 155° C. in EtOH as a yellow powder (96.4%).

$^1$H NMR (DMSO-d$_6$) δ 10.83 (br s, 1H), 7.98 (d, J=8.29 Hz, 2H,), 7.74 (s, 1H), 7.49 (d, J=8.29 Hz, 2H), 7.4 (s, 1H), 7.37 (d, J=7.53 Hz, 1H), 6.29 (d, J=7.54 Hz, 1H), 3.48-3.52 (m, 2H), 3.26-3.36 (m, 4H), 2.21 (t, J=7.91 Hz, 2H), 1.79-192 (m, 4H)

HPLC (max plot) 99.9%; Rt: 3.03 min.

Example 82

[4-(4-chlorophenyl)-1,3-thiazol-2(3H)-ylidene][2-(cyclopropylamino)pyrimidin-4-yl]acetonitrile

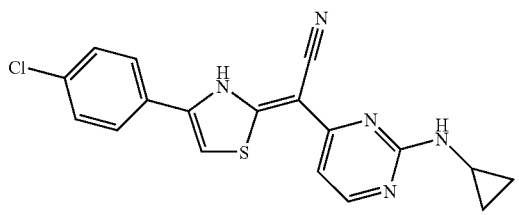

Following the general strategies and protocols outlined in the procedure E, the title compound was obtained from [4-(4-chlorophenyl)-1,3-thiazol-2(3H)-ylidene](2-chloropyrimidin-4-yl)acetonitrile and cyclopropyl amine in the presence of triethylamine for 5 min at 155° C. in EtOH as a yellow powder (62.3%).

$^1$H NMR (DMSO-d$_6$) δ 10.72 (br s, 1H), 7.96 (d, J=8.66 Hz, 2H), 7.73 (s, 1H), 7.48 (d, J=8.67 Hz, 2H), 7.38 (d, J=7.16 Hz, 1H), 6.34 (d, J=7.15 Hz, 1H), 2.85 (s, 1H), 0.84 (m, 2H), 0.63-0.66 (m, 2H)

M$^-$(ES): 366.1; M$^+$(ES): 368.2; HPLC (max plot) 99.4%; Rt: 3.22 min.

Example 83

[4-(3,4-dichlorophenyl)-1,3-thiazol-2(3H)-ylidene](2-{[3-(2-oxopyrrolidin-1-yl)propyl]amino}pyrimidin-4-yl)acetonitrile

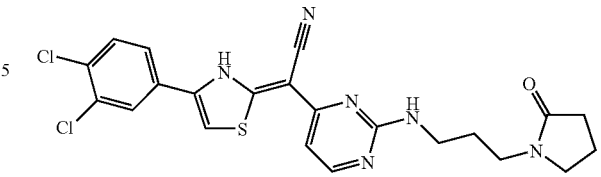

Following the general strategies and protocols outlined in the procedure E, the title compound was obtained from (2-chloropyrimidin-4-yl)[4-(3,4-dichlorophenyl)-1,3-thiazol-2(3H)-ylidene]acetonitrile and 1-(3-aminopropyl)-2-pyrrolidinone in the presence of triethylamine for 5 min at 155° C. in EtOH as a yellow powder (64%).

$^1$H NMR (DMSO-d$_6$) δ 10.8 (br s, 1H), 8.18 (s, 1H), 7.97 (d, J=8.66 Hz, 1H), 7.89 (s, 1H), 7.70 (d, J=8.29 Hz, 1H), 7.38 (br s, 1H), 7.37 (d, J=7.54 Hz, 1H), 6.28 (d, J=7.53 Hz, 1H), 3.51 (m, 2H), 3.26-3.36 (m, 4H), 2.22 (t, J=7.91 Hz, 2H), 1.88 (quint, J=6.79, 2H), 1.82 (quint, J=6.78, 2H)

M$^-$(ES): 484.8; M$^+$(ES): 487.1; HPLC (max plot) 97.8%; Rt: 3.44 min.

Example 84

[4-(3,4-dichlorophenyl)-1,3-thiazol-2(3H)-ylidene]{2-[(2-pyridin-3-ylethyl)amino]pyrimidin-4-yl}acetonitrile

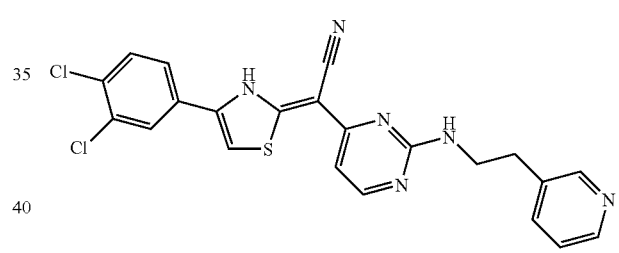

Following the general strategies and protocols outlined in the procedure E, the title compound was obtained from (2-chloropyrimidin-4-yl)[4-(3,4-dichlorophenyl)-1,3-thiazol-2(3H)-ylidene]acetonitrile and 3-(2-aminoethyl)pyridine in the presence of triethylamine for 5 min at 155° C. in EtOH as a yellow powder (30%).

$^1$H NMR (DMSO-d$_6$) δ 10.82 (br s, 1H), 8.77 (s, 1H), 8.72 (d, J=5.27 Hz, 1H), 8.30 (d, J=7.91 Hz, 1H), 8.18 (d, J=2.26 Hz, 1H), 7.96 (dd, J=8.29 Hz, J=2.26 Hz, 1H), 7.87 (s, 1H), 7.80-7.82 (m, 1H), 7.70 (d, J=8.29 Hz, 1H), 7.58 (br s, 1H), 7.36 (d, J=7.16Hz, 1H), 6.29 (d, J=7.15 Hz, 1H), 3.89 (m, 2H), 3.13 (t, J=6.41 Hz, 2H)

M$^-$(ES): 464.3; M$^+$(ES): 466.8; HPLC (max plot) 96%; Rt: 2.87 min.

Example 85

[2-(cyclopropylamino)pyrimidin-4-yl][4-(3,4-dichlorophenyl)-1,3-thiazol-2(3H)-ylidene]acetonitrile

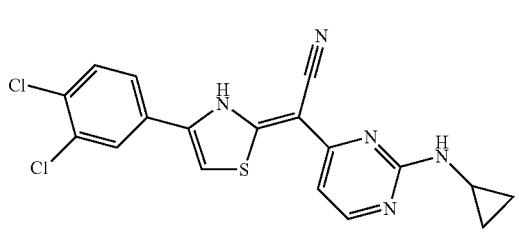

Following the general strategies and protocols outlined in the procedure E, the title compound was obtained from (2-chloropyrimidin-4-yl)[4-(3,4-dichlorophenyl)-1,3-thiazol-2(3H)-ylidene]acetonitrile and cyclopropyl amine in the presence of triethylamine for 5 min at 155° C. in EtOH as a yellow powder (85%).

$^1$H NMR (DMSO-$d_6$) δ 10.66 (br s, 1H), 8.16 (s, 1H), 7.94 (d, J=8.29 Hz, 1H), 7.88 (s, 1H), 7.67 (d, J=8.29 Hz, 1H), 7.34 (br t, 1H), 6.33 (d, J=7.53 Hz, 1H), 2.84 (m, 1H), 0.84-0.86 (m, 2H), 0.63 (m, 2H)

M$^-$(ES): 400.1; M$^+$(ES): 402.5; HPLC (max plot) 99.9%; Rt: 3.64 min.

Example 86

[4-(4-methylphenyl)-1,3-thiazol-2(3H)-ylidene](2-{[3-(2-oxopyrrolidin-1-yl)propyl]amino}pyrimidin-4-yl)acetonitrile

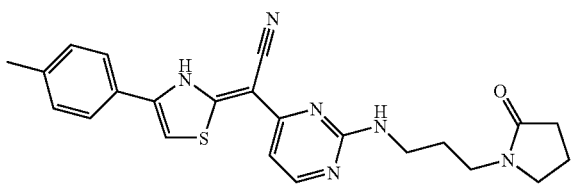

Following the general strategies and protocols outlined in the procedure E, the title compound was obtained from (2-chloropyrimidin-4-yl)[4-(4-methylphenyl)-1,3-thiazol-2(3H)-ylidene]acetonitrile and 1-(3-aminopropyl)-2-pyrrolidinone in the presence of triethylamine for 5 min at 155° C. in EtOH as a yellow powder (70%).

$^1$H NMR (DMSO-$d_6$) δ 10.79 (br s, 1H), 7.82 (d, J=8.29 Hz, 2H), 7.6 (s, 1H), 7.37 (s, 1H), 7.35 (d, J=7.54 Hz, 1H), 7.23 (d, J=7.91 Hz, 2H), 6.27 (d, J=7.53 Hz, 1H), 3.5 (m, 2H), 3.26-3.36 (m, 4H), 2.32 (s, 3H), 2.21 (t, J=7.53 Hz, 2H), 1.92 (quint, J=7.14 2H), 1.81 (quint, J=7.17, 2H)

M$^-$(ES): 431.1; M$^+$(ES): 433.2; HPLC (max plot) 97%; Rt: 2.87 min.

Example 87

[4-(4-methylphenyl)-1,3-thiazol-2(3H)-ylidene]{2-[(2-pyridin-3-ylethyl)amino]pyrimidin-4-yl}acetonitrile

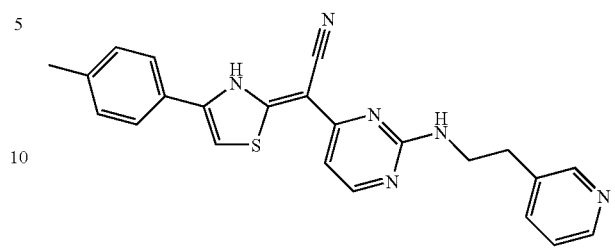

Following the general strategies and protocols outlined in the procedure E, the title compound was obtained from (2-chloropyrimidin-4-yl)[4-(4-methylphenyl)-1,3-thiazol-2(3H)-ylidene]acetonitrile and 3-(2-aminoethyl)pyridine in the presence of triethylamine for 5 min at 155° C. in EtOH as a yellow powder (64.8%).

$^1$H NMR (DMSO-$d_6$) δ 10.75 (br s, 1H), 8.78 (s, 1H), 8.73 (d, J=5.65 Hz, 1H), 8.33 (d, J=7.91 Hz, 1H), 7.87 (s, 1H), 7.84 (d, J=7.91 Hz, 2H), 7.58 (s, 1H), 7.53 (br s, 1H), 7.34 (d, J=7.16 Hz, 1H), 7.23 (d, J=8.29 Hz, 2H), 6.28 (d, J=7.16 Hz, 1H), 3.9 (m, 2H), 3.14 (t, J=6.32 Hz, 2H), 2.33 (s, 3H)

M$^-$(ES): 413.2; M$^+$(ES): 413.2; HPLC (max plot) 95%; Rt: 2.26 min.

Example 88

[2-(cyclopropylamino)pyrimidin-4-yl][4-(4-methylphenyl)-1,3-thiazol-2(3H)-lylidene]acetonitrile

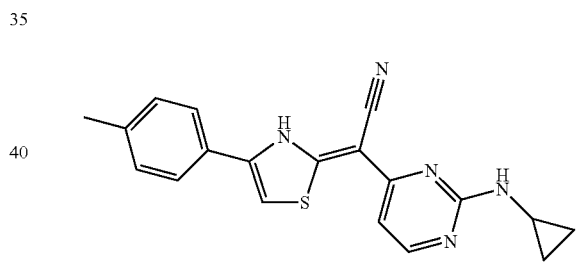

Following the general strategies and protocols outlined in the procedure E, the title compound was obtained from (2-chloropyrimidin-4-yl)[4-(4-methylphenyl)-1,3-thiazol-2(3H)-ylidene]acetonitrile and cyclopropyl amine in the presence of triethylamine for 5 min at 155° C. in EtOH as a yellow powder (55%).

$^1$H NMR (DMSO-$d_6$) δ 10.71 (br s, 1H), 8.01 (br s, 1H), 7.80 (d, J=7.91 Hz, 2H), 7.6 (s, 1H), 7.39 (br s, 1H), 7.23 (d, J=7.91 Hz, 2H), 6.34 (d, J=7.15 Hz, 1H), 2.86 (br s, 1H), 2.32 (s, 3H), 0.78-0.82 (m, 2H), 0.60-0.63 (m, 2H)

M$^-$(ES): 346.2; M$^+$(ES): 348.2; HPLC (max plot) 98.4%; Rt: 3.08 min.

Example 89

{2-[(3-aminopropyl)amino]pyrimidin-4-yl}(4-tertbutyl-1,3-thiazol-2(3H)-ylidene)acetonitrile

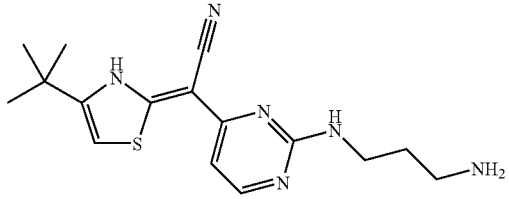

Following the general strategies and protocols outlined in the procedure E, the title compound was obtained from (4-tert-butyl-1,3-thiazol-2(3H)-ylidene)(2-chloropyrimidin-4-yl)acetonitrile and 1,3-diaminopropane in the presence of triethylamine for 4 min at 155° C. in EtOH (95.6%).

$^1$H NMR (DMSO-d$_6$) δ 7.45 (d, J=6 Hz, 1H), 6.39 (s, 1H), 6.11 (d, J=6 Hz, 1H), 3.60-3.24 (m, 2H+2H exchangeable), 2.82-2.77 (m, 2H), 1.80-1.76 (m, 2H), 1.24 (s, 9H).

HPLC (max plot) 89%; Rt: 1.78 min.

Example 90

{2-[(2-aminoethyl)amino]pyrimidin-4-yl}(4-tert-butyl-1,3-thiazol-2(3H)-ylidene)acetonitrile

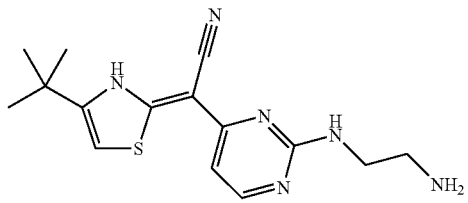

Following the general strategies and protocols outlined in the procedure E, the title compound was obtained from (4-tert-butyl-1,3-thiazol-2(3H)-ylidene)(2-chloropyrimidin-4-yl)acetonitrile and 1,2-diaminoethane in the presence of triethylamine for 4 min at 155° C. in ETOH (83.7%).

$^1$H NMR (DMSO-d6) δ 7.46 (d, J=6 Hz, 1H), 6.43 (s, 1H), 6.16 (d, J=6 Hz, 1H), 3.60-3.25 (2H+2H exchangeable), 3.00-2.96 (m, 2H), 1.24 (s, 9H).

M$^-$(ES): 315.2; M$^+$(ES): 317.2; HPLC (max plot) 89%; Rt: 1.64 min.

Example 91

{2-[(piperidin-4-yl)amino]pyrimidin-4-yl}(4-ethyl-1,3-thiazol-2(3H)-ylidene)acetonitrile

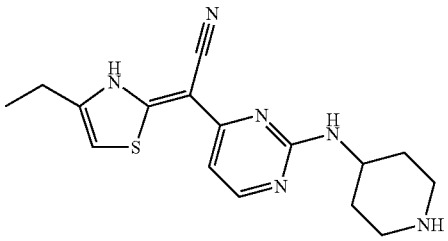

Following the general strategies and protocols outlined in the procedure E, the title compound was obtained from (2-chloropyrimidin-4-yl)(4-ethyl-1,3-thiazol-2(3H)-ylidene)acetonitrile and 1-(tert-butoxycarbonyl)-aminopiperidine in the presence of triethylamine for 6 min at 155° C. in EtOH (84.2%).

$^1$H NMR (DMSO-d6) δ 10.26 (br s, 1H, exchangeable), 7.80 (br s, 1H, exchangeable), 7.35-7.25 (m, 1H), 6.85 (s, 1H), 6.21 (d, J=7.2 Hz, 1H), 4.25-4.0 (br s, 1H), 4.00-3.80 (m, 2H), 3.05-2-80 (m, 2H), 2.70-2.55 (m, 2H), 2.10-1.75 (m, 2H), 1.55-1.25 (m, 11H [9+2]), 1.24-1.10 (m, 3H).

M$^+$(ES): 429; HPLC (max plot) 79%; Rt: 3.12 min.

The Boc protected tert-butyl 4-({4-[cyano(4-ethyl-1,3-thiazol-2(3H)-ylidene)methyl]pyrimidin-2-yl}amino)piperidine-1-carbamate was treated with a solution of 20% TFA in DCM overnight at rt, affording the title compound as a diTFA salt after evaporation of the solvent (52.5%).

$^1$H NMR (DMSO-d6) δ 11.57 (br s, 1H, exchangeable), 9.00-8.15 (m, 4H, exchangeable), 8.10-7.90 (m, 1H), 7.62-7.55 (m, 1H), 6.93 (s, 1H), 6.39 (d, J=6.8 Hz, 1H), 4.30-4.20 (m, 1H), 3.45-2.85 (m, 2+2H), 2.80-2.55 (m, 2H), 2.35-1.50 (m, 2+2H), 1.25-1.15 (m, 3H).

M$^+$(ES): 330.3; HPLC (max plot) 76.8%; Rt: 1.47 min.

Example 92 methyl N-{4-[(4-tert-butyl-1,3-thiazol-2(3H)-ylidene) (cyano)methyl]pyrimidin-2-yl}-beta-alaninate

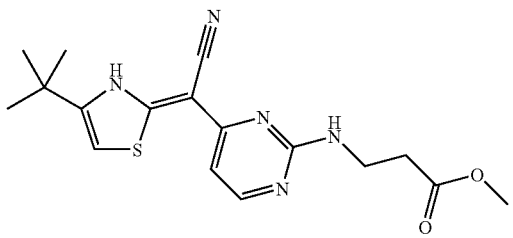

Following the general strategies and protocols outlined in the procedure E, the title compound was obtained from (4-tert-butyl-1,3-thiazol-2(3H)-ylidene)(2-chloropyrimidin-4-yl)acetonitrile and Beta-alanine methyl ester hydrochloride in the presence of triethylamine for 4 min at 155° C. in EtOH (63.6%).

M⁻(ES): 358; M⁺(ES): 360; HPLC (max plot) 80%; Rt: 2.68 min.

Example 93

(2-{[3-(2-oxopyrrolidin-1-yl)propyl]amino}pyrimidin-4-yl)[4-(pentafluoroethyl)-1,3-thiazol-2(3H)-ylidene]acetonitrile

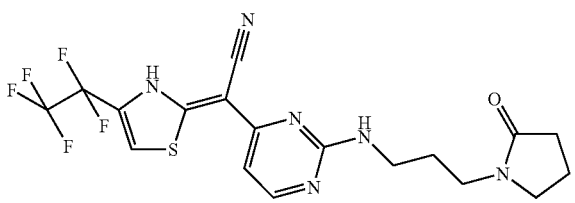

Following the general strategies and protocols outlined in the procedure E, the title compound was obtained from (2-chloropyrimidin-4-yl)[4-(pentafluoroethyl)-1,3-thiazol-2(3H)-ylidene]acetonitrile and 1-(3-aminopropyl)-2-pyrrolidinone in the presence of triethylamine for 4 min at 155° C. in EtOH (99%).

¹H NMR (DMSO-d6) δ 10.94 (s, 1H); 7.97 (s, 1H); 7.52 (s, 1H); 7.42 (d, J=7.5 Hz, 1H); 6.30 (d, J=7.2 Hz, 1H); 3.50 (m, 2H); 3.31 (m, 4H); 2.20 (t, J=7.5 Hz, 2H); 1.89 (quint, J=7.5 Hz, 2H); 1.81(quint, J=7.2 Hz, 2H)

M⁺(ES): 461; HPLC (max plot) 99.8%; Rt: 3.70 min.

Example 94

{5-methyl-2-[(2-pyridin-3-ylethyl)amino]pyrimidin-4-yl}(4-methyl-1,3-thiazol-2(3H)-ylidene)acetonitrile

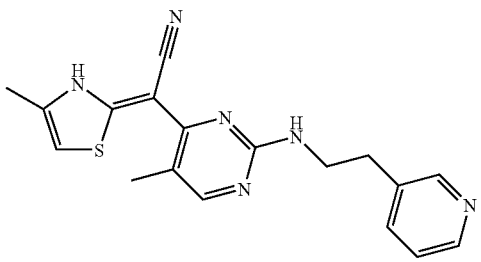

Following the general strategies and protocols outlined in the procedure E, the title compound was obtained from (2-chloro-5-methylpyrimidin-4-yl)(4-methyl-1,3-thiazol-2(3H)-ylidene)acetonitrile and 3-(2-aminoethyl)pyridine in the presence of triethylamine for 15 min at 155° C. in EtOH (66.6%).

¹H NMR (DMSO-d6) δ 8.65 (d, J=1.6 Hz, 1H); 8.61 (dd, J=1.6 Hz, J=5.3 Hz, 1H); 8.09 (d, J=7.5 Hz, 1H); 7.67 (dd, J=5.6 Hz, J=7.5 Hz, 1H); 7.56 (s, 1H); 7.04 (s, 1H); 3.82 (s, 2H); 3.05 (t, J=6.8 Hz, 2H); 2.34 (s, 3H); 2.33 (s, 3H)

M⁺(ES): 351; HPLC (max plot) 100%; Rt: 1.52 min.

Example 95

(5-methyl-2-{[3-(2-oxopyrrolidin-1-yl)propyl]amino}pyrimidin-4-yl)(4-methyl-1,3-thiazol-2(3H)-ylidene)acetonitrile

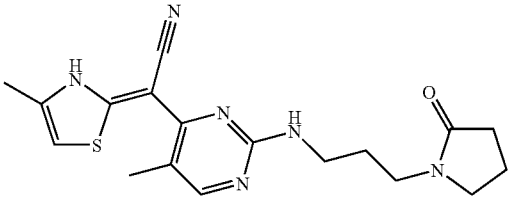

Following the general strategies and protocols outlined in the procedure E, the title compound was obtained from (2-chloro-5-methylpyrimidin-4-yl)(4-methyl-1,3-thiazol-2(3H)-ylidene)acetonitrile and 1-(3-aminopropyl)-2-pyrrolidinone in the presence of triethylamine for 16 min at 155° C. in EtOH (67.2%).

¹H NMR (DMSO-d6) δ 7.78 (br s, 1H); 7.52 (s, 1H); 7.05 (s, 1H); 3.44 (br s, 2H); 3.34 (t, J=Hz, 2H); 3.28 (t, 2H); 2.35 (s, 3H); 2.32 (s, 3H); 2.20 (t, J=8 Hz, 2H); 1.90 (quint, J=7.5 Hz, 2H); 1.80 (quint, J=7.2 Hz, 2H).

M⁺(ES): 371; HPLC (max plot) 97.3%; Rt: 2.10 min.

Example 96

[2-(cyclopropylamino)-5-methylpyrimidin-4-yl](4-methyl-1,3-thiazol-2(3H)-ylidene)acetonitrile

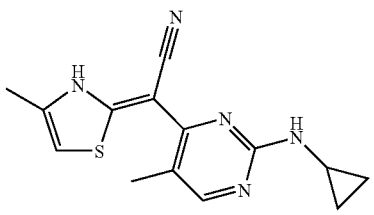

Following the general strategies and protocols outlined in the procedure E, the title compound was obtained from (2-chloro-5-methylpyrimidin-4-yl)(4-methyl-1,3-thiazol-2(3H)-ylidene)acetonitrile and cyclopropylamine in the presence of triethylamine for 22 min at 155° C. in EtOH (65.7%).

¹H NMR (DMSO-d6) δ 13 (br s, 1H); 8.49 (s, 1H); 7.57 (s, 1H); 7.07 (s, 1H); 2.78 (s, 1H); 2.34 (s, 6H); 0.89 (m, 2H); 0.65 (m, 2H)

M⁺(ES): 286; HPLC (max plot) 100%; Rt: 2.15 min.

Example 97

(4-tert-butyl-1,3-thiazol-2(3H)-ylidene){5-methyl-2-[(2-pyridin-3-ylethyl)amino]pyrimidin-4- yl}acetonitrile

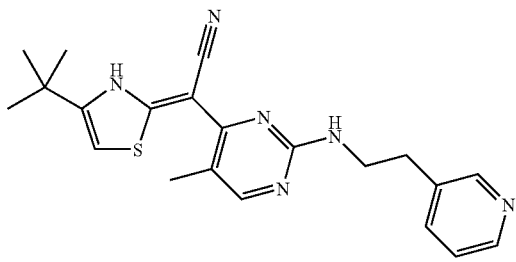

Following the general strategies and protocols outlined in the procedure E, the title compound was obtained from (4-tert-butyl-1,3-thiazol-2(3H)-ylidene)(2-chloro-5-methylpyrimidin-4-yl)acetonitrile and 3-(2-aminoethyl)pyridine in the presence of triethylamine for 28 min at 155° C. in EtOH (70.8%).

$^1$H NMR (DMSO-d6) δ 8.72 (br d, 1H), 8.69-8.68 (m, 1H), 8.22 (d, J=7.9 Hz, 1H), 7.79 (dd, J=5.6 Hz, J=7.9 Hz, 1H), 7.45 (br s, 1H), 7.25 (s, 1H), 6.84 (s, 1H), 3.86-3.78 (m, 2H), 3.09-3.04 (m, 2H), 2.27 (s, 3H), 1.28 (s, 9H).

M$^+$(ES): 393.3; HPLC (max plot) 93.9%; Rt: 2.08 min.

Example 98

(4-tert-butyl-1,3-thiazol-2(3H)-ylidene)(5-methyl-2-{[3-(2-oxopyrrolidin-1-yl)propyl]amino}pyrimidin-4-yl)acetonitrile

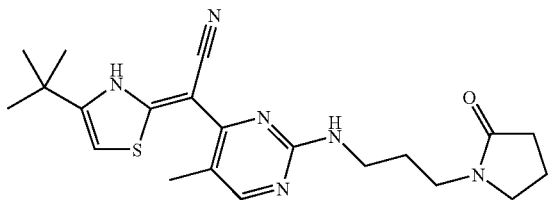

Following the general strategies and protocols outlined in the procedure E, the title compound was obtained from (4-tert-butyl-1,3-thiazol-2(3H)-ylidene)(2-chloro-5-methylpyrimidin-4-yl)acetonitrile and 1-(3-aminopropyl)-2-pyrrolidinone in the presence of triethylamine for 20 min at 155° C. in EtOH (64.9%).

$^1$H NMR (DMSO-d6) δ 7.50-7.32 (m, 2H), 6.92 (s, 1H), 3.46-3.44 (m, 2H), 3.38-3.24 (m, 4H), 2.22 (s, 3H), 2.19 (t, J=7.9 Hz, 2H), 1.94-1.72 (m, 4H), 1.30 (s, 9H)

M$^+$(ES): 413.3; HPLC (max plot) 98.8%; Rt: 2.78 min.

Example 99

(4-tert-butyl-1,3-thiazol-2(3H)-ylidene)[2-(cyclopropylamino)-5-methylpyrimidin-4-yl]acetonitrile

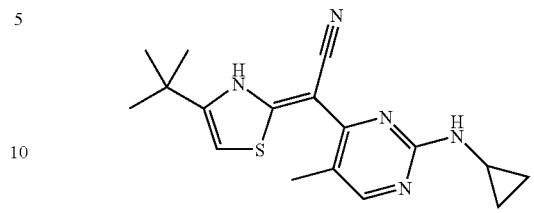

Following the general strategies and protocols outlined in the procedure E, the title compound was obtained from (4-tert-butyl-1,3-thiazol-2(3H)-ylidene)(2-chloro-5-methylpyrimidin-4-yl)acetonitrile and cyclopropylamine in the presence of triethylamine for 20 min at 155° C. in EtOH (70.9%).

$^1$H NMR (DMSO-d6) δ 8.11 (br s, 1H), 7.36 (s, 1H), 6.96 (s, 1H), 2.82-2.72 (m, 1H), 2.31 (s, 3H), 1.31 (s, 9H), 0.88-0.81 (m, 2H), 0.64-0.59 (m, 2H)

M$^+$(ES): 328.2; HPLC (max plot) 99.6%; Rt: 2.82 min.

Example 100

(4-tert-butyl-1,3-thiazol-2(3H)-ylidene)(5-methyl-2-{[3-(1H-1,2,4-triazol-1-yl)propyl]amino}pyrimidin-4-yl)acetonitrile

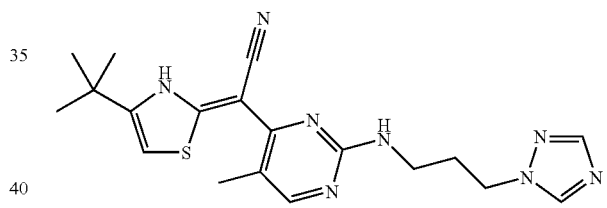

Following the general strategies and protocols outlined in the procedure E, the title compound was obtained from (4-tert-butyl-1,3-thiazol-2(3H)-ylidene)(2-chloro-5-methylpyrimidin-4-yl)acetonitrile and HBr salt of 1-(3'-aminopropyl)-1H-1,2,4-triazole in the presence of triethylamine for 20 min at 155° C. in EtOH (23.3%).

$^1$H NMR (DMSO-d6) δ 8.53 (s, 1H), 7.98 (s, 1H), 7.54-7.22 (m, 2H, exchangeable), 6.90 (s, 1H), 4.28 (t, J=6.8 Hz, 2H), 3.48-3.46 (m, 2H), 2.28 (s, 3H), 2.16-2.07 (m, 2H), 1.30 (s, 9H)

M$^+$(ES): 397.3; HPLC (max plot) 99.7%; Rt: 2.50 min.

Example 101

N-[3-({4-[(4-tert-butyl-1,3-thiazol-2(3H)-ylidene)(cyano)methyl]pyrimidin-2-yl}amino)propyl]-2- ethoxy-N-glycoloylacetamide

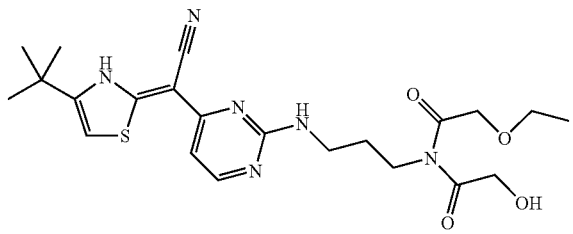

Following the general strategies and protocols outlined in the procedure E, the title compound was obtained from (4-tert-butyl-1,3-thiazol-2(3H)-ylidene)(2-chloropyrimidin-4-yl)acetonitrile and 4-(3-aminopropyl)morpholine-3,5-dione in the presence of triethylamine for 30 min at 155° C. in EtOH (27.6%).

$^1$H NMR (DMSO-d6) δ 10.8 (br s, 1H), 7.92 (br t, 1H, exchangeable), 7.58-7.32 (m, 2H, including 1 exchangeable), 6.87 (s, 1H), 6.31 (br d, 1H), 4.17 (s, 2H), 4.11 (q, J=7.2 Hz, 2H), 3.95 (s, 2H), 3.55-3.45 (m, 2H), 3.24-3.20 (m, 2H), 1.78-1.74 (m, 2H), 1.28 (s, 9H), 1.18 (t, J=7.2 Hz, 3H)

M$^+$(ES): 475.2; HPLC (max plot) 95.7%; Rt: 2.72 min.

Example 102

N-[3-({4-[cyano(4-isopropyl-1,3-thiazol-2(3H)-ylidene)methyl]pyrimidin-2-yl}amino)propyl]-2-ethoxy-N-glycoloylacetamide

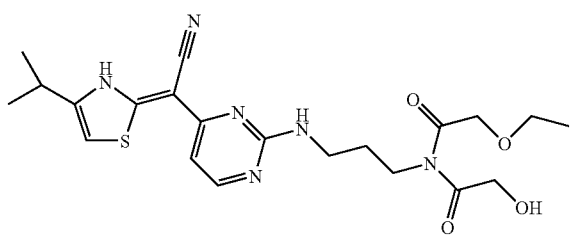

Following the general strategies and protocols outlined in the procedure E, the title compound was obtained from (2-chloropyrimidin-4-yl)(4-isopropyl-1,3-thiazol-2(3H)-ylidene)acetonitrile and 4-(3-aminopropyl)morpholine-3,5-dione in the presence of triethylamine for 5 min at 155° C. in EtOH (40%).

$^1$H NMR (DMSO-d6) δ 11.30 (br s, 1H), 7.81-7.61 (m, 2H, exchangeable), 7.46 (br d, 1H), 6.83 (s, 1H), 6.26 (br d, 1H), 4.02 (s, 2H), 3.96 (q, J=7.2 Hz, 2H), 3.80 (s, 2H), 3.42-3.28 (m, 2H), 3.10-3.03 (m, 2H), 2.92-2.88 (m, 1H), 1.64-1.60 (m, 2H), 1.08 (d, J=6.7 Hz, 6H), 1.03 (t, J=7.2 Hz, 3H).

M$^+$(ES): 461.2; HPLC (max plot) 97.5%; Rt: 2.57 min.

Example 103

[2-(cyclohexylamino)pyrimidin-4-yl](4-ethyl-1,3-thiazol-2(3H)-ylidene)acetonitrile

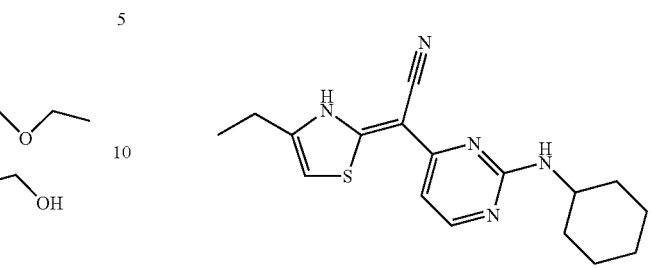

Following the general strategies and protocols outlined in the procedure E, the title compound was obtained from (2-chloropyrimidin-4-yl)(4-ethyl-1,3-thiazol-2(3H)-ylidene)acetonitrile and cyclohexylamine in the presence of triethylamine for 4 min at 155° C. in EtOH (75.7%).

$^1$H NMR (DMSO-d6) δ 11.40 (br s, 1H), 7.99 (br s, 1H, exchangeable), 7.65 (br d, 1H), 7.11 (s, 1H), 6.43 (d, J=7.2 Hz, 1H), 4.08-3.95 (m, 1H), 2.72-2.65 (m, 2H), 2.00-1.97 (m, 2H), 1.76-1.71 (m, 2H), 1.63-1.59 (m, 1H), 1.39-1.28 (m, 5H), 1.23-1.18 (m, 3H)

M$^+$(ES): 328.2; HPLC (max plot) 96.4%; Rt: 3.04 min.

Example 104

[2-(cyclopentylamino)pyrimidin-4-yl](4-ethyl-1,3-thiazol-2(3H)-ylidene)acetonitrile

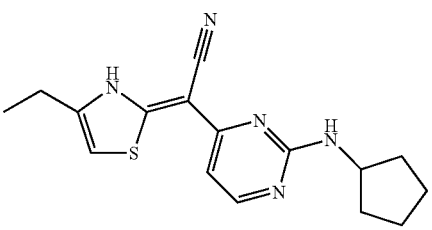

Following the general strategies and protocols outlined in the procedure E, the title compound was obtained from (2-chloropyrimidin-4-yl)(4-ethyl-1,3-thiazol-2(3H)-ylidene)acetonitrile and cyclopentylamine in the presence of triethylamine for 4 min at 155° C. in EtOH (78.2%).

1H NMR (DMSO-d6) δ 8.28 (br s, 1H exchangeable), 7.95 (br s, 1H exchangeable), 7.70 (d, J=7.1 Hz, 1H), 7.07 (s, 1H), 6.46 (d, J=7.1 Hz, 1H), 4.53-3.98 (m, 1H), 2.73-2.66 (m, 2H), 2.06-2.02 (m, 2H), 1.70-1.55 (m, 6H), 1.22-1.18 (m, 3H)

M$^+$(ES): 314.2; HPLC (max plot) 97.2%; Rt: 2.82 min.

Example 105

(4-ethyl-1,3-thiazol-2(3H)-ylidene)[2-(isobutylamino)pyrimidin-4-yl]acetonitrile

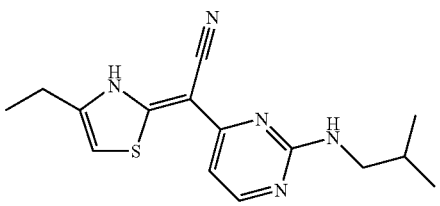

Following the general strategies and protocols outlined in the procedure E, the title compound was obtained from (2-chloropyrimidin-4-yl)(4-ethyl-1,3-thiazol-2(3H)-ylidene)acetonitrile and isobutylamine in the presence of triethylamine for 4 min at 155° C. in EtOH (91.2%).

¹H NMR (DMSO-d6) δ 7.97 (br s, 1H exchangeable), 7.51 (d, J=7.2 Hz, 1H), 6.91 (s, 1H), 6.26 (d, J=7.2 Hz, 1H), 3.19-3.08 (m, 2H), 2.51-2.43 (m, 2H), 1.76-1.67 (m, 1H), 0.97 (t, J=7.6 Hz, 3H), 0.72 (d, J=6.7 Hz, 6H)

M⁺(ES): 302.3; HPLC (max plot) 100%; Rt: 2.75 min.

Example 106

(4-tert-butyl-1,3-thiazol-2(3H)-ylidene)(2-{[3-(1H-1,2,4-triazol-1-yl)propyl]amino}pyrimidin-4-yl)acetonitrile

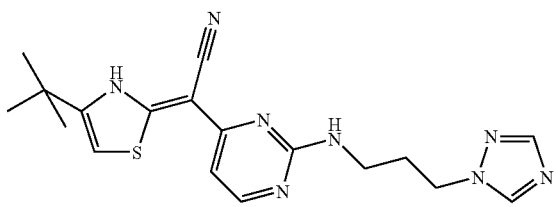

Following the general strategies and protocols outlined in the procedure E, the title compound was obtained from (4-tert-butyl-1,3-thiazol-2(3H)-ylidene)(2-chloropyrimidin-4-yl)acetonitrile and the HCl salt of 3-(1H-1,2,4-triazol-1-yl)propan-1-amine in the presence of triethylamine for 8 min at 155° C. in EtOH (88.6%).

¹H NMR (DMSO-d6) δ 8.55 (s, 1H), 8.00 (s, 1H), 7.53 (br d, 1H), 6.92 (s, 1H), 6.38 (d, J=7.1 Hz, 1H), 4.30 (t, J=6.8 Hz, 2H), 3.51-3.49 (m, 2H), 2.18-2.09 (m, 2H), 1.31 (s, 9H).

M⁺(ES): 383.3; HPLC (max plot) 99.4%; Rt: 2.34 min.

Example 107

(4-isopropyl-1,3-thiazol-2(3H)-ylidene)(2-{[3-(2-oxopyrrolidin-1-yl)propyl]amino}pyrimidin-4-yl)acetonitrile

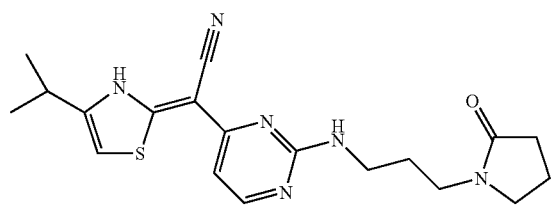

Following the general strategies and protocols outlined in the procedure E, the title compound was obtained from (2-chloropyrimidin-4-yl)(4-isopropyl-1,3-thiazol-2(3H)-ylidene)acetonitrile and 1-(3-aminopropyl)-2-pyrrolidinone in the presence of triethylamine for 4 min at 155° C. in EtOH (57%).

¹H NMR (DMSO-d6) δ 8.00-7.45 (m, 2H, 1 exchangeable), 6.94 (s, 1H), 6.38 (d, J=7.1 Hz, 1H), 3.65-3.15 (m, 6H, [2+2+2]), 3.10-2.95 (m, 1H), 2.25-2.10 (m, 2H), 2.00-1.65 (m, 4H, [2+2]), 1.23 (d, J=7.1 Hz, 6H).

M⁺(ES): 385; HPLC (max plot) 99.7%; Rt: 2.43 min.

Example 108

(4-isopropyl-1,3-thiazol-2(3H)-ylidene){2-[(2-pyridin-3-ylethyl)amino]pyrimidin-4-yl}acetonitrile

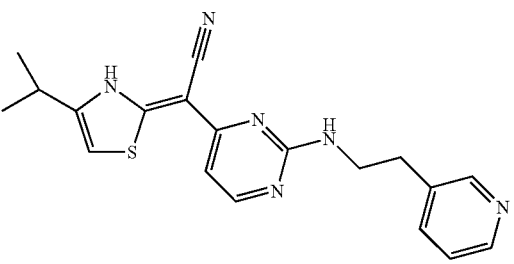

Following the general strategies and protocols outlined in the procedure E, the title compound was obtained from (2-chloropyrimidin-4-yl)(4-isopropyl-1,3-thiazol-2(3H)-ylidene)acetonitrile and 3-(2-aminoethyl)pyridine in the presence of Triethylamine for 4 min at 155° C. in EtOH (88.6%).

¹H NMR (DMSO-d6) δ 8.67 (s, 1H), 8.62 (d, J=5.3 Hz, 1H), 8.09 (d, J=7.9 Hz, 1H), 7.93 (br s, 1H, exchangeable), 7.70-7.50 (m, 2H), 6.95 (s, 1H), 6.40 (d, J=7.1 Hz, 1H), 3.95-3.75 (m, 2H), 3.20-2.95 (m, 3H [2+1]), 1.23 (d, J=6.8 Hz, 6H).

M⁺(ES): 365; HPLC (max plot) 97%; Rt: 1.74 min.

Example 109

[2-(cyclopropylamino)pyrimidin-4-yl](4-isopropyl-1,3-thiazol-2(3H)-ylidene)acetonitrile

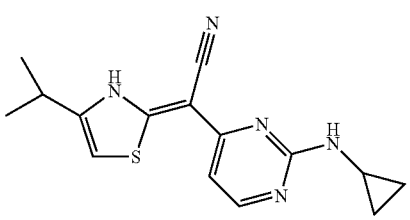

Following the general strategies and protocols outlined in the procedure E, the title compound was obtained from (2-chloropyrimidin-4-yl)(4-isopropyl-1,3-thiazol-2(3H)-ylidene)acetonitrile and cyclopropylamine in the presence of triethylamine for 4 min at 155° C. in EtOH (87.8%).

¹H NMR (DMSO-d6) δ 11.90 (br s, 1H, exchangeable), 8.60-8.40 (br s, 1H, exchangeable), 7.67 (d, J=6 Hz, 1H), 7.02

(s, 1H), 6.47 (d, J=6.8 Hz, 1H), 3.15-2.95 (m, 1H), 1.23 (d, J=6.8 Hz, 6H), 0.95-0.85 (m, 2H), 0.68-0.63 (m, 2H).

M⁺(ES): 300; HPLC (max plot) 99.8%; Rt: 2.49 min.

Example 110 methyl 4-({4-[(4-tert-butyl-1,3-thiazol-2(3H)-ylidene)(cyano)methyl]pyrimidin-2-yl}amino)butanoate

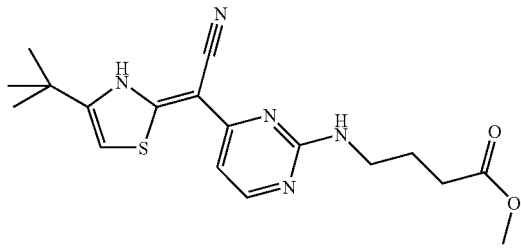

Following the general strategies and protocols outlined in the procedure E, the title compound was obtained from (4-tert-butyl-1,3-thiazol-2(3H)-ylidene)(2-chloropyrimidin-4-yl)acetonitrile and the HCl salt of methyl 4-aminobutyrate in the presence of triethylamine for 4 min at 155° C. in EtOH (56.8%).

¹H NMR (DMSO-d6) δ 10.9 (br s, 1H, exchangeable), 7.90-7.35 (m, 2H, including 1 exchangeable), 6.92 (s, 1H), 6.34 (d, J=6.8 Hz, 1H), 3.65-3.4 (m, 4H [3+1]), 2.41 (t, J=7.2 Hz), 1.87 (quint, J=7.2 Hz, 2H), 1.29 (s, 9H).

M⁺(ES): 374; HPLC (max plot) 96.5%; Rt: 2.78 min.

Example 111

4-{2-[cyano(2-{[3-(2-oxopyrrolidin-1-yl)propyl]amino}pyrimidin-4-yl)methylene]-2,3-dihydro-1,3-thiazol-4-yl}benzonitrile

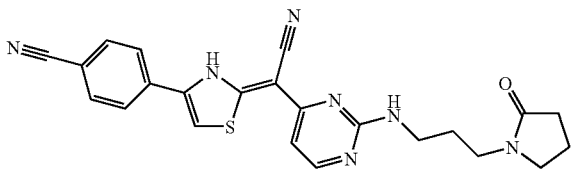

Following the general strategies and protocols outlined in the procedure E, the title compound was obtained from 4-{2-[(2-chloropyrimidin-4-yl)(cyano)methylene]-2,3-dihydro-1,3-thiazol-4-yl}benzonitrile and 1-(3-aminopropyl)-2-pyrrolidinone in the presence of triethylamine for 5 min at 155° C. in EtOH (50%).

¹H NMR (DMSO-d6) δ 10.8 (s, 1H); 8.14 (d, J=8.29 Hz, 2H), 7.97 s, 1H), 7.87 (d, J=8.29 Hz, 2H), 7.37 (s, 1H), 7.35 (d, J=7.16 Hz, 1H), 6.28 (d, J=7.53 Hz, 1H), 3.5 (m, 2H), 3.34 (m, 4H), 2.21 (t, J=7.9 Hz, 2H), 1.9 (t, J=7.92 Hz, 2H), 1.81 (t, J=6.7 Hz, 2H).

M⁻(ES): 442.3; M⁺(ES): 444.3; HPLC (max plot) 97%; Rt: 2.79 min.

Example 112

4-[2-(cyano{2-[(2-pyridin-3-ylethyl)amino]pyrimidin-4-yl}methylene)-2,3-dihydro-1,3-thiazol-4-yl]benzonitrile

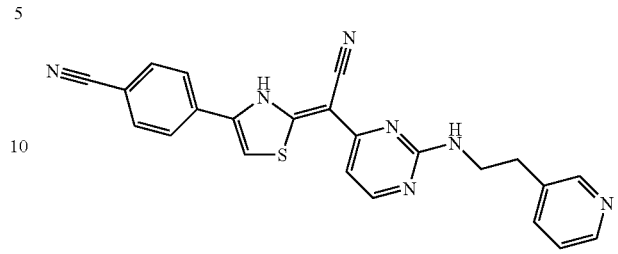

Following the general strategies and protocols outlined in the procedure E, the title compound was obtained from 4-{2-[(2-chloropyrimidin-4-yl)(cyano)methylene]-2,3-dihydro-1,3-thiazol-4-yl}benzonitrile and 3-(2-aminoethyl)pyridine in the presence of triethylamine for 5 min at 155° C. in EtOH (65%).

¹H NMR (DMSO-d6) δ 10.8 (s, 1H), 8.76 (s, 1H), 8.71 (d, J=4.14, 1H), 8.3 (d, J=8.29 Hz, 1H), 8.16 (d, J=8.29 Hz, 2H), 7.95 (s, 1H), 7.9 (d, J=8.67 Hz, 2H), 7.86 (d, 1H), 7.56 (s, 1H), 7.37 (d, J=7.15 Hz, 1H), 6.3 (d, J=7.16 Hz, 1H), 3.89 (m, 2H), 3.13 (t, J=6.78 Hz, 2H).

M⁻(ES): 422.2; M⁺(ES): 424.1; HPLC (max plot) 92.6%; Rt: 2.25 min.

Example 113

4-(2-{cyano[2-(cyclopropylamino)pyrimidin-4-yl]methylene}-2,3-dihydro-1,3-thiazol-4-yl)benzonitrile

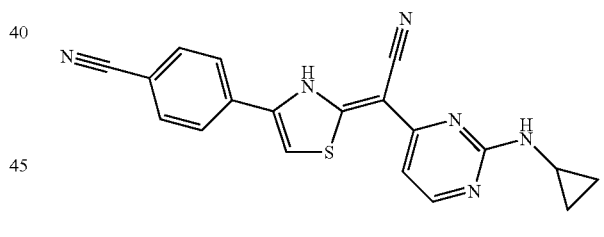

Following the general strategies and protocols outlined in the procedure E, the title compound was obtained from 4-{2-[(2-chloropyrimidin-4-yl)(cyano)methylene]-2,3-dihydro-1,3-thiazol-4-yl}benzonitrile and cyclopropylamine in the presence of triethylamine for 5 min at 155° C. in EtOH (63.6%).

¹H NMR (DMSO-d6) δ 10.68 (s, 1H), 8.14 (d, J=8.28 Hz, 2H), 7.96 (s, 1H), 7.89 (d, J=8.29 Hz, 2H), 7.34 (d, 1H), 6.34 (d, J=7.15 Hz, 1H), 2.85 (m, 1H), 0.84 (m, 2H), 0.62 (m, 2H).

M⁻(ES): 357.2; M⁺(ES): 359.2; HPLC (max plot) 98.3%; Rt: 2.92 min.

Example 114

[4-(2-chlorophenyl)-1,3-thiazol-2(3H)-ylidene](2-{[3-(2-oxopyrrolidin-1-yl)propyl]amino}pyrimidin-4-yl)acetonitrile

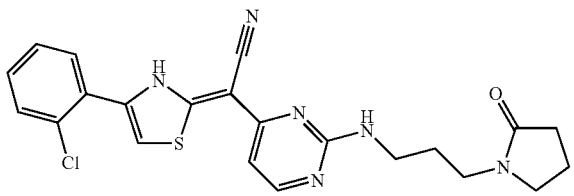

Following the general strategies and protocols outlined in the procedure E, the title compound was obtained from [4-(2-chlorophenyl)-1,3-thiazol-2(3H)-ylidene](2-chloropyrimidin-4-yl)acetonitrile and 1-(3-aminopropyl)-2-pyrrolidinone in the presence of triethylamine for 5 min at 155° C. in EtOH (63.4%).

$^1$H NMR (DMSO-d6) δ 10.98 (s, 1H), 7.92 (d, J=7.54 Hz, 1H), 7.68 (s, 1H), 7.56 (d, 3H), 7.38 (m, 3H), 6.3 (d, J=7.16 Hz, 1H), 3.51 (m, 2H), 3.31 (m, 4H), 2.2 (t, J=7.9 Hz, 2H), 1.94-1.79(m, 4H).

M$^-$(ES): 450.8; M$^+$(ES): 453.2; HPLC (max plot) 97.1%; Rt: 2.83 min.

Example 115

[4-(3-chlorophenyl)-1,3-thiazol-2(3H)-ylidene](2-{[3-(2-oxopyrrolidin-1-yl)propyl]amino}pyrimidin-4-yl)acetonitrile

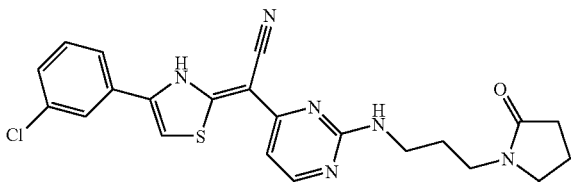

Following the general strategies and protocols outlined in the procedure E, the title compound was obtained from [4-(3-chlorophenyl)-1,3-thiazol-2(3H)-ylidene](2-chloropyrimidin-4-yl)acetonitrile and 1-(3-aminopropyl)-2-pyrrolidinone in the presence of triethylamine for 5 min at 155° C. in EtOH (66.3%).

$^1$H NMR (DMSO-d6) δ 10.8 (s, 1H), 8.00 (s, 1H), 7.92 (d, J=7.53 Hz, 1H), 7.82 (s, 1H), 7.47 (m, 2H), 7.36 (br d, 2H), 6.29 (d, J=7.53 Hz, 1H), 3.52 (m, 2H), 3.35-3.26 (m, 4H), 2.21 (t, J=7.54 Hz, 2H), 1.92 (quint, J=7.53 Hz, 2H), 1.84 (quint, J=6.78 Hz, 2H).

M$^-$(ES): 451.1; M$^+$(ES): 453.1; HPLC (max plot) 97.8%; Rt: 3.06 min.

Example 116

[4-(3-chlorophenyl)-1,3-thiazol-2(3H)-ylidene]{2-[(2-pyridin-3-ylethyl)amino]pyrimidin-4-yl}acetonitrile

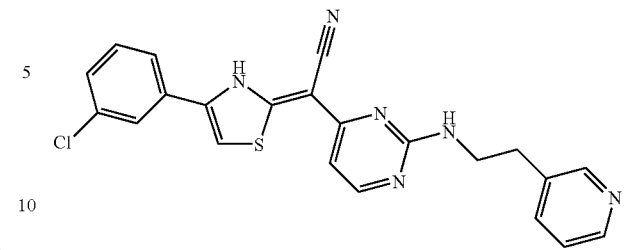

Following the general strategies and protocols outlined in the procedure E, the title compound was obtained from [4-(3-chlorophenyl)-1,3-thiazol-2(3H)-ylidene](2-chloropyrimidin-4-yl)acetonitrile and 3-(2-aminoethyl)pyridine in the presence of triethylamine for 5 min at 155° C. in EtOH (57.4%).

$^1$H NMR (DMSO-d6) δ 10.9 (s, 1H), 8.82 (s, 1H), 8.78 (d, J=5.08 Hz, 1H), 8.41 (d, J=8.1 Hz, 1H), 8.00 (s, 1H), 7.95 (d, J=7.72 Hz, 2H), 7.8 (s, 1H), 7.63 (s, 1H), 7.46 (t, J=7.7 Hz, 1H), 7.37 (d, J=7.17 Hz, 2H), 6.31 (d, J=7.34 Hz, 1H), 3.91 (m, 2H), 3.16 (br t, 2H).

M$^-$(ES): 431.1; M$^+$(ES): 432.9; HPLC (max plot) 95.5%; Rt: 2.45 min.

Example 117

[4-(2-chlorophenyl)-1,3-thiazol-2(3H)-ylidene]{2-[(2-pyridin-3-ylethyl)amino]pyrimidin-4-yl}acetonitrile

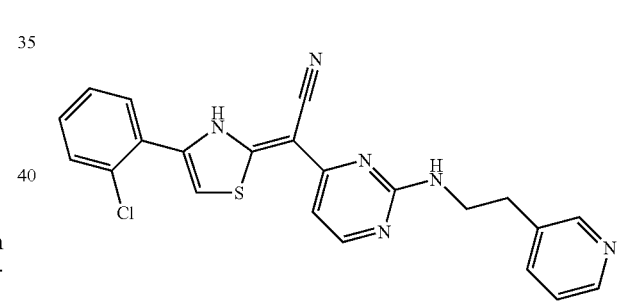

Following the general strategies and protocols outlined in the procedure E, the title compound was obtained from [4-(2-chlorophenyl)-1,3-thiazol-2(3H)-ylidene](2-chloropyrimidin-4-yl)acetonitrile and 3-(2-aminoethyl)pyridine in the presence of triethylamine for 5 min at 155° C. in EtOH (34.1%).

$^1$H NMR (DMSO-d6) δ 10.74 (s, 1H), 8.71 (s, 1H), 8.66 (d, J=4.52 Hz, 1H), 8.26 (d, J=8.67 Hz, 1H), 7.89 (d, J=7.53 Hz, 1H), 7.79 (m, 1H), 7.61 (s, 1H), 7.49 (d, J=7.53 Hz, 1H), 7.45-7.40 (m, 1H), 7.33 (m, 2H), 6.25 (d, J=7.54 Hz, 1H), 3.84 (m, 2H), 3.08 (br t, 2H).

M$^-$(ES): 431.1; M$^+$(ES): 433.1; HPLC (max plot) 91.6%; Rt: 2.16 min.

Example 118

[2-(cyclopropylamino)pyrimidin-4-yl][4-(4-methoxyphenyl)-1,3-thiazol-2(3H)-ylidene]acetonitrile

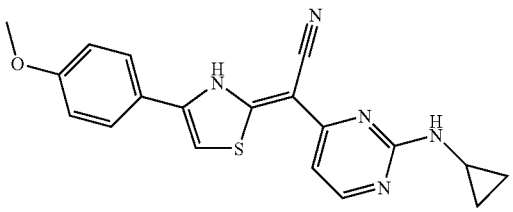

Following the general strategies and protocols outlined in the procedure E, the title compound was obtained from (2-chloropyrimidin-4-yl)[4-(4-methoxyphenyl)-1,3-thiazol-2(3H)-ylidene]acetonitrile and cyclopropylamine in the presence of triethylamine for 5 min at 155° C. in EtOH (37.9%).

$^1$H NMR (DMSO-d6) δ 8.2 (br s, 1H), 7.83 (d, J=8.66 Hz, 2H), 7.52 (s, 1H), 7.45 (d, J=7.54 Hz, 1H), 6.99 (d, J=9.04 Hz, 2H), 6.36 (d, J=9.04 Hz, 1H), 3.79 (s, 3H), 2.87 (br s, 1H), 0.87-0.75 (m, 2H), 0.65-0.56 (m, 2H).

M$^-$(ES): 362.2; M$^+$(ES): 634.1; HPLC (max plot) 100%; Rt: 3.00 min.

Example 119

[4-(2-chlorophenyl)-1,3-thiazol-2(3H)-ylideneN][2-(cyclopropylamino)pyrimidin-4-yl]acetonitrile

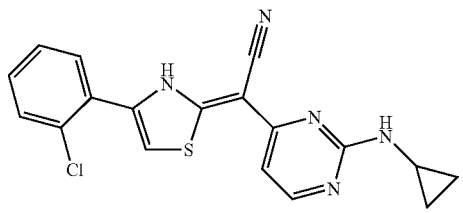

Following the general strategies and protocols outlined in the procedure E, the title compound was obtained from [4-(2-chlorophenyl)-1,3-thiazol-2(3H)-ylidene](2-chloropyrimidin-4-yl)acetonitrile and cyclopropylamine in the presence of triethylamine for 5 min at 155° C. in EtOH (58.5%).

$^1$H NMR (DMSO-d6) δ 7.89 (br d, 1H), 7.67 (s, 1H), 7.56 (dd, J=7.16 Hz, J=1.89 Hz, 1H), 7.37-7.46 (m, 3H), 6.37 (d, J=6.78 Hz, 1H), 2.85 (br s, 1H), 2.91-2.75 (m, 2H), 0.70-0.50 (m, 2H).

M$^-$(ES): 366.1; M$^+$(ES): 368.1; HPLC (max plot) 100%; Rt: 3.06 min.

Procedure F

Example 120

N-[3-({4-[cyano(4-ethyl-1,3-thiazol-2(3H)-ylidene)methyl]pyrimidin-2-yl}amino)propyl]acetamide

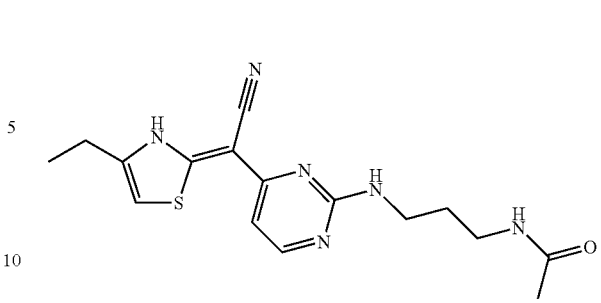

To a solution of {2-[(3-aminopropyl)amino]pyrimidin-4-yl}(4-ethyl-1,3-thiazol-2(3H)-ylidene)acetonitrile (165 mg, 0.37 mmol) in DMA (3 mL) were added and Et$_3$N (0.048 mL, 0.37 mmol) and acetyl chloride (0.04 mL, 0.46 mmol) at 0° C. The resulting solution was stirred at 0° C. for 3 h. The solvent was evaporated under reduced pressure (Genevac) affording the title compound as a crude yellow solid. HPLC (max plot) 92%. The solid was taken up in DCM and an excess TFA was added. The yellow precipitate formed after addition of ether was filtered off and washed with ether (×3) then dried under vacuum at 40° C. After purification by preparative HPLC then lyophilization, 148 mg of the title compound was obtained as a TFA salt (yellow powder, Y=87.3%)

$^1$H NMR (DMSO-d$_6$) δ 7.93-7.90 (m, 2H), 7.65 (br d, 1H), 7.01 (s, 1H), 6.43 (d, J=7.1 Hz, 1H), 3.56-3.44 (m, 2H), 3.16-3.10 (m, 2H), 2.69 (q, J=7.5 Hz, 2H), 1.78 (s, 3H), 1.75-1.71 (m, 2H), 1.20 (t, J=7.5 Hz, 3H).

M$^+$(ES): 345.2; HPLC (max plot) 99%; Rt: 1.97 min.

Example 121

N-[2-({4-[(4-tert-butyl-1,3-thiazol-2(3H)-ylidene)(cyano)methyl]pyrimidin-2-yl}amino)ethyl)acetamide

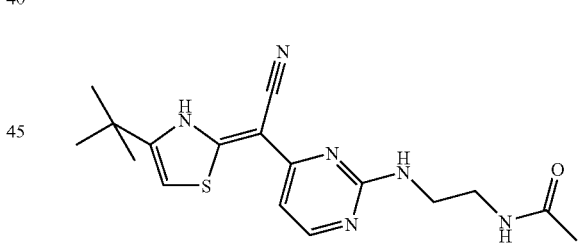

Following the general strategies and protocols outlined in the procedure F, the title compound was obtained from {2-[(2-aminoethyl)amino]pyrimidin-4-yl}(4-tert-butyl-1,3-thiazol-2(3H)-ylidene)acetonitrile and acetyl chloride in the presence of triethylamine for 1 h 30 at 0° C. in DMA (58.9%).

$^1$H NMR (DMSO-d6) δ 8.01-7.98 (m, 1H, exchangeable), 7.69 (br s, 1H, exchangeable), 7.49 (br d, 1H), 6.88 (s, 1H), 6.36 (d, J=7.1 Hz, 1H), 3.67-3.38 (m, 2H), 3.34-3.30 (m, 2H), 1.81 (s, 3H), 1.30 (s, 9H).

M$^+$(ES): 359.2; HPLC (max plot) 100%; Rt: 2.24 min.

Example 122

{2-[(1-acetylpiperidin-4-yl)amino]pyrimidin-4-yl}(4-ethyl-1,3-thiazol-2(3H)-ylidene)acetonitrile

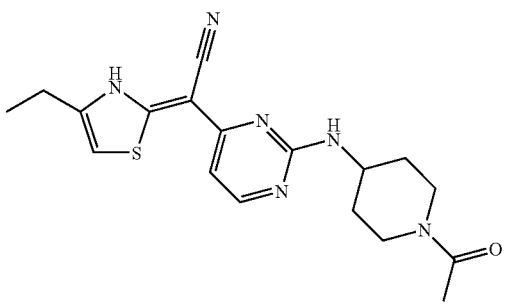

Following the general strategies and protocols outlined in the procedure F, the title compound was obtained from the TFA salt of {2-[(piperidin-4-yl)amino]pyrimidin-4-yl}(4-ethyl-1,3-thiazol-2(3H)-ylidene)acetonitrile and acetyl chloride in the presence of triethylamine for 1 h 30 at 0° C. to r.t. in DCM (3.8%).

1H NMR (DMSO-d6) δ 8.00-7.40 (2 br s, 2H including 1 exchangeable), 7.01 (s, 1H), 6.40 (d, J=6.1 H, 1H), 4.40-4.25 (m, 1H), 4.00-3.75 (m, 2H), 3.00-2.60 (m, 7H [2+2+3]), 2.10-1.90 (m, 5H, [2+3]), 1.55-1.10 (m, 5H, [3+2]).

M$^+$(ES): 371; HPLC (max plot) 99%; Rt: 2.19 min.

Procedure G

Example 123

(4-tert-butyl-1,3-thiazol-2(3H)-ylidene)(2-{[3-(2,5-dioxopyrrolidin-1-yl)propyl]amino}pyrimidin-4-yl)acetonitrile

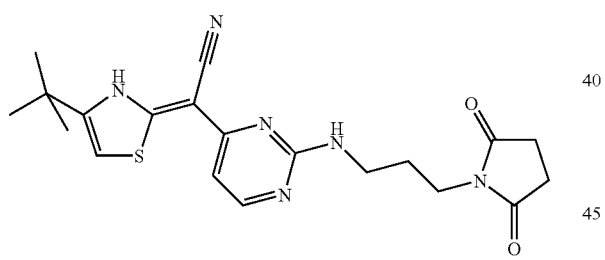

To a suspension of {2-[(3-aminopropyl)amino]pyrimidin-4-yl}(4-tert-butyl-1,3-thiazol-2(3H)-ylidene)acetonitrile (200 mg, 0.61 mmol) in DMA in a microwave tube (X2) were added succinic anhydride (122 mg, 1.21 mmol) and NMM (0.133 mL, 1.21 mmol) and after sonication the solution was heated up to 250° C. on normal absorption for 15 min. Both tubes were gathered and 10 mL of water were added then the suspension was left at 4° C. for ON. The solid obtained was filtered off through paper and washed with water (3×) then dried under vacuum at 40° C. for 5 days, affording the crude title compound as a brown powder. The solid was taken up in DCM then an excess TFA was added. To the black solution was added ether and the suspension was left at 4° C. for 2 h. The precipitate formed was filtered off then washed with ether (3×), affording 353.9 mg of the title compound as a TFA salt (HPLC (max plot) 92%).

After purification by preparative HPLC then lyophilization, 210 mg of the title compound were obtained as a TFA salt (yellow powder, Y=33%).

$^1$H NMR (DMSO-d$_6$) δ 11.0-10.7 (br s, 1H, exchangeable), 7.55-7.35 (m, 2H, including one H exchangeable), 6.87 (s, 1H), 6.32 (d, J=6.0 Hz, 1H), 3.70-3.30 (m, 4H), 2.58 (s, 4H), 1.95-1.70 (m, 2H), 1.29 (s, 9H).

M$^-$(ES): 411; M$^+$(ES): 413; HPLC (max plot) 95%; Rt: 2.50 min.

Example 124

(2-{[3-(2,5-dioxopyrrolidin-1-yl)propyl]amino}pyrimidin-4-yl)(4-ethyl-1,3-thiazol-2(3H)-ylidene)acetonitrile

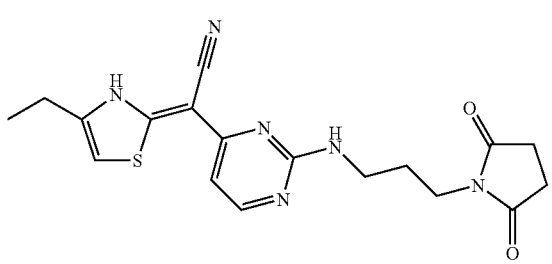

Following the general strategies and protocols outlined in the procedure G, the title compound was obtained from {2-[(3-aminopropyl)amino]pyrimidin-4-yl}(4-ethyl-1,3-thiazol-2(3H)-ylidene)acetonitrile and succinic anhydride in the presence of NMM for 15 min at 250° C. in DMA as a yellow powder (23.6%).

$^1$H NMR (DMSO-d$_6$) δ 7.88 (s, 1H), 7.64 (br d, 1H), 7.00 (s, 1H), 6.42 (d, J=7.2 Hz, 1H), 3.48-3.43 (m, 4H), 2.69 (q, J=7.5 Hz, 2H), 2.59 (s, 4H), 1.85-1.81 (m, 2H), 1.20 (t, J=7.5 Hz, 3H).

M$^+$(ES): 385.2; HPLC (max plot) 97.3%; Rt: 2.11 min.

Example 125

(4-ethyl-1,3-thiazol-2(3H)-ylidene)(2-{[1-(methylsulfonyl)piperidin-4-yl]amino}pyrimidin-4-yl)acetonitrile trifluoroacetate

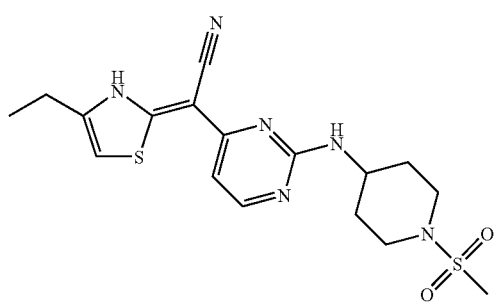

To a suspension of {2-[(piperidin-4-yl)amino]pyrimidin-4-yl}(4-ethyl-1,3-thiazol-2(3H)-ylidene)acetonitrile (102 mg, 0.18 mmol) in DCM (3 mL) were added at 0° C. triethylamine (0.09 mL, 0.64 mmol) and a solution of methylsulphonyl chloride (0.017 mL, 0.22 mmol) in DCM (1 mL). The bright yellow solution was stirred at r.t for 2 h. Water was added and the product was extracted with DCM (3×). The organic phase was washed with water (2×) then brine (1×) and dried over MgSO$_4$. After removal of the solvent, the residue was taken up in DCM (1 mL) and 20 μL of TFA were added. A fluffy precipitate formed upon addition of ether. It was filtered off and washed with ether (3×) then dried under vacuum at 40° C., affording 42.9 mg of the title compound as a TFA salt (yellow fluffy solid, 41%).

¹H NMR (DMSO-d6) δ 11.3-11.0 (br s, 1H exchangeable), 8.1-7.9 (br s, 1H, exchangeable), 7.70-7.60 (m, 1H), 7.06 (s, 1H), 6.43 (d, J=7.2 Hz, 1H), 4.17-3.90 (m, 1H), 3.7-3.5 (m, 2H), 3.05-2.85 (m, 5H [2+3]), 2.70 (q, J=7.9, 7.5 Hz, 2H), 2.15-2.07 (m, 2H), 1.70-1.50 (m, 2H), 1.21 (t, J=7.5 Hz, 3H).

M⁺(ES): 407; HPLC (max plot) 92%; Rt: 2.29 min.

Example 126

N~3~-{4-[(4-tert-butyl-1,3-thiazol-2(3H)-ylidene)(cyano)methyl]pyrimidin-2-yl}-N~1~,N~1~-dimethyl-beta-alaninamide

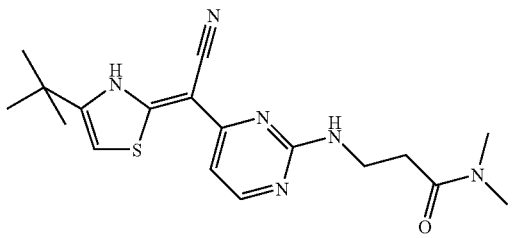

To a solution of dimethylamine (0.051 mL, 1 mmol) in DCE was added a solution of TMA 2M in hexane (499 mmol, 1 mmol) and the mixture was stirred 30 min at r.t. To this solution was added a solution of methyl N-{4-[(4-tert-butyl-1,3-thiazol-2(3H)-ylidene)(cyano)methyl]pyrimidin-2-yl}-beta-alaninate (72 mg, 0.2 mmol) in DCE and the mixture was refluxed under inert atmosphere overnight then stirred for a week at r.t. The mixture was diluted with DCM then water was added. The suspension was filtered through celite. The filtrate was washed with aqueous NaHCO3 5% (×2) then brine and it was dried over MgSO4. The solvent was removed under reduced pressure affording the title compound as yellow solid (HPLC max plot 86%).

The solid was taken up in DCM and 10 μL of TFA were added then ether in large excess. As no precipitation occurred, the solvents were evaporated under reduced pressure. The solid residue obtained was taken up in ether, sonicated then filtered off and washed with ether (2×). It was then dried under vacuum at 40° C. ON, affording 38 mg of the title compound as a TFA salt (pale yellow powder Y=39%).

¹H NMR (DMSO-d6) δ 7.65-7.45 (m, 2H, including 1 exchangeable), 6.88 (s, 1H), 6.34 (d, J=7.2 Hz, 1H), 3.80-3.70 (m, 1H), 2.91 (s, 3H), 2.84 (s, 3H), 2.67 (t, J=6.0 Hz, 2H), 1.29 (s, 9H).

M⁺(ES): 373; HPLC (max plot) 96%; Rt: 2.50 min.

Procedure H

Example 127

N-{3-[{4-[(4-tert-butyl-1,3-thiazol-2(3H)-ylidene)(cyano)methyl]pyrimidin-2-yl}(methyl)amino]propyl}acetamide

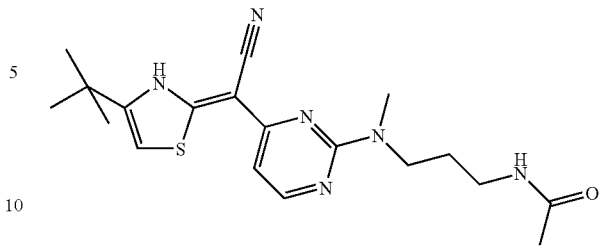

To suspension of N-[3-({4-[(4-tert-butyl-1,3-thiazol-2(3H)-ylidene)(cyano)methyl]pyrimidin-2-yl}amino)propyl]acetamide (290 mg, 0.68 mmol) in THF (7 ml) were added potassium tert-butoxide (91 mg, 0.81 mmol) and methyl iodide (0.085 mL, 1.35 mmol). The resulting mixture was stirred 2 h at rt. LC/MS analysis showed the presence two peaks with the same mass in a proportion of 7:3. The THF was evaporated and the residue was taken up in water and extracted with EtOAc (3×). The combined organic layer was washed with brine, dried with MgSO4 and the solvent was evaporated under reduced pressure to give a gummy residue which was the mixture of to compounds of the same mass. It was taken up in DCM and an excess TFA then ether were added to the solution. As no precipitation occurred, the solution was concentrated under reduced pressure and the residue was purified by preparative HPLC to give 93 mg of the title compound as a TFA salt pyrimidine (yellow solid, Y=27.3%).

¹H NMR (DMSO-d6) δ 7.94-7.85 (m, 1H, exchangeable), 7.75-7.46 (m, 2H, 1 exchangeable), 6.89 (s, 1H), 6.40 (br d, 1H), 3.61-3.59 (m, 2H), 3.45 (s, 3H), 3.16-3.12 (m, 2H), 1.78 (s, 3H), 1.78-1.70 (m, 2H), 1.30 (s, 9H)

M⁺(ES): 387.3; HPLC (max plot) 100%; Rt: 2.35 min.

HPLC (max plot) 99.3%, rt=3.24 min., LCMS(ES+): 387.27, H-NMR (DMSO) 8.34 (br d, 1H), 7.84-7.75 (m, 1H, exchangeable), 7.52 (br s, 1H, exchangeable), 7.35 (s, 1H), 6.66 (br d, 1H), 3.32-3.21 (m, 2H), 3.08-3.01 (m, 2H), 2.12 (s, 3H), 1.77 (s, 3H), 1.66-1.59 (m, 2H), 1.27 (s, 9H).

Example 128

N-[3-({4-[(4-tert-butyl-3-methyl-1,3-thiazol-2(3H)-ylidene)(cyano)methyl]pyrimidin-2-yl}amino)propyl]acetamide

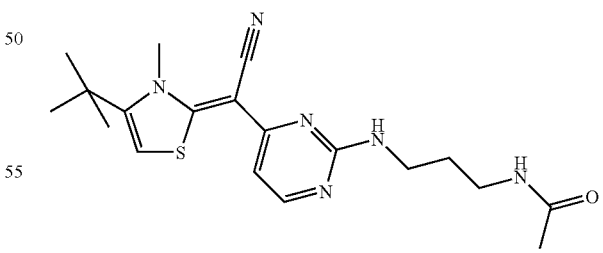

Following the general strategies and protocols outlined in the procedure H, 70 mg the title compound were obtained after purification of the second product obtained during the synthesis of Example 115 (orange oil, 20.6%).

¹H NMR (DMSO-d6) δ 8.34 (br d, 1H), 7.84-7.75 (m, 1H, exchangeable), 7.52 (br s, 1H, exchangeable), 7.35 (s, 1H), 6.66 (br d, 1H), 3.32-3.21 (m, 2H), 3.08-3.01 (m, 2H), 2.12 (s, 3H), 1.77 (s, 311), 1.66-1.59 (m, 2H), 1.27 (s, 9H).

M+(ES): 387.3; HPLC (max plot) 99.3%; Rt: 3.24 min.

Procedure I

Example 129

(4-ethyl-1,3-thiazol-2(3H)-ylidene)(2-{[4-(morpholin-4-ylmethyl)benzyl]oxy}pyrimidin-4-yl)acetonitrile

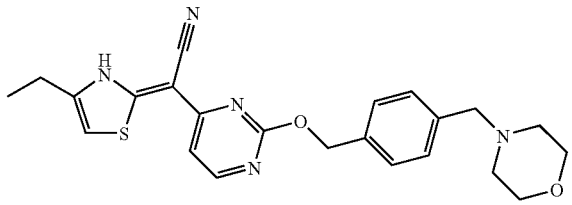

To a suspension of NaH (99 mg, 2.27 mmol) in ACN (4 mL) was added a solution of N-(4-hydroxymethylbenzyl) morpholine 313 mg, 1.51 mmol) in ACN (4 mL). The mixture was stirred 1 h at rt. Then (2-chloropyrimidin-4-yl)(4-ethyl-1,3-thiazol-2(3H)-ylidene)acetonitrile (200 mg, 0.76 mmol) was added portion wise. The resulting mixture was heated up at 80° C. for 5 h. After cooling down to rt the ACN was evaporated. EtOAc (5 mL) was added to the residue. After one night at 4° C., the yellow solid was filtered off affording the title compound as a free base (HPLC (max plot) 73.9%). The solid was taken up in DCM and excess TFA then ether were added. The precipitate formed was filtered off, washed with ether (3×) then dried under reduced pressure at 40° C. overnight, affording 409 mg of the title compound as a diTFA salt (Yellow powder, Y=81.1%)

$^1$H NMR (DMSO-$d_6$) δ 10.26 (br s, 1H), 7.76 (br d, 1H), 7.61 (d, J=7.9 Hz, 2H), 7.53 (d, J=7.9 Hz, 2H), 6.90 (s, 1H), 6.61 (br d, 1H), 5.64 (s, 2H), 4.36 (s, 2H), 4.03-3.85 (m, 2H), 3.74-3.53 (m, 2H), 3.32-3.04 (m, 4H), 2.66 (q, J=7.5 Hz, 2H), 1.19 (br t, 3H).

M+(ES): 436.0; HPLC (max plot) 98.2%; Rt: 1.82 min.

Example 130

{2-[3-(dimethylamino)propoxy]pyrimidin-4-yl}(4-ethyl-1,3-thiazol-2(3H)-ylidene)acetonitrile

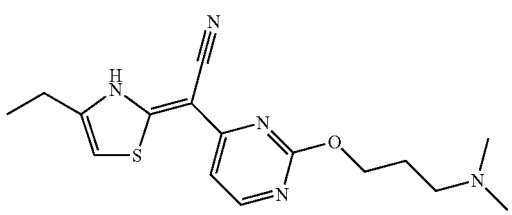

Following the general strategies and protocols outlined in the procedure I, the title compound was obtained from 2-chloropyrimidin-4-yl)(4-ethyl-1,3-thiazol-2(3H)-ylidene)acetonitrile and 3-dimethylamino-1-propanol in the presence of sodium hydride for 4 h at rt then 80° C. in ACN as a yellow powder (61%).

$^1$H NMR (DMSO-$d_6$) δ 9.51 (br s, 1H), 7.75 (br d, 1H), 6.91 (s, 1H), 6.59 (br d, 1H), 4.60-4.56 (m, 2H), 3.25-3.20 (m, 2H), 2.81 (s, 6H), 2.67 (q, J=7.5 Hz, 2H), 2.19-2.15 (m, 2H), 1.20 (t, J=7.5 Hz, 3H).

M−(ES): 330.3; HPLC (max plot) 99.9%; Rt: 1.29 min.

General Procedure J 10 mg of Building Blocks were dissolved in 0.3 mL of DMA. Et$_3$N (4 eq.) and the amines (4 eq.) dissolved in DMA (0.3 mL) were then added to the reaction mixtures and the plate was sealed and heated in a microwave (Mars 5) as follows: 2 plates at a time were heated 4 min at 300 Watts and then left to cool down for 10 min. This was repeated 4 times. The reaction mixtures were then transferred into a 2 mL plate and the solvent was removed in the Genevac. Work up: 1 mL of water/CH$_3$COOH (2%) was then added and the plate was shaken for 3h00. The aqueous layer was removed using the Zymark, leaving the solid behind. This solid was further washed with water (2×). 1 mL of MeOH/TFA (20%) was added to the plates, which were shaken at rt for 48 h and the supernatant was collected using the Lissy. Analytical plates were made and the solvents were removed in the Genevac.

Example 131

[4-(4-chlorophenyl)-1,3-thiazol-2(3H)-ylidene]{5-methyl-2-[(3-pyrrolidin-1-ylpropyl)amino]pyrimidin-4-yl}acetonitrile

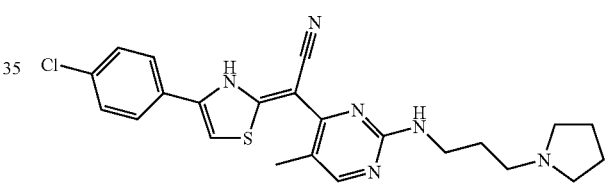

Following the general strategies and protocols outlined in the procedure J, the title compound was obtained from (2-chloro-5-methylpyrimidin-4-yl)[4-(4-chlorophenyl)-1,3-thiazol-2(3H)-ylidene]acetonitrile and 1-(3-aminopropyl) pyrrolidine in the presence of triethylamine in DMA.

M+(ES): 453.2; LC (215 nm): 91%

Example 132

[4-(4-chlorophenyl)-1,3-thiazol-2(3H)-ylidene]{2-[(3-pyrrolidin-1-ylpropyl)amino]pyrimidin-4-yl}acetonitrile

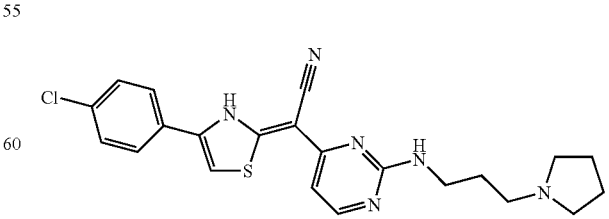

Following the general strategies and protocols outlined in the procedure J, the title compound was obtained from [4-(4-chlorophenyl)-1,3-thiazol-2(3H)-ylidene](2-chloropyrimidin-4-yl)acetonitrile and 1-(3-aminopropyl)pyrrolidine in the presence of triethylamine in DMA.

M⁺(ES): 439.2; LC (215 nm): 86.8%

Example 133

[4-(dimethylamino)-6-(octahydroquinolin-1(2H)-yl)-1,3,5-triazin-2-yl](4-phenyl-1,3-thiazol-2(3H)-ylidene)acetonitrile

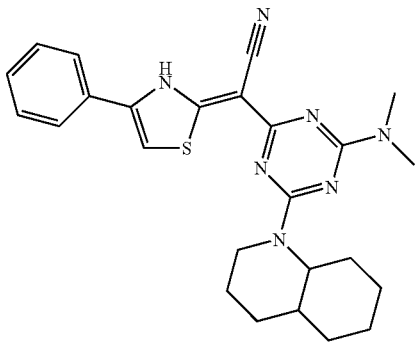

Following the general strategies and protocols outlined in the procedure J, the title compound was obtained from [4-chloro-6-(dimethylamino)-1,3,5-triazin-2-yl](4-phenyl-1,3-thiazol-2(3H)-ylidene)acetonitrile and decahydroquinoline in the presence of triethylamine in DMA.

M⁺(ES): 460.2; LC (215 nm): 91.4%

Example 134

[2-(cyclohexylamino)-5-methylpyrimidin-4-yl](4-phenyl-1,3-thiazol-2(3H)-ylidene)acetonitrile

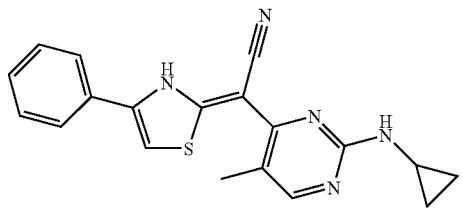

Following the general strategies and protocols outlined in the procedure J, the title compound was obtained from (2-chloro-5-methylpyrimidin-4-yl)(4-phenyl-1,3-thiazol-2 (3H)-ylidene)acetonitrile and cyclohexamine in the presence of triethylamine in DMA.

M⁺(ES): 390.2; LC (215 nm): 67.7%

Example 135

[2-(cyclohexylamino)pyrimidin-4-yl](4-phenyl-1,3-thiazol-2(3H)-ylidene)acetonitrile

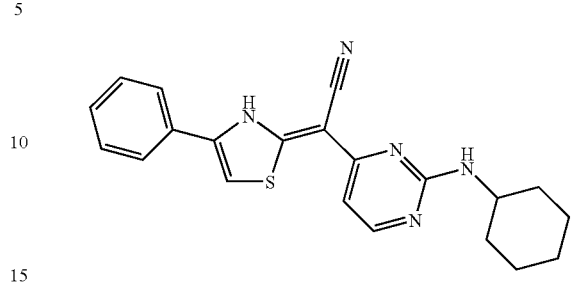

Following the general strategies and protocols outlined in the procedure J, the title compound was obtained from (2-chloropyrimidin-4-yl)(4-phenyl-1,3-thiazol-2(3H)-ylidene)acetonitrile and cyclohexamine in the presence of triethylamine in DMA.

M⁺(ES): 376.11; LC (215 nm): 92%

Example 136

[4-(methylamino)-6-(4-methylpiperidin-1-yl)-1,3,5-triazin-2-yl](4-methyl-1,3-thiazol-2(3H)-ylidene)acetonitrile

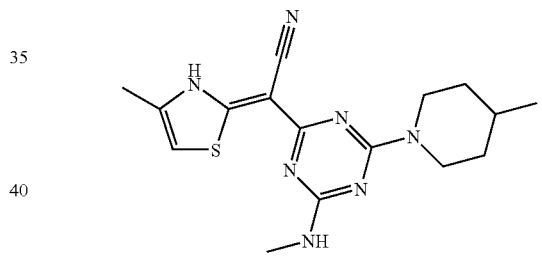

Following the general strategies and protocols outlined in the procedure J, the title compound was obtained from [4-chloro-6-(methylamino)-1,3,5-triazin-2-yl](4-methyl-1,3-thiazol-2(3H)-ylidene)acetonitrile and 4-methylpiperidine in the presence of triethylamine in DMA.

M⁺(ES): 344.1; LC (215 nm): 90.7%

Example 137

[4-(cyclohexylamino)-6-(methylamino)-1,3,5-triazin-2-yl](4-methyl-1,3-thiazol-2(3H)-ylidene)acetonitrile

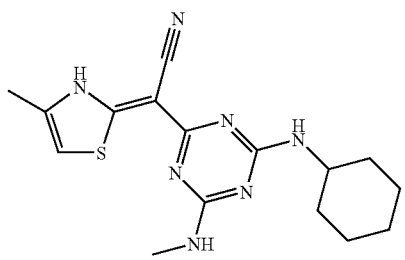

Following the general strategies and protocols outlined in the procedure J, the title compound was obtained from [4-chloro-6-(methylamino)-1,3,5-triazin-2-yl](4-methyl-1,3-thiazol-2(3H)-ylidene)acetonitrile and cyclohexamine in the presence of triethylamine in DMA.

$M^+$(ES): 344.1; LC (215 nm): 97.9%

Example 138

[5-methyl-2-(4-methylpiperidin-1-yl)pyrimidin-4-yl](4-phenyl-1,3-thiazol-2(3H)-ylidene)acetonitrile

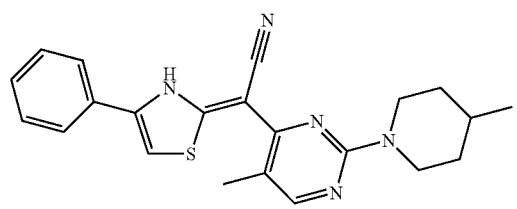

Following the general strategies and protocols outlined in the procedure J, the title compound was obtained from (2-chloro-5-methylpyrimidin-4-yl)(4-phenyl-1,3-thiazol-2(3H)-ylidene)acetonitrile and 4-methylpiperidine in the presence of triethylamine in DMA.

$M^+$(ES): 390.1; LC (215 nm): 86.2%

Example 139

[2-(cyclopropylamino)-5-methylpyrimidin-4-yl](4-phenyl-1,3-thiazol-2(3H)-ylidene)acetonitrile

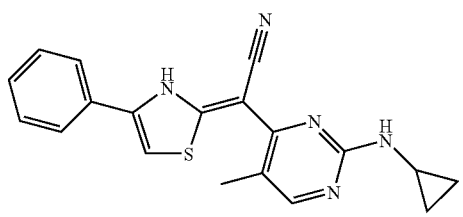

Following the general strategies and protocols outlined in the procedure J, the title compound was obtained from (2-chloro-5-methylpyrimidin-4-yl)(4-phenyl-1,3-thiazol-2(3H)-ylidene)acetonitrile and cyclopropylamine in the presence of triethylamine in DMA.

$M^+$(ES): 348.1; LC (215 nm): 87.2%

Example 140

[2-(cyclopropylamino)pyrimidin-4-yl](4-phenyl-1,3-thiazol-2(3H)-ylidene)acetonitrile

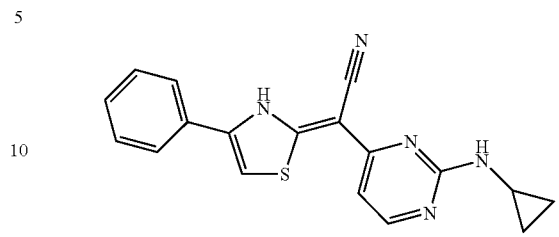

Following the general strategies and protocols outlined in the procedure J, the title compound was obtained from (2-chloropyrimidin-4-yl)(4-phenyl-1,3-thiazol-2(3H)-ylidene)acetonitrile and cyclopropylamine in the presence of triethylamine in DMA.

$M^+$(ES): 334.1; LC (215 nm): 81%

Example 141

[2-(cyclopentylamino)-5-methylpyrimidin-4-yl](4-phenyl-1,3-thiazol-2(3H)-ylidene)acetonitrile

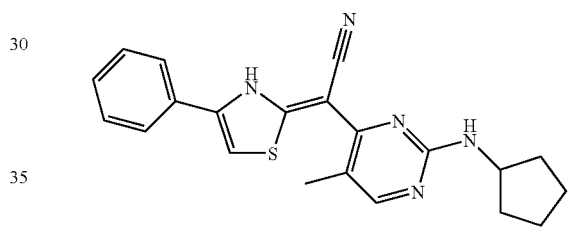

Following the general strategies and protocols outlined in the procedure J, the title compound was obtained from (2-chloro-5-methylpyrimidin-4-yl)(4-phenyl-1,3-thiazol-2(3H)-ylidene)acetonitrile and cyclopentylamine in the presence of triethylamine in DMA.

$M^+$(ES): 376.2; LC (215 nm): 70%

Example 142

{5-methyl-2-[(1-methylbutyl)amino]pyrimidin-4-yl}(4-phenyl-1,3-thiazol-2(3H)-ylidene)acetonitrile

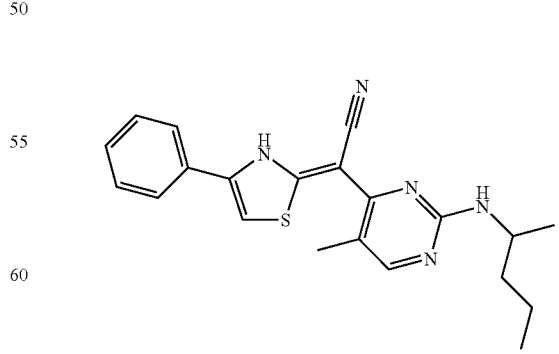

Following the general strategies and protocols outlined in the procedure J, the title compound was obtained from (2-chloro-5-methylpyrimidin-4-yl)(4-phenyl-1,3-thiazol-2

(3H)-ylidene)acetonitrile and (+/−)-2-aminopentane in the presence of triethylamine in DMA.

M⁺(ES): 378.2; LC (215 nm): 73.8%

Example 143

[2-(cyclopentylamino)pyrimidin-4-yl](4-phenyl-1,3-thiazol-2(3H)-ylidene)acetonitrile

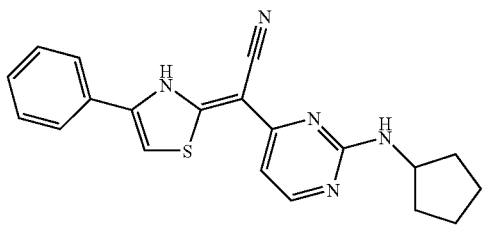

Following the general strategies and protocols outlined in the procedure J, the title compound was obtained from (2-chloropyrimidin-4-yl)(4-phenyl-1,3-thiazol-2(3H)-ylidene)acetonitrile and cyclopentylamine in the presence of triethylamine in DMA.

M⁺(ES): 362.1; LC (215 nm): 84.8%

Example 144

{5-methyl-2-[(3-pyrrolidin-1-ylpropyl)amino]pyrimidin-4-yl}(4-phenyl-1,3-thiazol-2(3H)-ylidene)acetonitrile

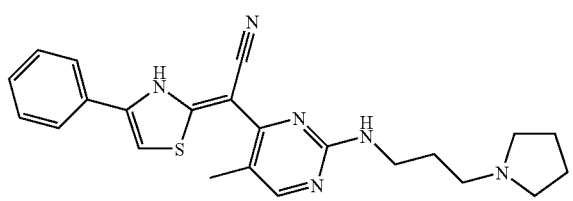

Following the general strategies and protocols outlined in the procedure J, the title compound was obtained from (2-chloro-5-methylpyrimidin-4-yl)(4-phenyl-1,3-thiazol-2 (3H)-ylidene)acetonitrile and 1-(3-aminopropyl)pyrrolidine in the presence of triethylamine in DMA.

M⁺(ES): 419.2; LC (215 nm): 88.9%

Example 145

{2-[(1-methylbutyl)amino]pyrimidin-4-yl}(4-phenyl-1,3-thiazol-2(3H)-ylidene)acetonitrile

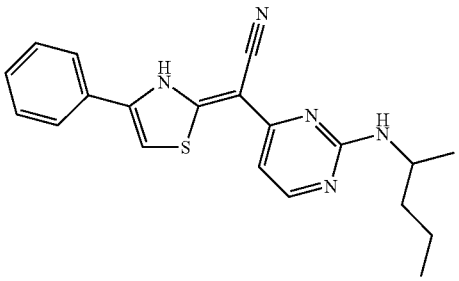

Following the general strategies and protocols outlined in the procedure J, the title compound was obtained from (2-chloropyrimidin-4-yl)(4-phenyl-1,3-thiazol-2(3H)-ylidene)acetonitrile and (+/−)-2-aminopentane in the presence of triethylamine in DMA.

M⁺(ES): 364.1; LC (215 nm): 79.2%

Example 146

{6-[(2-furylmethyl)amino]pyrimidin-4-yl}(4-methyl-1,3-thiazol-2(3H)-ylidene)acetonitrile

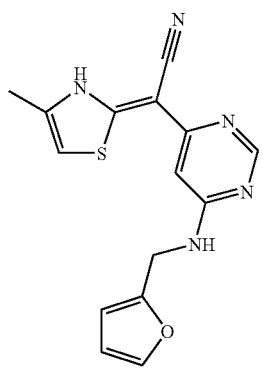

Following the general strategies and protocols outlined in the procedure J, the title compound was obtained from (6-chloropyrimidin-4-yl)(4-methyl-1,3-thiazol-2(3H)-ylidene)acetonitrile and furfurylamine in the presence of triethylamine in DMA.

M⁺(ES): 312.1; LC (215 nm): 60.8%

Example 147

[6-(4-ethylpiperazin-1-yl)pyrimidin-4-yl](4-methyl- 1,3-thiazol-2(3H)-ylidene)acetonitrile

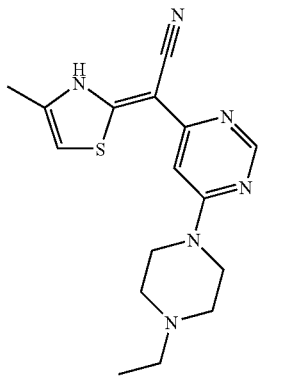

Following the general strategies and protocols outlined in the procedure J, the title compound was obtained from (6-chloropyrimidin-4-yl)(4-methyl-1,3-thiazol-2(3H)-ylidene)acetonitrile and 1-ethylpiperazine in the presence of triethylamine in DMA.

M$^+$(ES): 329.2; LC (215 nm): 77.9%

Example 148

(4-phenyl-1,3-thiazol-2(3H)-ylidene){2-[(3-pyrrolidin-1-ylpropyl)amino]pyrimidin-4-yl}acetonitrile

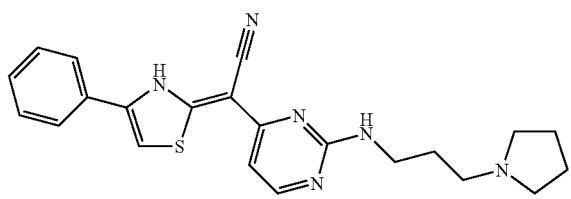

Following the general strategies and protocols outlined in the procedure J, the title compound was obtained from (2-chloropyrimidin-4-yl)(4-phenyl-1,3-thiazol-2(3H)-ylidene)acetonitrile and 1-(3-aminopropyl)pyrrolidine in the presence of triethylamine in DMA.

M$^+$(ES): 405.2; LC (215 nm): 82.2%

Example 149

[2-(cyclopentylamino)-6-methylpyrimidin-4-yl](4-phenyl-1,3-thiazol-2(3H)-ylidene)acetonitrile

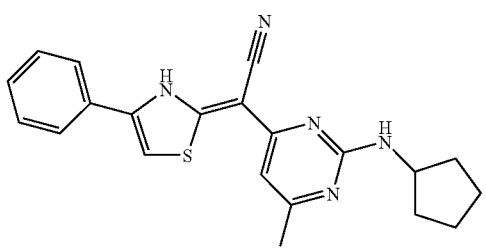

Following the general strategies and protocols outlined in the procedure J, the title compound was obtained from (2-chloro-6-methylpyrimidin-4-yl)(4-phenyl-1,3-thiazol-2(3H)-ylidene)acetonitrile and cyclopentylamine in the presence of triethylamine in DMA.

M$^+$(ES): 376.2; LC (215 nm): 81.2%

Example 150

[4-(4-ethylpiperazin-1-yl)-6-morpholin-4-yl-1,3,5-triazin-2-yl](4-phenyl-1,3-thiazol-2(3H)-ylidene)acetonitrile

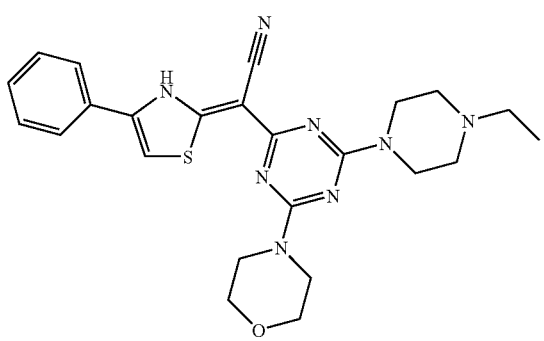

Following the general strategies and protocols outlined in the procedure J, the title compound was obtained from (4-chloro-6-morpholin-4-yl-1,3,5-triazin-2-yl)(4-phenyl-1,3-thiazol-2(3H)-ylidene)acetonitrile and 1-ethylpiperazine in the presence of triethylamine in DMA.

M$^+$(ES): 477.2; LC (215 nm): 72.1%

Example 151

{2-[(cyclohexylmethyl)amino]pyrimidin-4-yl}(4-phenyl-1,3-thiazol-2(3H)-ylidene)acetonitrile

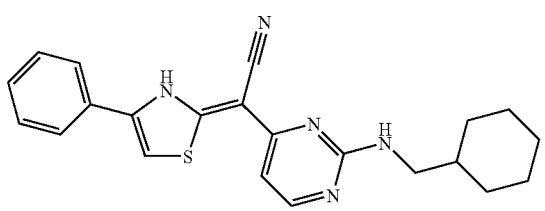

Following the general strategies and protocols outlined in the procedure J, the title compound was obtained from (2-chloropyrimidin-4-yl)(4-phenyl-1,3-thiazol-2(3H)-ylidene)acetonitrile and (aminomethyl)cyclohexane in the presence of triethylamine in DMA.

M$^+$(ES): 390.2; LC (215 nm): 96.4%

Example 152

{2-[(cyclohexylmethyl)amino]-5-methylpyrimidin-4-yl}(4-phenyl-1,3-thiazol-2(3H)-ylidene)acetonitrile

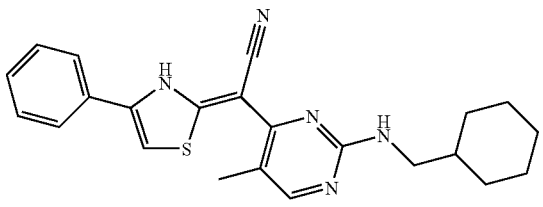

Following the general strategies and protocols outlined in the procedure J, the title compound was obtained from (2-chloro-5-methylpyrimidin-4-yl)(4-phenyl-1,3-thiazol-2(3H)-ylidene)acetonitrile and (aminomethyl)cyclohexane in the presence of triethylamine in DMA.
M+(ES): 404.2; LC (215 nm): 84.6%

Example 153

[2-(4-ethylpiperazin-1-yl-5-methylpyrimidin-4-yl](4-phenyl-1,3-thiazol-2(3H)-ylidene)acetonitrile

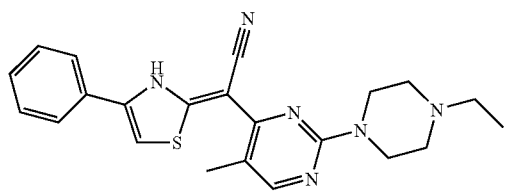

Following the general strategies and protocols outlined in the procedure J, the title compound was obtained from (2-chloro-5-methylpyrimidin-4-yl)(4-phenyl-1,3-thiazol-2(3H)-ylidene)acetonitrile and 1-ethylpiperazine in the presence of triethylamine in DMA.
M+(ES): 405.2; LC (215 nm): 91.4%

Example 154

[4-(cyclopentylamino)-6-(methylamino)-1,3,5-triazin-2-yl](4-methyl-1,3-thiazol-2(3H)-ylidene)acetonitrile

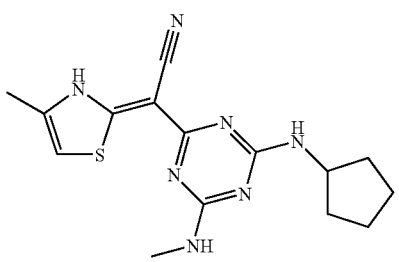

Following the general strategies and protocols outlined in the procedure J, the title compound was obtained from [4-chloro-6-(methylamino)-1,3,5-triazin-2-yl](4-methyl-1,3-thiazol-2(3H)-ylidene)acetonitrile and cyclopentylamine in the presence of triethylamine in DMA.
M+(ES): 330.2; LC (215 nm): 80.8%

Example 155

[4-(cyclopropylamino)-6-morpholin-4-yl-1,3,5-triazin-2-yl](4-phenyl-1,3-thiazol-2(3H)-ylidene)acetonitrile

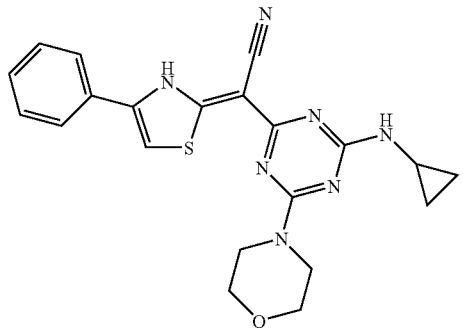

Following the general strategies and protocols outlined in the procedure J, the title compound was obtained from (4-chloro-6-morpholin-4-yl-1,3,5-triazin-2-yl)(4-phenyl-1,3-thiazol-2(3H)-ylidene)acetonitrile and cyclopropylamine in the presence of triethylamine in DMA.
M+(ES): 420.2; LC (215 nm): 70.1%

Example 156

[4-(cyclopropylamino)-6-(methylamino)-1,3,5-triazin-2-yl](4-phenyl-1,3-thiazol-2(3H)-ylidene)acetonitrile

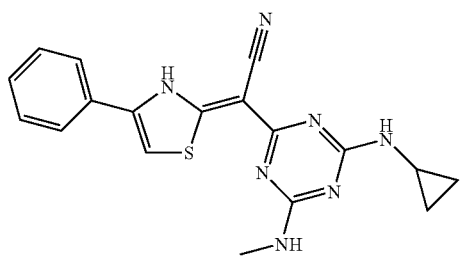

Following the general strategies and protocols outlined in the procedure J, the title compound was obtained from [4-chloro-6-(methylamino)-1,3,5-triazin-2-yl](4-phenyl-1,3-thiazol-2(3H)-ylidene)acetonitrile and cyclopropylamine in the presence of triethylamine in DMA.
M+(ES): 364.1; LC (215 nm): 91.6%

Example 157

[4-(cyclopropylamino)-6-(methylamino)-1,3,5-triazin-2-yl](4-methyl-1,3-thiazol-2(3H)-ylidene)acetonitrile

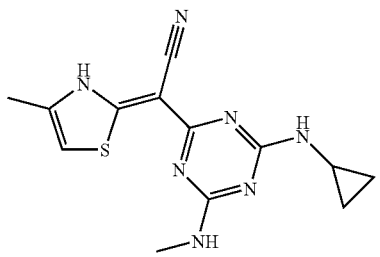

Following the general strategies and protocols outlined in the procedure J, the title compound was obtained from [4-chloro-6-(methylamino)-1,3,5-triazin-2-yl](4-methyl-1,3-thiazol-2(3H)-ylidene)acetonitrile and cyclopropylamine in the presence of triethylamine in DMA.
M⁺(ES): 302.1; LC (215 nm): 94.2%

Example 158

[2-(1,4-dioxa-8-azaspiro[4,5]dec-8-yl)-5-methylpyrimidin-4-yl](4-phenyl-1,3-thiazol-2(3H)-ylidene)acetonitrile

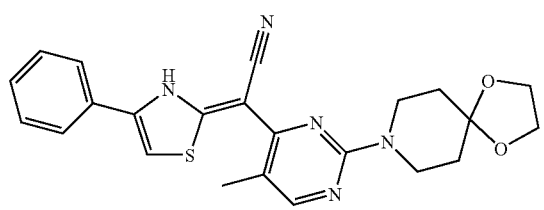

Following the general strategies and protocols outlined in the procedure J, the title compound was obtained from (2-chloro-5-methylpyrimidin-4-yl)(4-phenyl-1,3-thiazol-2(3H)-ylidene)acetonitrile and 1,4-dioxa-8-azaspiro[4.5]decane in the presence of triethylamine in DMA.
M⁺(ES): 434.2; LC (215 nm): 61.7%

Example 159

(5-methyl-2-{[3-(1H-1,2,4-triazol-1-yl)propyl]amino}pyrimidin-4-yl)(4-phenyl-1,3-thiazol-2(3H)-ylidene)acetonitrile

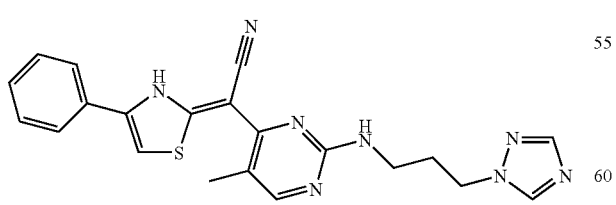

Following the general strategies and protocols outlined in the procedure J, the title compound was obtained from (2-chloro-5-methylpyrimidin-4-yl)(4-phenyl-1,3-thiazol-2(3H)-ylidene)acetonitrile and 1-(3'-aminopropyl)-1H-1,2,4-triazole in the presence of triethylamine in DMA.
M⁺(ES): 417.2; LC (215 nm): 78.2%

Example 160

{2-[(1,4-dimethylpentyl)amino]-5-methylpyrimidin-4-yl}(4-phenyl-1,3-thiazol-2(3H)-ylidene)acetonitrile

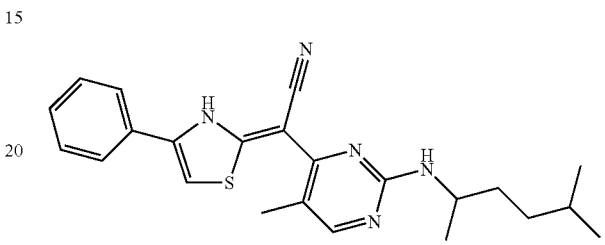

Following the general strategies and protocols outlined in the procedure J, the title compound was obtained from (2-chloro-5-methylpyrimidin-4-yl)(4-phenyl-1,3-thiazol-2(3H)-ylidene)acetonitrile and 1,4-dimethylpentylamine in the presence of triethylamine in DMA.
M⁺(ES): 406.2; LC (215 nm): 80.1%

Example 161

(5-methyl-2-{[2-(1H-pyrazol-1-yl)ethyl]amino}pyrimidin-4-yl)(4-phenyl-1,3-thiazol-2(3H)-ylidene)acetonitrile

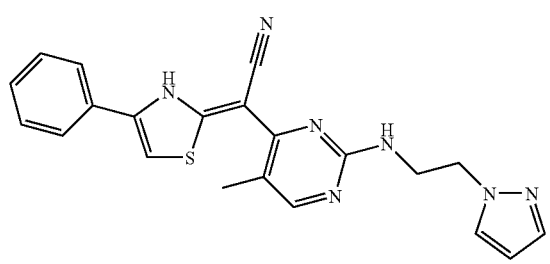

Following the general strategies and protocols outlined in the procedure J, the title compound was obtained from (2-chloro-5-methylpyrimidin-4-yl)(4-phenyl-1,3-thiazol-2(3H)-ylidene)acetonitrile and 1-(2'-aminoethyl)pyrazole in the presence of triethylamine in DMA.
M⁺(ES): 402.2; LC (215 nm): 83.7%

Example 162

(4-phenyl-1,3-thiazol-2(3H)-ylidene)(2-{[3-(1H-1,2,4-triazol-1-yl)propyl]amino}pyrimidin-4-yl)acetonitrile

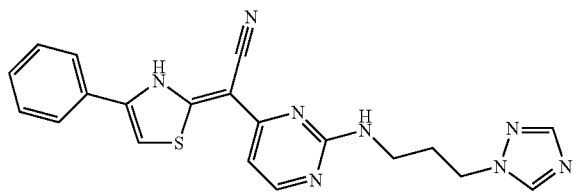

Following the general strategies and protocols outlined in the procedure J, the title compound was obtained from (2-chloropyrimidin-4-yl)(4-phenyl-1,3-thiazol-2(3H)-ylidene)acetonitrile and 1-(3'-aminopropyl)-1H-1,2,4-triazole in the presence of triethylamine in DMA.
M$^+$(ES): 403.2; LC (215 nm): 77.5%

Example 163

(4-phenyl-1,3-thiazol-2(3H)-ylidene)(2-{[2-(1H-pyrazol-1-yl)ethyl]amino}pyrimidin-4-yl)acetonitrile

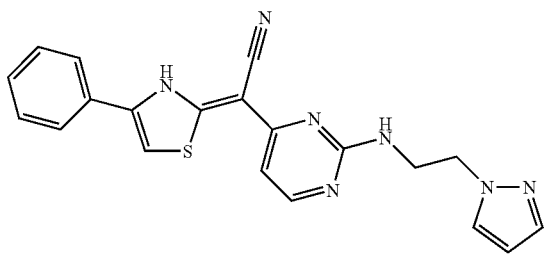

Following the general strategies and protocols outlined in the procedure J, the title compound was obtained from (2-chloropyrimidin-4-yl)(4-phenyl-1,3-thiazol-2(3H)-ylidene)acetonitrile and 1-(2'-aminoethyl)pyrazole in the presence of triethylamine in DMA.
M$^+$(ES): 388.1; LC (215 nm): 78.8%

Example 164

[2-(dipropylamino)-5-methylpyrimidin-4-yl](4-phenyl-1,3-thiazol-2(3H)-ylidene)acetonitrile

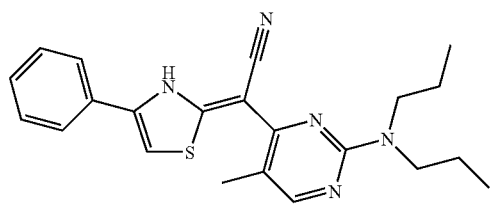

Following the general strategies and protocols outlined in the procedure J, the title compound was obtained from (2-chloro-5-methylpyrimidin-4-yl)(4-phenyl-1,3-thiazol-2(3H)-ylidene)acetonitrile and dipropylamine in the presence of triethylamine in DMA.
M$^+$(ES): 392.2; LC (215 nm): 74%

Example 165

{2-[(1,4-dimethylpentyl)amino]pyrimidin-4-yl}(4-phenyl-1,3-thiazol-2(3H)-ylidene)acetonitrile

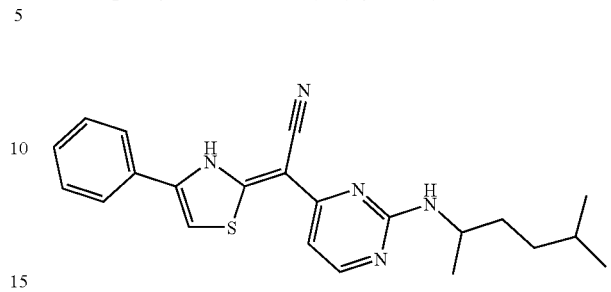

Following the general strategies and protocols outlined in the procedure J, the title compound was obtained from (2-chloropyrimidin-4-yl)(4-phenyl-1,3-thiazol-2(3H)-ylidene)acetonitrile and 1,4-dimethylpentylamine in the presence of triethylamine in DMA.
M$^+$(ES): 392.2; LC (215 nm): 68.9%

Example 166

[2-(methylamino)pyrimidin-4-yl](4-phenyl-1,3-thiazol-2(3H)-ylidene)acetonitrile

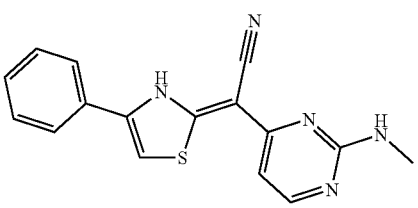

Following the general strategies and protocols outlined in the procedure J, the title compound was obtained from (2-chloropyrimidin-4-yl)(4-phenyl-1,3-thiazol-2(3H)-ylidene)acetonitrile and methylamine in the presence of triethylamine in DMA.
M$^+$(ES): 308.1; LC (215 nm): 68.3%

Example 167

[4-[(1,4-dimethylpentyl)amino]-6-(methylamino)-1,3,5-triazin-2-yl](4-phenyl-1,3-thiazol-2(3H)-ylidene)acetonitrile

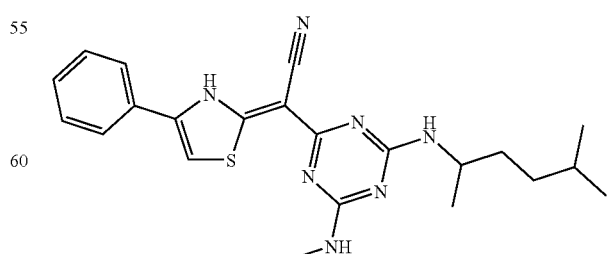

Following the general strategies and protocols outlined in the procedure J, the title compound was obtained from

[4-chloro-6-(methylamino)-1,3,5-triazin-2-yl](4-phenyl-1,3-thiazol-2(3H)-ylidene)acetonitrile and 1,4-dimethylpentylamine in the presence of triethylamine in DMA.

M⁺(ES): 422.2; LC (215 nm): 95.1%

Example 168

[4-{[(6-aminopyridin-3-yl)methyl]amino}-6-(methylamino)-1,3,5-triazin-2-yl](4-methyl-1,3-thiazol-2(3H)-ylidene)acetonitrile

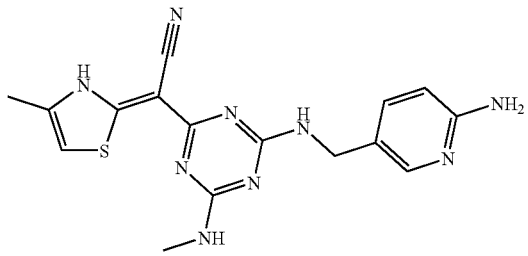

Following the general strategies and protocols outlined in the procedure J, the title compound was obtained from [4-chloro-6-(methylamino)-1,3,5-triazin-2-yl](4-methyl-1,3-thiazol-2(3H)-ylidene)acetonitrile and 5-(aminomethyl)pyridin-2-amine in the presence of triethylamine in DMA.

M⁺(ES): 368.2; LC (215 nm): 81.3%

Example 169

[2-(methylamino)pyrimidin-4-yl](4-methyl-1,3-thiazol-2(3H)-ylidene)acetonitrile

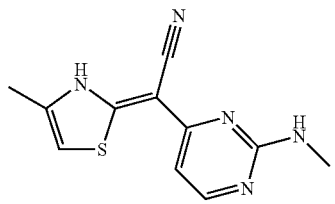

Following the general strategies and protocols outlined in the procedure J, the title compound was obtained from (2-chloropyrimidin-4-yl)(4-methyl-1,3-thiazol-2(3H)-ylidene)acetonitrile and methylamine in the presence of triethylamine in DMA.

M⁺(ES): 246.1; LC (215 nm): 74.4%

Example 170

[2-(cyclopentylamino)pyrimidin-4-yl](4-methyl-1,3-thiazol-2(3H)-ylidene)acetonitrile

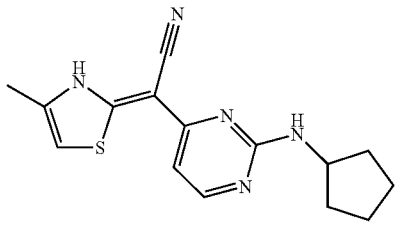

Following the general strategies and protocols outlined in the procedure J, the title compound was obtained from (2-chloropyrimidin-4-yl)(4-methyl-1,3-thiazol-2(3H)-ylidene)acetonitrile and cyclopentylamine in the presence of triethylamine in DMA.

M⁺(ES): 300.2; LC (215 nm): 81.1%

Example 171

[2-(cyclohexylamino)pyrimidin-4-yl](4-methyl-1,3-thiazol-2(3H)-ylidene)acetonitrile

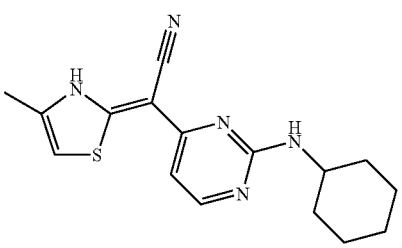

Following the general strategies and protocols outlined in the procedure J, the title compound was obtained from (2-chloropyrimidin-4-yl)(4-methyl-1,3-thiazol-2(3H)-ylidene)acetonitrile and cyclohexylamine in the presence of triethylamine in DMA.

M⁺(ES): 314.1; LC (215 nm): 64.7%

Example 172

{2-[(1-methylbutyl)amino]pyrimidin-4-yl}(4-methyl-1,3-thiazol-2(3H)-ylidene)acetonitrile

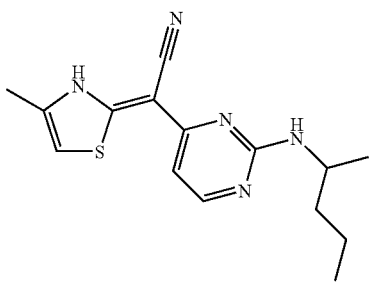

Following the general strategies and protocols outlined in the procedure J, the title compound was obtained from (2-chloropyrimidin-4-yl)(4-methyl-1,3-thiazol-2(3H)-ylidene)acetonitrile and (+/−)-2-aminopentane in the presence of triethylamine in DMA.

M$^+$(ES): 302.2; LC (215 nm): 72.7%

Example 173

[2-(cyclopentylamino)-6-methylpyrimidin-4-yl](4-methyl-1,3-thiazol-2(3H)-ylidene)acetonitrile

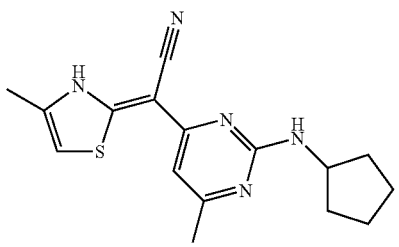

Following the general strategies and protocols outlined in the procedure J, the title compound was obtained from (2-chloro-6-methylpyrimidin-4-yl)(4-methyl-1,3-thiazol-2(3H)-ylidene)acetonitrile and cyclopentylamine in the presence of triethylamine in DMA.

M$^+$(ES): 314.2; LC (215 nm): 84.6%

Example 174

{2-[(cyclohexylmethyl)amino]pyrimidin-4-yl}(4-methyl-1,3-thiazol-2(3H)-ylidene)acetonitrile

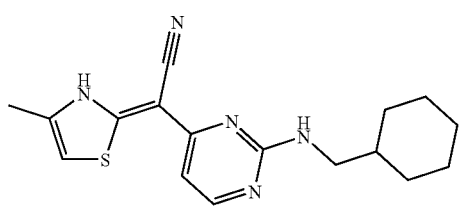

Following the general strategies and protocols outlined in the procedure J, the title compound was obtained from (2-chloropyrimidin-4-yl)(4-methyl-1,3-thiazol-2(3H)-ylidene)acetonitrile and (aminomethyl)cyclohexane in the presence of triethylamine in DMA.

M$^+$(ES): 328.2; LC (215 nm): 76.6%

Example 175

{6-[methyl(phenyl)amino]-2-[(2-pyridin-3-ylethyl)amino]pyrimidin-4-yl}(4-methyl-1,3-thiazol-2(3H)-ylidene)acetonitrile

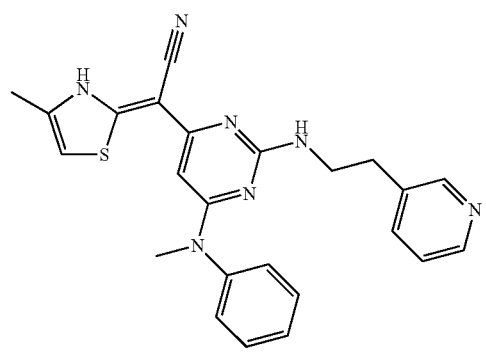

Following the general strategies and protocols outlined in the procedure J, the title compound was obtained from {2-chloro-6-[methyl(phenyl)amino]pyrimidin-4-yl}(4-methyl-1,3-thiazol-2(3H)-ylidene)acetonitrile and 3-(2-aminoethyl)pyridine in the presence of triethylamine in DMA.

M$^+$(ES): 442.3; LC (215 nm): 66.1%

Example 176

{2-[(2,3-dimethylcyclohexyl)amino]pyrimidin-4-yl}(4-methyl-1,3-thiazol-2(3H)-ylidene)acetonitrile

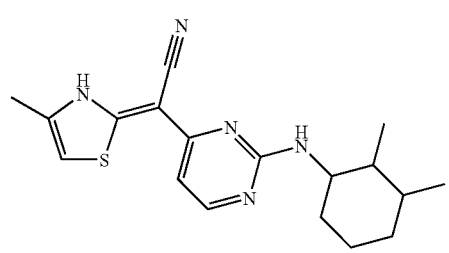

Following the general strategies and protocols outlined in the procedure J, the title compound was obtained from (2-chloropyrimidin-4-yl)(4-methyl-1,3-thiazol-2(3H)-ylidene)acetonitrile and 2,3-dimethylcyclohexylamine in the presence of triethylamine in DMA.

M$^+$(ES): 342.2; LC (215 nm): 72.3%

Example 177

(4-methyl-1,3-thiazol-2(3H)-ylidene){2-[(pyridin-3- ylmethyl)amino]pyrimidin-4-yl}acetonitrile

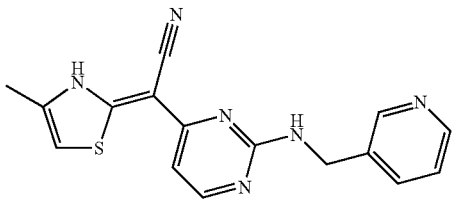

Following the general strategies and protocols outlined in the procedure J, the title compound was obtained from (2-chloropyrimidin-4-yl)(4-methyl-1,3-thiazol-2(3H)-ylidene)acetonitrile and (3-aminomethyl)pyridine in the presence of triethylamine in DMA.

M$^+$(ES): 323.2; LC (215 nm): 62%

Example 178

{6-methyl-2-[(2-pyridin-2-ylethyl)amino]pyrimidin-4-yl}(4-methyl-1,3-thiazol-2(3H)-ylidene)acetonitrile

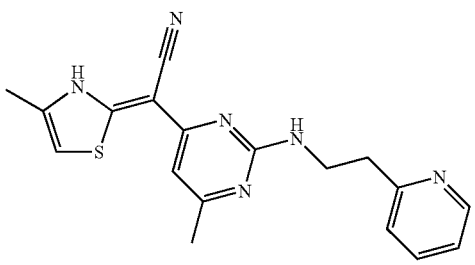

Following the general strategies and protocols outlined in the procedure J, the title compound was obtained from (2-chloro-6-methylpyrimidin-4-yl)(4-methyl-1,3-thiazol-2(3H)-ylidene)acetonitrile and 2-(2-aminoethyl)pyridine in the presence of triethylamine in DMA.

M$^+$(ES): 351.2; LC (215 nm): 73%

Example 179

[2-(isopropylamino)pyrimidin-4-yl](4-methyl-1,3-thiazol-2(3H)-ylidene)acetonitrile

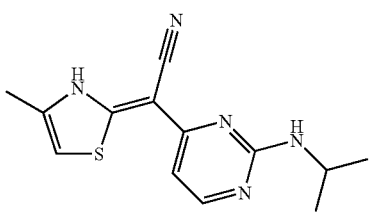

Following the general strategies and protocols outlined in the procedure J, the title compound was obtained from (2-chloropyrimidin-4-yl)(4-methyl-1,3-thiazol-2(3H)-ylidene)acetonitrile and iso-propylamine in the presence of triethylamine in DMA.

M$^+$(ES): 274.1; LC (215 nm): 68.1%

Example 180

{2-[(1,2-dimethylpropyl)amino]pyrimidin-4-yl}(4-methyl-1,3-thiazol-2(3H)-ylidene)acetonitrile

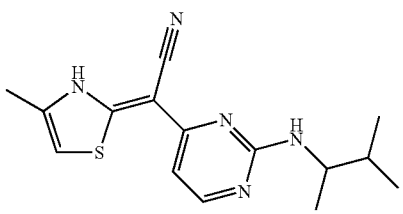

Following the general strategies and protocols outlined in the procedure J, the title compound was obtained from (2-chloropyrimidin-4-yl)(4-methyl-1,3-thiazol-2(3H)-ylidene)acetonitrile and 1,2-dimethylpropylamine in the presence of triethylamine in DMA.

M$^+$(ES): 302.2; LC (215 nm): 80.5%

Example 181

(4-methyl-1,3-thiazol-2(3H)-ylidene){2-[4-(pyrimidin-2-ylamino)piperidin-1-yl]pyrimidin-4-yl}acetonitrile

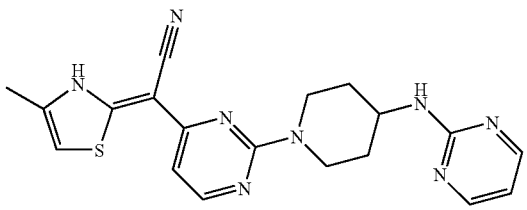

Following the general strategies and protocols outlined in the procedure J, the title compound was obtained from (2-chloropyrimidin-4-yl)(4-methyl-1,3-thiazol-2(3H)-ylidene)acetonitrile and 2-(N-4-piperidinyl)-aminopyrimidine in the presence of triethylamine in DMA.

M$^+$(ES): 393.2; LC (215 nm): 68.6%

Example 182

{2-[(1-ethylpropyl)amino]pyrimidin-4-yl}(4-methyl-1,3-thiazol-2(3H)-ylidene)acetonitrile

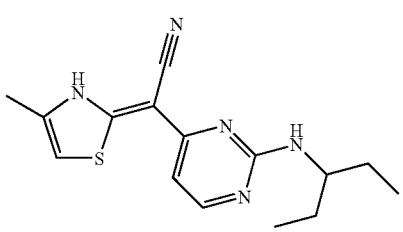

Following the general strategies and protocols outlined in the procedure J, the title compound was obtained from (2-chloropyrimidin-4-yl)(4-methyl-1,3-thiazol-2(3H)-ylidene)acetonitrile and 3-aminopentane in the presence of triethylamine in DMA.

M+(ES): 302.2; LC (215 nm): 75.5%

Example 183

{2-[(3-butoxypropyl)amino]-6-[methyl(phenyl)amino]pyrimidin-4-yl}(4-methyl-1,3-thiazol-2(3H)-ylidene)acetonitrile

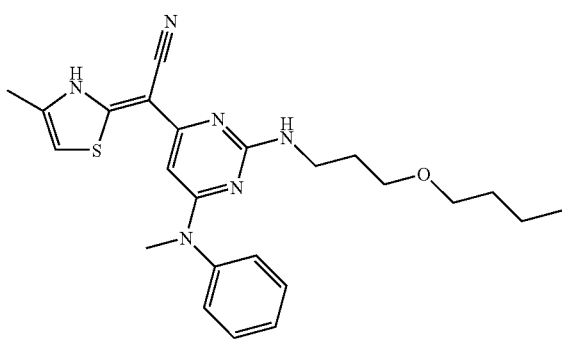

Following the general strategies and protocols outlined in the procedure J, the title compound was obtained from {2-chloro-6-[methyl(phenyl)amino]pyrimidin-4-yl}(4-methyl-1,3-thiazol-2(3H)-ylidene)acetonitrile and 3-butoxypropylamine in the presence of triethylamine in DMA.

M+(ES): 451.3; LC (215 nm): 85.7%

Example 184

{4-[(3-butoxypropyl)amino]-6-morpholin-4-yl-1,3,5-triazin-2-yl}(4-methyl-1,3-thiazol-2(3H)-ylidene)acetonitrile

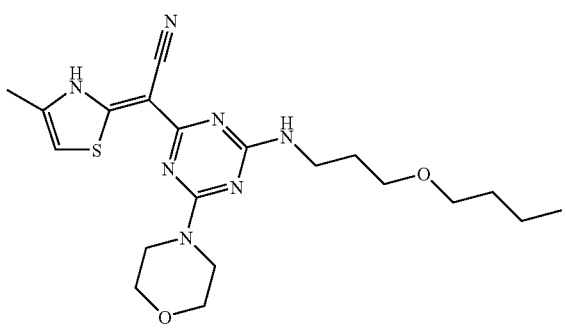

Following the general strategies and protocols outlined in the procedure J, the title compound was obtained from (4-chloro-6-morpholin-4-yl-1,3,5-triazin-2-yl)(4-methyl-1,3-thiazol-2(3H)-ylidene)acetonitrile and 3-butoxypropylamine in the presence of triethylamine in DMA.

M+(ES): 432.3; LC (215 nm): 72.4%

Example 185

{2-(isopropylamino)-6-[methyl(phenyl)amino]pyrimidin-4-yl}(4-methyl-1,3-thiazol-2(3H)-ylidene)acetonitrile

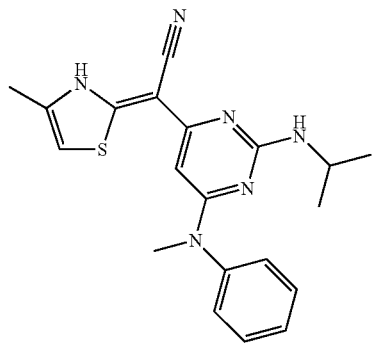

Following the general strategies and protocols outlined in the procedure J, the title compound was obtained from {2-chloro-6-[methyl(phenyl)amino]pyrimidin-4-yl}(4-methyl-1,3-thiazol-2(3H)-ylidene)acetonitrile and isopropylamine in the presence of triethylamine in DMA.

M+(ES): 379.2; LC (215 nm): 64.9%

Example 186

{2-[(3-isopropoxypropyl)amino]pyrimidin-4-yl}(4-methyl-1,3-thiazol-2(3H)-ylidene)acetonitrile

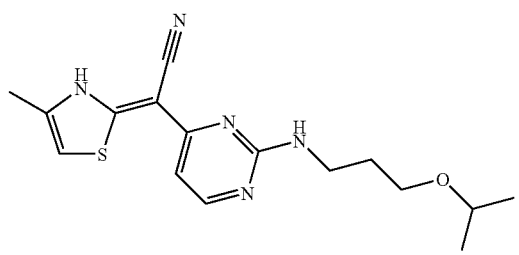

Following the general strategies and protocols outlined in the procedure J, the title compound was obtained from (2-chloropyrimidin-4-yl)(4-methyl-1,3-thiazol-2(3H)-ylidene)acetonitrile and 3-isopropoxypropylamine in the presence of triethylamine in DMA.

M+(ES): 332.2; LC (215 nm): 73.2%

Example 187

[4-(4-chlorophenyl)-1,3-thiazol-2(3H)-ylidene][2-(cyclopropylamino)pyrimidin-4-yl]acetonitrile

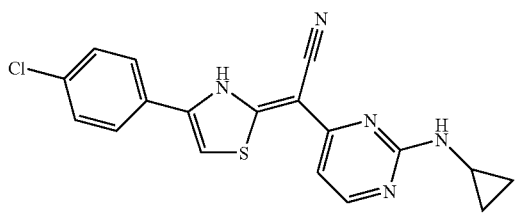

Following the general strategies and protocols outlined in the procedure J, the title compound was obtained from [4-(4-chlorophenyl)-1,3-thiazol-2(3H)-ylidene](2-chloropyrimidin-4-yl)acetonitrile and cyclopropylamine in the presence of triethylamine in DMA.

M$^+$(ES): 368.1; LC (215 nm): 79.8%

Example 188

[4-(4-chlorophenyl)-1,3-thiazol-2(3H)-ylidene][2-(cyclopentylamino)pyrimidin-4-yl]acetonitrile

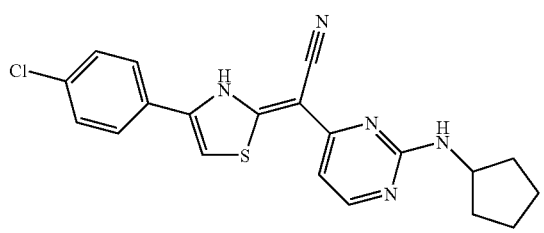

Following the general strategies and protocols outlined in the procedure J, the title compound was obtained from [4-(4-chlorophenyl)-1,3-thiazol-2(3H)-ylidene](2-chloropyrimidin-4-yl)acetonitrile and cyclopentylamine in the presence of triethylamine in DMA.

M$^+$(ES): 396.1; LC (215 nm): 78.1%

Example 189

[4-(4-chlorophenyl)-1,3-thiazol-2(3H)-ylidene]{2-[(cyclohexylmethyl)amino]-5-methylpyrimidin-4-yl}acetonitrile Following the general strategies and protocols outlined in the procedure J, the title compound was obtained from (2-chloro-5-methylpyrimidin-4-yl)[4-(4-chlorophenyl)-1,3-thiazol-2(3H)-ylidene]acetonitrile and (aminoethyl)cyclohexane in the presence of triethylamine in DMA.

M$^+$(ES): 438.1; LC (215 nm): 88.9%

Example 190

Preparation of a Pharmaceutical Formulation

The following formulation examples illustrate representative pharmaceutical compositions according to the present invention being not restricted thereto.

Formulation 1—Tablets

An azole compound of formula I is admixed as a dry powder with a dry gelatin binder in an approximate 1:2 weight ration. A minor amount of magnesium stearate is added as a lubricant. The mixture is formed into 240-270 mg tablets (80-90 mg of active azole compound per tablet) in a tablet press.

Formulation 2—Capsules

An azole compound of formula I is admixed as a dry powder with a starch diluent in an approximate 1:1 weight ratio. The mixture is filled into 250 mg capsules (125 mg of active azole compound per capsule).

Formulation 3—Liquid

An azole compound of formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

An azole compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active azole compound) in a tablet press.

Formulation 5—Injection

An azole compound of formula (I) is dissolved in a buffered sterile saline injectable aqueous medium to a concentration of approximately 5 mg/ml.

Biological Assays

The compounds of the present invention may be subjected to the following assays:

a) JNK2 and -3 in vitro assay:

The compounds of the present invention are inhibitors of JNKs. The phosphorylation of c-jun by JNK2 or JNK3 may be determined by monitoring the incorporation of $^{33}$P into c-jun following the protocol below. The inhibitory activity of the compounds according to formula I, towards c-jun phosphorylation through JNK, is determined by calculating phosphorylation activity in the presence or absence of compounds according to formula I.

JNK3 and/or -2 assays are performed in 96 well MTT plates: incubation of 0.5 μg of recombinant, pre-activated GST-JNK3 or GST-JNK2 with 1 μg of recombinant, biotinylated GST-c-Jun and 2 μM $^{33}$γ-ATP (2 nCi/μl), in the presence or absence of compounds according to formula I and in a reaction volume of 50 μl containing 50 mM Tris-HCl, pH 8.0; 10 mM MgCl$_2$; 1 mM Dithiothreitol, and 100 μM NaVO$_4$. The test compound according to formula I is used in concentrations of 10, 3, 033, 0.1, 0.033, 0.01, 0.0033, 0.001 μM. The incubation is performed for 120 min. at R.T and stopped upon addition of 200 μl of a solution containing 250 μg of Streptavidine-coated SPA beads (Amersham, Inc.)*, 5 mM EDTA, 0.1% Triton X-100 and 50 μM ATP, in phosphate saline buffer.

After incubation for 60 minutes at RT, beads are sedimented by centrifugation at 1500×g for 5 minutes, resuspended in 200 μl of PBS containing 5 mM EDTA, 0.1% Triton X-100 and 50 µM ATP and the radioactivity measured in a scintillation β counter, following sedimentation of the beads as described above.

The tested compounds according to formula I display an inhibition ($IC_{50}$) with regard to JNK3 of less than 20 µM, preferably less than 1 µM.

b) GSK3 in vitro assay:

GSK3β Assay (see Naerum et al., *Bioorg. Med. Chem. Lett* 12 p. 1525-1528 (2002))

In a final reaction volume of 25 µl, the protein kinase GSK3β (h) (5-10 mU) is incubated with 8 mM MOPS at a pH of 7.0, in 0.2 mM EDTA, as well as 20 µM of the peptide YRRAAVPPSPSLSRHSSPHQS(p)EDEEE (SEQ ID NO: 1; a phosphor GS2 peptide being the GSK3 substrate in this assay), 10 mM Mg Acetate and [γ-$^{33}$P-ATP] (Specific activity approx. 500 cpm/pmol, concentration as required). The reaction is initiated by the addition of Mg$^{2+}$[γ-$^{33}$P-ATP]. The test compound according to formula I is used in concentrations of 100, 25, 5, 1.25, 0.315, 0.078, 0.0195, 0.0049, 0.0012, 0.00031 µM. After incubations for 40 minutes at room temperature, the reaction is stopped by the addition of 5 µl of a 3% phosphoric acid solution. 10 µl of the reaction is then spotted onto a P30 filtermat and washed three times for 5 minutes in 50 mM phosphoric acid and once in methanol prior to drying and the degree of phosphorylation of the substrate is determined by scintillation counting.

The tested compounds according to formula I display an inhibition ($IC_{50}$) with regard to GSK3 of less than 20 µM, preferably less than 10 and even more preferred less than 1 µM.

The binding affinities of the compounds of formula (I) were assessed using the above described in vitro biological assay. Representative values for some example compounds are given in Tables 1 and 2 below.

The values in Table 1 refer to the binding affinity ($IC_{50}$; µM) of the example compounds according to formula I to GSK3.

TABLE 1

In vitro potency of azole derivatives on human GSK3 β

| Structure | Compound | $IC_{50}$ (µM) GSK3β |
|---|---|---|
| 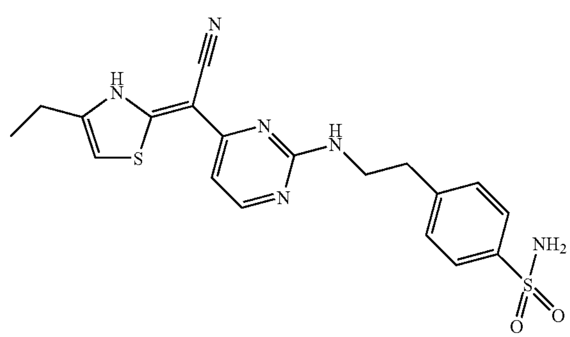 | 4-[2-({4-[cyano(4-ethyl-1,3-thiazol-2(3H)-ylidene)methyl]pyrimidin-2-yl}amino)ethyl]benzenesulfonamide | <10 |
| 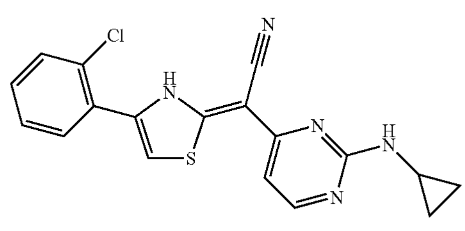 | [4-(2-chlorophenyl)-1,3-thiazol-2(3H)-ylidene][2-(cyclopropylamino)pyrimidin-4-yl]acetonitrile | <10 |
| 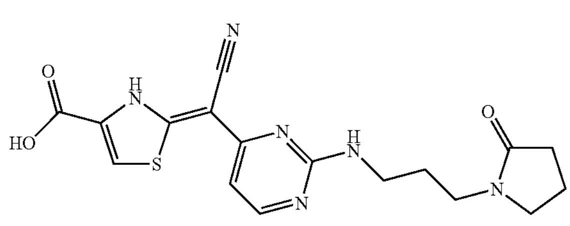 | 2-[cyano(2-{[3-(2-oxopyrrolidin-1-yl)propyl]amino}pyrimidin-4-yl)methylene]-2,3-dihydro-1,3-thiazole-4-carboxylic acid | <10 |

TABLE 1-continued

In vitro potency of azole derivatives on human GSK3 β

| Structure | Compound | IC$_{50}$ (µM) GSK3β |
|---|---|---|
| 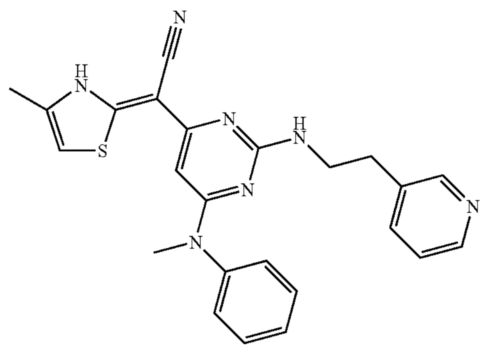 | {6-[methyl(phenyl)amino]-2-[(2-pyridin-3-ylethyl)amino]pyrimidin-4-yl}(4-methyl-1,3-thiazol-2(3H)-ylidene)acetonitrile | <10 |
| 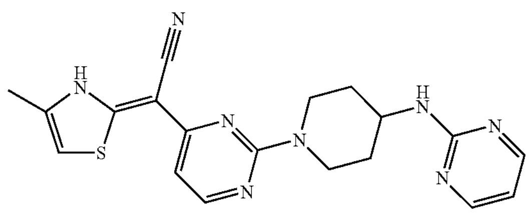 | (4-methyl-1,3-thiazol-2(3H)-ylidene){2-[4-(pyrimidin-2-ylamino)piperidin-1-yl]pyrimidin-4-yl}acetonitrile | <10 |
| 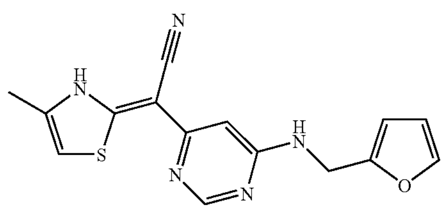 | {6-[(2-furylmethyl)amino]pyrimidin-4-yl}(4-methyl-1,3-thiazol-2(3H)-ylidene)acetonitrile | <10 |
| 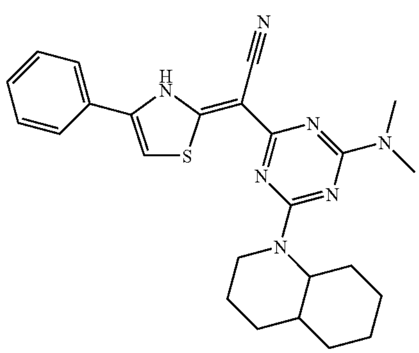 | [4-(dimethylamino)-6-(octahydroquinolin-1(2H)-yl)-1,3,5-triazin-2-yl](4-phenyl-1,3-thiazol-2(3H)-ylidene)acetonitrile | <10 |

The values in Table 2 refer to the binding affinity (IC$_{50}$; µM) of the example compounds according to formula I to JNK3.

TABLE 2

In vitro potency of azole derivatives on rat JNK3

| Structure | IUPAC-Name | JNK3 IC$_{50}$ (µM) |
|---|---|---|
| 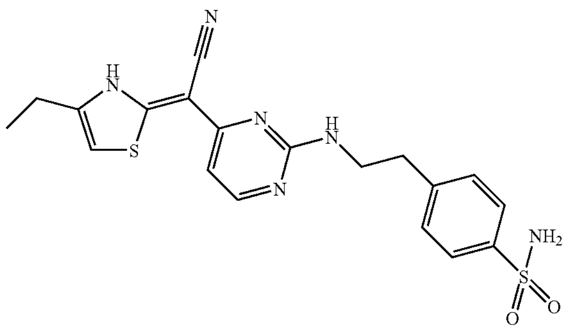 | 4-[2-({4-[cyano(4-ethyl-1,3-thiazol-2(3H)-ylidene)methyl]pyrimidin-2-yl}amino)ethyl]benzenesulfonamide | <10 |
| 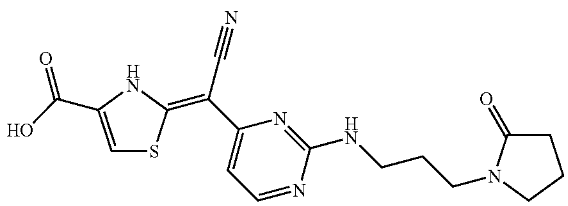 | 2-[cyano(2-{[3-(2-oxopyrrolidin-1-yl)propyl]amino}pyrimidin-4-yl)methylene]-2,3-dihydro-1,3-thiazole-4-carboxylic acid | <10 |
| 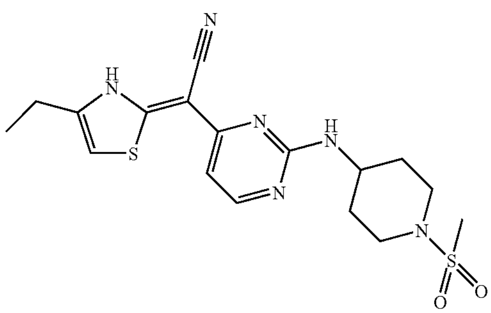 | (4-ethyl-1,3-thiazol-2(3H)-ylidene)(2-{[1-(methylsulfonyl)piperidin-4-yl]amino}pyrimidin-4-yl)acetonitrile trifluoroacetate | <10 |
| 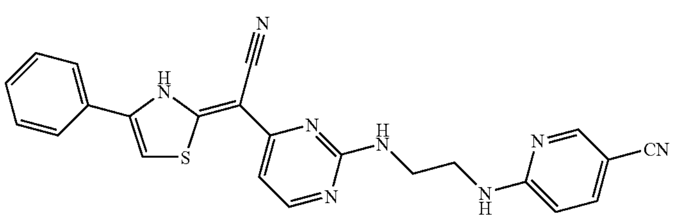 | 6-{[2-({4-[cyano(4-phenyl-1,3-thiazol-2(3H)-ylidene)methyl]pyrimidin-2-yl}amino)ethyl]amino}nicotinonitrile | <10 |

REFERENCE LIST

1) Xie X et al, (*Structure* 6 (8) p. 983-991 (1998)
2) Kumagae Y et al, *Brain Res*, 67(1), 10-17 (1999)
3) Yang D D et al *Nature*, 389 p. 865-870 (1997)
4) Yang et al, *Immunity* 9, 575-585 (1998)
5) Sabapathy et al. *Current Biology* 3, 116-125 (1999)
6) Woodgett et al. *Trends Biochem. Sci.*, 16 p. 177-81 (1991)
7) Saito et al. *Biochem. J.*, 303 p. 27-31 (1994)
8) Welsh et al., *Biochem. J.*, 294 p. 625-29 (1993)
9) Cross et al., *Biochem. J.*, 303 p. 21-26 (1994)
10) Carol Grimes, Richard Jope, *Prog. Neurobiol.* 65(4) p. 391-426 (2001)
11) Peter Klein, Douglas Melton *PNAS* 93 p. 8455-9 (1996)
12) Flückiger-Isler et al., *Biochem. J.* 292 p. 85-91 (1993)
13) Massillon et al., *Biochem. J.* 299 p. 123-8 (1994)
14) Lovestone et al., *Current Biology* 4 p. 1077-86 (1994)
15) Brownlees et al., *Neuroreport* 8 p. 3251-55 (1997)
16) Stambolic et al., *Current Biology* 6 p. 1664-8 (1996)
17) Chen et al. *J. Neurochemistry* 72 p. 1327-30 (1999)
18) Takashima et al., *PNAS* 95 p. 9637-41 (1998
19) Zhang et al., *Nature* 395 p. 698-702 (1998)
20) Takashima et al., *PNAS* 90 p. 7789-93 (1993)
21) Pei et al., *J. Neuropathol. Exp.* 56 p. 70-78 (1997)
22) Nonaka et al, *PNAS* 95 p. 2642-47 (1998)
23) Thomas et al., *J. Am. Geriatr. Soc.* 43 p. 1279-89 (1995)
24) Sasaki C. et al., *Neurol. Res.* 23(6) p. 588-92 (2001)
25) Cross et al., *Journal of Neurochemistry* 77 p. 94-102 (2001)
26) Ali et al., *American Chemical Society* p. A-N (December 2000)

27) Naerum et al., *Bioorg. Med. Chem. Lett* 12 p. 1525-1528 (2002)
28) WO 0035921 (Roche)
29) WO 0035909 (Roche)
30) WO 0035906 (Roche)
31) WO 0064872 (Vertex)
32) EP 1110957 (Applied Research Systems ARS Holding NV)
33) WO 02/20495 (Chiron)
34) WO 02/10141 (Pfizer)
35) WO 02/22608 (Vertex)
36) EP0169502 A2
37) Chabaka L. M. et al., *Pol. J. Chem.* p. 1317-1326 (1994)
38) Abdelhamid, A. O. et al, *J. Chem. Research (S)*, 144-145 (1995)
39) Brown M. D. et al., *J. Chem. Soc. Perkin Trans I*, 52(5) p. 1623-1626 (1985)
40) Dawood K. M. et al., *J. Chem. Research* (S), 206-201 (2000)
41) Gaudry M. and Marquet A., *Tetrahedron*, 1970, 26, 5611-5615 alkyl-aryl, aryl, heteroaryl, $C_1$-$C_6$-alkyl-heteroaryl, —C(O)—OR$^5$, —C(O)—R$^5$, —C(O)—NR$^5$R$^{5'}$, and —(SO$_2$)R$^5$, wherein R$^5$ and R$^{5'}$, being independently selected from the group consisting of hydrogen, $C_1$-$C_6$ alkyl, $C_2$-$C_6$ alkenyl, $C_2$-$C_6$ alkynyl, aryl, heteroaryl, $C_1$-$C_6$-alkyl aryl, and $C_1$-$C_6$-alkyl heteroaryl;

R$^1$ is selected from the group consisting of hydrogen, $C_1$-$C_6$-alkyl, $C_2$-$C_6$-alkenyl, $C_2$-$C_6$-alkynyl, $C_1$-$C_6$-alkoxy, $C_1$-$C_6$-sulfanyl, primary, secondary or tertiary amino groups, aminoacyl, aminocarbonyl, $C_1$-$C_6$ alkoxycarbonyl, $C_3$-$C_8$-cycloalkyl, $C_3$-$C_8$ heterocycloalkyl, aryl, heteroaryl, carboxyl, cyano, halogen, hydroxy, nitro, sulfonamide and hydrazide;

R$^2$ is selected from the group consisting of hydrogen, sulfonyl, amino, $C_1$-$C_6$-alkyl, $C_2$-$C_6$-alkenyl, and $C_2$-$C_6$-alkynyl, wherein said alkyl, alkenyl, alkynyl chains may be interrupted by a heteroatom selected from the group consisting of N, O, S, aryl, heteroaryl, saturated or unsaturated 3-8-membered cycloalkyl, and heterocycloalkyl, wherein said cycloalkyl, heterocycloalkyl, aryl or heteroaryl groups may be fused with 1-2 further cycloalkyl,

---

---

The invention claimed is:
1. An azole compound according to formula (I),

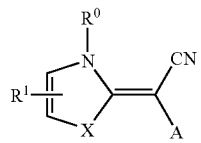

a tautomer thereof, a geometrical isomer thereof, an optically active form thereof as an enantiomer thereof, a diastereomer thereof, a racemate form thereof, or a pharmaceutically acceptable salt thereof, wherein X is S;
A is a pyrimidinyl, which may be substituted with 1, 2 or 3 moieties R$^2$ and/or fused with an aryl or a heteroaryl group;
R$^0$ is selected from the group consisting of hydrogen, $C_1$-$C_6$-alkyl, $C_2$-$C_6$-alkenyl, $C_2$-$C_6$-alkynyl, $C_1$-$C_6$- heterocycloalkyl, aryl or heteroaryl group, an acyl moiety, $C_1$-$C_6$-alkyl aryl, $C_1$-$C_6$-alkyl heteroaryl, $C_1$-$C_6$-alkenyl aryl, $C_1$-$C_6$-alkenyl heteroaryl, $C_1$-$C_6$-alkynyl aryl, $C_1$-$C_6$-alkynyl heteroaryl, $C_1$-$C_6$-alkyl cycloalkyl, $C_1$-$C_6$-alkyl heterocycloalkyl, $C_1$-$C_6$-alkenyl cycloalkyl, $C_1$-$C_6$-alkenyl heterocycloalkyl, $C_1$-$C_6$-alkynyl cycloalkyl, $C_1$-$C_6$-alkynyl heterocycloalkyl, alkoxycarbonyl, aminocarbonyl, $C_1$-$C_6$-alkyl carboxy, $C_1$-$C_6$-alkyl acyl, aryl acyl, heteroaryl acyl, $C_3$-$C_8$-(hetero)cycloalkyl acyl, $C_1$-$C_6$-alkyl acyloxy, $C_1$-$C_6$-alkyl alkoxy, $C_1$-$C_6$-alkyl alkoxycarbonyl, $C_1$-$C_6$-alkyl aminocarbonyl, $C_1$-$C_6$-alkyl acylamino, acylamino, $C_1$-$C_6$-alkyl ureido, $C_1$-$C_6$-alkyl carbamate, $C_1$-$C_6$-alkyl amino, $C_1$-$C_6$-alkyl ammonium, $C_1$-$C_6$-alkyl sulfonyloxy, $C_1$-$C_6$-alkyl sulfonyl, $C_1$-$C_6$-alkyl sulfinyl, $C_1$-$C_6$-alkyl sulfanyl, $C_1$-$C_6$-alkyl sulfonylamino, $C_1$-$C_6$-alkyl aminosulfonyl, hydroxy or halogen, wherein the following compounds are excluded:

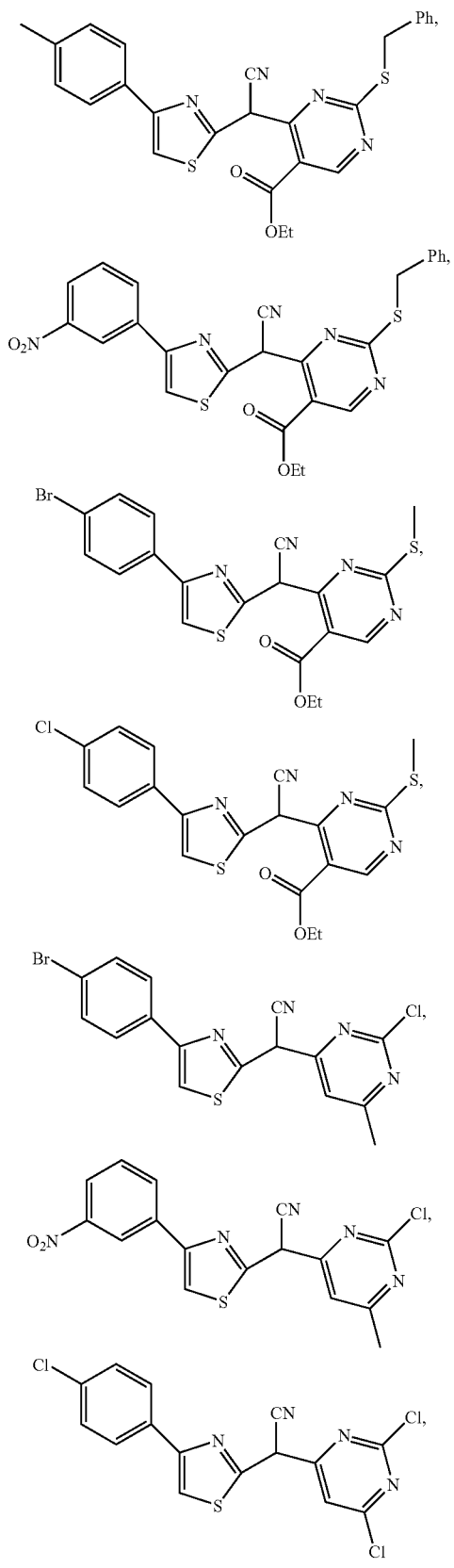

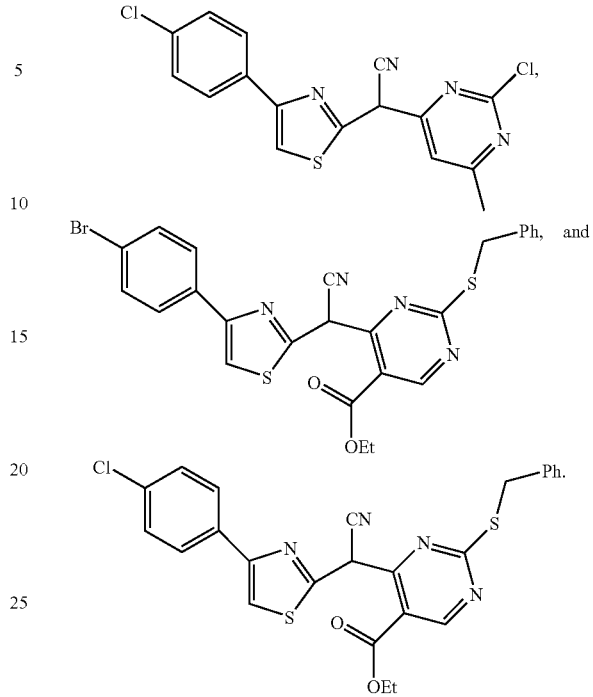

2. The azole compound according to claim 1 wherein $R^0$ is hydrogen.

3. The azole compound according to claim 1 wherein $R^2$ is —$NHR^4$, with $R^4$ being a straight or branched $C_1$-$C_6$ alkyl which may be substituted by $C_3$-$C_8$-cycloalkyl, heterocycloalkyl, aryl, heteroaryl, amino, alkoxycarbonyl, acylamino, or diacylamino.

4. The azole compound according to claim 3 wherein $R^4$ is a straight or branched $C_2$-$C_4$ alkyl group substituted with a heteroaryl or heterocycloalkyl group.

5. The azole compound according to claim 4 wherein said heteroaryl or heterocycloalkyl group is selected from the group consisting of a pyridyl, triazolyl and 2-pyrrolidinone.

6. The azole compound according to claim 1 wherein $R^1$ is ($C_3$-$C_8$)-cycloalkyl, ($C_3$-$C_8$)-heterocycloalkyl, aryl or heteroaryl group which may be substituted with at least one moiety selected from the group consisting of $C_1$-$C_6$-alkyl, $C_2$-$C_6$-alkenyl, $C_2$-$C_6$-alkynyl, $C_1$-$C_6$-alkoxy, $C_1$-$C_6$-sulfanyl, primary, secondary or tertiary amino groups, acylamino, aminocarbonyl, $C_1$-$C_6$ alkoxycarbonyl, $C_3$-$C_8$-cycloalkyl, $C_3$-$C_8$ heterocycloalkyl, aryl, heteroaryl, carboxy, cyano, halogen, hydroxy, nitro, sulfinyl, sulfonyl, sulfonamide and hydrazide.

7. The azole compound according to claim 6 wherein $R^1$ is a phenyl or phenyl which is substituted by straight or branched $C_1$-$C_6$ alkyl or halogen or $R^1$ is a straight or branched $C_1$-$C_6$ alkyl.

8. The azole compound according to claim 1 wherein $R^1$ is ($C_3$-$C_8$)-cycloalkyl, ($C_3$-$C_8$)-heterocycloalkyl, aryl or heteroaryl group which may be substituted with at least one moiety selected from the group consisting of $C_1$-$C_6$-alkyl, $C_2$-$C_6$-alkenyl, $C_2$-$C_6$-alkynyl, $C_1$-$C_6$-alkoxy, $C_1$-$C_6$-sulfanyl, primary, secondary or tertiary amino groups, aminoacyl, aminocarbonyl, $C_1$-$C_6$ alkoxycarbonyl, $C_3$-$C_8$-cycloalkyl, $C_3$-$C_8$ heterocycloalkyl, aryl, heteroaryl, carboxyl, cyano, halogen, hydroxy, nitro, sulfinyl, sulfonyl, sulfonamide and hydrazide, A is a pyrimidinyl group substituted by halogen or —NHR⁴ with R⁴ being a straight or branched $C_1$-$C_6$ alkyl in which said alkyl is substituted with $C_3$-$C_8$-cycloalkyl, heterocycloalkyl, aryl or heteroaryl straight or branched $C_1$-$C_6$ alkyl group substituted with a heteroaryl group and R⁰ is hydrogen.

9. The azole compound according to claim 8 wherein R¹ is a phenyl group which may be substituted with straight or branched $C_1$-$C_6$ alkyl or halogen, X is S, A is a pyrimidinyl group substituted by —NHR⁴ with R⁴ being a straight or branched $C_2$-$C_4$ alkyl wherein said alkyl is substituted with a pyridyl group and R⁰ is hydrogen.

10. An azole compound according to claim 1, selected from the group consisting of
(2-chloropyrimidin-4-yl)-(4-ethyl-3H-thiazol-2ylidene)-acetonitrile,
[4-(4-chlorophenyl)-1,3-thiazol-2(3H)-ylidene](2-chloropyrimidin-4-yl)acetonitrile,
(2-chloropyrimidin-4-yl)(4-phenyl-1,3-thiazol-2(3H)-ylidene)acetonitrile,
(2-chloropyrimidin-4-yl)(4-methyl-1,3-thiazol-2(3H)-ylidene)acetonitrile,
(2-chloropyrimidin-4-yl)[4-(4-methoxyphenyl)-1,3-thiazol-2(3H)-ylidene]acetonitrile
ethyl-2-[(2-chloropyrimidin-4-yl)(cyano)methylene]-2,3-dihydro-1,3-thiazole-4-carboxylate,
methyl-2-[(2-chloropyrimidin-4-yl)(cyano)methylene]-2,3-dihydro-1,3-thiazole-4-carboxylate,
(2-chloropyrimidin-4-yl)[4-(3-methoxyphenyl)-1,3-thiazol-2-yl]acetonitrile,
(2-chloropyrimidin-4-yl)[4-(2-methoxyphenyl)-1,3-thiazol-2(3H)-ylidene]acetonitrile,
(2-chloropyrimidin-4-yl)[4-(4-fluorophenyl)-1,3-thiazol-2(3H)-ylidene]acetonitrile,
(2-chloro-5-methylpyrimidin-4-yl)(4-ethyl-1,3-thiazol-2(3H)-ylidene)acetonitrile,
(2-chloropyrimidin-4-yl)[4-(3,4-dichlorophenyl)-1,3-thiazol-2(3H)-ylidene]acetonitrile,
(2-chloropyrimidin-4-yl)[4-(4-methylphenyl)-1,3-thiazol-2(3H)-ylidene]acetonitrile,
(4-{[3-(2-oxopyrrolidin-1-yl)propyl]amino}pyrimidin-2-yl)(4-phenyl-1,3-thiazol-2(3H)-ylidene)acetonitrile,
4-{2-[(2-chloropyrimidin-4-yl)(cyano)methylene]-2,3-dihydro-1,3-thiazol-4-yl}benzonitrile,
[4-(2-chlorophenyl)-1,3-thiazol-2(3H)-ylidene](2-chloropyrimidin-4-yl)acetonitrile,
[4-(3-chlorophenyl)-1,3-thiazol-2(3H)-ylidene](2-chloropyrimidin-4-yl)acetonitrile,
(2-chloropyrimidin-4-yl)[4-(4-methoxyphenyl)-1,3-thiazol-2(3H)-ylidene]acetonitrile,
(2-chloropyrimidin-4-yl)[4-(pentafluoroethyl)-1,3-thiazol-2(3H)-ylidene]acetonitrile,
(2-chloro-5-methylpyrimidin-4-yl)(4-methyl-1,3-thiazol-2(3H)-ylidene)acetonitrile,
(4-tert-butyl-1,3-thiazol-2(3H)-ylidene)(2-chloro-5-methylpyrimidin-4-yl)acetonitrile,
(4-tert-butyl-1,3-thiazol-2(3H)-ylidene)(2-chloropyrimidin-4-yl)acetonitrile,
(2-chloropyrimidin-4-yl)(4-isopropyl-1,3-thiazol-2(3H)-ylidene)acetonitrile,
(2-chloro-5-methylpyrimidin-4-yl)[4-(4-chlorophenyl)-1,3-thiazol-2(3H)-ylidene]acetonitrile,
(2-chloro-6-methylpyrimidin-4-yl)(4-phenyl-1,3-thiazol-2(3H)-ylidene)acetonitrile,
(2-chloro-5-methylpyrimidin-4-yl)(4-phenyl-1,3-thiazol-2(3H)-ylidene)acetonitrile,
(6-chloropyrimidin-4-yl)(4-methyl-1,3-thiazol-2(3H)-ylidene)acetonitrile,
(2-chloro-6-methylpyrimidin-4-yl)(4-methyl-1,3-thiazol-2(3H)-ylidene)acetonitrile,
{2-chloro-6-[methyl(phenyl)amino]pyrimidin-4-yl}(4-methyl-1,3-thiazol-2(3H)-ylidene)acetonitrile,
(4-ethyl-1,3-thiazol-2(3H)-ylidene)(2-{[3-(2-oxopyrrolidin-1-yl)propyl]amino}pyrimidin-4-yl)acetonitrile,
[4-(4-chlorophenyl)-1,3-thiazol-2(3H)-ylidene]{2-[(2-pyridin-3-ylethyl)amino]pyrimidin-4-yl}acetonitrile,
(4-phenyl-1,3-thiazol-2(3H)-ylidene){2-[(2-pyridin-3-ylethyl)amino]pyrimidin-4-yl}acetonitrile,
{2-[(3-aminopropyl)amino]pyrimidin-4-yl}(4-ethyl-1,3-thiazol-2(3H)-ylidene)acetonitrile,
(2-{[2-(6-aminopyridin-3-yl)ethyl]amino}pyrimidin-4-yl)(4-ethyl-1,3-thiazol-2(3H)-ylidene)acetonitrile,
{2-[(3-aminopropyl)amino]pyrimidin-4-yl}(4-ethyl-1,3-thiazol-2(3H)-ylidene)acetonitrile,
{2-[(3-aminopropyl)amino]pyrimidin-4-yl}(4-tert-butyl-1,3-thiazol-2(3H)-ylidene)acetonitrile,
ethyl-2-[cyano(2-{[3-(2-oxopyrrolidin-1-yl)propyl]amino}pyrimidin-4-yl)methylene]-2,3-dihydro-1,3-thiazole-4-carboxylate,
(4-methyl-1,3-thiazol-2(3H)-ylidene){2-[(2-pyridin-3-ylethyl)amino]pyrimidin-4-yl}acetonitrile,
4-(4-methoxyphenyl)-1,3-thiazol-2(3H)-ylidene]{2-[(2-pyridin-3-ylethyl)amino]pyrimidin-4-yl}acetonitrile,
2-[cyano(2-{[3-(2-oxopyrrolidin-1-yl)propyl]amino}pyrimidin-4-yl)methylene]-2,3-dihydro-1,3-thiazole-4-carboxylic acid,
methyl-2-[cyano(2-{[3-(2-oxopyrrolidin-1-yl)propyl]amino}pyrimidin-4-yl)methylene]-2,3-dihydro-1,3-thiazole-4-carboxylate,
methyl-2-(cyano{2-[(2-pyridin-3-ylethyl)amino]pyrimidin-4-yl}methylene)-2,3-dihydro-1,3-thiazole-4-carboxylate,
[2-(cyclopropylamino)pyrimidin-4-yl](4-methyl-1,3-thiazol-2(3H)-ylidene)acetonitrile,
4-[2-({4-[cyano(4-methyl-1,3-thiazol-2(3H)-ylidene)methyl]pyrimidin-2-yl}amino)ethyl]benzenesulfonamide,
[4-(pentafluoroethyl)-1,3-thiazol-2(3H)-ylidene]{2-[(2-pyridin-3-ylethyl)amino]pyrimidin-4-yl}acetonitrile,
[2-(cyclopropylamino)pyrimidin-4-yl][4-(pentafluoroethyl)-1,3-thiazol-2(3H)-ylidene]acetonitrile,
(2-{[3-(2-oxopyrrolidin-1-yl)propyl]amino}pyrimidin-4-yl)(4-phenyl-1,3-thiazol-2(3H)-ylidene)acetonitrile,
(4-ethyl-1,3-thiazol-2(3H)-ylidene){2-[(2-pyridin-3-ylethyl)amino]pyrimidin-4-yl}acetonitrile,
[4-(3-methoxyphenyl)-1,3-thiazol-2(3H)-ylidene]{2-[(2-pyridin-3-ylethyl)amino]pyrimidin-4-yl}acetonitrile,
[4-(3-methoxyphenyl)-1,3-thiazol-2(3H)-ylidene](2-{[3-(2-oxopyrrolidin-1-yl)propyl]amino}pyrimidin-4-yl)acetonitrile,
methyl 4-[2-({4-[cyano(4-ethyl-1,3-thiazol-2(3H)-ylidene)methyl]pyrimidin-2-yl}amino)ethyl]benzoate,
6-{[2-({4-[-cyano(4-ethyl-1,3-thiazol-2(3H)-ylidene)methyl]pyrimidin-2-yl)amino)ethyl]amino}nicotinonitrile,
[2-({2-[6-(dimethylamino)pyridin-3-yl]ethyl}amino)pyrimidin-4-yl](4-ethyl-1,3-thiazol-2(3H)-ylidene)acetonitrile,
4-[2-({4-[cyano(4-ethyl-1,3-thiazol-2(3H)-ylidene)methyl]pyrimidin-2-yl}amino)ethyl]benzenesulfonamide,
(2-{[2-(4-aminophenyl)ethyl]amino}pyrimidin-4-yl)(4-ethyl-1,3-thiazol-2(3H)-ylidene)acetonitrile, (4-ethyl-1,3-thiazol-2(3H)-ylidene)(2-{[2-(6-morpholin-4-ylpyridin-3-yl)ethyl]amino}pyrimidin-4-yl)acetonitrile,
(4-ethyl-1,3-thiazol-2(3H)-ylidene)[2-({2-[6-(4-methylpiperazin-1-yl)pyridin-3-yl]ethyl}amino)pyrimidin-4-yl]acetonitrile,
[2-(cyclopropylamino)pyrimidin-4-yl](4-ethyl-1,3-thiazol-2(3H)-ylidene)acetonitrile,
[4-(2-methoxyphenyl)-1,3-thiazol-2(3H)-ylidene]{2-[(2-pyridin-3-ylethyl)amino]pyrimidin-4-yl}acetonitrile,
[4-(2-methoxyphenyl)-1,3-thiazol-2(3H)-ylidene](2-{[3-(2-oxopyrrolidin-1-yl)propyl]amino}pyrimidin-4-yl)acetonitrile,
[4-(4-fluorophenyl)-1,3-thiazol-2(3H)-ylidene]{2-[(2-pyridin-3-ylethyl)amino]pyrimidin-4-yl}acetonitrile,
[4-(4-fluorophenyl)-1,3-thiazol-2(3H)-ylidene](2-{[3-(2-oxopyrrolidin-1-yl)propyl]amino}pyrimidin-4-yl)acetonitrile,
(4-ethyl-1,3-thiazol-2(3H)-ylidene){5-methyl-2-[(2-pyridin-3-ylethyl)amino]pyrimidin-4-yl}acetonitrile,
(4-ethyl-1,3-thiazol-2(3H)-ylidene)(5-methyl-2-{[3-(2-oxopyrrolidin-1-yl)propyl]amino}pyrimidin-4-yl)acetonitrile,
[2-(cyclopropylamino)-5-methylpyrimidin-4-yl](4-ethyl-1,3-thiazol-2(3H)-ylidene)acetonitrile,
(4-ethyl-1,3-thiazol-2(3H)-ylidene){2-[(3-pyrrolidin-1-ylpropyl)amino]pyrimidin-4-yl}acetonitrile,
[2-({2-[(5-nitropyridin-2-yl)amino]ethyl}amino)pyrimidin-4-yl](4-phenyl-1,3-thiazol-2(3H)-ylidene)acetonitrile,
6-{[2-({4-[cyano(4-phenyl-1,3-thiazol-2(3H)-ylidene)methyl]pyrimidin-2-yl}amino)ethyl]amino}nicotinonitrile,
tert-butyl 4-({4-[cyano(4-phenyl-1,3-thiazol-2(3H)-ylidene)methyl]pyrimidin-2-yl}amino)butanoate,
[4-(4-methoxyphenyl)-1,3-thiazol-2(3H)-ylidene](2-{[3-(2-oxopyrrolidin-1-yl)propyl]amino}pyrimidin-4-yl)acetonitrile,
(4-methyl-1,3-thiazol-2(3H)-ylidene)(2-{[3-(2-oxopyrrolidin-1-yl)propyl]amino}pyrimidin-4-yl)acetonitrile,
(4-tert-butyl-1,3-thiazol-2(3H)-ylidene)(2-{[3-(2-oxopyrrolidin-1-yl)propyl]amino}pyrimidin-4-yl)acetonitrile,
(4-tert-butyl-1,3-thiazol-2(3H)-ylidene){2-[(2-pyridin-3-ylethyl)amino]pyrimidin-4-yl}acetonitrile,
(4-tert-butyl-1,3-thiazol-2(3H)-ylidene)[2-(cyclohexylamino)pyrimidin-4-yl]acetonitrile,
(4-tert-butyl-1,3-thiazol-2(3H)-ylidene)[2-(cyclopropylamino)pyrimidin-4-yl]acetonitrile,
[4-(4-chlorophenyl)-1,3-thiazol-2(3H)-ylidene](2-{[3-(2-oxopyrrolidin-1-yl)propyl]amino}pyrimidin-4-yl)acetonitrile,
[4-(4-chlorophenyl)-1,3-thiazol-2(3H)-ylidene][2-(cyclopropylamino)pyrimidin-4-yl]acetonitrile,
[4-(3,4-dichlorophenyl)-1,3-thiazol-2(3H)-ylidene](2-{[3-(2-oxopyrrolidin-1-yl)propyl]amino}pyrimidin-4-yl)acetonitrile,
[4-(3,4-dichlorophenyl)-1,3-thiazol-2(3H)-ylidene]{2-[(2-pyridin-3-ylethyl)amino]pyrimidin-4-yl}acetonitrile,
[2-(cyclopropylamino)pyrimidin-4-yl][4-(3,4-dichlorophenyl)-1,3-thiazol-2(3H)-ylidene]acetonitrile,
[4-(4-methylphenyl)-1,3-thiazol-2(3H)-ylidene](2-{[3-(2-oxopyrrolidin-1-yl)propyl]amino}pyrimidin-4-yl)acetonitrile,
[4-(4-methylphenyl)-1,3-thiazol-2(3H)-ylidene]{2-[(2-pyridin-3-ylethyl)amino]pyrimidin-4-yl}acetonitrile,
[2-(cyclopropylamino)pyrimidin-4-yl][4-(4-methylphenyl)-1,3-thiazol-2(3H)-ylidene]acetonitrile,
{2-[(3-aminopropyl)amino]pyrimidin-4-yl}(4-tert-butyl-1,3-thiazol-2(3H)-ylidene)acetonitrile,
{2-[(2-aminoethyl)amino]pyrimidin-4-yl}(4-tert-butyl-1,3-thiazol-2(3H)-ylidene)acetonitrile,
{2-[(piperidin-4-yl)amino]pyrimidin-4-yl}(4-ethyl-1,3-thiazol-2(3H)-ylidene)acetonitrile,
methyl N-{4-[(4-tert-butyl-1,3-thiazol-2(3H)-ylidene)(cyano)methyl]pyrimidin-2-yl}-beta-alaninate,
(2-{[3-(2-oxopyrrolidin-1-yl)propyl]amino}pyrimidin-4-yl)[4-(pentafluoroethyl)-1,3-thiazol-2(3H)-ylidene]acetonitrile,
{5-methyl-2-[(2-pyridin-3-ylethyl)amino]pyrimidin-4-yl}(4-methyl-1,3-thiazol-2(3H)-ylidene)acetonitrile,
(5-methyl-2-{[3-(2-oxopyrrolidin-1-yl)propyl]amino}pyrimidin-4-yl)(4-methyl-1,3-thiazol-2(3H)-ylidene)acetonitrile,
[2-(cyclopropylamino)-5-methylpyrimidin-4-yl](4-methyl-1,3-thiazol-2(3H)-ylidene)acetonitrile,
(4-tert-butyl-1,3-thiazol-2(3H)-ylidene){5-methyl-2-[(2-pyridin-3-ylethyl)amino]pyrimidin-4-yl}acetonitrile,
(4-tert-butyl-1,3-thiazol-2(3H)-ylidene)(5-methyl-2-{[3-(2-oxopyrrolidin-1-yl)propyl]amino}pyrimidin-4-yl)acetonitrile,
(4-tert-butyl-1,3-thiazol-2(3H)-ylidene)[2-(cyclopropylamino)-5-methylpyrimidin-4-yl]acetonitrile,
(4-tert-butyl-1,3-thiazol-2(3H)-ylidene)(5-methyl-2-{[3-(1H-1,2,4-triazol-1-yl)propyl]amino}pyrimidin-4-yl)acetonitrile,
N-[3-({4-[(4-tert-butyl-1,3-thiazol-2(3H)-ylidene)(cyano)methyl]pyrimidin-2-yl}amino)propyl]-2-ethoxy-N-glycoloylacetamide,
N-[3-({4-[cyano(4-isopropyl 1,3-thiazol-2(3H)-ylidene)methyl]pyrimidin-2-yl}amino)propyl]-2-ethoxy-N-glycoloylacetamide,
[2-(cyclohexylamino)pyrimidin-4-yl](4-ethyl-1,3-thiazol-2(3H)-ylidene)acetonitrile,
[2-(cyclopentylamino)pyrimidin-4-yl](4-ethyl-1,3-thiazol-2(3H)-ylidene)acetonitrile,
(4-ethyl-1,3-thiazol-2(3H)-ylidene)[2-(isobutylamino)pyrimidin-4-yl]acetonitrile,
(4-tert-butyl-1,3-thiazol-2(3H)-ylidene)(2-{[3-(1H-1,2,4-triazol-1-yl)propyl]amino}pyrimidin-4-yl)acetonitrile,
(4-isopropyl-1,3-thiazol-2(3H)-ylidene)(2-{[3-(2-oxopyrrolidin-1-yl)propyl]amino}pyrimidin-4-yl)acetonitrile,
(4-isopropyl-1,3-thiazol-2(3H)-ylidene){2-[(2-pyridin-3-ylethyl)amino]pyrimidin-4-yl}acetonitrile,
[2-(cyclopropylamino)pyrimidin-4-yl](4-isopropyl-1,3-thiazol-2(3H)-ylidene)acetonitrile,
methyl 4-({4-[(4-tert-butyl-1,3-thiazol-2(3H)-ylidene)(cyano)methyl]pyrimidin-2-yl}amino)butanoate,
4-{2-[cyano(2-{[3-(2-oxopyrrolidin-1-yl)propyl]amino}pyrimidin-4-yl)methylene]-2,3-dihydro-1,3-thiazol-4-yl}benzonitrile,
4-[2-(cyano {2-[(2-pyridin-3-ylethyl)amino]pyrimidin-4-yl}methylene)-2,3-dihydro-1,3-thiazol-4-yl]benzonitrile,
4-(2-{cyano[2-(cyclopropylamino)pyrimidin-4-yl]methylene}-2,3-dihydro-1,3-thiazol-4-yl)benzonitrile,
[4-(2-chlorophenyl)-1,3-thiazol-2(3H)-ylidene](2-{[3-(2-oxopyrrolidin-1-yl)propyl]amino}pyrimidin-4-yl)acetonitrile,
[4-(3-chlorophenyl)-1,3-thiazol-2(3H)-ylidene](2-{[3-(2-oxopyrrolidin-1-yl)propyl]amino}pyrimidin-4-yl)acetonitrile,

[4-(3-chlorophenyl)-1,3-thiazol-2(3H)-ylidene]{2-[(2-pyridin-3-ylethyl)amino]pyrimidin-4-yl}acetonitrile,
[4-(2-chlorophenyl)-1,3-thiazol-2(3H)-ylidene]{2-[(2-pyridin-3-ylethyl)amino]pyrimidin-4-yl}acetonitrile,
[2-(cyclopropylamino)pyrimidin-4-yl][4-(4-methoxyphenyl)-1,3-thiazol-2(3H)-ylidene]acetonitrile,
[4-(2-chlorophenyl)-1,3-thiazol-2(3H)-ylidene][2-(cyclopropylamino)pyrimidin-4-yl]acetonitrile,
N-[3-({4-[cyano(4-ethyl-1,3-thiazol-2(3H)-ylidene)methyl]pyrimidin-2-yl}amino)propyl]acetamide,
N-[2-({4-[(4-tert-butyl-1,3-thiazol-2(3H)-ylidene)(cyano)methyl]pyrimidin-2-yl}amino)ethyl]acetamide,
{2-[(1-acetylpiperidin-4-yl)amino]pyrimidin-4-yl}(4-ethyl-1,3-thiazol-2(3H)-ylidene)acetonitrile,
(4-tert-butyl-1,3-thiazol-2(3H)-ylidene)(2-{[3-(2,5-dioxopyrrolidin-1-yl)propyl]amino}pyrimidin-4-yl)acetonitrile,
(2-{[3-(2,5-dioxopyrrolidin-1-yl)propyl]amino}pyrimidin-4-yl)(4-ethyl-1,3-thiazol-2(3H)-ylidene)acetonitrile,
(4-ethyl-1,3-thiazol-2(3H)-ylidene)(2-{[1-(methylsulfonyl)piperidin-4-yl]amino}pyrimidin-4-yl)acetonitrile trifluoroacetate,
N~3~-{4-[(4-tert-butyl-1,3-thiazol-2(3H)-ylidene)(cyano)methyl]pyrimidin-2-yl}-N~1~,N~1~-dimethyl-beta-alaninamide,
N-{3-[{4-[(4-tert-butyl-1,3-thiazol-2(3H)-ylidene)(cyano)methyl]pyrimidin-2-yl}(methyl)amino]propyl}acetamide,
N-[3-({4-[(4-tert-butyl-3-methyl-1,3-thiazol-2(3H)-ylidene)(cyano)methyl]pyrimidin-2-yl}amino)propyl]acetamide,
(4-ethyl-1,3-thiazol-2(3H)-ylidene)(2-{[4-(morpholin-4-ylmethyl)benzyl]oxy}pyrimidin-4-yl)acetonitrile,
{2-[3-(dimethylamino)propoxy]pyrimidin-4-yl}(4-ethyl-1,3-thiazol-2(3H)-ylidene)acetonitrile,
[4-(4-chlorophenyl)-1,3-thiazol-2(3H)-ylidene]{5-methyl-2-[(3-pyrrolidin-1-ylpropyl)amino]pyrimidin-4-yl}acetonitrile,
[4-(4-chlorophenyl)-1,3-thiazol-2(3H)-ylidene]{2-[(3-pyrrolidin-1-ylpropyl)amino]pyrimidin-4-yl}acetonitrile,
[2-(cyclohexylamino)-5-methylpyrimidin-4-yl](4-phenyl-1,3-thiazol-2(3H)-ylidene)acetonitrile,
[2-(cyclohexylamino)pyrimidin-4-yl](4-phenyl-1,3-thiazol-2(3H)-ylidene)acetonitrile,
[5-methyl-2-(4-methylpiperidin-1-yl)pyrimidin-4-yl](4-phenyl-1,3-thiazol-2(3H)-ylidene)acetonitrile,
[2-(cyclopropylamino)-5-methylpyrimidin-4-yl](4-phenyl-1,3-thiazol-2(3H)-ylidene)acetonitrile,
[2-(cyclopropylamino)pyrimidin-4-yl](4-phenyl-1,3-thiazol-2(3H)-ylidene)acetonitrile,
[2-(cyclopentylamino)-5-methylpyrimidin-4-yl](4-phenyl-1,3-thiazol-2(3H)-ylidene)acetonitrile,
{5-methyl-2-[(1-methylbutyl)amino]pyrimidin-4-yl}(4-phenyl-1,3-thiazol-2(3H)-ylidene)acetonitrile,
[2-(cyclopentylamino)pyrimidin-4-yl](4-phenyl-1,3-thiazol-2(3H)-ylidene)acetonitrile,
{5-methyl-2-[(3-pyrrolidin-1-ylpropyl)amino]pyrimidin-4-yl}(4-phenyl-1,3-thiazol-2(3H)-ylidene)acetonitrile,
{2-[(1-methylbutyl)amino]pyrimidin-4-yl}(4-phenyl-1,3-thiazol-2(3H)-ylidene)acetonitrile,
{6-[(2-furylmethyl)amino]pyrimidin-4-yl}(4-methyl-1,3-thiazol-2(3H)-ylidene)acetonitrile,
[6-(4-ethylpiperazin-1-yl)pyrimidin-4-yl](4-methyl-1,3-thiazol-2(3H)-ylidene)acetonitrile,
(4-phenyl-1,3-thiazol-2(3H)-ylidene){2-[(3-pyrrolidin-1-ylpropyl)amino]pyrimidin-4-yl}acetonitrile,
[2-(cyclopentylamino)-6-methylpyrimidin-4-yl](4-phenyl-1,3-thiazol-2(3H)-ylidene)acetonitrile,
{2-[(cyclohexylmethyl)amino]pyrimidin-4-yl}(4-phenyl-1,3-thiazol-2(3H)-ylidene)acetonitrile,
{2-[(cyclohexylmethyl)amino]-5-methylpyrimidin-4-yl}(4-phenyl-1,3-thiazol-2(3H)-ylidene)acetonitrile,
[2-(4-ethylpiperazin-1-yl)-5-methylpyrimidin-4-yl](4-phenyl-1,3-thiazol-2(3H)-ylidene)acetonitrile,
[2-(1,4-dioxa-8-azaspiro[4,5]dec-8-yl)-5-methylpyrimidin-4-yl](4-phenyl-1,3-thiazol-2(3H)-ylidene)acetonitrile,
(5-methyl-2-{[3-(1H-1,2,4-triazol-1-yl)propyl]amino}pyrimidin-4-yl)(4-phenyl-1,3-thiazol-2(3H)-ylidene)acetonitrile,
{2-[(1,4-dimethylpentyl)amino]-5-methylpyrimidin-4-yl}(4-phenyl-1,3-thiazol-2(3H)-ylidene)acetonitrile,
(5-methyl-2-{[2-(1H-pyrazole-1-yl)ethyl]amino}pyrimidin-4-yl)(4-phenyl-1,3-thiazol-2(3H)-ylidene)acetonitrile,
(4-phenyl-1,3-thiazol-2(3H)-ylidene)(2-{[3-(1H-1,2,4-triazol-1-yl)propyl]amino}pyrimidin-4-yl)acetonitrile,
(4-phenyl-1,3-thiazol-2(3H)-ylidene)(2-{[2-(1H-pyrazol-1-yl)ethyl]amino}pyrimidin-4-yl)acetonitrile,
[2-(dipropylamino)-5-methylpyrimidin-4-yl](4-phenyl-1,3-thiazol-2(3H)-ylidene)acetonitrile,
{2-[(1,4-dimethylpentyl)amino]pyrimidin-4-yl}(4-phenyl-1,3-thiazol-2(3H)-ylidene)acetonitrile,
[2-(methylamino)pyrimidin-4-yl](4-phenyl-1,3-thiazol-2(3H)-ylidene)acetonitrile,
[2-(methylamino)pyrimidin-4-yl](4-methyl-1,3-thiazol-2(3H)-ylidene)acetonitrile,
[2-(cyclopentylamino)pyrimidin-4-yl](4-methyl-1,3-thiazol-2(3H)-ylidene)acetonitrile,
[2-(cyclohexylamino)pyrimidin-4-yl](4-methyl-1,3-thiazol-2(3H)-ylidene)acetonitrile,
{2-[(1-methylbutyl)amino]pyrimidin-4-yl}(4-methyl-1,3-thiazol-2(3H)-ylidene)acetonitrile,
[2-(cyclopentylamino)-6-methylpyrimidin-4-yl](4-methyl-1,3-thiazol-2(3H)-ylidene)acetonitrile,
{2-[(cyclohexylmethyl)aanino]pyrimidin-4-yl}(4-methyl-1,3-thiazol-2(3H)-ylidene)acetonitrile,
{6-[methyl(phenyl)amino]-2-[(2-pyridin-3-ylethyl)amino]pyrimidin-4-yl}(4-methyl-1,3-thiazol-2(3H)-ylidene)acetonitrile,
{2-[(2,3-dimethylcyclohexyl)amino]pyrimidin-4-yl}(4-methyl-1,3-thiazol-2(3H)-ylidene)acetonitrile,
(4-methyl-1,3-thiazol-2(3H)-ylidene){2-[(pyridin-3-ylmethyl)amino]pyrimidin-4-yl}acetonitrile,
{6-methyl-2-[(2-pyridin-2-ylethyl)amino]pyrimidin-4-yl}(4-methyl-1,3-thiazol-2(3H)-ylidene)acetonitrile,
[2-(isopropylamino)pyrimidin-4-yl](4-methyl-1,3-thiazol-2(3H)-ylidene)acetonitrile,
{2-[(1,2-dimethylpropyl)amino]pyrimidin-4-yl}(4-methyl-1,3-thiazol-2(3H)-ylidene)acetonitrile,
(4-methyl-1,3-thiazol-2(3H)-ylidene){2-[4-(pyrimidin-2-ylamino)piperidin-1-yl]pyrimidin-4-yl}acetonitrile,
{2-[(1-ethylpropyl)amino]pyrimidin-4-yl}(4-methyl-1,3-thiazol-2(3H)-ylidene)acetonitrile,
{2-[(3-butoxypropyl)amino]-6-[methyl(phenyl)amino]pyrimidin-4-yl}(4-methyl-1,3-thiazol-2(3H)-ylidene)acetonitrile,
{2-(isopropylamino)-6-[methyl(phenyl)amino]pyrimidin-4-yl}(4-methyl-1,3-thiazol-2(3H)-ylidene)acetonitrile,
{2-[(3-isopropoxypropyl)amino]pyrimidin-4-yl}(4-methyl-1,3-thiazol-2(3H)-ylidene)acetonitrile,

[4-(4-chlorophenyl)-1,3-thiazol-2(3H)-ylidene][2-(cyclopropylamino)pyrimidin-4-yl]acetonitrile,

[4-(4-chlorophenyl)-1,3-thiazol-2(3H)-ylidene][2-(cyclopentylamino)pyrimidin-4-yl]acetonitrile, and

[4-(4-chlorophenyl)-1,3-thiazol-2(3H)-ylidene]{2-[(cyclohexylmethyl)amino]-5-yl]acetonitrile.

11. A method for treating diabetes or obesity, said method comprising administering said azole compound according to claim 1 to a patient in need thereof in an amount sufficient to treat diabetes or obesity in the patient.

12. The method according to claim 11 wherein obesity is treated.

13. The method according to claim 11 wherein diabetes is treated.

14. A pharmaceutical composition comprising at least one azole compound according to claim 1 and a pharmaceutically acceptable carrier, diluent or excipient.

15. A method of preparing the azole compound according to claim 1, comprising reacting the compound of formula II with the compound of formula III:

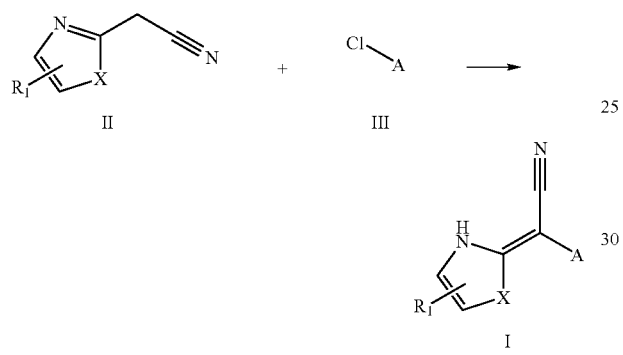

wherein X, A, and $R_1$ have the same meanings as in claim 1.

16. A method of preparing the azole derivative according to claim 1, comprising reacting the compound of formula II with the compound of formula III' to obtain a compound of formula II'; and

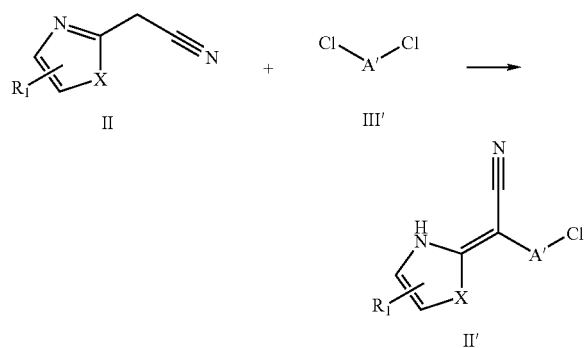

reacting the compound of formula II' with the compound of formula IV;

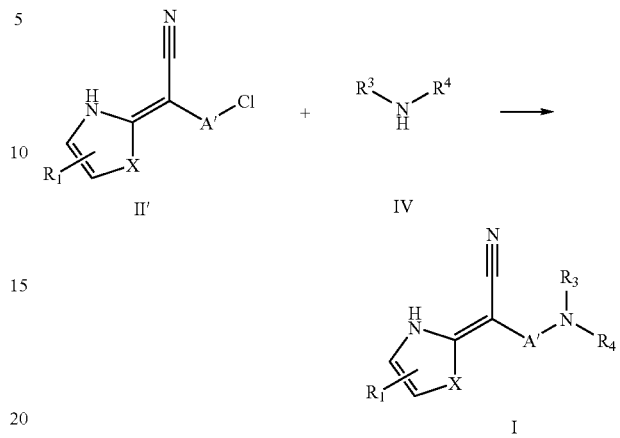

[A' = A'a, A'b, A'c, A'd]

wherein X, A, and $R_1$ have the same meanings as in claim 1.

17. A method of preparing the azole compound according to claim 1, comprising reacting a compound of formula II'a with a compound of formula V:

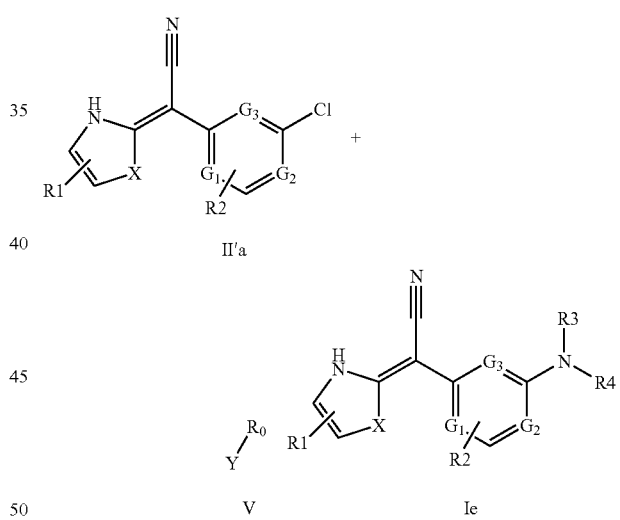

wherein X, A, and $R_1$ have the same meanings as in claim 1 and Y is an electrophile group.

18. The method according to claim 12, wherein diabetes is treated, which is type II diabetes.

* * * * *